US009878025B2

(12) United States Patent
Rowe et al.

(10) Patent No.: US 9,878,025 B2
(45) Date of Patent: Jan. 30, 2018

(54) MALARIA VACCINE

(71) Applicant: The University Court of the University of Edinburgh, Edinburgh (GB)

(72) Inventors: Jane Alexandra Rowe, Edinburgh (GB); Ashfaq Ghumra, Edinburgh (GB)

(73) Assignee: The University Court of the University of Edinburgh, Edinburgh (GB)

( * ) Notice: Subject to any disclaimer, the term of this patent is extended or adjusted under 35 U.S.C. 154(b) by 100 days.

(21) Appl. No.: 14/360,136

(22) PCT Filed: Nov. 22, 2012

(86) PCT No.: PCT/GB2012/052893
§ 371 (c)(1),
(2) Date: May 22, 2014

(87) PCT Pub. No.: WO2013/076492
PCT Pub. Date: May 30, 2013

(65) Prior Publication Data

US 2014/0322240 A1 Oct. 30, 2014

(30) Foreign Application Priority Data

Nov. 22, 2011 (GB) .................................. 1120109.2

(51) Int. Cl.
*A61K 39/00* (2006.01)
*A61K 39/015* (2006.01)
*C07K 16/20* (2006.01)
*G01N 33/569* (2006.01)

(52) U.S. Cl.
CPC .......... *A61K 39/015* (2013.01); *C07K 16/205* (2013.01); *G01N 33/56905* (2013.01); *C07K 2317/33* (2013.01)

(58) Field of Classification Search
None
See application file for complete search history.

(56) References Cited

U.S. PATENT DOCUMENTS

2009/0324628 A1* 12/2009 Theander ............. C07K 14/445 424/185.1

OTHER PUBLICATIONS

Notification Concerning Transmittal of International Preliminary Report on Patentability corresponding to International Application No. PCT/GB2012/052893 dated May 27, 2014.
Ghumra et al. "Identification of Residues in the Cμ4 Domain of Polymeric IgM Essential for Interaction with *Plasmodium falciparum* Erythrocyte Membrane Protein 1 (PfEMP1)[1]", *Journal of Immunology* 181(3):1988-2000 (2008).
Ghumra et al. "Immunisation with Recombinant PfEMP1 Domain Elicits Functional Rosette-Inhibiting and Phagocytosis-Inducing Antibodies to *Plasmodium falciparum", PLoS ONE* 6(1):e16414 pp. 1-15 (2011).
Notification of Transmittal of the International Search Report and the Written Opinion of the International Searching Authority, or the Declaration corresponding to International Application No. PCT/GB2012/052893 dated Apr. 10, 2013.
Albrecht et al. "var gene transcription and PfEMP1 expression in the rosetting cytoadhesive Plasmodium falciparum clone FCR3S1.2", Malaria Journal 10:17, 2011, pp. 1-9.
Avril, "Evidence for Globally Shared, Cross-Reacting Polymorphic Epitopes in the Pregnancy-Associated Malaria Vaccine Candidate VAR2CSA", Infection and Immunity, Apr. 2008, pp. 1791-1800.
Barfod et al. "Chondroitin Sulfate A-Adhering Plasmodium falciparum-Infected Erythrocytes Express Functionally Important Antibody Epitopes Shared by Multiple Variants", The Journal of Immunology, 2010, 185:7553-7561.
Barfod et al. "Evasion of Immunity to Plasmodium falciparum malaria by IgM masking of protective IgG epitopes in infected erythrocyte surface-exposed PfEMP1", PNAS, Jul. 26, 2011, vol. 108, No. 30, pp. 12485-12490.
Barry, "Population Genomics of the Immune Evasion (var) Genes of Plasmodium falciparum", PloS Pathogens, Mar. 2007, vol. 3, issue 3, e34, pp. 1-9.
Bull, "Antibody Recognition of Plasmodium falciparum Erythrocyte Surface Antigens in Kenya: Evidence for Rare and Prevalent Variants", Infection and Immunity, Feb. 1999, vol. 67, No. 2, pp. 733-739.
Bull, "Plasmodium falciparum-Infected Erythrocytes: Agglutination by Diverse Kenyan Plasma is Associated with Severe Disease and Young Host Age", The Journal of Infectious Diseases, 2000, 182:252-9.
Bull, "Plasmodium falciparum Variant Surface Antigen Expression Patterns During Malaria", PloS Pathogens, Nov. 2005, vol. 1, issue 3, e26, pp. 0202-0213.
Chattopadhyay et al., "Plasmodium falciparum Infection Elicits Both Variant-Specific and Cross-Reactive Antibodies against Variant Surface Antigens", Infection and Immunity, Feb. 2003, vol. 71, No. 2, pp. 597-604.
Chen et al., "A Molecular Epidemiological Study of var Gene Diversity to Characterize the Reservoir of Plasmodium falciparum in Humans in Africa", PloS One, Feb. 2011, vol. 6, issue 2, e16629, pp. 1-12.
Claessens et al. "Design of a variant surface antigen-supplemented microarray chip for whole transcriptome analysis of multiple Plasmodium falciparum cytoadherent strains, and identification of strain-transcendent rif and stevor genes", Malaria Journal, 2011, 10:180, pp. 1-16.
Clough et al. "Plasmodium falciparum: The Importance of IgM in the Rosetting of Parasite-Infected Erythrocytes", Experimental Parasitology, 89, 1998, pp. 129-132.

(Continued)

*Primary Examiner* — Ja'Na Hines
*Assistant Examiner* — Khatol Shahnan Shah
(74) *Attorney, Agent, or Firm* — Myers Bigel, P.A.

(57) ABSTRACT

The present invention provides an antigenically restricted subset of the highly variant PfEMP1 rosetting antigen which possess epitopes which may be exploited to raise immune responses effective against many diverse strains and isolates of the malaria parasite, *Plasmodium falciparum*. In this regard, the invention provides one or more *P. falciparum* Erythrocyte Membrane Protein-1 (PfEMP1) antigen(s) or a fragment or fragments thereof, for use in raising immune responses in humans.

7 Claims, 28 Drawing Sheets

(56) References Cited

OTHER PUBLICATIONS

Figure 1A:
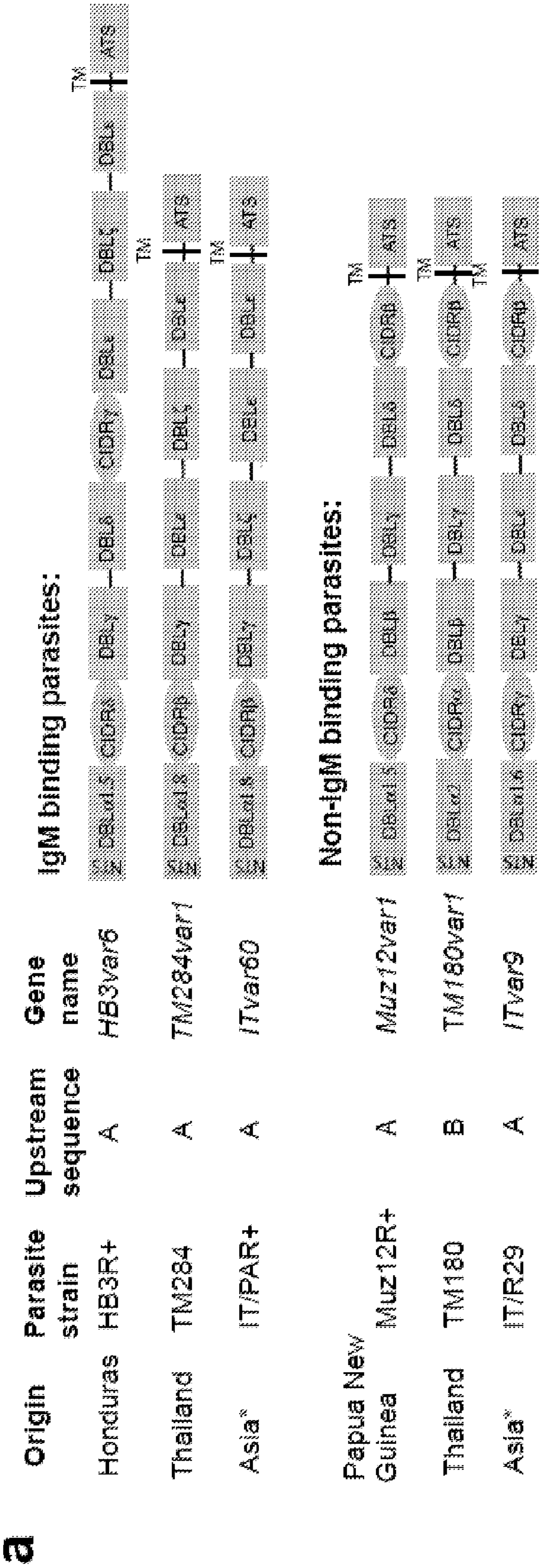

Cockburn et al. "A human complement receptor 1 polymorphism that reduces Plasmodium falciparum rosetting confers protection against severe malaria", PNAS, Jan. 6, 2004, vol. 101, No. 1, pp. 272-277.
Corrigan et al. "Strain variation in early innate cytokine induction by Plasmodium falciparum", Parasite Immunology, 2010, vol. 32, pp. 512-527.
Carlson et al. "Human cerebral malaria: association with erythrocyte rosetting and lack of anti-rosetting antibodies", Lancet, 1990, 336, pp. 1457-1460.
Deans et al. "Low Multiplication Rates of African Plasmodium falciparum Isolates and Lack of Association of Multiplication Rate and Red Blood Cell Selectivity with Malaria Virulence", Am. J. Trop. Med. Hyg., 74(4), 2006, pp. 554-563.
Doumbo et al. "High Levels of Plasmodium falciparum Rosetting in all Clinical Forms of Severe Malaria in African Children", Am. J. Trop. Med. Hyg., 81(6), 2009, pp. 987-993.
Freitas-Junior et al. "Frequent ectopic recombination of virulence factor genes in telomeric chromosome clusters of P. falciparum", Nature, vol. 407, Oct. 26, 2000, pp. 1018-1022.
Gamain et al. "The surface variant antigens of Plasmodium falciparum contain cross-reactive epitopes", PNAS, Feb. 27, 2001, vol. 98, No. 5, pp. 2664-2669.
Good et al. "Malaria Vaccine Design: Immunological Considerations", Immunity 33, Oct. 29, 2010, pp. 555-566.
Gupta et al. "Immunity to non-cerebral severe malaria is acquired after one or two infections", Nature Medicine, vol. 5, No. 3, Mar. 1999, pp. 340-343.
Handunnetti et al. "Uninfected Erythrocytes Form "Rosettes" Around Plasmodium falciparum infected Erythrocytes", Am. J. Trop. Med. Hyg. 40(2), 1989, pp. 115-118.
Heddini et al. "Enrichment of Immunoglobulin Binding Plasmodium falciparum-Infected Erythrocytes Using Anti-Immunoglobulin-Coated Magnetic Beads", Am. J. Trop. Med. Hyg. 59(5), 1998, pp. 663-666.
Horrocks et al. "Variable var transition rates underlie antigenic variation in malaria", PNAS, Jul. 27, 2004, vol. 101, No. 3, pp. 11129-11134.
Hviid, "The role of Plasmodium falciparum variant surface antigens in protective immunity and vaccine development", Human Vaccines, 6:1, Jan. 2010, pp. 84-89.
Janes et al. "Investigating the Host Binding Signature on the Plasmodium falciparum PfEMP1 Protein Family", PloS Pathogens, May 2011, vol. 7, issue 5, e1002032, pp. 1-15.
Jensen et al. "Plasmodium falciparum Associated with Severe Childhood Malaria Preferentially Expresses PfEMP1 Encoded by Group A var Genes", J. Exp Med., vol. 199, No. 9, May 3, 2004, pp. 1179-1190.
Farnert et al. "Genotyping of Plasmodium falciparum infections by PCR: a comparative multicentre study", Transactions of the Royal Society of Tropical Medicine and Hygiene (2001) 95, 225-232.
Joergensen et al. "Limited Cross-Reactivity among Domains of the Plasmodium falciparum Clone 3D7 Erythrocyte Membrane Protein 1 Family", Infection and Immunity, Dec. 2006, vol. 74, No. 12, p. 6778-6784.
Kaul et al. "Rosetting Plasmodium falciparum-Infected Red Blood Cells with Uninfected Red Blood Cells Enhances Microvascular Obstruction Under Flow Conditions" Blood, vol. 78, No. 3, (Aug. 1, 1991): pp. 812-819.
Kirchagatter et al. "Association of Severe Noncerebral Plasmodium falciparum Malaria in Brazil with Expressed PfEMP1 DBL1α Sequences Lacking Cysteine Residues", Molecular Medicine 8(1): 16-23, 2002.
Kramer et al. "New tools to identify var sequence tags and clone full-length genes using type-specific primers to Duffy binding-like domains", Molecular & Biochemical Parasitology, 129, (2003) 91-102.
Kraemer et al. "A family affair: var genes, PfEMP1 binding, and malaria disease", Current Opinion in Microbiology, 2006, 9:374-380.
Kraemer et al. "Patterns of gene recombination shape var gene repertoires in *Plasmodium falciparum*: comparisons of geographically diverse isolates", BMC Genomics 2007, 8:45, pp. 1-18.
Kyes et al. "Antigenic Variation at the Infected Red Cell Surface in Malaria", Annu. Rev. Microbiol. 2001, 55:673-707.
Kyriacou et al. "Differential var gene transcription in *Plasmodium falciparum* isolates from patients with cerebral malaria compared to hyperparasitaemia", Molecular & Biochemical Parasitology 150 (2006) 211-218.
Langhorne et al. "Immunity to malaria: more questions than answers", Nature Immunology vol. 9, No. 7, Jul. 2008, pp. 725-732.
Le Scanf et al. "Rosetting is associated with increased Plasmodium falciparum in vivo multiplication rate in the *Saimiri sciureus* monkey", Microbes and Infection 10 (2008) 447-451.
Marsh et al. "Antigens Induced on Erythrocytes by P. falciparum: Expression of Diverse and Conserved Determinants", Science, vol. 231, Jan. 10, 1986, pp. 150-153.
Mu et al. "Recombination Hotspots and Population Structure in Plasmodium falciparum", PLoS Biology, Oct. 2005, vol. 3, Issue 10, pp. 1734-1741.
Newbold et al. "Plasmodium falciparum: The Human Agglutinating Antibody Response to the Infected Red Cell Surace is Predominantly Variant Specific", Experimental Parasitology, 75, 781-292, (1992), pp. 281-292.
Nielsen et al. "Plasmodium falciparum Variant Surface Antigen Expression Varies Between Isolates Causing Severe and Nonsevere Malaria and is Modified by Acquired Immunity", The Journal of Immunology, 2002, 168: 3444-3450.
Pierce et al. "World Malaria Day 2009: What Malaria Knows about the Immune System That Immunologists Still Do Not", The Journal of Immunology, 2009, 182: 5171-5177.
Rappuoli et al. "A 2020 vision for vaccines against HIV, tuberculosis and malaria", Nature, vol. 473, May 26, 2011, pp. 463-469.
Rask et al. "Plasmodium falciparum Erythrocyte Membrane Protein 1 Diversity in Seven Genomes—Divide and Conquer", PLoS Computational Biology, vol. 6, Issue 9, Sep. 2010, pp. 1-23.
Recker et al. "Conficting Immune Response can Prolong the Length of Infection in Plasmodium Falciparum Malaria", Bulletin of Mathematical Biology (2006) 68: 821-835.
Robinson et al. "Widespread functional specialization of Plasmodium falciparum erythrocyte membrane protein 1 family members to bind CD36 analysed across a parasite genome", Molecular Microbiology (2003) 47(5), 1265-1278.
Rottmann et al. "Differential Expression of var Gene Groups is Associated with Morbidity Caused by *Plasmodium falciparum* Infection in Tanzanian Children", Infection and Immunity, vol. 74, No. 7, Jul. 2006, p. 3904-3911.
Rowe et al. "Implications of mycoplasma contamination of Plasmodium falciparum cultures and methods for its detection and eradication", Molecular and Biochemical Parasitology, 92 (1998) 177-180.
Rowe et al. "P. falciparum rosetting mediated by a parasite-variant erythrocyte membrane protein and complement-receptor 1", Nature, vol. 388, Jul. 17, 1997, pp. 292-295.
Rowe et al. "Blood group 0 protects against severe Plasmodium falciparum malaria through the mechanism of reduced rosetting", PNAS, Oct. 30, 2007, vol. 104, No. 44, pp. 17471-17476.
Rowe et al. "Short Report: Positive Correlation Between Rosetting and Parasitemia in Plasmodium Falciparum Clinical Isolates", Am. J. Trop. Med. Hyg., 66(5) 2002, pp. 458-460.
Rowe et al. "Plasmodium falciparum Rosetting is Associated with Malaria Severity in Kenya", Infection and Immunity, Jun. 1995, vol. 63, No. 6, pp. 2323-2326.
Rowe et al. "Nonimmune $I_gM$, But Not $I_gG$ Binds to the Surface of Plasmodium Falciparum—Infected Erythrocytes and Correlates with Rosetting and Severe Malaria", Am. J. Trop. Med. Hyg. 6696), 2002, pp. 692-699.
Rowe et al. "Adhesion of Plasmodium falciparum-infected erythrocytes to human cells: molecular mechanisms and therapeutic

(56) References Cited

OTHER PUBLICATIONS implications", Accession information: doi:10.1017/S1462399409001082; vol. 11; e16; May 2009, 2009 Cambridge University Press.

Scholander et al. "Novel fibriller structure confers adhesive property to malaria-infected erythrocytes", Nature Medicine, vol. 2, No. 2, Feb. 1996, pp. 204-208.

Semblat et al. "Identification of Plasmodium falciparum var1CSA and var2CSA domains that bind IgM natural antibodies", Molecular & Biochemical Parasitology, 146 (2006) 192-197.

Smith et al. "Classification of adhesive domains in the Plasmodium falciparum Erythrocyte Membrane Protein 1 family", Molecular and Biochemical Parasitology 110 (2000) 293-310.

Somner et al. "Multiple human serum components act as bridging molecules in rosette formation by Plasmodium falciparum-infected erythrocytes", Blood, Jan. 15, 2000, vol. 95, No. 2, pp. 674-682.

Taylor et al. "A study of var gene transcription in vitro using universal var gene primers", Molecular and Biochemical Parasitology, 105 (2000) 13-23.

Treutiger et al. "Rosette Formation in Plasmodium Falciparum Isolates and Anti-Rosette Activity of Sera From Gambians with Cerebral or Uncomplicated Malaria", Am. J. Trop. Med. Hyg. 46(5), 1992, pp. 503-510.

Trimnell et al. "Global genetic diversity and evolution of var genes associated with placental and severe childhood malaria", Molecular & Biochemical Parasitology, 148, (2006), 169-180.

Udomsangpetch et al. "Plasmodium Falciparum-Infected Erythrocytes Form Spontaneous Erythrocyte Rosettes", J. Exp. Med., vol. 169, May 1989, 1835-1840.

Warimwe et al. "Plasmodium falciparum var gene expression is modified by host immunity", PNAS, Dec. 22, 2009, vol. 106, No. 51, 21801-21806.

Vigan-Womas et al. "An In Vivo and In Vitro Model of Plasmodium falciparum Rosetting and Autoagglutination Mediated by varO, a group A var Gene Encoding a Frequent Serotype", Infection and Immunity, Dec. 2008, vol. 76, No. 12, pp. 5565-5580.

Vigan-Womas et al. "Allelic Diversity of the Plasmodium falciparum Erythrocyte Membrane Protein 1 Entails Variant-Specific Red Cell Surface Epitopes", PLoS One, Jan. 2011, vol. 6, Issue 1, pp. 1-14.

* cited by examiner

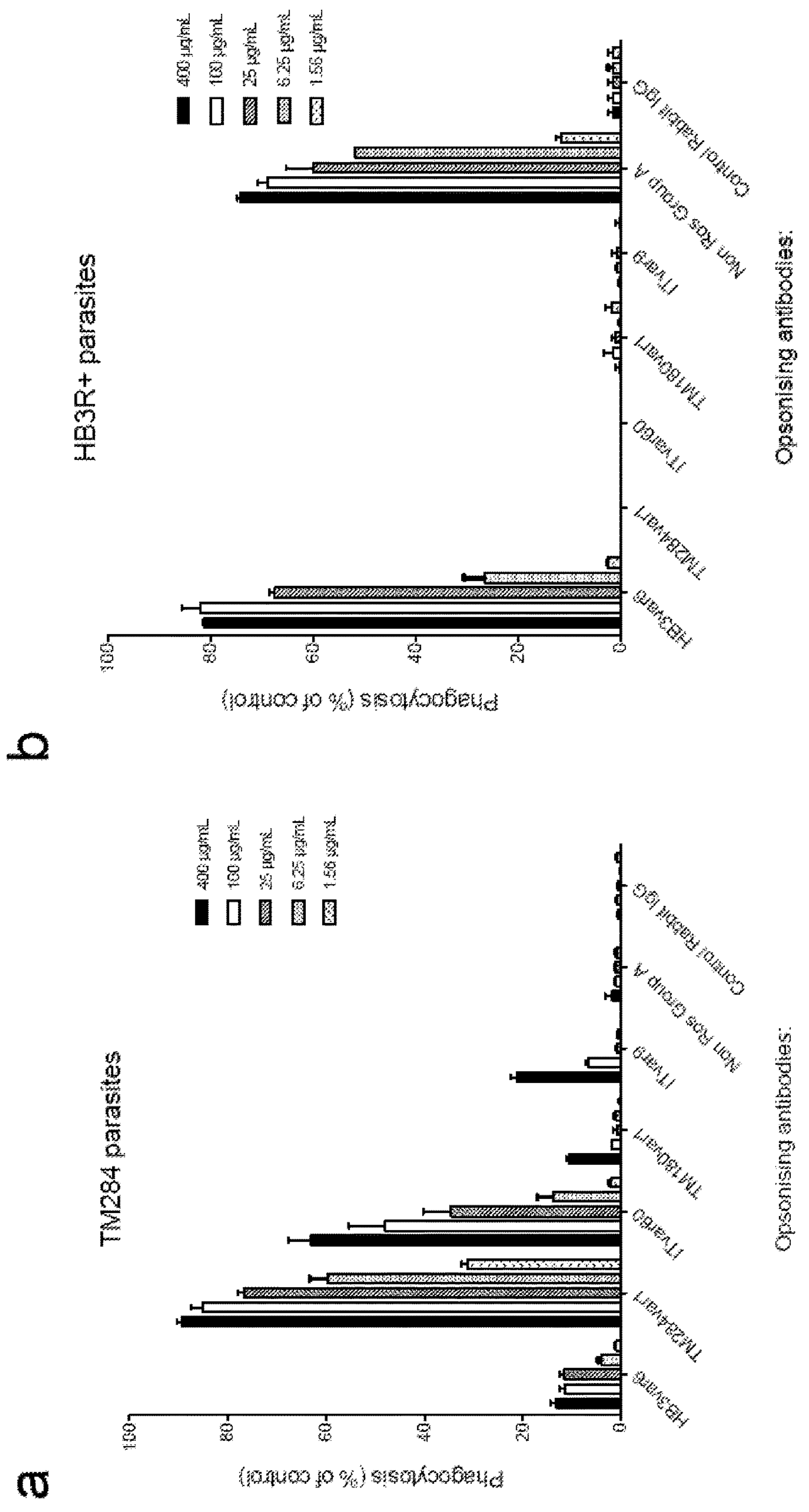
Figure 7a and b

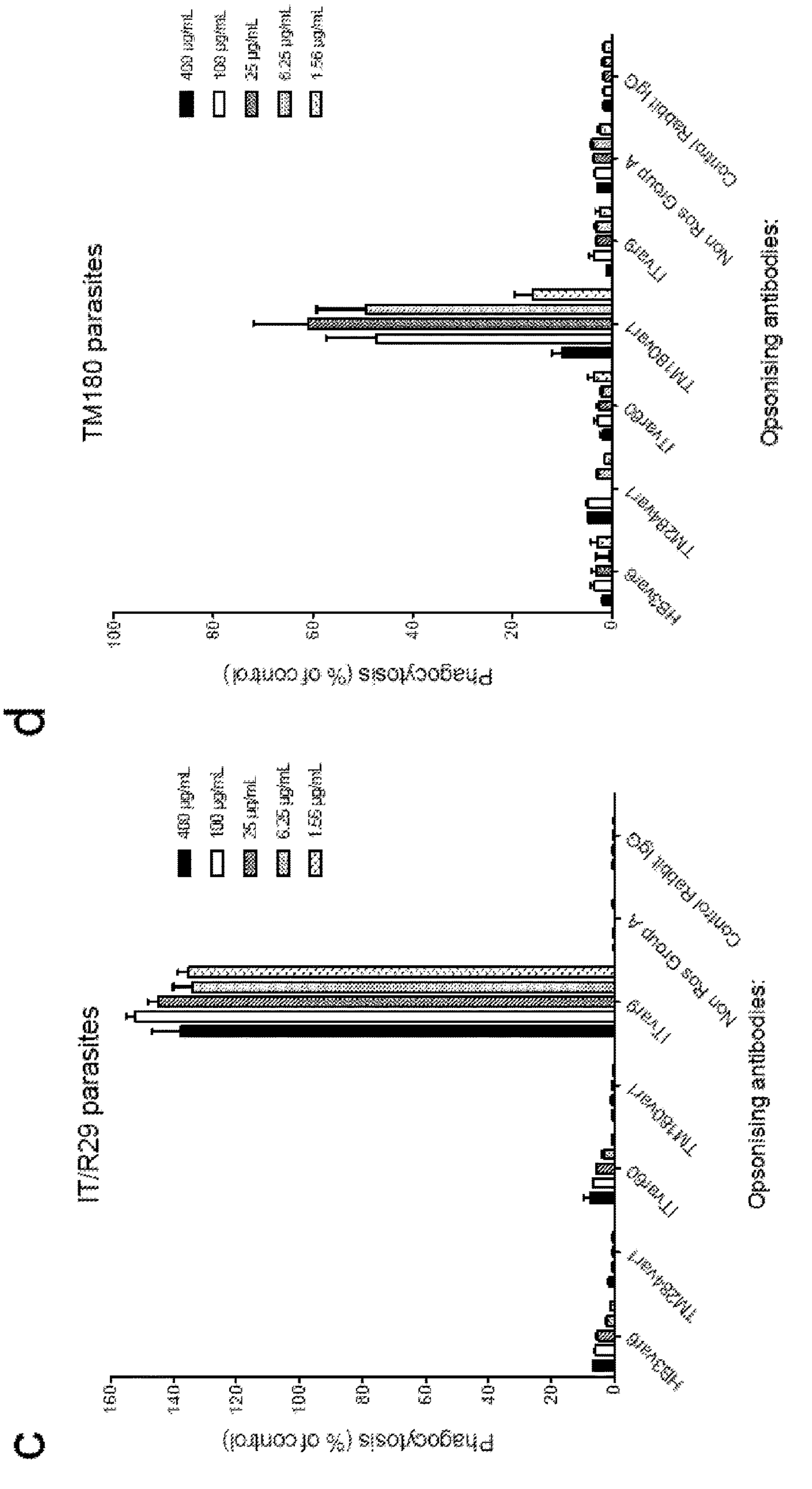
Figure 7c and d

Non IgM-binding variants

Figure 16 A & B

Figure 17 A & B

MALARIA VACCINE

RELATED APPLICATIONS

This application is a 35 U.S.C. §371 national stage application of PCT Application No. PCT/GB2012/052893, filed on Nov. 22, 2012, which claims priority from British Application No. 1120109.2, filed on Nov 22, 2011, the contents of which are incorporated herein by reference in their entireties. The above-referenced PCT International Application was published as International Publication No. WO 2013/076492 A1 on May 30, 2013.

STATEMENT REGARDING ELECTRONIC FILING OF A SEQUENCE LISTING

A Sequence Listing in ASCII text format, submitted under 37 C.F.R. §1.821, entitled 9013-134TS_$_{ST}$25.txt, 175,973 bytes in size, generated on May 20, 2014 and filed via EFS-Web, is provided in lieu of a paper copy. This Sequence Listing is hereby incorporated by reference into the specification for its disclosures.

FIELD OF THE INVENTION

This invention provides antigens which may be exploited to raise immune responses in humans. In particular, the invention provides antigens which raise immune responses which exhibit cross-reactivity to a variety of *Plasmodium falciparum* strains and which may be exploited in the treatment and/or prevention of malaria and in particular severe malaria.

BACKGROUND OF THE INVENTION

Sequence diversity in pathogen antigens is an obstacle to development of interventions against many infectious diseases. In malaria caused by *Plasmodium falciparum*, the PfEMP1 family of variant surface antigens encoded by var genes are adhesion molecules that play a pivotal role in malaria pathogenesis and clinical disease. PfEMP1 is a major target of protective immunity, however, development of drugs or vaccines based on PfEMP1 is problematic due to extensive sequence diversity within the PfEMP1 family.

Every *P. falciparum* isolate has 50-60 diverse PfEMP1 variants, and the PfEMP1 repertoires of different isolates are largely non-overlapping [3,4,5,6]. PfEMP1 variants are expressed in a mutually exclusive fashion, and transcriptional switching from one var gene to another results in antigenic variation of *P. falciparum* infected erythrocytes [7]. PfEMP1 variants sampled from broad global parasite populations show essentially unlimited sequence diversity [5,8], making PfEMP1 an extremely challenging therapeutic target [9](see also: Pierce S K, Miller L H. J Immunol 2009; 182:5171-7).

Surface-reactive antibodies to PfEMP1 on live infected erythrocytes that occur after natural infections [10,11] or after immunization with recombinant PfEMP1 domains [11, 12] are predominantly variant-specific, as expected for highly polymorphic parasite antigens. However, children living in endemic areas develop antibodies during the first few years of life that protect against life-threatening malaria [13] suggesting that strain-transcending antibody responses may occur, or that the parasites that cause severe malaria are of restricted antigenic types [14,15]. Antigenically-restricted subsets of parasite surface antigens that induce strain-transcending antibodies have not yet been identified.

In addition to their role in immunity and immune evasion, PfEMP1 variants are adhesion proteins that mediate interactions with a variety of human cell types and surface receptors [16,17]. Three major PfEMP1 families (A, B and C, based on conserved upstream sequence and genomic location) differ in their adhesive function [16]. Group B and C variants (approximately 40-50 variants per haploid parasite genome) bind to the endothelial protein and scavenger receptor CD36 [18,19]. In contrast, Group A variants (approximately 10 variants per haploid parasite genome) do not bind CD36 [18,19] but do mediate rosetting [11,12,20,21], an adhesion phenotype in which infected erythrocytes bind to uninfected erythrocytes [22]. Transcription of Group A var genes is linked to severe malaria in a variety of geographical settings [23,24,25,26] and laboratory experiments [27], whereas transcription of B and C var genes occurs in less virulent infections causing uncomplicated disease [23, 24,25,26].

Rosetting is an important parasite virulence factor, associated with life-threatening malaria in African children [28, 29,30,31,32] and high parasite burden in a primate malaria model [33]. Rosetting causes pathological obstruction to microvascular blood flow [34] and human erythrocyte polymorphisms that reduce the ability of *P. falciparum* to form rosettes confer substantial protection against severe malaria [35,36]. *P. falciparum* rosetting parasites can be divided into two distinct phenotypes: those that bind IgM natural antibodies ("non-immune" IgM) from normal human serum [37,38] and those that do not. Non-immune IgM binding is thought to strengthen the adhesion interactions between infected and uninfected erythrocytes in rosettes [37,39,40] and may also play a role in immune evasion by masking key epitopes [41]. Previous studies on PfEMP1 and rosetting have focussed on parasites with the non-IgM binding phenotype [11,12,20,21,42]. Detailed examination of IgM binding rosetting parasites has been neglected to date, despite the clinical importance of this phenotype, as rosetting parasites from clinically ill children are predominantly of the IgM binding type [38].

SUMMARY OF THE INVENTION

The present invention is based on the discovery of an antigenically restricted subset of the highly variant PfEMP1 rosetting antigen. Moreover, the inventors have discovered that despite substantial sequence diversity, PfEMP1 variants possess epitopes which can be exploited to raise immune responses effective against many diverse strains and isolates of the malaria parasite, *Plasmodium falciparum*.

In a first aspect, the present invention provides one or more *P. falciparum* Erythrocyte Membrane Protein-1 (PfEMP1) antigen(s) or a fragment or fragments thereof, for use in raising immune responses in humans.

In a second aspect, the invention provides use of one or more *P. falciparum* Erythrocyte Membrane Protein-1 (PfEMP1) antigen(s) or a fragment or fragments thereof for the manufacture of a medicament for raising immune responses in humans.

In a further aspect, the invention provides a method of raising an immune response in a human, the method comprising the step of administering an immunogenic amount of one or more *P. falciparum* Erythrocyte Membrane Protein-1 (PfEMP1) antigen(s) or a fragment or fragments thereof to a human subject.

In one embodiment, the immune response raised in the human subject comprises a systemic antibody response, comprising one or more antibody isotypes. By way of example, the immune response raised in the human may comprise IgM, IgG, IgA, IgD and/or IgE antibody isotypes.

Advantageously, the immune responses described herein are cross reactive; that is to say, the immune response comprises antibodies which exhibit a degree of affinity, selectivity and/or specificity not only to the specific PfEMP1 antigen(s) exploited by this invention, but also to other PfEMP1 variants. Given the comparable lack of sequence identity/homology between PfEMP1 antigens, the ability to raise cross reactive antibody responses from only a limited selection of PfEMP1 antigens is both advantageous and surprising.

The immune responses described herein may further assist in alleviating, reducing and/or eliminating the symptoms of malaria/severe malaria. Additionally or alternatively, the immune response raised in the human subject may reduce the parasite (*Plasmodium* sp.) burden and/or clear or eliminate the parasite from the host. One of skill will appreciate that immune responses of this type may be known as "protective immune responses".

As such, the antigens, uses and/or methods described herein may be exploited to raise cross-reactive and/or protective antibodies in human hosts, which antibodies exhibit a degree of affinity, selectivity and/or specificity for the PfEMP1 antigen of *P. falciparum.*

In one embodiment, the PfEMP1 antigens to be exploited by this invention are IgM rosetting variants. One of skill in this field will appreciate that IgM rosetting PfEMP1 variants are characterised by their ability to bind IgM antibodies from human serum. As such, in a yet further embodiment, the invention provides PfEMP1 IgM rosetting variants (or a fragment(s) thereof) for use in raising immune responses in humans; use of PfEMP1 IgM rosetting variants (or a fragment(s) thereof) for the manufacture of medicaments for raising immune responses in humans; and methods of raising immune responses in humans, the methods comprising the step of administering an immunogenic amount of one or more PfEMP1 IgM rosetting variants or a fragment or fragments thereof, to a human subject.

In one embodiment, the PfEMP1 antigens of this invention represent specific PfEMP1 variants. In this regard, the inventors have discovered that the (IgM rosetting) PfEMP1 variants designated HB3var6, TM284var1 and ITvar60 comprise epitopes capable of inducing protective and/or cross reactive immune responses.

Accordingly, one embodiment of this invention provides one or more PfEMP1 antigen(s) or a fragment(s) thereof, for use in raising an immune response in a human subject, wherein the PfEMP1 antigen is selected from the group consisting of:

(i) HB3var6

(ii) TM284var1; and (iii) ITvar60.

In addition, it should be understood that the various medicaments and methods described in this invention may also exploit the specific PfEMP1 variants (or fragment(s) thereof) listed as (i)-(iii) above.

One of skill will appreciate that the HB3var6 PfEMP1 antigen may be obtained from the *P. falciparum* strain HB3. Similarly the TM284var1 PfEMP1 antigen and the ITvar60 PfEMP1 antigen may be obtained from *P. falciparum* strains TM284 and IT/PAR+ respectively.

The PfEMP1 variant designated HB3var6 has the following amino acid sequence:

SEQ ID NO: 1

```
MGNTIPKPPDPIYINESYQSTRNVLERYAESIKQQAAADAEKCEKSLKGD
LTKAEFRGAHIETVGVQKYSYSNPCGLNHTWNTNLLHDRVKDRDPCHGRN
QKRFDEGQVYECGSGIIKGNGNNRNGGSYAPPRRRHICDKNLEALTVQNT
KNSNDLLGNILVTAKYEGESIVNSYANSGMFNVCTALARSFADIGDIVRG
KDLYSGNKQEKEKRKQLEKNLQKIFRNIYDKLLEYNKTNGEIEARYGSDK
ENFFQLREDWWKANRDQVWRAITCKAPQDANYFRKISGDTKVFTSQGQCG
HSETNVPTNLDYVPQFLRWFDEWAEEFCRVREHKLKKIKEACRGKNDEKD
CSREGYDCNKTNLRLNEIFMDLECPNCEKACTSYKEWIENKQKEFNKQKK
KYEKEIENDESNSHSTYDNELYNNLKRNYPSFENFVETLKEGAYCTNGII
EGKIDFNKQYDTFSHSQYCKSCPILGAKCKNGQCNSFNDINCTKIPTMTN
IRIHSTESPKDIYILVNDKKNREHSLELKDAFNDCDIFKRIRKQKWYCKY
KCNLDVCELKNFNRDMDDERLISIEVLIKRWLKYFLNDYNQIKENLNQCI
NNGTNTLCINDCHKNCECIEKWIKEKEKEWKVIKDRYVEQYNNNDKDVSS
KLKTFLKQDLFTNYVKNALDPDETLDKMKESSVCNVPNKLNGTSCKKKDV
INILLNRLNEKIDPCKNQHKATKGKECCDKLPKIADGDTSDDEDDDEEDV
SVTSGEKQNVKQDCAGKKSDEVCEMVKKLIGDNNGMSGRIESCNPKTGTY
PPWKNHASLVEDNRTWMPPRRQKLCVSALTQEGKIKNKEDIRKHFITCAA
IETHFAWHRYKNHNANAESKLKTGKIPDDFLRSMKYTFGDYRDIFFGTDI
SSCDKIKNASNTIKSILENKTKKKKGDKLIEDNEKHKEWWNEHGKEIWEG
MLCALEKVGGSVNIKSTYNYDTIKNDLEDFASRPQFLRWFTEWSDEFCQE
RKKLEAKVKEYCKKDYVGCNKQNTKANNSCVSACEAFQHYMKSKMSEYDT
QKKKFEAEKSGKEPEYEGFSTKDASEYLKEKCLHGTCDCMEKVKNIDDYW
KNPHKTYDDNKLETKCECPQTPPKPCEIVKTLLEDNNGRHVDACNLKYEG
KKEKHTSWNCNPNKFKNGEEGACIPPRRQKLYIYNLEKFTGGTSEIELRK
AFIECAAIETFFSWHKFKKDKEREDKEKQDLVGYTSTVDEKHQKDLQSGK
IPEEFKRQMFYTFGDYRDICLGNDMGNDNYNKNISTKVRSILNSGETPEE
WWQKHGPQIWEGMLCALSYDTEKQKKVQDVHNNLIAPPNNNKYNDVKLVS
KSGKLHTSLSDFATVPQFLRWEEENVEEFCRKKKIKIDKIEDECRGEYDN
GGKKYCSGDGYDCDKRYLSHNKMFADLNCLGCEKECRNYKKWIEEKVEEF
YKQKKKYEKGFENTRTNLDNKYVKEFYETSAGKYKSVDLFLDTLKERSHC
SMGMVNRKIDEKNPLETFSPSIYCKTCPLYGVNCNSRECVDITENEFKKK
NVLDEIIINDKSHTSIDIEMIDRRGQYMQENLDNPLFKESYLLKSVRDQK
WDCNFIHNKIDLCEINKFNENIDTDESITFKVLIERWLQDFLEGYYISKK
QIDLFTKKEENKCECVKKWAEKKEGEWEKINEHFNKQKHDDAFDMDFKVK
NYFEKNASDLKDWIDNFKRLNNIDDYQVCNVHNNCKSADKKNKIDMVSIL
LSELKKEIETCKNQGNEKTKIKCDASPTNDELDEEYELGTTDTSPSAAPD
ICKDVIQSKSEETICRDDKRVDCNKVGKDDPIKVPMDPKSGEDHLNEMGD
KHNCSGIIIKTNGEWKNTKQLNYPNPCESIYASPRRQKFCVHELDKAKNQ
KELRTKLLTVAANQGYNLAIKHHEYKDKYTVNPCNALKYSFYDYQHIILG
DDPMEPEKWDTESALKRIFGNRNTEDAKPLSRKRKDFWKENKECVWSAMK
```

-continued

CGYNEGIKKGNKSNNIPECKDSIPTQFDGVPQFLMWFTEWSEDFCNHKKT

HLKKLEQGCRGCTLRIDGTCEKDGSGCQKCSQACEEYKAWLQNWKDQYKK

QSKKYSGDKKKELYKTVPKVKNSTHAYEYLQTQLEKLCEKGKCDYTCMKN

PSTENSTENMPESLDVKPDIVKDKCPCPPQKIEKPDSTLNCIDRSAFELY

AKAKSDLHGVKDKLKGNNTKNIYEETTNGKNDDNIICKINESISKQNNVC

KKNENLFDDIDKWDCKKRTNTVPIENICIPPRRKLMCAYPLKNLGVKKNT

SEVLFNKVLRTAAYEGKHIKESWEKAEKSKKKKTQICDAMKYSFADLGDI

IRGRDILIFNNGNNEIERDLKAVFQSIYDKWKSDSNNNKDKYPDLTSFRS

AWWDANRKDIWKAMTCGAPEDATLFKKLEKWGIPNLILSQHKCGHNDDPP

IDDYIPQRLRWMKEWGEYVCKILNENVNDMKNDCDKCTLNDKKCSDEDDG

NKCRSCKEKCKEYTKLIYNLKSQFYILEKHYNELYTKAQNNTTYFTNDND

KKVIEFFKKVKKDCDVGTPDKYLDKAIHCIHYDFTKNGTKSKPYVFNNQP

EKYKNLCSCTITNHPLDKCPLPDKTDDYCKIIRHINPCITINLDNNLDTW

TGFVVHNISHKNKGVLVPPRRRHLCTRELTGIRYRKNDKDNLKQNLIDSA

FNQGILLGKTFKDYSDQGLEYMKYSFADYGDIIKAKDMIGGSNIDDFNND

LKKMFPEHHSENMGKTTISREQWWEANKTHVWHAMLCGYHQGIINPNLSR

RRPKPLEEGTQSSIATKTIPSNWCQLPNDYSTDQFLRWFQEWIENFCTRK

KVLEKEAQEQCKNITCNNDTGKTNTKCTEACKNYSNFILIKKKEYESLNS

QYDMNYKKIVEHKNALEYFKDKCKNNCECLSKHIDNGKNWKEPYETIDDS

ELIGKCKCKKVKPKTPDVIPAGATETKEKDTPHAPEKPQQPPQPLPPSDE

PFDPTILQTTIPFGIALALGSIAFLFMKKKPKSPVDLLRVLNIPKRDYEM

PTLKSKNRYIPYASDRYKGKTYIYMEGDSSGDEKYAFMSDTTDVTSSESE

YEELDINDIYVPGSPKYKTLIEVVLEPSKSNGNTLGDDMVPTTNTFTDEE

WNELKHDFISQYVQREPLDVPQYDESTQLPMNIVGNVLDDGMDEKPFITS

IHDRDLYTGEEISYNINMSTNSMDDPKYVSNNVYSGIDLINDTLSGDRID

IYDELLKRKENELFGTNHVKQTSIHSVAKLTNSDPIHNQLDLFHTWLDRH

RDMCNTWNTKEELLDKLNEQWNKDNDGGDIPNDNKKLNTDVSFEIDMDET

KGKKEFSNMDTILDDMEDDIYYDVNDENPSVDNIPMDHNKVDVPKKVHVE

MKILNNTSNGSLEQEFPISDVWNI

Moreover, the HB3var6 PfEMP1 variant is encoded by the following nucleic acid sequence:

SEQ ID NO: 2

ATGGGGAATACAATACCAAAGCCTCCGGATCCAATTTATATAAATGAAAG

TTATCAAAGTACCAGAAATGTTTTGGAACGTTATGCCGAAAGTATAAAGC

AACAGGCAGCTGCTGATGCAGAAAAATGTGAGAAATCGTTGAAAGGAGAT

TTGACAAAAGCAGAATTTCGTGGTGCTCATATAGAGACAGTTGGTGTCCA

GAAATATAGTTATTCTAATCCATGTGGTTTGAATCATACATGGAATACTA

ATTTATTGCATGATAGAGTGAAGGATAGAGATCCGTGCCATGGTAGAAAT

CAAAAACGTTTTGATGAAGGTCAAGTATATGAATGTGGTAGTGGTATAAT

CAAAGGTAATGGAAATAACAGAAATGGGGGATCCTATGCGCCACCCAGAA

GAAGACATATATGTGATAAAAACTTGGAAGCTCTAACTGTGCAAAATACA

-continued

AAAAATTCTAACGACTTGTTAGGAAATATCTTGGTCACAGCAAAATATGA

AGGCGAATCTATTGTGAATAGTTATGCAAATAGCGGAATGTTCAATGTAT

GTACTGCACTTGCACGAAGTTTTGCAGATATAGGTGATATCGTACGCGGC

AAAGATCTATATAGTGGTAATAAACAAGAAAAAGAAAAAAGAAAACAATT

AGAGAAGAATTTACAAAAAATTTTTAGGAATATATATGACAAATTATTAG

AGTATAACAAGACGAATGGGGAGATAGAAGCTCGCTACGGAAGTGATAAA

GAAAATTTTTTTCAATTAAGAGAAGATTGGTGGAAAGCGAACAGAGATCA

AGTATGGAGAGCTATAACATGTAAAGCTCCACAAGACGCTAATTATTTTA

GAAAAATTTCAGGAGATACTAAGGTGTTTACAAGTCAAGGACAATGTGGG

CATAGTGAAACAAACGTTCCTACGAATCTAGATTATGTCCCTCAATTTTT

ACGATGGTTTGATGAATGGGCAGAAGAGTTTTGCAGAGTAAGAGAACATA

AGTTGAAAAAGATTAAAGAAGCGTGTCGTGGGAAAAATGATGAAAAAGAT

TGTAGTCGTGAGGGTTACGATTGTAATAAAACAAATCTAAGACTTAATGA

AATTTTTATGGATTTAGAATGTCCAAATTGTGAAAAAGCGTGTACAAGTT

ATAAGGAATGGATAGAAAATAAACAAAAGGAATTTAATAAACAAAAGAAA

AAATACGAAAAGGAAATAGAAAATGATGAAAGTAATTCTCATAGTACATA

TGATAACGAATTATATAATAATCTGAAAAGAAATTATCCTTCCTTTGAAA

ATTTTGTAGAAACATTAAAAGAAGGAGCGTATTGTACTAATGGCATTATA

GAAGGTAAAATAGATTTTAATAAACAATATGACACTTTTTCCCATTCACA

GTACTGTAAATCATGTCCTATATTAGGTGCCAAATGCAAGAATGGACAAT

GCAATTCATTTAATGATATAAATTGTACAAAAATACCGACTATGACTAAT

ATAAGAATTCACAGCACTGAAAGTCCTAAGGATATTTATATTCTGGTGAA

TGATAAAAAAAAATAGAGAACATTCTCTTGAATTAAAGGATGCTTTTAATG

ATTGTGATATTTTTAAAAGAATAAGAAAACAAAAATGGTATTGTAAATAT

AAATGTAACTTAGATGTATGTGAACTAAAAAATTTTAATAGGGATATGGA

TGATGAAAGATTAATTTCAATCGAAGTATTGATTAAACGTTGGTTAAAGT

ATTTTTTAAATGATTATAATCAAATAAAAGAAAATTTAAATCAATGTATA

AATAATGGAACAAATACATTATGTATAAACGATTGTCATAAAAATTGTGA

ATGCATAGAGAAATGGATAAAAGAAAAAGAGAAAGAGTGGAAAGTTATAA

AAGATCGTTATGTAGAACAATATAATAATAACGATAAAGACGTTTCTTCT

AAACTTAAAACTTTTTTGAAACAGGATTTGTTTACTAACTATGTTAAAAA

TGCCTTGGACCCCGATGAAACGTTAGATAAGATGAAAGAATCTAGTGTAT

GCAATGTACCTAATAAACTCAATGGAACATCATGTAAAAAAAAGGACGTG

ATAAATATTTTACTTAATAGACTTAATGAAAAAATAGATCCTTGCAAAAA

TCAACATAAAGCAACCAAAGGTAAAGAATGTTGTGATAAATTACCTAAAA

TTGCAGATGGTGATACATCAGACGATGAAGATGACGATGAAGAGGATGTT

TCTGTGACTTCTGGAGAAAAACAAAATGTAAAACAAGATTGTGCTGGTAA

GAAATCGGATGAGGTGTGCGAAATGGTGAAGAAACTTATTGGAGATAACA

ATGGAATGAGTGGTCGAATAGAGAGTTGTAATCCAAAAACTGGAACTTAT

CCTCCATGGAAAAACCACGCAAGTTTAGTGGAAGACAACAGAACGTGGAT

-continued

GCCTCCAAGAAGACAGAAATTATGCGTAAGTGCTTTAACACAAGAAGGTA

AAATAAAAAATAAAGAAGATATAAGAAAACATTTTATTACATGTGCGGCT

ATAGAAACACATTTTGCGTGGCATAGATATAAAAACCATAATGCGAATGC

TGAAAGCAAATTAAAAACTGGAAAAATTCCTGATGATTTTTTAAGATCCA

TGAAATATACTTTTGGTGATTATAGAGATATATTTTTTGGAACAGATATT

TCATCATGTGATAAAATTAAAAATGCCTCAAATACTATAAAATCTATATT

AGAAAATAAAACAAAGAAGAAAAAAGGAGATAAACTCATTGAAGATAATG

AAAAACACAAAGAGTGGTGGAATGAACATGGGAAGGAGATATGGGAAGGA

ATGTTATGTGCACTAGAAAAAGTTGGAGGAAGCGTCAATATCAAATCCAC

GTACAACTACGATACTATAAAAAATGATCTAGAAGACTTTGCATCTAGGC

CACAATTTTTACGGTGGTTCACCGAATGGAGTGATGAATTTTGTCAGGAA

CGGAAGAAATTGGAGGCAAAGGTTAAAGAATATTGTAAGAAGGATTATGT

CGGATGTAATAAACAAAACACGAAGGCTAATAATAGTTGTGTTAGCGCTT

GTGAAGCATTTCAACATTACATGAAGTCCAAAATGTCAGAATACGATACA

CAAAAAAAAAAATTTGAGGCTGAAAAAAGCGGGAAGGAACCAGAATATGA

AGGTTTTTCAACTAAAGACGCTTCTGAATACTTAAAAGAAAAATGTTTGC

ATGGTACATGTGATTGTATGGAGAAAGTAAAAAACATTGATGATTATTGG

AAAAATCCTCATAAAACGTATGACGATAACAAACTTGAAACTAAATGTGA

GTGTCCTCAAACACCACCAAAACCATGTGAAATAGTAAAAACACTTTTGG

AAGATAACAATGGAAGACATGTAGATGCTTGCAATCTCAAATATGAGGGT

AAAAAAGAAAAACATACTTCATGGAATTGTAATCCAAATAAGTTTAAAAA

TGGAGAAGAAGGTGCCTGTATACCTCCGAGAAGACAAAAATTATACATAT

ATAATTTAGAGAAATTCACTGGTGGAACATCAGAAATTGAATTGAGAAAA

GCTTTTATTGAATGTGCTGCAATAGAAACGTTTTTTTCTTGGCATAAATT

TAAAAAGGATAAAGAAAGAGAGGATAAAGAAAAACAAGATCTAGTAGGAT

ATACATCAACCGTCGATGAAAAACATCAAAAGGATTTACAAAGTGGAAAA

ATTCCTGAAGAATTTAAACGTCAAATGTTCTATACATTTGGTGATTATAG

AGATATATGTTTAGGAAACGATATGGGTAATGATAACTATAATAAAAATA

TATCTACAAAAGTTAGGAGTATTTTAAATAGTGGGGAAACACCTGAAGAA

TGGTGGCAAAAACATGGACCTCAGATATGGGAAGGTATGTTATGTGCTTT

AAGTTACGATACCGAAAAACAAAAAAAGGTTCAAGATGTGCACAATAATC

TTATAGCCCCCCCAAACAACAACAAGTACAACGACGTAAAATTGGTTTCG

AAAAGTGGGAAACTTCATACCTCTTTATCCGATTTTGCAACTGTTCCGCA

GTTTTTAAGATGGTTCGAAGAATGGGTCGAAGAGTTTTGTAGAAAAAAAA

AAATTAAAATTGATAAAATTGAAGACGAATGTCGTGGAGAATATGATAAT

GGTGGTAAAAAATATTGTAGTGGTGATGGTTATGATTGTGACAAAAGATA

TTTATCCCATAATAAAATGTTTGCAGATTTAAATTGTCTAGGTTGTGAGA

AAGAATGTAGAAATTATAAAAAATGGATAGAAGAAAAAGTAGAAGAATTT

TATAAACAAAAAAAGAAATACGAAAAGGGGTTTGAGAACACACGAACTAA

CCTTGATAATAAATATGTTAAAGAATTTTATGAAACATCTGCTGGAAAAT

ATAAGTCTGTTGACTTATTTTTAGATACATTGAAAGAAAGATCTCATTGT

-continued

AGTATGGGTATGGTAAATAGAAAAATAGATTTTAAGAATCCGCTCGAAAC

ATTTTCCCCTTCAATATATTGTAAAACGTGCCCTTTATATGGAGTTAACT

GTAATTCGAGAGAATGTGTAGACATTACTGAAAATGAGTTTAAGAAAAAA

AATGTTTTAGATGAGATTATTATAAACGATAAGTCACATACAAGTATTGA

TATCGAAATGATTGATCGTAGGGGACAGTATATGCAAGAGAATTTAGACA

ATCCTTTGTTTAAAGAATCATATCTTTTAAAAAGTGTCAGAGATCAAAAA

TGGGATTGTAACTTTATTCATAATAAGATCGATTTATGTGAAATAAATAA

GTTTAATGAAAACATAGACACTGATGAAAGCATTACATTTAAGGTTTTGA

TAGAACGGTGGTTACAAGATTTCTTAGAAGGATATTATATATCAAAAAAA

CAAATCGATCTATTTACAAAAAAAGAAGAAAATAAATGTGAATGCGTGAA

GAAATGGGCAGAAAAAAAGGAAGGAGAATGGGAAAAAATAAACGAACATT

TTAATAAACAAAAACATGATGATGCATTTGATATGGATTTTAAAGTCAAA

AATTATTTTGAGAAAAATGCAAGTGATTTAAAGGATTGGATAGATAATTT

TAAACGTCTAAACAATATAGATGATTATCAGGTTTGCAATGTTCATAACA

ATTGTAAAAGTGCGGATAAAAAAAATAAAATAGATATGGTATCTATTTTA

CTTTCTGAGCTTAAAAAAGAAATAGAAACTTGTAAAAATCAAGGTAACGA

AAAAACAAAAATAAAATGTGATGCATCACCTACAAACGACGAACTAGATG

AAGAATACGAACTAGGCACAACGGACACATCTCCATCCGCAGCTCCGGAT

ATTTGTAAGGATGTGATCCAAAGTAAATCTGAAGAAACAATATGTAGAGA

TGATAAAAGGGTAGATTGTAACAAGGTGGGTAAAGATGATCCAATAAAGG

TCCCTATGGATCCAAAATCTGGTGAAGATCATCTCAACGAGATGGGAGAT

AAACATAATTGTAGTGGAATTATCATTAAAACAAATGGTGAATGGAAAAA

TACAAAACAATTAAATTACCCGAACCCATGTGAAAGCATATATGCTTCAC

CTCGAAGACAAAAATTCTGTGTACATGAACTTGACAAAGCAAAAAACCAA

AAGGAATTAAGAACTAAATTATTGACTGTTGCTGCAAATCAAGGATATAA

TCTAGCTATTAAACATCATGAATATAAAGACAAATATACTGTTAATCCTT

GTAATGCATTGAAATATAGTTTTTACGATTATCAGCATATAATTCTAGGA

GATGACCCGATGGAACCTGAAAAATGGGATACGGAAAGTGCATTGAAAAG

AATATTTGGAAATAGAAATACAGAAGATGCCAAACCTCTTAGTAGAAAAC

GTAAAGATTTTTGGAAAGAAAACAAAGAATGCGTTTGGTCAGCAATGAAA

TGTGGTTACAACGAAGGAATAAAAAAGGGTAATAAGAGTAATAATATTCC

AGAATGTAAGGACAGTATACCTACCCAATTTGATGGTGTTCCTCAATTTT

TGATGTGGTTTACTGAATGGAGTGAAGATTTTTGTAATCATAAGAAGACA

CATTTGAAAAAATTGGAGCAGGGGTGTAGGGGATGTACTCTTCGTATTGA

TGGCACATGTGAGAAAGATGGCTCAGGATGCCAAAAATGTTCACAAGCGT

GTGAAGAATATAAAGCATGGCTTCAAAATTGGAAAGACCAATATAAGAAA

CAAAGCAAAAAATATAGTGGTGATAAAAAAAAAGAGCTATATAAAACTGT

TCCTAAAGTAAAAAATTCAACACATGCCTATGAATATTTACAAACACAAT

TAGAAAAACTTTGTGAAAAAGGTAAATGTGATTATACTTGTATGAAAAAC

CCATCGACAGAAAATAGTACTGAAAATATGCCCGAATCATTGGACGTAAA

-continued

ACCCGATATAGTTAAGGATAAATGCCCTTGTCCACCACAGAAAATAGAAA

AACCCGATTCCACATTAAATTGCATAGATAGAAGTGCATTTGAATTATAT

GCAAAAGCAAAAAGTGATTTACATGGTGTAAAAGATAAATTAAAGGGTAA

TAATACAAAAAATATATACGAAGAAACAACTAATGGTAAAAATGATGATA

ATATTATCTGTAAAATTAATGAGAGTATTTCTAAACAAAACAATGTATGT

AAAAAAAATGAAAATCTTTTTGATGATATAGACAAATGGGACTGTAAAAA

ACGAACAAATACAGTGCCCATTGAAAATATATGTATTCCTCCAAGAAGGA

AACTTATGTGTGCATATCCATTAAAAAATTTAGGAGTAAAAAAAAATACT

TCAGAAGTATTGTTCAACAAAGTATTGCGTACAGCAGCATATGAAGGAAA

ACATATAAAGGAATCATGGGAAAAAGCAGAAAAATCCAAGAAAAAAAAAA

CCCAAATATGTGATGCTATGAAATACAGTTTTGCAGATTTAGGAGATATA

ATTAGAGGAAGAGATATATTGATATTTAATAATGGTAATAATGAAATTGA

GAGAGACTTAAAAGCTGTTTTTCAGTCAATATACGATAAATGGAAATCTG

ACAGTAATAATAATAAAGATAAATACCCCGACTTAACCTCTTTTCGTTCT

GCCTGGTGGGATGCTAATAGAAAAGATATTTGGAAAGCTATGACATGTGG

TGCACCGGAAGATGCTACGCTTTTTAAAAAACTAGAAAAATGGGGAATTC

CTAATTTAATTTTGTCACAACATAAATGTGGGCATAATGACGATCCTCCT

ATTGATGATTACATACCTCAACGGTTAAGATGGATGAAGGAATGGGGAGA

ATATGTTTGCAAAATATTAAATGAAAACGTGAATGATATGAAGAACGATT

GTGATAAATGTACACTAAATGATAAAAAATGTTCAGATGAAGATGATGGT

AATAAATGTAGAAGTTGTAAAGAAAAATGTAAAGAATATACTAAACTTAT

ATACAATCTGAAATCACAATTTTATATACTAGAAAAACATTATAACGAAT

TATATACAAAAGCACAAAATAATACAACATATTTTACAAATGATAACGAT

AAAAAGGTTATTGAATTTTTTAAAAAAGTTAAAAAGGATTGTGATGTGGG

AACTCCTGATAAATATCTCGATAAAGCTATTCATTGTATCCATTATGATT

TTACTAAAAATGGAACCAAATCTAAGCCATATGTCTTCAACAATCAACCA

GAAAAGTATAAAAATCTTTGTAGTTGTACTATTACTAATCATCCGTTAGA

CAAATGTCCTTTACCTGATAAAACAGATGATTATTGCAAAATCATTAGAC

ATATTAATCCGTGTATAACAATAAATTTGGATAATAATTTGGATACGTGG

ACTGGATTTGTTGTGCATAATATAAGTCACAAAAATAAAGGTGTGCTTGT

ACCTCCAAGAAGAAGACATTTATGTACAAGAGAATTAACTGGAATTAGAT

ATCGTAAAAATGATAAAGATAATTTGAAACAAAATCTTATTGATTCTGCT

TTTAATCAAGGAATACTTTTAGGAAAAACATTTAAAGATTACAGCGATCA

AGGTTTGGAATATATGAAATATAGTTTTGCTGATTATGGAGATATAATTA

AAGCTAAAGATATGATAGGAGGTTCAAATATTGATGATTTCAATAATGAT

TTAAAAAAAATGTTTCCAGAACATCATAGTGAGAATATGGGAAAAACTAC

TATTAGTCGTGAACAGTGGTGGGAAGCAAATAAAACACACGTATGGCACG

CTATGTTATGCGGGTATCATCAAGGAATAATTAATCCAAACTTATCAAGA

AGAAGACCAAAACCATTAGAAGAAGGAACACAATCGTCGATAGCAACTAA

AACTATTCCTTCAAATTGGTGTCAATTACCTAATGATTATAGCACTGATC

AGTTTCTTCGTTGGTTTCAGGAATGGATTGAAAATTTTTGTACAAGGAAA

-continued

AAAGTATTAGAGAAAGAAGCACAAGAACAATGTAAGAATATTACATGTAA

TAACGATACTGGAAAAACGAACACTAAATGTACTGAAGCATGTAAAAATT

ATAGTAATTTTATTTTAATAAAAAAAAAGGAGTATGAGTCACTAAATAGT

CAATACGATATGAATTATAAAAAAATAGTAGAACATAAAAATGCCCTAGA

ATATTTCAAAGATAAATGTAAAAATAATTGTGAATGTCTCTCTAAACATA

TTGATAATGGAAAAAATTGGAAAGAACCATATGAAACTATCGATGACTCA

GAACTCATAGGTAAATGTAAATGCAAAAAAGTTAAACCCAAAACTCCTGA

CGTAATTCCTGCAGGGGCAACTGAAACAAAAGAAAAAGATACACCTCATG

CACCTGAAAAACCTCAACAACCCCCACAACCCTTACCACCATCCGACGAA

CCCTTTGACCCGACCATCCTACAAACGACCATTCCTTTTGGAATCGCTTT

GGCATTAGGATCGATAGCGTTTCTTTTCATGAAAaaaaaaccgaaatctc cagttgacctcttacgtgtactgaatatcccgaaacgagattatgaaatg cctacgttgaaatcaaaaaatcgatatataccctatgctagtgatcgata taaaggtaaaacatacatttatatggaaggagatagcagtggagatgaaa aatatgcatttatgtctgatactactgatgtaacttcctcagaaagtgaa tatgaagaattggatattaatgatatatatgtaccaggtagtcctaaata taaaacattgatagaagtagtattggaaccatcaaaaagtaatggtaaca cactaggtgatgatatggtacctaccactaatacatttacagatgaggaa tggaatgaattgaaacatgattttatatcacaatatgtacaacgtgaacc actggatgtaccacaatatgatgaatcaacacagttaccaatgaatatag taggtaacgttttagatgatggtatggatgaaaaaccttttattacttct attcatgatagagatttatatactggagaagaaattagttataatattaa tatgagtactaatagtatggatgatccaaaatatgtatcaaataatgtat attctggtatagatttaattaatgatacattaagtggtgatcgtattgat atatatgatgaattattgaaacgaaaagaaaatgaattatttggtacaaa tcatgtgaaacaaacaagtatacatagtgttgccaaactaacaaatagtg accccatccacaaccaattagatttgttccatacatggttagatagacat agagatatgtgcaatacgtggaataccaaggaagaattattagataaatt gaatgaacaatggaataaagataatgatggtggtgatataccaaatgata acaaaaagttgaatacggatgtttcgtttgaaatagatatggatgaaact aaaggaaagaaggaatttagtaatatggatactatcttggatgatatgga agatgatatatattatgatgtaaatgatgaaaacccatctgtggataata tacctatggatcataataaagtagatgtaccaaagaaagtacatgttgaa atgaaaatccttaataatacatccaatggatcgttggaacaagaatttcc catatcggatgtatggaatatataa PfEMP1 variant designated TM284var1 has the following amino acid sequence:

SEQ ID NO: 3

MTSKRGNRTVINLSVTDVLEKIALQIYKEENEKKIPHESELIGTLWKAQF

SDGLSGSFGDVRSGPSNSCNLHHKYYTNIKNGYPPARNPCDGRNEKRFSN

-continued

```
EGEAECGSDKIRVIGKGDGTACVPFRRQNMCDKNLEYLINKNTKTTHDLL
GNVLVTAKYEGASIVAKHPHKDTSEVCTALARSFADIGDIVRGRDMFLPN
KDDKVQKGLREVEKKIHDNLSSSVKPHYKDDGSGNYVKLREDWWAINRKE
VWNALTCEAPQSVHYFIKTSHGTRGFTSQGKCGRNETNVPTNLDYVPQYL
RWFDEWAEEFCRLRNHKLQNVKKECRGENIGDKYCSGDGEDCEKIVRQDY
NIRSDFLCPSCKKECTNYKKWIDTKQGEFNKQKKKYEKEIKKVESNSDTT
YDKKVYKILKEMYPLNSEFVATLKEAPYCNNNNVDGTIDENKPDDTFSRS
DYCKSCPVFGVICTRGECTEVKEDTCSKMNVKVPKKITNKEDPINTGILV
SDDRVSVIPNELENVCKDTGLFKGIRKDQRSCNYLCNLDVCDLSHNKNNT
HIDKRISIRVLFKRWLEYFFKDYSKLKKKLNSCTNNGEKSICINKCKKKC
ECVGKWVEEKRTEWEKVRKRYFSQYNVDDSQKSYTVKSIVNGNVDRSDIN
NSLDESEDIETLKESDTCYNSDSAKKQKCEKNDVITILTDRLKKKIDDCE
KQHDNRTNQICCDELPESKEDDEDEEEEGKKKKNAKQLEVTNEKKEQEDK
NLFQVCQKMKKVITDNNGERIRNQRCNEKTDRKWDCSTNEIPTNHTGACM
PPRRISLCIRPLRYLVDNGGKKSIDDYKNAFTECASIETYLLWQKYKRTN
GAEDKLKDGEIPNDFLRIMYYTYGDYRDIFLGTDISKNPNIKNISNKVKN
ILKFKKSMDESGKNQDENAKVQSSWDEHKRDIWKGMLCGLTYDIQNEKKD
ILKILNNKYNYPCDLEVFASKPQFFRWFIEWAEDYCRKYNDEYEKLQTAC
STVDCSKDPTDSEKQKCKNACDNFKTFVEGWKKQYDSQKNKFNKIKIEAN
IKNTYKGIENKEAYVFLSEECKGKCDCIKYKTDYDTNANDPKGFDTPPKE
QKDNCECVLRKKSACENNEVPKGRTQSQMTCADLKNESPSKGNNNTGNNH
KETITFSCNKSNLIGLGAQWKKITDDGLYASPRTRQLCLKHVIDIGRNNT
KKNNITEEEFINVLQKDAYAEGKLLYMYYNSNGKISIFQNGEKLKLDDIE
KHTHEAMKRSYADYGDLIKGTTKYTQYNDYNKISDIINVVTKKKNSASIN
DIYEREEFWEKYRADVWNAMLCGYKDVSNKTFDGNDDMCNLPNTDKEEEF
LRWEKEWNENFCITQIKRAEKLKNECNNFNCSSIKSKKDDIKSKCVKACI
NYKKFVKESKTQYEDQKRTYNERHNKTNKDIPTFLKDNCIHKNCDCISIK
FNHKDNWEKSFFESLDSSDIKNKCECLKLEEESNTTERYISKEDPQYHPE
YKGDGKVNYKYEKGKPKALPSIYPLNCAEKVADELRMYAENSLDTNTKLK
AKISKSIDTNEQNATNDEIDCNIYNNISNGQKNTCEHNGNTFHDKDEWDC
NKGTNKLYENDICLPPRRKHMCTKQLENISTASITTTDDLLKEVLITAVN
EGKRLKQQWEKTENEAQKKKHFLCDAMKYSFADLADIIRGTDIWKGNREQ
QKIQERLVKIFRNIYDNLEKDEYEKYKYGTKYQNLRSAWWDAHRKKIWNA
MTCSAPGDFLFVKRGKGDGSDIEFLTFSEHKKCGHDKEPPVYDYVPQILR
WITEWSEHFCELQEKNYYLLKEKCADYIQKDSKPIDDSHNIKCNTCKTKC
EEYSKFIKKWNSQYINLEKKFKELYDEANNTKSYEELYRIGKPSHRNHYE
DENLIQFLQNVKSECNEPNTVDKYLMYTSDCRRVKFSNTIDTNVNKPTAD
VTHNTINGPSSNLPVVTETNIKNELREYAFLETPEGYGNACKCKGPEPLD
RCPENDNISNYCNDFVSVPECTAKIYKDEIDHWNNANVKFKTSINNGVLV
PPRRSHICLKNMITKNYDKKKNGNEKEKTDLLQVAYNEGYFLCQKYDKQP
RDVLEAMKYTFADIADIVKGRDMINKDISAKLRKLLDIKVEPKAPRKWWK
YNKAHVWHAMLCGYRKGGGTITNDECNVPDEEYTYQFLRWFQEWIKKFCT
GQQKLYDDVQTKCSSANCNRDDGTISLPECESSCVQYKNYITRKRQEYRS
LNHQYNMNFKEQKAQGMKATQYIDDKCNSKCDCLIKYIDREKEWTNIYDS
LENNDLKNKCDCKQIKPKRHPKEVNPEEEPANSEPDYIVPLVPQKPSTPE
VPPPPPPPLPTPSDEPFNRDILEKTIPFGIALALCSIAFLFIKKKPKSSV
DLLRVIDIHKGDYDIPTLKSKNRYIPYKSAQYKGKTYIYMEGDSDSGHYY
EDTTDITSSESEYEEMDINDIYVPGSPKYKTLIEVVLEPSKRDTQNDIPS
DNTPSYKLTDEEWNQLKHDFISQYLPNTEPNNNYRSGNSPTNTNNTTTSH
DNMGEKPFITSIHDRDLYTGEEISYNINMSTNTNNDIPKYVSNNVYSGID
LINDTLSGNKHIDIYDEVLKRKENELFGTNHPKNTSNNSVAKLTNSDPIM
NQLDLLHKWLDRHRDMCDKWNTKEELLDKLNEQWNKDNDVGGDISTSNGN
KTLNTNVSIEIDMDETKGKKEFSNMDTILDNIEDDIYYDVNDENPSMDDI
PMDHNKVDVPKKVHVEMKILNNTFNGSLEPEFPISDVWNI
```

Moreover, the TM284var1 PfEMP1 variant is encoded by the following nucleic acid sequence:

```
SEQ ID NO: 4
ATGACGTCAAAACGTGGAAATCGAACTGTAATTAATCTTAGTGTAACGGA
TGTTCTAGAAAAAATTGCATTACAAATATATAAAGAGGAAAATGAAAAAA
AGATTCCACATGAAAGTGAATTGATAGGCACATTATGGAAAGCACAATTT
TCTGATGGCTTGAGTGGTTCATTTGGTGATGTAAGGTCTGGTCCTTCAAA
TTCATGCAATCTTCATCACAAATACTATACTAATATAAAGAATGGATATC
CACCCGCAAGGAATCCTTGCGATGGTAGAAATGAAAAACGTTTTTCAAAC
GAAGGTGAAGCAGAATGTGGTAGTGATAAAATAAGGGTTATTGGAAAAGG
TGATGGTACAGCATGTGTACCATTTAGAAGGCAAAATATGTGTGATAAAA
ATTTAGAATATTTGATTAATAAAAACACGAAAACTACTCATGATTTATTG
GGAAATGTATTAGTTACAGCAAAATATGAAGGTGCCTCTATTGTTGCAAA
GCATCCACATAAAGATACTTCAGAAGTATGTACTGCACTTGCACGAAGTT
TTGCAGATATAGGTGATATTGTAAGAGGAAGAGATATGTTTTTACCTAAT
AAGGATGATAAAGTACAAAAAGGTCTAAGAGAAGTTTTCAAGAAAATACA
TGATAATTTGTCATCTTCCGTAAAACCACATTACAAAGATGATGGATCTG
GAAATTACGTCAAATTAAGAGAAGATTGGTGGGCAATTAATAGAAAGGAG
GTATGGAATGCATTAACATGTGAAGCTCCACAAAGTGTTCATTATTTTAT
AAAAACGTCACATGGAACAAGAGGTTTTACAAGTCAAGGAAAATGTGGCC
GTAATGAAACAAACGTTCCTACAAATCTTGACTATGTTCCTCAATATTTA
CGCTGGTTCGATGAATGGGCAGAAGAGTTTTGTCGATTAAGGAATCATAA
GTTACAAAACGTTAAGAAAGAGTGTCGTGGAGAAAATATAGGTGACAAAT
ATTGTAGTGGTGATGGTGAGGATTGTGAAAAGATTGTTCGTCAGGATTAT
AATATTCGTTCGGATTTTTTATGTCCGAGCTGTAAAAAGGAATGTACAAA
TTATAAAAAAATGGATAGACACAAAACAGGGAGAATTTAATAAACAGAAAA
AAAAATACGAAAAAGAAATTAAAAAAGTTGAAAGTAATTCTGATACCACA
```

-continued

TATGATAAAAAAGTTTATAAAATTCTAAAAGAAATGTACCCTTTAAATTC
AGAATTTGTAGCAACATTAAAAGAAGCTCCCTATTGTAATAACAATAATG
TAGACGGTACAATAGATTTTAATAAACCAGATGATACATTTTCTCGTTCA
GACTATTGTAAATCATGTCCTGTATTTGGTGTTATTTGTACAAGAGGTGA
GTGTACTGAAGTTAAGGAAGATACATGTAGTAAAATGAATGTTAAGGTTC
CGAAAAAAATTACAAATAAGGAAGATCCTATTAATATAGGTATTCTTGTT
AGTGATGACAGAGTAAGTGTAATTCCAAATGAATTAGAGAATGTTTGCAA
AGATACAGGTCTCTTTAAAGGTATTAGAAAAGATCAACGGTCATGTAATT
ACTTATGTAATTTAGATGTATGTGACCTGAGTCATAATAAAAACAATACA
CATATAGATAAACGTATTTCTATTAGAGTATTGTTTAAACGTTGGTTAGA
ATATTTTTTTAAAGATTATAGTAAATTAAAAAAAAAACTGAATTCATGTA
CAAATAATGGAGAAAAATCCATATGTATAAATAAATGTAAAAAAAAATGT
GAATGTGTGGGAAAATGGGTAGAAGAAAAAAGGACAGAATGGGAAAAAGT
AAGAAAGCGTTACTTCAGTCAATATAATGTTGATGATTCACAAAAATCGT
ATACAGTGAAAAGTATTGTAAATGGAAATGTAGATCGTAGTGATATTAAT
AATTCATTAGATGAGAGCGAAGATATAGAAACGTTGAAAGAATCAGATAC
ATGTTATAATTCTGATAGCGCAAAAAAACAAAAATGTGAAAAAAACGACG
TCATAACTATTTTAATTGATAGACTTAAAAAAAAAATTGATGATTGTGAA
AAGCAACATGATAATAGAACTAATCAAATTTGTTGTGATGAGTTACCTGA
AAGTAAAGAAGATGATGAAGATGAAGAGGAAGAAGGGAAAAAGAAAAAAA
ATGCAAAGCAATTGGAAGTAACTAATGAGAAAAAAGAACAAGAAGACAAA
AACTTGTTTCAAGTGTGCCAAAAAATGAAGAAGGTAATTACGGATAATAA
TGGAGAAAGAATCAGAAACCAGCGTTGCAATGAAAAAACTGATAGAAAAT
GGGATTGTAGTACTAATGAAATTCCTACAAATCATACTGGAGCTTGTATG
CCACCAAGAAGAATATCATTATGTATTCGGCCTTTACGATATTTGGTAGA
TAACGGAGGAAAAAAAAGCATAGATGATTATAAAAATGCGTTTACTGAAT
GTGCATCAATAGAAACGTATTTGTTATGGCAAAAATACAAAAGAACTAAT
GGAGCAGAAGATAAATTAAAAGATGGAGAGATTCCAAATGATTTTCTAAG
AATAATGTATTATACATATGGAGATTATAGAGATATATTTTTGGGAACAG
ATATTTCTAAAAATCCTAATATTAAAAATATATCAAATAAGGTTAAAAAT
ATATTGAAATTCAAAAAGAGCATGGACGAATCAGGTAAAAATCAGGATGA
AAATGCGAAAGTTCAATCTTCGTGGGATGAACATAAAAGGGACATATGGA
AAGGAATGTTATGTGGATTAACCTATGATATCCAAAATGAAAAGAAAGAT
ATTCTCAAAATTCTCAATAACAAGTACAATTACCCATGCGATCTTGAAGT
GTTTGCATCTAAACCACAATTTTTTCGTTGGTTTATTGAATGGGCAGAAG
ATTATTGTAGAAAATACAATGATGAGTATGAAAAATTACAGACGGCGTGT
AGTACGGTAGATTGTAGTAAAGACCCTACTGATTCTGAAAAACAAAAATG
TAAAAACGCTTGTGATAATTTCAAAACATTCGTTGAAGGTTGGAAAAAAC
AATATGATAGTCAAAAAAATAAATTTAATAAGATAAAAATTGAAGCTAAT
ATAAAGAATACATATAAAGGTATAGAAAATAAAGAAGCTTATGTATTTTT
AAGTGAAGAATGTAAAGGAAAATGTGACTGTATAAAATATAAAACAGACT

-continued

ATGATACAAATGCAAATGATCCTAAAGGTTTCGATACACCACCGAAAGAA
CAAAAAGATAATTGTGAATGTGTGTTGAGAAAAAAATCGGCATGTGAAAA
TAATGAAGTACCTAAAGGTCGAACACAATCTCAAATGACATGTGCTGATC
TAAAAAATGAATCTCCTAGTAAAGGAAATAATAATACTGGGAACAATCAT
AAAGAAACCATTACATTCTCGTGCAATAAAAGCAATTTAATTGGCTTAGG
AGCACAATGGAAAAAAATAACTGATGATGGTTTATATGCTTCTCCAAGAA
CTCGACAATTATGTTTGAAACACGTAATAGACATAGGAAGGAATAATACT
AAAAAAAACAATATAACAGAAGAAGAGTTCATTAATGTATTACAAAAAGA
TGCATATGCTGAAGGTAAATTACTTTATATGTACTACAACAGTAATGGTA
AAATATCTATATTTCAAAATGGCGAAAAGTTAAAATTGGATGACATAGAA
AAACATACACATGAAGCCATGAAAAGATCATATGCTGATTATGGTGATTT
AATTAAAGGAACAACAAAATATACACAATACAATGATTATAACAAAATTA
GCGATATTATAAACGTTGTGACTAAAAAGAAAAATTCCGCTTCAATTAAT
GATATTTATGAGCGTGAAGAATTTTGGGAAAAATATAGAGCTGATGTATG
GAATGCTATGTTATGTGGTTACAAAGATGTATCAAATAAAACATTTGATG
GAAACGATGATATGTGTAACTTACCAAATACTGATAAGGAGGAAGAATTT
CTCAGATGGTTTAAGGAATGGAATGAAAATTTTTGTATTACACAAATAAA
ACGCGCAGAGAAATTAAAAAATGAATGCAATAATTTTAACTGTTCTTCCA
TTAAGAGTAAAAAGGACGATATTAAATCTAAATGTGTAAAAGCATGTATA
AATTATAAAAAGTTTGTAAAGGAATCAAAAACGCAATATGAAGATCAAAA
GAGAACATACAATGAAAGACATAATAAGACAAATAAGGATATTCCTACTT
TTTTGAAAGATAATTGTATTCATAAAAACTGTGATTGTATTTCTATAAAA
TTTAATCATAAAGATAATTGGGAAAAATCTTTTTTTGAGAGTTTAGATAG
TTCCGATATTAAAAATAAGTGTGAATGTTTAAAACTTGAAGAAGAGTCAA
ATACTACAGAACGATATATTTCTAAAGAAGACCCACAATATCATCCAGAA
TATAAAGGTGATGGAAAGGTTAATTATAAATATGAGAAAGGAAAACCAAA
AGCTCTTCCTTCTATATACCCTTTGAACTGTGCTGAAAAGGTTGCTGACG
AGTTACGAATGTATGCTGAAAATTCTTTGGATACTAATACTAAATTGAAG
GCAAAAAATATCAAAAAGTATAGATACAAATGAACAAAATGCTACGAATGA
TGAGATTGATTGCAATATTTACAATAATATATCTAATGGACAGAAAAATA
CTTGTGAACATAATGGAAACACTTTTCATGATAAGGATGAATGGGATTGT
AACAAAGGAACAAATAAATTATATGAAAATGATATTTGTTTACCTCCAAG
AAGAAAACATATGTGTACAAAACAACTAGAAAATATCAGCACGGCATCAA
TTACAACTACGGATGATTTACTGAAAGAAGTGTTAATTACAGCTGTAAAT
GAAGGAAAGCGTTTAAAACAGCAATGGGAGAAAACAGAAAATGAAGCACA
AAAAAAGAAACACTTTTTATGTGATGCTATGAAATATAGTTTTGCTGATT
TAGCTGATATTATAAGAGGAACAGACATATGGAAAGGAAATAGAGAGCAA
CAAAAAATACAAGAAAGATTAGTAAAAATCTTCAGAAATATATATGATAA
CTTAGAGAAGGATGAATATGAGAAATATAAATATGGTACAAAATATCAAA
ATTTAAGATCGGCTTGGTGGGATGCACATAGAAAGAAAATATGGAATGCT

-continued

ATGACATGTTCAGCACCAGGTGATTTCCTTTTTGTAAAAAGAGGAAAAGG
AGATGGAAGTGACATCGAATTTTTAACTTTTTCAGAACATAAAAAATGTG
GACATGATAAAGAACCACCTGTTTATGATTATGTGCCTCAAATACTTAGA
TGGATTACAGAATGGTCTGAACATTTTTGTGAATTGCAAGAAAAAAATTA
TTATCTTCTAAAAGAAAAATGTGCTGATTATATACAAAAGGATTCCAAAC
CTATTGATGATTCACATAATATAAAATGTAATACTTGTAAGACGAAATGT
GAAGAATATAGTAAATTTATTAAGAAATGGAACTCTCAGTATATAAATCT
GGAAAAAAAATTTAAAGAATTATATGACGAGGCAAATAATACTAAAAGTT
ATGAAGAACTTTACAGAATTGGGAAGCCTTCACACAGAAACCACTATGAA
GATGAAAACCTGATTCAGTTCTTACAAAATGTAAAATCTGAGTGTAACGA
ACCTAACACTGTTGATAAATATCTTATGTATACAAGTGATTGTAGAAGAG
TTAAATTTTCTAATACTATCGATACAAATGTTAACAAACCTACTGCGGAT
GTTACTCATAATACTATTAATGGTCCTAGTAGTAACCTCCCAGTTGTTAC
TGAAACAAATATTAAAAATGAACTAAGAGAATATGCTTTCTTAGAAACAC
CAGAAGGATATGGTAATGCTTGTAAATGTAAGGGTCCTGAACCATTAGAT
CGTTGCCCTGAAAATGATAATATTAGTAATTACTGTAACGATTTTGTTAG
TGTTCCTGAATGCACAGCAAAAATATATAAAGATGAAATTGATCATTGGA
ATAATGCAAATGTAAAATTTAAGACATCAATAAATAACGGTGTGTTAGTT
CCTCCAAGAAGAAGTCATATATGTCTTAAGAATATGATAACAAAAAACTA
TGATAAAAAGAAAAATGGGATGGAAAAATTTAAAACTGATCTTCTACAGG
TTGCATACAATGAAGGTTATTTCCTATGTCAAAAATATGATAAGCAACCT
AGAGACGTATTGGAAGCGATGAAATACACATTTGCAGATATTGCTGATAT
AGTAAAAGGTAGAGATATGATTAACAAAGATATATCCGCAAAACTACGAA
AATTATTGGATATTAAGGTTGAACCCAAAGCTCCTAGAAAATGGTGGAAA
TACAATAAAGCACATGTATGGCACGCTATGTTATGTGGATATAGAAAAGG
TGGAGGAACAATTACGAATGATGAGTGTAATGTTCCAGATGAAGAGTACA
CTTATCAATTTCTTCGATGGTTTCAAGAATGGATTAAAAAATTTTGTACT
GGACAACAAAAATTATATGACGACGTACAAACGAAATGTTCATCTGCCAA
TTGTAATAGAGATGATGGGACGATTAGCCTACCTGAATGTGAAAGTTCTT
GTGTTCAATATAAGAATTACATTACAAGGAAGAGACAAGAGTATCGGTCA
CTAAACCATCAATATAACATGAATTTTAAAGAACAAAAGGCACAAGGTAT
GAAAGCCACACAGTACATAGATGATAAATGTAATAGTAAATGTGATTGTC
TCATTAAATATATTGATAGAGAAAAAGAATGGACAAACATATATGACTCA
TTGGAAAATAATGATCTGAAAAATAAATGTGATTGTAAGCAAATTAAACC
CAAACGTCATCCAAAAGAAGTAAATCCTGAGGAAGAACCTGCTAATTCTG
AACCCGATTACATTGTTCCCCTTGTACCACAAAAACCTTCAACACCAGAG
GTACCCCCACCTCCTCCTCCACCTTTACCAACCCCTTCGGACGAACCATT
CAATCGTGACATTCTGGAAAAAACCATTCCTTTTGGAATTGCATTGGCAT
TATGTTCGATAGCTTTTCTCTTCATAAAGaaaaaacctaaatcatctgtt
gacctcttgcgagtaattgacatccacaaaggagattatgatatacctac
attgaaatccaaaaataggtacataccatataaaagtgctcaatataaag -continued gtaaaacatacatttatatggaaggagatagtgatagtggacactactac
gaagatacaactgatattacttcctccgaaagtgaatatgaagagatgga
tattaatgatatatatgttcctggtagtccaaaatacaaaacgttgatag
aagttgttctggagccatcaaaaagagatacacaaaatgatatacctagt
gataatacacctagttataaacttacagatgaggaatggaatcaattgaa
acatgattttatatcacaatatttaccaaatacagaaccaaataataatt
atagaagtggaaatagtccaacaaataccaataatactaccacgtcacat
gataatatgggagaaaaaccttttattacttctattcatgatagggattt
atatactggagaagaaattagttataatattaatatgagtactaacacta
ataatgatattccaaaatatgtatcaaataatgtatattctggtatagat
ttaattaatgacacattaagtggtaacaaacatattgatatatatgatga
agtgctaaaaagaaaagaaaatgaattatttggaacaaatcatccgaaaa
atacatcaaacaatagtgtagctaaattaacaaatagtgatccaattatg
aaccaattagatttgttacataaatggttagatagacatagagatatgtg
cgataaatggaataccaaggaagaattgttagataaattaaatgaacaat
ggaataaagataatgatgttggtggtgatatttccactagtaatggtaat
aaaacgttgaatactaatgtttcgattgaaatagatatggatgaaactaa
aggaaagaaggaatttagtaatatggatactatcttggataatatagaag
atgatatatattatgatgtaaatgatgaaaacccatctatggatgatata
cctatggatcataataaagtagatgtacctaagaaagtacatgttgaaat
gaaaatccttaataatacattcaatggatccttggaaccagaatttccca
tatcggatgtatggaatatataa The PfEMP1 variant designated ITvar60 has the following amino acid sequence:

SEQ ID NO: 5

MAPKGRSTNEIELSARDVLENIGIGIYNQEKIKKNPYEQQLKGTLSNARF
HDGLHKAADLGVIPGPSHFSQLYYKKHTNNTKYYKDDRHPCHGRQGKRFD
EGQKFECGNDKIIGNSDKYGSCAPPRRRHICDQNLEFLDNNHTDTIHDVL
GNVLVTAKYEGESIVNDHPDKKNNGNKSGICTSLARSFADIGDIVRGRDM
FKPNDKDAVRHGLKVVFKKIYDKLSPKVQEHYKDVDGSGNYYKLREDWWT
ANRDQVWKAITYKAPQDANYFRNVSGTTMAFTSAGKCRHNDNSVPTNLDY
VPQFLRWYDEWADDFCRIRNHKLQKVKDTCQGYNNSGYRIYCSGDGEDCT
NILKQNFNIVSDFFCPSCKTECTNYKKWINKKQGEFNKQKKKYEKEINNI
ASNSDNTYDKKVYKTLKSMYPLDTKFVATLKEAPFCNNNNVDGIIDFNKP
DDTFSSSTYCDSCPAFGVICENGTCTKVNEDTCSKMNVQVPKIITNKEDP
TNIGILVSDDRVNVIPNELENVCKNTGIFKGIRKDEWSCKYLCNLDVCDL
SHNKNNTHIDKRISIRVLFKRWLEYFLKDYSKLKKKLNSCTNNGKESICI
NECKKKCECVGKWAEEKRKEWEKVRKRFFNQYNVDDSLKSYEVKTFVNGN
VDRSDIKNALNEGENLEALQDSDECIKPHNSKKDTCVKNDVVNILINRLK
KKIDDCKIQHDNRTNQICCDELPESKEDNEDEEEEGEKKKNSKHLEETKE

-continued

KKELDDNNFLDLCNNVKKYIEDNNKQISIQHKCNTKGDGNWNDSTKKIDI

QHTGAHMPPRRKSLCIRELRYLVEIGGDKNIDDYKNAFTKCASIETYLLW

QKYKKSNRSEEDKLKGGEIPEDFRGIMYYTFGDYRDIFLGTDISSDGNIK

NISNKIKDLMKEKYSKATGHKGENHNSNLQSSWDEHKRTIWKGMLCGLTY

GISNEQQKKNIRKMLNNKYKYPCDLETESKKPQFLRWFNEWSEDFCKNYK

NAIDILKKDCTEADCMNKLVNNREKNKKCKEACEHFKEWIKGWKNQYEQQ

RKKFNIDKNVEQKETAYINVNGLEPYEFFQNQYFVGTCECMKNKSESSAN

NDENIPEAFDEKPKEFKDKCPCTYDIPEPSETMSCIEKAAFKLRYASEDK

IHSKISSKLKGNGSAFSCTNSASDNIFDETSCYKNEFNKTENINSVKASN

MNRFDTNIIWDCDGKTKYEQINLCVPPRRENMCIKGLEHLNETKHSDNKT

LLKELQEIASTEGKGISKNFKQMDRENDDGICDAMKYSFADLADIVRGTD

NYKNSNGNNNKVEENLKKIFEKIHNINSLKKEYSKDKPDYQRLRSDWWDT

NRKEIWKALTCSARDNNKIYKKGQKNTNNGKNKCGNEEDPPDDDYIPQPF

RWLQEWSEHFCRVQYDNLNKLKEECGECNENKNGLACMMNSNIKDTKCMN

CKDACKDYRNMINTWNSQWKKQQEDYKELYNTKNKININKCKVIEFLDKT

NDTCHYKPGSAEKFLKESSHCTDLTFDKTKNSNNIPYAFENPPDGYKVLC

GTTYRKSCKKLKKLGMNYTSENKIDLSGENAKWEKLNDLIYVPPRTQQLC

LQPLQTLISRTNKTTKVTEYDFSRALQICAYNEANSLHNYYSKYGKDFVF

SAGKSQDTKDEIKTHILENMKRSFADYGNLIKGKTQYEYNGLNKKLQDYI

KTNLKYNGTDRKTGEDLWNKHKSDIWNSMLCGYNEENPSEPLHDKDIRCK

LPDNDSEDEFLRWFQEWREDFCVIKGILIQNVKDACNFNNCEDANNKSIR

SCQKPCVKYKTWVEQRKIEYENQIQKYKNLNNNSNEGKESLLFLNDKCKG

KCECIVQKKSTDNIDKIFEEYPEEYKTQCECQPDPCSDLSITDSGFPDAS

PFGGGQPRSACPTRRGNHNNCPTEEICKKYDSYINGCRPKTYHDNTNNWD

SRGMLNSSSENEGVLIPPRRRHLCTRNIIKNLSRIKNKDHFKDYLMKSAY

EEGKLLREKYRNNSRDGLNAMMFTFADYADIVKGTDIFGSILSQKLGEIT

GISNDINERKKWWSEIKNNIWEVMLCSYNRTKNNNNFEGNIVRENCNVPN

TDEKDQFLRWLLEWGIQACKEKKIRKQALQTKCYCSNPNEISGSDIIKHY

PCKSELTKYIQWNLMIKELLDQLNIKYQNIKASNNPKNPSEINAEEYIET

ELKEGECNLVDIERDYNKIKQEHNPLKEILMYLCPNLEFPDDTFEYIGKT

ETEDTTIEPETPTSDNPEDSIPSISPEDVHPTTGEDTNIFNSNILSSTIP

FGIALALSSTAFLFLKKKTLSPVDLLRVLDIHKGDYGIPTLKSKNRYIPY

RSGTYKGKTYLYVEGDSDSGHYYEDTTDITSSESEYEEMDINDIYVPGSP

KYKTLIEVVLEPSKSDGHIPHSAGEPLDDMVGTTIFTDEEWNELKHDFIS

QYVQRESMGVPQYDVSTELPMNIGGNVLDDGMEEKPFITSIHDRDLYTGE

EFSYNINMGTNSMDDPKYVSNNVYSGIDLINDTLSGNQHIDIYDEVLKRK

ENELFGTNYKKNISNNRVAKLTNNDPIMNQLDLLHKWLDRHRDMCNTWNT

KEELLDKLNEQWNKDNDAGDIPSDSNKKLNTDVSIQIDMDDPKGKKEFSN

MDTILDDIEDDIYYDVNDENPFVDDIPMDHNKVDVPKKVHVEMKILNNTS

NGSLEPEFPISDVWNI

Moreover, the ITvar60 PfEMP1 variant is encoded by the following nucleic acid sequence:

SEQ ID NO: 6

ATGGCACCAAAGGGTAGAAGTACAAATGAAATTGAACTTAGCGCAAGAGA

TGTTTTGGAAAATATTGGAATAGGAATATATAATCAGGAAAAAATAAAAA

AGAATCCATATGAACAACAATTGAAAGGCACATTATCAAACGCCCGATTT

CATGATGGCTTGCACAAGGCAGCTGATTTGGGGGTAATACCTGGTCCTTC

ACATTTTTCTCAGCTTTATTACAAAAAGCATACTAATAACACAAAATATT

ATAAGGATGATAGGCATCCTTGTCATGGTAGACAAGGAAAACGTTTTGAT

GAAGGTCAAAAATTTGAATGTGGTAATGATAAAATAATTGGTAATAGCGA

TAAATATGGATCCTGTGCTCCACCTAGAAGAAGACATATATGTGATCAAA

ATTTAGAATTCTTAGATAACAATCATACTGATACTATTCATGATGTATTG

GGAAATGTGTTGGTCACAGCAAAATATGAAGGTGAATCTATTGTTAATGA

TCATCCAGATAAAAAGAACAATGGTAATAAATCAGGTATATGTACTTCTC

TTGCACGAAGTTTTGCCGATATAGGTGATATTGTAAGAGGAAGAGATATG

TTTAAACCTAATGACAAAGATGCAGTGCGGCATGGTTTAAAGGTAGTTTT

TAAGAAAATATATGATAAATTGTCACCTAAAGTACAAGAACATTACAAAG

ATGTTGATGGATCTGGAAATTACTATAAATTAAGGGAAGATTGGTGGACA

GCGAACAGAGATCAAGTATGGAAAGCCATAACATATAAAGCTCCACAAGA

CGCTAATTATTTTAGAAATGTTTCAGGAACAACTATGGCGTTTACAAGTG

CAGGAAAATGTAGACACAATGACAATAGCGTCCCAACGAATCTAGATTAT

GTCCCTCAATTTTTACGTTGGTACGATGAATGGGCAGATGATTTTTGTCG

AATAAGAAATCATAAGTTGCAAAAGGTTAAAGACACATGTCAGGGATATA

ATAATAGTGGTTATAGAATATATTGTAGTGGTGATGGTGAGGATTGTACA

AATATTCTTAAACAGAATTTTAATATTGTTTCGGATTTTTTTTGTCCGAG

CTGTAAAACCGAATGTACAAATTATAAAAAATGGATAAATAAAAAACAAG

GTGAATTTAATAAACAAAAAAAAAAAATACGAAAAGGAAATTAACAATATT

GCAAGTAATTCTGATAACACATATGATAAAAAAGTTTATAAAACTCTAAA

AAGCATGTACCCTTTAGATACAAAATTTGTAGCAACACTAAAAGAGGCTC

CCTTTTGCAATAACAATAATGTAGATGGTATAATAGATTTTAATAAACCA

GATGATACATTTTCTAGTTCAACATATTGTGATTCATGTCCTGCATTTGG

TGTTATTTGTGAAAATGGTACGTGTACTAAGGTTAATGAAGATACATGTA

GTAAAATGAATGTTCAGGTTCCAAAAATAATTACAAATAAGGAAGATCCT

ACTAATATAGGTATTCTTGTTAGTGATGACAGAGTAAATGTAATTCCAAA

TGAATTAGAGAATGTTTGCAAAAATACAGGTATCTTTAAAGGTATTAGAA

AAGATGAATGGTCATGTAAATATTTATGTAATTTAGATGTCTGTGACCTG

AGTCATAATAAAAACAATACACATATAGATAAACGTATTTCAATTAGAGT

ACTGTTTAAACGTTGGTTAGAATATTTTTTAAAAGATTATAGTAAATTAA

AAAAAAAACTGAATTCATGTACAAATAATGGAAAAGAATCCATATGTATA

AATGAATGTAAAAAAAAAATGTGAATGTGTGGGAAAATGGGCAGAAGAGAA

AAGAAAAGAATGGGAAAAAGTAAGAAAGCGTTTCTTTAATCAATATAATG

-continued

TTGATGATTCACTAAAATCTTACGAAGTGAAAACATTTGTAAATGGAAAT

GTAGATCGTAGTGATATTAAGAATGCATTAAATGAGGGTGAAAATTTAGA

AGCGTTGCAAGATTCTGATGAATGTATTAAACCTCATAATTCCAAGAAAG

ACACATGTGTAAAAAATGACGTCGTAAATATTTTAATTAATAGACTTAAA

AAAAAAATTGATGATTGTAAAATCCAACATGATAATAGAACTAATCAAAT

TTGTTGTGATGAGTTACCTGAAAGTAAAGAAGATAATGAAGATGAAGAGG

AAGAAGGGGAAAAGAAAAAAAATTCAAAACATTTGGAGGAGACTAAAGAG

AAAAAAGAACTGGATGACAACAATTTTTTGGATTTGTGCAACAATGTGAA

GAAATATATTGAGGATAATAATAAGCAAATAAGTATACAACATAAATGCA

ATACGAAAGGAGATGGAAATTGGAATGATAGTACAAAAAAGATCGATATT

CAACATACTGGAGCTCATATGCCACCAAGAAGAAAATCATTATGTATTCG

TGAGTTACGATATTTGGTAGAAATTGGAGGAGATAAAAACATAGATGATT

ATAAAAATGCGTTTACTAAATGTGCATCAATAGAAACATATTTGTTATGG

CAAAAATACAAAAAATCTAATAGATCAGAAGAAGATAAATTAAAAGGTGG

AGAGATTCCAGAAGATTTTAGAGGAATAATGTATTATACATTTGGTGATT

ACAGAGATATATTTTTGGGAACAGATATTTCTTCAGATGGTAATATTAAA

AATATATCAAATAAAATAAAAGATTTAATGAAAGAAAAGTATAGTAAAGC

AACAGGTCATAAAGGAGAAAACCATAATTCAAATCTTCAATCTTCGTGGG

ATGAACATAAAAGGACCATATGGAAAGGAATGTTATGTGGATTAACCTAT

GGTATATCAAATGAACAACAAAAAAAAAATATTCGCAAAATGCTCAACAA

CAAGTACAAATACCCATGCGATCTAGAAACATTTTCAAAGAAACCACAAT

TTCTTCGTTGGTTTAACGAATGGAGTGAAGATTTTTGTAAAAATTACAAA

AATGCTATTGATATATTAAAAAAGGATTGTACAGAAGCAGATTGTATGAA

TAAATTAGTAAATAATCGTGAAAAAAACAAGAAATGTAAAGAAGCGTGTG

AACATTTTAAAGAGTGGATAAAAGGATGGAAAAATCAATATGAACAACAA

AGAAAAAAATTTAATATTGATAAAAATGTTGAACAAAAGGAGACAGCATA

TATAAACGTAAATGGTCTGGAACCCTATGAATTTTTTCAAAACCAATATT

TTGTGGGAACATGTGAATGCATGAAAAATAAATCAGAGTCATCTGCAAAT

AATGATGAAAATATACCAGAAGCATTCGATGAAAAACCAAAAGAGTTCAA

GGACAAATGTCCATGTACTTATGATATACCTGAACCTAGCGAAACTATGA

GTTGTATAGAGAAAGCTGCCTTCAAATTACGTTATGCTTCTGAAGATAAA

ATTCATAGTAAAATTAGTAGTAAATTGAAAGGAAACGGTTCAGCGTTTTC

ATGTACGAACAGCGCAAGTGACAATATTTTTGATGAGACAAGTTGTTATA

AGAATGAATTTAACAAAACAGAAAATATTAATTCAGTGAAAGCTTCAAAC

ATGAATCGTTTTGATACAAATATTATATGGGATTGTGATGGAAAAACAAA

ATATGAGCAAATTAATTTATGTGTTCCGCCTAGAAGAGAAAATATGTGTA

TAAAGGGGCTAGAACACTTGAACGAAACTAAACATTCTGATAATAAAACG

CTATTAAAAGAGCTTCAAGAAATTGCAAGTACTGAAGGGAAAGGCATATC

AAAAAATTTTAAACAAATGGATAGAGAAAATGATGACGGAATATGTGATG

CCATGAAGTACAGTTTTGCCGATTTGGCAGATATAGTAAGAGGTACAGAT

AATTACAAAAATTCTAATGGTAATAATAATAAAGTAGAGGAAAACCTTAA

-continued

AAAAATTTTCGAAAAAATACACAATATTAATAGTCTTAAAAAAGAATATA

GTAAGGACAAACCGGATTATCAAAGATTACGATCTGACTGGTGGGATACG

AATAGAAAAGAAATATGGAAAGCATTAACGTGTTCAGCAAGGGATAATAA

TAAAATATACAAGAAAGGGCAAAAAAATACTAATAATGGAAAGAATAAAT

GTGGAAATGAAGAGGATCCTCCTGATGATGATTATATTCCACAACCTTTT

CGTTGGTTACAAGAATGGAGTGAACATTTTTGTAGAGTTCAATATGATAA

TCTGAATAAACTGAAAGAAGAATGTGGAGAATGTAATGAAAATAAAAATG

GTTTAGCTTGTATGATGAATTCAAATATTAAAGATACAAAATGTATGAAT

TGCAAAGATGCATGCAAGGACTACAGAAATATGATTAACACATGGAATAG

TCAATGGAAAAAACAACAAGAAATATATAAAGAATTATATAATACTAAAA

ATAAAATAAATATtAATAAATGTAAGGTGATAGAATTTTTAGATAAAACA

AATGATACGTGTCACTATAAACCAGGAAGTGCAGAAAAGTTTCTTAAAGA

ATCTAGTCATTGTACTGACCTTACATTCGACAAAACAAAGAATTCAAATA

ATATTCCTTATGCCTTTGAAAATCCACCTGATGGATATAAAGTTTTATGT

GGTACAACATATAGAAAATCATGTAAAAAGCTAAAAAAATTAGGGATGAA

TTATACGTCAGAAAACAAAATTGATTTAAGTGGAGAAAACGCTAAGTGGG

AAAAACTTAATGATTTGATATATGTCCCTCCACGAACACAACAATTATGT

TTACAACCTTTGCAAACGTTGATATCACGTACCAATAAAACCACGAAAGT

AACAGAATATGATTTCTCCAGAGCATTACAAATATGTGCATATAATGAAG

CAAATTCTCTTCACAATTATTATAGTAAGTATGGCAAAGATTTTGTATTT

AGTGCTGGTAAGTCTCAAGATACTAAAGATGAAATAAAAACACACATTCT

TGAAAATATGAAAAGAAGCTTTGCTGATTATGGTAATTTAATTAAAGGAA

AGACCCAATACGAATATAATGGTTTAAACAAAAAGCTTCAGGATTACATA

AAGACTAATTTAAAATATAATGGAACTGACAGAAAAACAGGTGAAGATCT

TTGGAATAAACATAAATCCGATATTTGGAATTCTATGCTATGTGGATATA

ATGAAGAAAACCCAAGTGAACCACTTCATGATAAAGACATAAGATGTAAA

TTACCTGATAATGATAGTGAAGATGAATTTTTACGTTGGTTTCAAGAATG

GAGAGAAGATTTTTGTGTTATCAAAGGTATACTGATACAAAATGTGAAAG

ATGCATGTAATTTTAATAATTGTGAAGATGCAAATAATAAATCCATAAGA

TCTTGTCAAAAACCATGTGTCAAATACAAAACATGGGTTGAACAAAGAAA

AATTGAATACGAAAATCAAATCCAGAAATATAAAAATCTCAACAATAATT

CAAATGAAGGAAAAGAATCACTTTTATTTTTAAACGATAAATGTAAAGGG

AAATGTGAATGTATAGTTCAAAAAAAAGTACTGATAATATCGATAAGAT

TTTTGAGGAATATCCTGAAGAATACAAAACGCAATGTGAATGTCAGCCTG

ATCCATGTAGTGACCTAAGTATTACAGATAGTGGATTTCCTGATGCAAGT

CCTTTTGGTGGAGGTCAACCACGTTCCGCGTGTCCTACAAGGCGAGGAAA

TCATAATAATTGCCCTACTGAAGAAATATGTAAAAAATATGATAGCTATA

TTAATGGTTGTCGCCCTAAAACATATCACGACAATACAAATAATTGGGAT

AGCAGAGGCATGCTAAACAGTTCATCTGAAAATGAAGGTGTATTAATTCC

TCCTAGAAGGCGACATTTATGCACAAGAAATATAATTAAAAATTTGTCAC

-continued

```
GTATTAAAAATAAAGATCATTTTAAAGATTACCTAATGAAATCTGCTTAT
GAAGAAGGAAAACTTTTAAGGGAAAAATATAGAAATAATAGTAGAGATGG
ATTAAATGCAATGATGTTCACTTTTGCTGATTATGCAGATATAGTTAAAG
GTACTGATATATTTGGCAGTATATTATCTCAAAAATTAGGTGAAATAACT
GGAATAAGCAATGATATAAATGAGCGTAAAAAATGGTGGAGTGAAATTAA
AAATAATATATGGGAAGTTATGTTGTGTTCTTATAATAGAACAAAGAATA
ATAATAATTTTTTCGGAAACATTGTGAGAGAAAACTGTAATGTTCCTAAC
ACAGATGAAAAGGACCAATTTTTGAGATGGTTACTTGAATGGGGTATACA
AGCATGTAAAGAAAAAAAAATCAGAAAACAAGCCCTTCAAACGAAGTGTT
ACTGTTCAAACCCAAACGAAATATCGGGTTCCGATATTATAAAACATTAC
CCTTGTAAAAGTGAACTCACCAAATATATACAATGGAATTTAATGATTAA
AGAATTATTAGATCAATTAAATATAAAATATCAAAATATAAAAGCATCTA
ATAATCCGAAAAATCCCTCGGAAATAAATGCAGAGGAATACATAGAAACA
GAACTTAAGGAAGGTGAATGTAATTTGGTTGATATAGAACGAATATATAA
TAAAATTAAACAAGAACATAATCCATTAAAAGAAATATTAATGTATTTAT
GTCCTAATTTAGAATTTCCTGATGATACATTCGAATACATTGGGAAAACC
GAAACTGAAGATACAACTATTGAACCAGAAACCCCTACATCCGATAACCC
TGAGGATAGTATTCCTTCCATTTCACCTGAAGACGTTCACCCAACAACAG
GAGAAGACACAAACATTTTCAACAGTAACATATTATCATCTACTATCCCT
TTTGGAATTGCTTTGGCCTTAAGTTCGATCGCTTTCCTGTTCCTGAAGaa
aaaaaccctatcccctgtggacctcttacgtgtacttgatatccataaag
gcgattatggaatacctacactgaaatccaaaaataggtatataccatat
agaagtggtacatataaaggcaaaacatatttatatgttgaaggagatag
tgatagtggacactactacgaagatacaactgatattacttcatccgaaa
gtgaatatgaagaaatggatatcaatgatatatatgtaccaggtagtcct
aaatataaaacattgatagaagtagtactggaaccatccaaaagtgatgg
tcatataccacatagtgctggtgaaccactagatgatatggtaggtacca
ctatatttacagatgaggaatggaatgaactgaaacacgattttatatca
caatatgtgcaacgtgaatcaatgggtgtaccacaatatgatgtatcaac
cgagttaccaatgaatataggaggtaatgttttagatgatggcatggaag
aaaaaccttttattacttctattcatgatagggatttatatactggagaa
gaatttagttataatattaatatgggtactaatagtatggatgatccaaa
atatgtatcaaataatgtatattctggtatcgatttaattaatgacacat
taagtggtaatcaacatattgatatatatgatgaagtattgaaaagaaaa
gaaaatgaattatttgggacaaattataagaaaaatatatcgaataaccg
tgtagctaaattaacaaataatgatccaattatgaaccaattagatttgt
tacataaatggttagatagacatagagatatgtgcaatacgtggaatacc
aaggaagaattattagataaattgaatgaacaatggaataaagataatga
tgctggtgatataccaagtgatagtaacaaaaagttgaatacggatgttt
cgatacaaatagatatggatgatcctaaaggaaagaaggaatttagtaat
atggatactatcttggatgatatagaagatgatatatattatgatgtaaa
tgatgaaaacccatttgtggatgatatacctatggatcataataaagtag
atgtaccaaagaaagtacatgttgaaatgaaaatccttaataatacatcc
aatggatccttggaaccagaatttcctatatcggatgtatggaatatat
aa
```

In view of the above, the invention relates to PfEMP1 antigens encoded by or having the sequences given as SEQ ID NOS 1, 2, 3, 4, 5 or 6 above. One of skill will appreciate that PfEMP1 antigens encoded by sequences exhibiting a degree of homology or identity with the sequences provided herein, are also within the scope of this invention. In particular, PfEMP1 antigens encoded by sequences exhibiting at least 40%, 45%, 50%, 55%, 60%, 65%, 70%, 75%, 80%, 90%, 91%, 92%, 93%, 94%, 095%, 96%, 97%, 98% or 99% homology/identity with any of SEQ ID NOS; 1, 2, 3, 4, 5 or 6 are to be regarded as PfEMP1 antigens having potential utility in this invention. The invention further relates to recombinantly or synthetically generated PfEMP1 antigens encoded by or having a sequence having homology and/or identity to those given as SEQ ID NOS: 1, 2, 3, 4, 5 or 6.

In all cases, the invention encompasses PfEMP1 antigens which, relative to those encoded by or having the sequences given as SEQ ID NOS: 1, 2, 3, 4, 5 or 6, comprise (i) one or more mutations—a mutation being characterised as an amino acid/nucleic acid deletion, addition, substitution and/or inversion and (ii) with respect to SEQ ID NOS: 2, 4 and/or 6, one or more conservative amino acid substitutions—the term "conservative substitution" embracing the act of replacing one or more amino acids of a protein or peptide with an alternate amino acid with similar properties and which does not substantially alter the physico-chemical properties and/or structure or function of the native (or wild type) protein. Of course, one of skill will appreciate that the degeneracy of the genetic code permits substitution of one or more bases in a codon without changing the primary amino acid sequence. Consequently, although SEQ ID NOS: 1, 3 and 5 encode specific PfEMP1 antigens, the degeneracy of the code may be exploited to yield variant nucleic acid sequences which encode the same primary amino acid sequences.

One of skill will appreciate that the PfEMP1 antigens described herein may be produced recombinantly using expression vector and/or systems. In this regard, the invention provides vectors, for example bacterial expression vectors (pET or pGEX system vectors for example) comprising nucleic acid sequences encoding PfEMP1 antigens of this invention. One of skill will appreciate that the nucleic acid sequences encoding PfEMP1 antigens of this invention may be codon optimised to ensure maximum expression in a particular expression system. The invention further provides host cells (for example bacterial cells (*E. coli*)) transformed with the vectors of this invention.

In other embodiments, the invention provides medicaments for use in raising immune responses in humans—the medicaments comprising PfEMP1 antigen(s) (or fragments thereof) selected from the group consisting of HB3var6; TM284var1; and ITvar60. Additionally, the invention provides methods of raising immune responses in humans, comprising administering to a human subject, an immunogenic amount of one or more PfEMP1 antigen(s) (or a fragment thereof), the PfEMP1 antigens being selected from the group consisting of HB3var6; TM284var1; and ITvar60.

One of skill will appreciate that the term "fragment" encompasses immunogenic and/or antigenic fragments of the PfEMP1 antigens described herein—including those encoded by SEQ ID NOS 1, 2, 3, 4, 5 or 6. In one embodiment, a fragment may comprise a complete domain or region of the PfEMP1 antigen—including for example, one or more of the Duffy Binding Like (DBL) domains. In other embodiments, suitable fragments may comprise between about 10 and n−1 amino acids—where "n" is the total number of amino acids of the complete PfEMP1 antigen (HB3var6: n=3424; TM284var1: n=2790; ITvar60: n=2716). By way of example, a PfEMP1 antigen fragment may comprise or consist of about 10, 20, 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2700, 2800, 2900, 3000, 3100, 3200, 3300 or 3400 (contiguous) PfEMP1 amino acids. In other embodiments, a PfEMP1 antigen fragment suitable for use in this invention may comprise at least one epitope capable of raising a cross-reactive/protective immune response.

In addition to identifying PfEMP1 antigens suitable for raising cross reactive and/or protective immune responses in humans, the inventors have further identified specific fragments, regions and/or domains of the PfEMP1 antigen(s) which are also suitable for raising cross reactive and/or protective immune responses in humans.

As such, in a fourth aspect, the invention provides one or more Duffy Binding Like (DBL) domains of *P. falciparum* Erythrocyte Membrane Protein-1 (PfEMP1) for use in raising immune responses in humans.

In a fifth aspect, the invention provides use of one or more Duffy Binding Like (DBL) domains of *P. falciparum* Erythrocyte Membrane Protein-1 (PfEMP1) for the manufacture of a medicament for raising immune responses in humans.

In a sixth aspect, the invention provides a method of raising an immune response in a human, the method comprising the step of administering an amount of one or more Duffy Binding Like (DBL) domains of *P. falciparum* Erythrocyte Membrane Protein-1 (PfEMP1) to a human subject.

As with the PfEMP1 antigens, exploited in the first, second and/or third aspects of this invention, the DBL domains exploited in the fourth, fifth and sixth aspects are suitable for raising cross reactive and/or protective immune responses/antibodies. That is to say, an immune response raised against a PfEMP1 DBL domain provided by this invention may comprise antibodies which exhibit a degree of specificity, selectivity and/or affinity for the PfEMP1 antigens of many different *P. falciparum* strains.

In one embodiment, the DBL domains for use in the fourth, fifth and/or sixth aspects of this invention are one or more selected from the group consisting of:

(i) the NTS-DBL1α domain;
(ii) the DBL4ϵ domain; and
(iii) a(n immunogenic/antigenic) fragment of (i) and/or (ii).

In one embodiment, the NTS-DBL1α domains for use in the fourth, fifth and/or sixth aspects of this invention are derived from the PfEMP1 variant HB3var6, TM284var1 and/or ITvar60. In one embodiment, the NTS-DBL1α domains for use in the fourth, fifth and/or sixth aspects of this invention are derived from HB3var6, and/or TM284var1.

In other embodiments, the DBL4ϵ domain is obtained from the PfEMP1 variant ITvar60.

In view of the above, the invention provides antigens for use, uses and methods comprising one or more PfEMP1 DBL domains selected from the group consisting of:

(i) the NTS-DBL1α domain of PfEMP1 variant HB3var6;
(ii) the NTS-DBL1α domain of PfEMP1 variant TM284var1;
(iii) the DBL4ϵ domain of PfEMP1 variant ITvar60; and
(iv) a (n immunogenic/antigenic) fragment of any of (i)-(iii) above.

It should be understood that all references to DBL domains encompass DBL domain fragments. As defined above, a DBL fragment for use in this invention may be immunogenic and/or antigenic and thus capable of generating protective/cross-reactive immune responses in humans. In other words, a DBL fragment may be capable of raising (or generating) a host immune response which is substantially similar or identical to an immune response raised when a host is administered a complete DBL antigen. DBL domain fragments suitable for use may include those comprising or consisting of 10, 20, 30, 40 or 50 (preferable contiguous) amino acids of the complete DBL sequence. In one embodiment the fragments may comprise or consist of any number of amino acids of a DBL domain from about 10 amino acids to about n−1 amino acids, where n is the total number of amino acids of the relevant DBL domain.

For convenience, the various PfEMP1 antigens, mutants/variants, fragments and domains thereof described in this specification shall be collectively referred to as "PfEMP1 antigens". Specifically, the following are to be regarded as PfEMP1 antigens according to this invention:

(i) PfEMP1 (including mutants or sequence variants thereof as defined above);
(ii) an IgM binding rosetting PfEMP1;
(iii) PfEMP1 variant HB3var6;
(iv) PfEMP1 variant TM284var1;
(v) PfEMP1 variant ITvar60;
(vi) a PfEMP1 DBL domain;
(vii) the NTS-DBL1α domain;
(viii) the DBL4ϵ domain;
(ix) the NTS-DBL1α domain of PfEMP1 variant HB3var6;
(x) the NTS-DBL1α domain of PfEMP1 variant TM284var1;
(xi) the DBL4ϵ domain of PfEMP1 variant ITvar60; and
(x) a(n immunogenic/antigenic) fragment of any of (i)-(ix).

One of skill will appreciate that the PfEMP1 antigens, fragments and/or domains may find particular application as vaccines for raising immune responses. While immunity to malaria can develop naturally, repeated exposure to the malarial parasite (for example, *P. falciparum*) is required. Indeed, without wishing to be bound by theory, this invention is based, in part, upon the discovery that antibodies to PfEMP1 antigens are detected in children recovering from severe (cerebral) malaria—moreover the inventors have noted that these antibodies exhibit a degree of specificity for the specific PfEMP1 antigens described herein (namely PfEMP1 variants, HB3var6; TM284var1 and ITvar60). As such, PfEMP1 variants HB3var6; TM284var1 and ITvar60 may represent exemplary vaccine candidates.

Of course, in the young and people from areas of the world where malaria is not a problem (for example Europe), levels of natural immunity are low as there has been insufficient exposure to the malaria parasite. Moreover in a person with low/no immunity to a *Plasmodium* sp. (for example *P. falciparum*), infection can bring about severe malaria. One of skill in this field will appreciate that instances of severe malaria can result in secondary complications including death, coma (cerebral malaria), respiratory difficulties, hypoglycaemia and severe anaemia. As such, children and/or travelers not regularly exposed to malarial parasites are susceptible to developing malaria and/or severe malaria.

The vaccines provided by this invention may be used to raise immune responses in children, wherein the immune response is protective against malaria and the development of severe malaria. In other embodiments, the invention provides vaccines which may be used to raise immune responses in humans who are infrequently exposed to malaria or who have not been exposed to malaria—this may include, for example travelers from those areas of the world where malaria does not exist. As above, immune responses raised through use of the vaccines provided by this invention may offer protection against the development of malaria and severe malaria.

In a seventh aspect, the invention provides the PfEMP1 antigens of this invention as compositions comprising a pharmaceutically acceptable diluent, carrier and/or excipient. In one embodiment, the compositions of this invention may be sterile.

The compositions may be formulated or prepared for parenteral administration—including, for example injection by subcutaneous, intradermal, intramuscular and/or intravenous injection. In one embodiment compositions of this invention may comprise aqueous or oleaginous suspensions formulated according to the known art using suitable dispersing, wetting and/or suspending agents. In this regard, one of skill will appreciate that an acceptable carrier, diluents and/or excipient may comprise 1,3-butanediol, water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectable compositions according to this invention.

In one embodiment, the compositions and vaccines provided by this invention may further comprise one or more adjuvants. One of skill will appreciate that the term "adjuvant" may encompass any agent which enhances or promotes the immune response of an immunised host to the antigens of a vaccine or immunogenic composition. Suitable adjuvants may include alum and/or freund's adjuvant.

The compositions and/or vaccines provided by this invention may be administered by either single or multiple dosages of an effective amount. Preferably two or more doses are administered over a predetermined period of time.

By way of example, an initial vaccine dose (primary immunisation) may be administered followed by one or more booster doses (secondary immunisation(s)) given at 2, 3, 4, 5, 6, 7, 8, 9 and/or 10 week intervals after the primary immunisation.

Other modes of administration are contemplated by the present invention and include intranasal, intraperitoneal, intrathecal, rectal, infusion and intrapulmonary administration. Administration may also be by nasal drip, aerosol, infusion through the skin or membrane surfaces or ingestion.

In an eight aspect, the invention provides a vaccine comprising a PfEMP1 antigen, for use in treating or preventing malaria or severe malaria. In one embodiment, the vaccines of this invention may prevent, limit or inhibit the development of severe malaria. One of skill will appreciate that a vaccine may be administered prophylactically to prevent the development of malaria or severe malaria in susceptible populations. A susceptible population may comprise children or juveniles and/or those not routinely, regularly exposed to the malarial parasite (for example European travelers).

In a ninth aspect, the invention provides the use of a vaccine comprising a PfEMP1 antigen in the manufacture of a medicament for treating or preventing malaria and/or severe malaria.

The PfEMP1 antigens provided by this invention may be combined with other antigens, for example other *Plasmodium* (*falciparum*) antigens and/or other bacterial or viral antigens to yield a combined vaccine for use. In a tenth aspect, the invention provides a method of treating or preventing malaria/severe malaria, the method comprising administering a vaccine to a human subject, the vaccine comprising an immunogenic amount of a PfEMP1 antigen.

In an eleventh aspect, the invention provides one or more of the PfEMP1 antigens described herein, for use in diagnosing or detecting malaria and/or severe malaria, in human subjects—particularly children (i.e. young or juvenile human subjects). The diagnostic procedures provided by the eleventh aspect of this invention may comprises the step of detecting a level of PfEMP1 antigen in a sample provided by a subject suspected of suffering from malaria/severe malaria, or being infected with a malaria parasite (for example *P. falciparum*). One of skill will appreciate that levels of PfEMP1 antigen may be detected by way of immunological techniques such as ELISA (exploiting antibodies exhibiting affinity, specificity and/or selectivity for a predetermined PfEMP1 antigen), immunoblot, SDS PAGE and/or PCR based techniques which probe samples for levels of *P. falciparum* nucleic acid—in particular, those sequences which encode PfEMP1 antigens.

In a twelfth aspect, the invention provides antibodies exhibiting a degree of affinity, specificity and/or selectivity for one or more of the PfEMP1 antigens described herein. Without wishing to be bound by theory, interventions that disrupt rosettes could be valuable adjunctive therapies for severe malaria. By way of example, antibodies which exhibit an affinity, specificity and/or selectivity for one or more of the PfEMP1 antigens described herein, may be exploited to unblocking the congested blood flow in the microvasculature that is the primary pathological event caused by rosetting parasites. "Rosette-busting" interventions of this type may be analogous to clot-busting drugs used after stokes and heart attacks, to remove the obstruction to microvascular blood flow caused by rosetting cells, and restore normal tissue oxygenation.

The term "antibodies" includes polyclonal antibodies as well as monoclonal antibodies and embraces antigen and/or epitope binding antibody fragments such as, for example, Fab, $Fab_2$, scFv, $V_H$ domain and/or $V_L$Domain fragments. The production and isolation of polyclonal/monoclonal antibodies specific for protein/peptide sequences is routine in the art, and further information can be found in, for example "Basic methods in Antibody production and characterisation" Howard & Bethell, 2000, Taylor & Francis Ltd. The antibodies described herein may be conjugated to detectable moieties such as, for example, chemiluminescent and/or fluorescent moieties. The antibodies described herein may be used in diagnostic procedures, to, for example, detect *P. falciparum* in samples, or to diagnose malaria or severe malaria (as caused by *P. falciparum*) in humans. Any diagnostic procedure may involve contacting a sample provided by a human subject, with an antibody of this invention—the detection of antibody bound to a PfEMP1 antigen indicating that the sample has been provided by a human infected with the *P. falciparum* parasite. The term "sample" may relate to any biological material and/or fluid provided by a human subject and may include, for example, samples of blood, serum, plasma, sweat, saliva and/or tissue biopsies or cell samples.

The antibodies provided by this invention may further be used in passive immunisation protocols to treat or prevent malaria and/or severe malaria. As such, one embodiment of this invention provides one or more antibodies according to the twelfth aspect of this invention for use in treating and/or preventing malaria/severe malaria.

As such, a thirteenth aspect of this invention provides an antibody exhibiting a specificity, selectivity and/or affinity for a PfEMP1 antigen described herein, for use in treating or preventing malaria and/or severe malaria. The invention further provides use of an antibody exhibiting a specificity, selectivity and/or affinity for a PfEMP1 antigen in the manufacture of a medicament for treating or preventing malaria. In a yet further aspect, the invention provides a method of treating or preventing malaria, the method comprising administering a therapeutically effective amount of an antibody exhibiting a specificity, selectivity and/or affinity for a PfEMP1 antigen, to a human subject in need thereof.

In a fourteenth aspect, the invention provides one or more compounds capable of recognising the interaction between PfEMP1 and uninfected erythrocytes, for use in treating and/or preventing malaria/severe malaria. By way of example, the compound may comprise a small molecule (for example a protein/peptide, nucleic acid carbohydrate, organic/inorganic molecule) or an antibody exhibiting affinity, selectivity and/or specificity for one or more of the PfEMP1 antigens, fragments, epitopes and/or domains provided by this invention. In addition, this invention may extend to the provision of small molecules which may be used in methods and medicaments for treating or preventing rosette formation.

DETAILED DESCRIPTION

The present invention will now be described in detail with reference to the following figures which show:

FIG. 1: Identification of key surface antigens (Group A PfEMP1 variants) of *P. falciparum* rosetting parasites and production of recombinant proteins for immunization. a) PfEMP1 domain architecture of the predominantly expressed variants from *P. falciparum* rosetting laboratory strains. The previously described rosetting variant ITvar9 [12,20] is shown for comparison. Domain types are based on conserved motifs [6,45]. NTS: N-terminal segment; DBL: Duffy Binding Like; CIDR: Cysteine-rich InterDomain Region; ATS: Acidic terminal Segment; TM: TransMembrane region. *The IT isolate was originally from Brazil, however following cross-contamination in the early 1980s, current IT/FCR3 strains are thought to be of South-East Asian origin [65]. b) Northern blots of RNA from isogenic rosetting (R+) and non-rosetting (R−) parasites probed with a PfEMP1 domain from the rosette-specific variant for each strain (R+DBL probe, high stringency) and with an Exon II probe (moderate stringency), which detects all var genes [44]. Arrows indicate the major rosette-specific variants. Equal loading of R+ and R− RNA was confirmed by staining with ethidium bromide (Et Br). c) Production of recombinant NTS-DBLα domains in *E. coli* to immunize rabbits. 1: TM180var1, 2: Muz12var1, 3:TM284var1, 4: ITvar60, 5:HB3var6. M: molecular weight marker; R: reduced; NR: non-reduced.

Figure 2A:
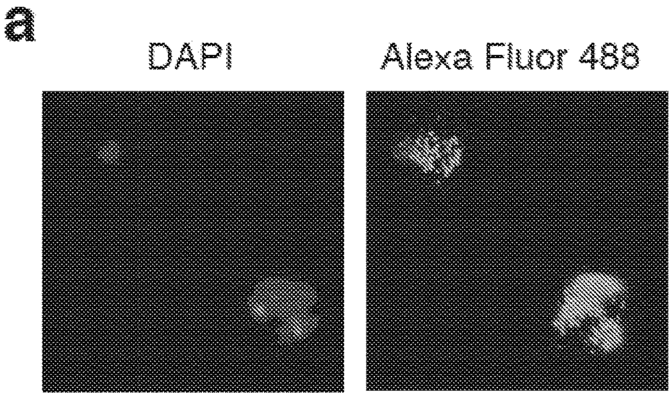
Figure 2B:
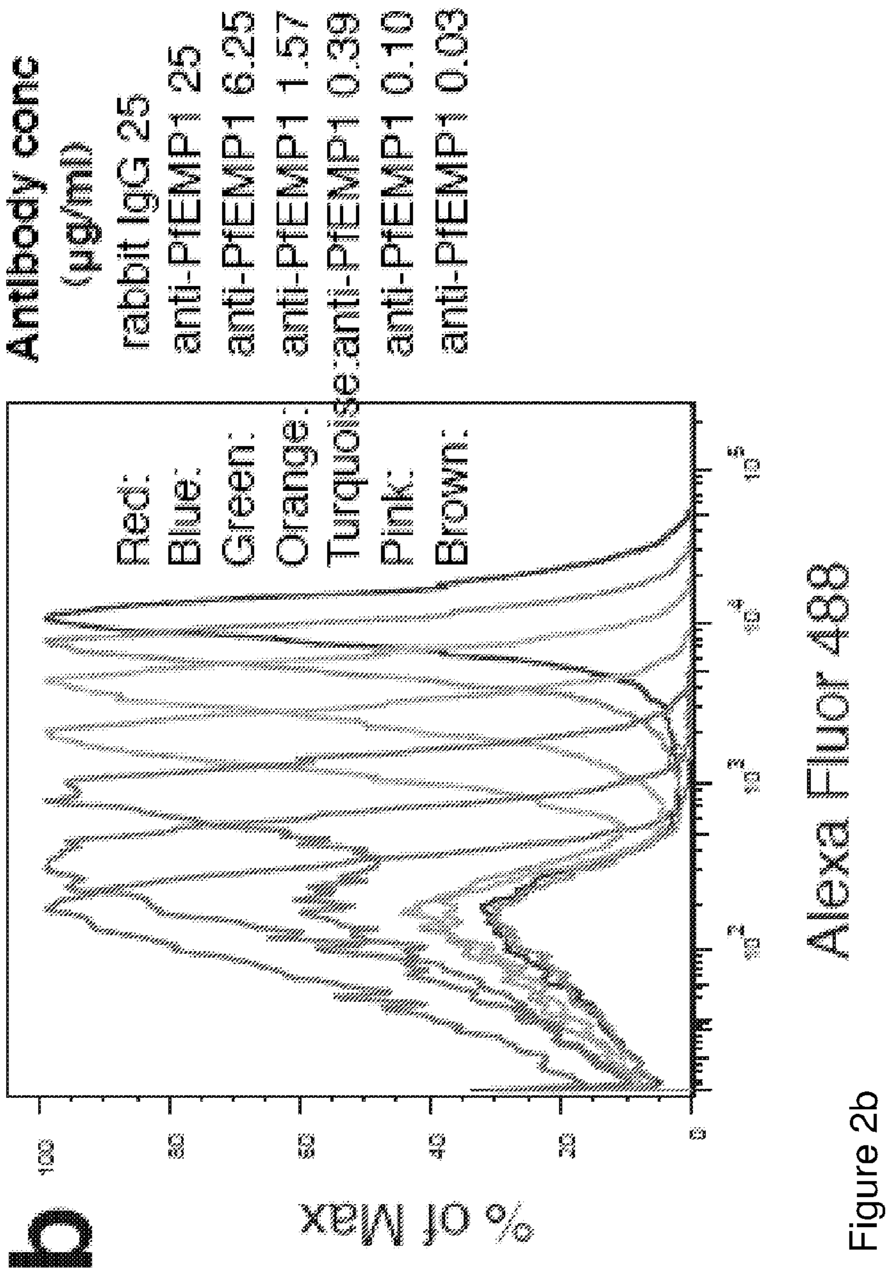

FIG. 2: Antibodies to PfEMP1 recognize the surface of live infected erythrocytes, and show cross reactivity between *P. falciparum* rosetting laboratory strains. a) Immunofluorescence assay (IFA) with antibodies to ITvar60 (25 μg/ml) tested on the homologous parasite (IT/PAR+). Left panel: DAPI staining to show position of infected erythrocytes. Right panel: punctate fluorescence over the surface of live infected erythrocytes. b) Flow cytometry to show the titration of antibodies to ITvar60 against IT/PAR+ parasites, compared to a non-immunized rabbit IgG control. The end titre (defined here as the lowest concentration at which more than 50% of infected erythrocytes were positive by IFA/flow cytometry) was 0.1 g/ml. c) PfEMP1 antibodies (four-fold dilutions of total IgG starting at 400 μg/ml) were tested against *P. falciparum* laboratory strains with various different adhesion phenotypes as indicated. The end titre for each antibody:parasite combination (defined as above) is shown inside each rectangle. Homologous antibody: parasite combinations are outlined in bold. Negative controls are non-immunised rabbit IgG, and antibodies against NTS-DBLα from a non-rosetting group A PfEMP1 variant (HB3var3, expressed by HB3-HBEC which are non-rosetting parasites selected for binding to human brain endothelial cells). *The HB3R+ parasites contain a subpopulation of HB3var3-expressing infected erythrocytes that are distinct from the HB3var6-expressing cells, Table S1).

FIG. 3: Antibodies to PfEMP1 show cross-reactivity in rosette inhibition and induction of phagocytosis in *P. falciparum* rosetting laboratory strains. a) Rosette inhibition assays to determine the dose-dependent effects of PfEMP1 antibodies on homologous and heterologous rosetting laboratory strains. Data are compared to a control with no added antibody, which contained at least 40% of infected erythrocytes in rosettes. Mean and standard deviation of triplicate values are shown. IC50: concentration of antibody giving 50% rosette inhibition. b) Rosette inhibition assay as above with 1 mg/ml of antibody, except for the Anti-Ros pool which consisted of a mixture of 0.1 mg/ml of each antibody (to HB3var6, TM284var1, ITvar60, Muz12var1, TM180var1 and ITvar9). Controls are as for FIG. 2*c*. c) Phagocytosis assay of opsonised IT/PAR+ infected erythrocytes co-incubated with the monocytic cell line Thp-1 [12]. Data are shown as percentage of the positive control opsonised with a rabbit anti-human erythrocyte antibody.

FIG. 4: Antibodies to PfEMP1 show cross-reactivity in surface recognition and rosette inhibition of *P. falciparum* clinical isolates. a) Flow cytometry of clinical isolate MAL43 with 0.4 mg/ml of total IgG from a non-immunised rabbit (negative control, left panel) and antibodies to TM284var1 (middle panel). Infected erythrocytes stained with Hoescht are in the right half, and antibody-positive infected erythrocytes stained with Alexa Fluor 488 are in the upper right quadrant. An overlay of histograms (right panel) shows a clear population of stained infected erythrocytes. b) Fresh clinical isolates tested with PfEMP1 antibodies for surface reactivity (IFA and flow cytometry at 0.4 mg/ml) and rosette inhibition (1 mg/ml). The percentage rosette inhibition is shown inside each rectangle for all isolate:antibody combinations with >25% rosette inhibition. The controls are as for FIG. 2*c*, and the Anti-Ros Pool as for FIG. 3*b*. The Anti-Ros pool was tested for rosette inhibition only. c) Flow cytometry histograms to show negative controls, anti-PfEMP1 positive and IgM-positive infected erythrocytes for five clinical isolates. Other isolates were tested by IFA only. The “negative PfEMP1 Ab” was antibody to TM180var1 and the IgM negative control was a mouse IgG1 isotype control.

Figure 5A:
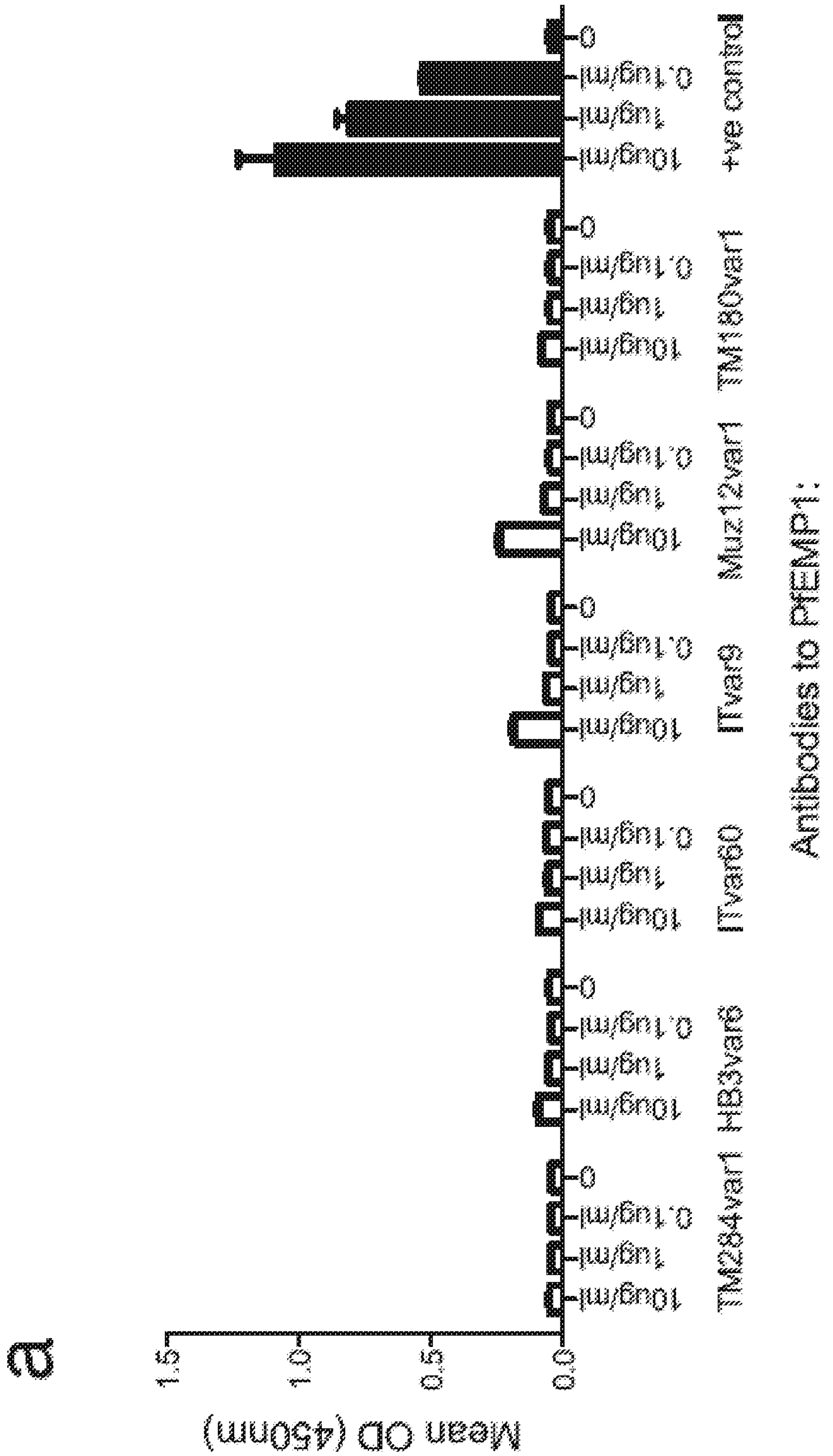

FIG. 5: Cross-reactive PfEMP1 antibodies do not recognise human IgM. a) ELISA for recognition of human IgM. The positive control is an anti-human IgM antibody. The mean and SD of Optical Density (OD) values from triplicate wells are shown. b) Flow cytometry of IT/PAR+ parasites grown with and without human IgM and stained with anti-TM284var1 antibodies.

Figure 6A:
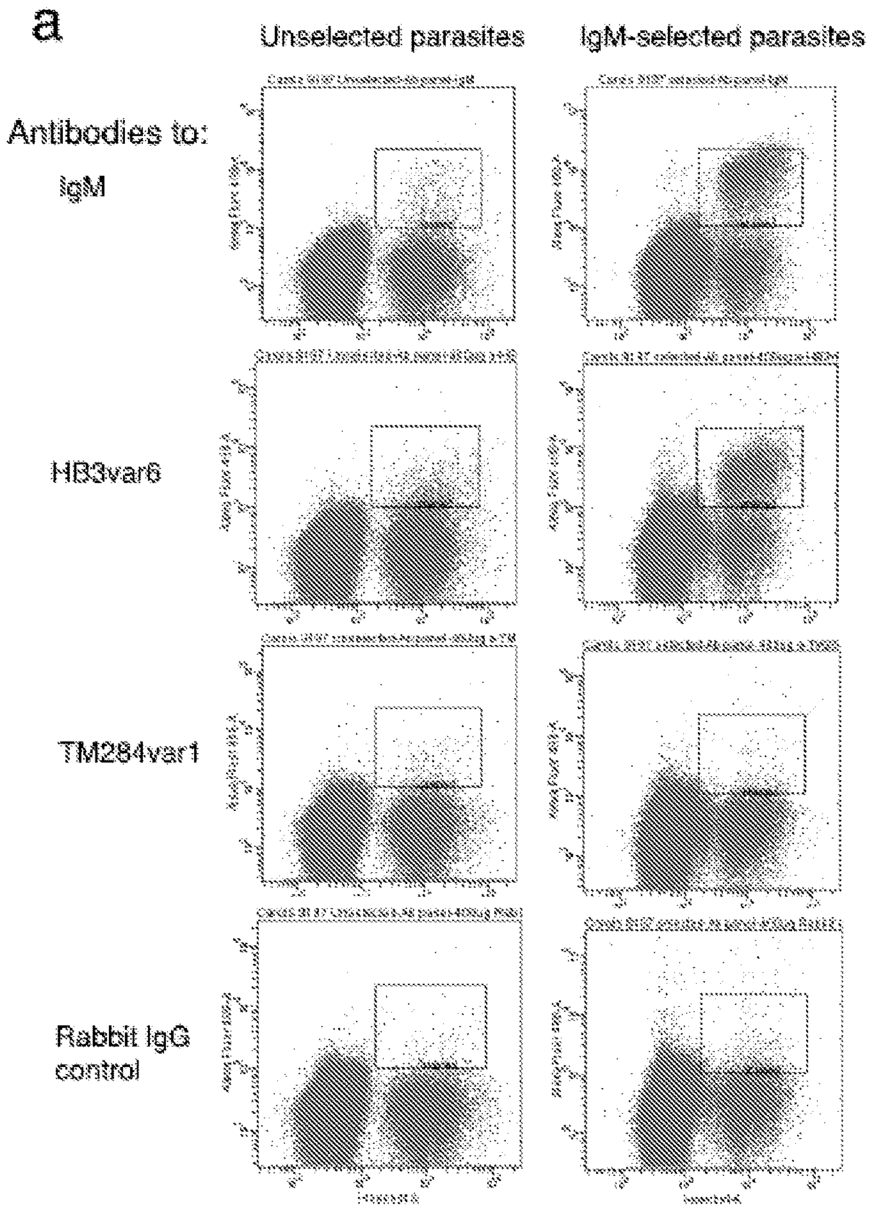

FIG. 6: Selection for IgM yields rosetting infected erythrocytes that cross-react with PfEMP1 antibodies. a) The culture-adapted Kenyan isolate 9197 was selected three times with anti-human IgM coated Dynabeads. Comparison of the unselected and selected lines by flow cytometry showed that the IgM-selected parasites were recognised by cross-reactive PfEMP1 antibodies to HB3var6. b) An IFA with dual staining (AlexaFluor 488 anti-rabbit IgG to detect PfEMP1 antibody and AlexaFluor 594 anti-mouse IgG to detect anti-human IgM) shows that the same subpopulation of infected erythrocytes bound both IgM and HB3var6 antibodies.

FIG. 7. Opsonisation and induction of phagocytosis by PfEMP1 antibodies. Infected erythrocytes were stained with ethidium bromide and opsonised with PfEMP1 antibodies before incubation with the monocytic cell line Thp-1. Thp-1 cells that phagocytosed infected erythrocytes were detected by flow cytometry. a) parasite strain TM284 b) parasite strain HB3R+c) parasite strain IT/R29 d) parasite strain TM180. Data are shown as percentage of the positive control opsonised with a rabbit anti-human erythrocyte antibody. The "Non Ros Group A" negative control consists of antibodies to HB3var3, a PfEMP1 variant that is not involved in rosetting. HB3R+ parasite culture contains a subpopulation of infected erythrocytes expressing HB3var3 (see Table S1) which explains why phagocytosis was induced in this case. The "Control Rabbit IgG" is a negative control consisting of purified IgG from a non-immunized rabbit.

Figure 8:
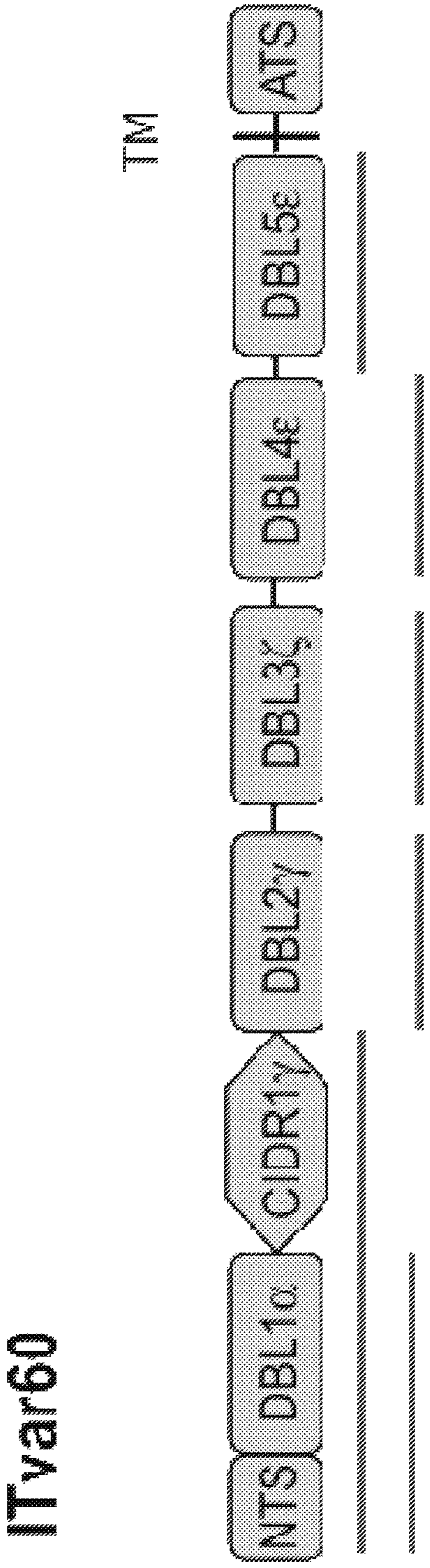

FIG. 8: DBL domains from the ITvar60 variant. The underlined regions indicate the recombinant proteins generated. Abbreviations as for FIG. 1*a*.

Figure 9:
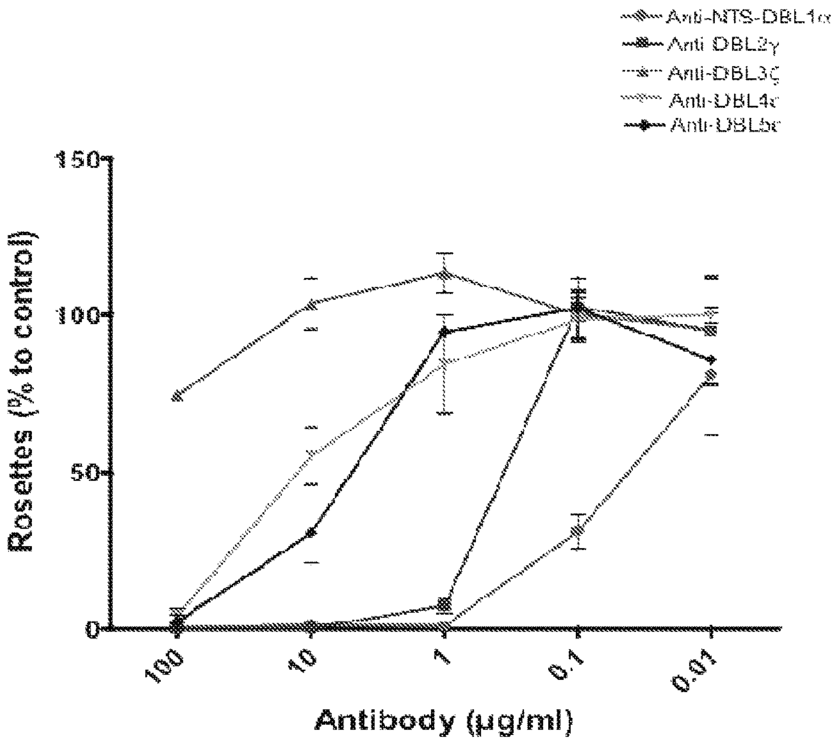

FIG. 9: Inhibition of rosetting by anti-DBL antibodies. Rosette inhibition assays to determine the dose-dependent effects of various ITvar60 PfEMP1 antibodies on IT/PAR+ parasites. Data are compared to a control with no added antibody, which contained at least 40% of infected erythrocytes in rosettes. Mean and standard deviation of triplicate values are shown.

Figure 10:
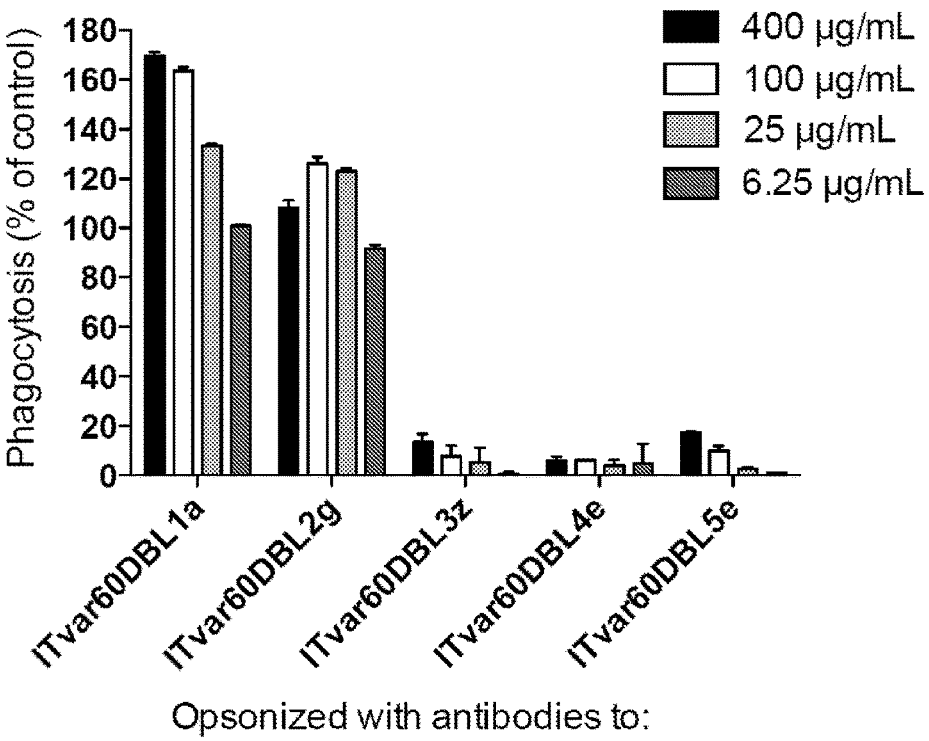

FIG. 10: Opsonisation and phagocytosis of infected erythrocytes by ITvar60 antibodies. Infected erythrocytes were stained with ethidium bromide and opsonised with PfEMP1 antibodies before incubation with the monocytic cell line Thp-1. Thp-1 cells that phagocytosed infected erythrocytes were detected by flow cytometry.

Figure 11:
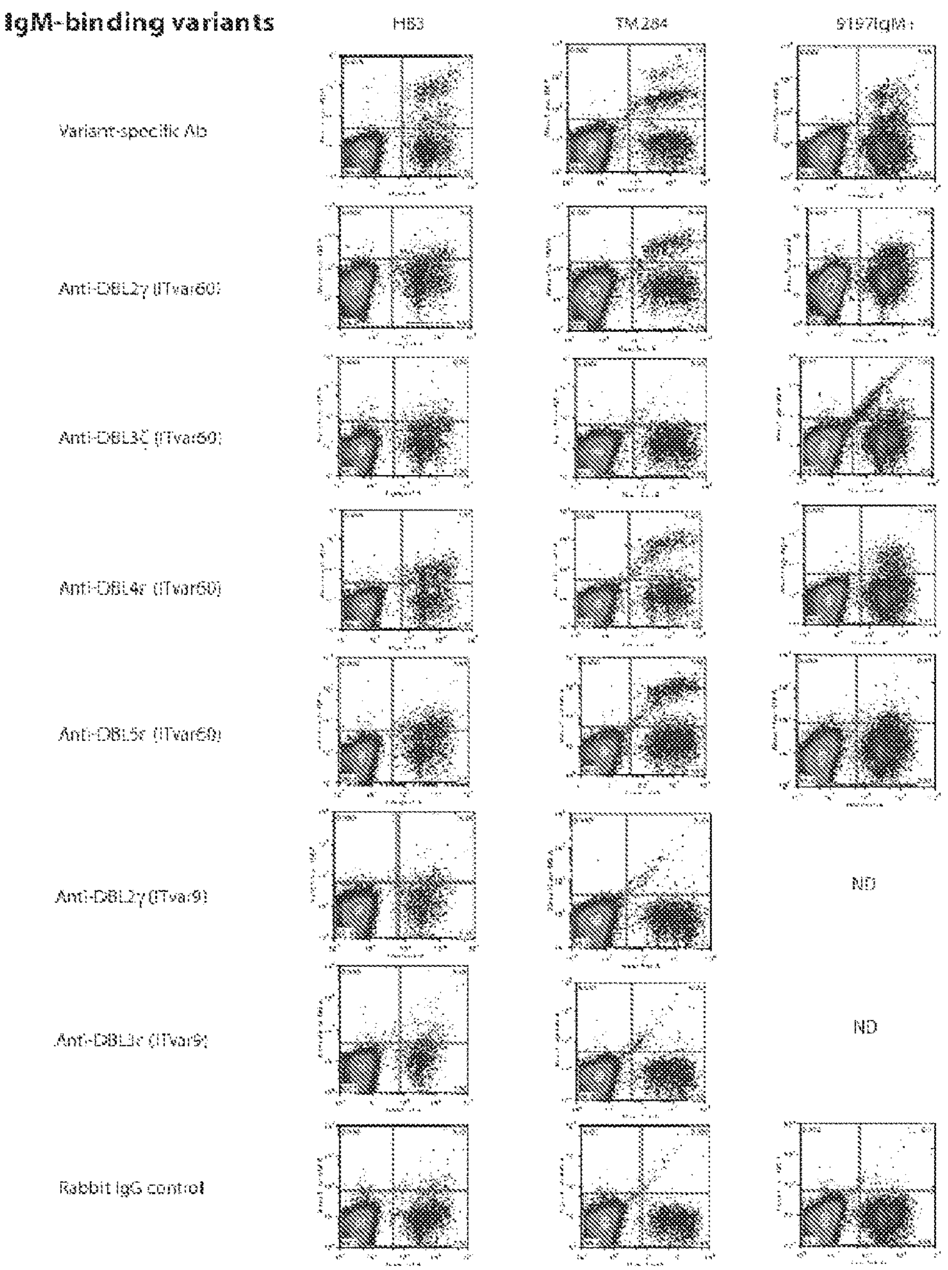

FIG. 11: Antibodies to various domains of ITvar60 tested against IgM binding rosetting parasites (strain HB3R+ 1st column, strain TM284 2nd column, strain 9197IgM+ 3rd column). Surface reactivity was assessed by flow cytometry, with positive infected cells detected in the upper right quadrant of each dot plot. Positive controls are variant-specific antibodies to each parasite strain (top row). Negative controls are non-immunized rabbit IgG (bottom row) and antibodies to domains from a non-IgM binding variant (ITvar9). Anti-DBL4ϵ of ITvar60 recognises all three strains, while anti-DBL5ϵ and anti-DBL2γ of ITvar60 recognise strain TM284 only.

Figure 12:
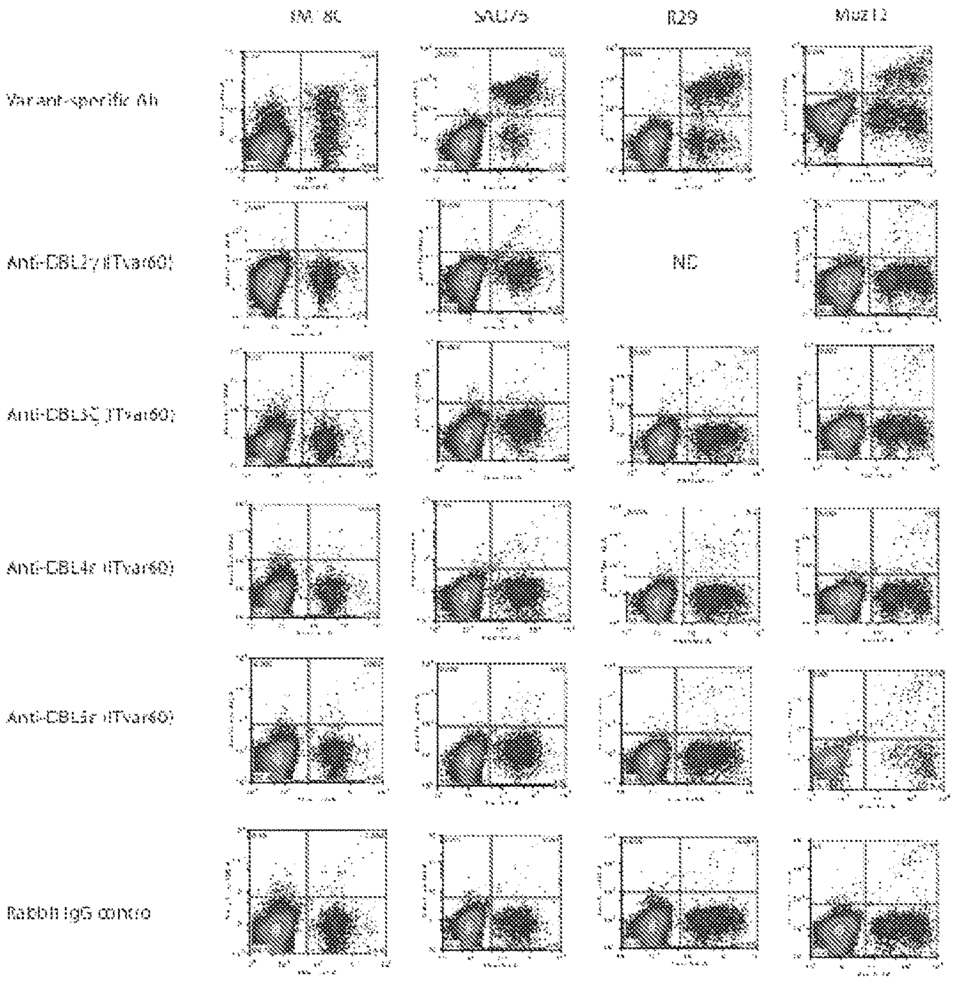

FIG. 12: Antibodies to various domains of ITvar60 tested against non-IgM binding rosetting parasites (strain TM180 1st column, strain SA075 2nd column, strain IT/R29 3rd column, strain Muz12 4th column). Surface reactivity was assessed by flow cytometry, with positive infected cells detected in the upper right quadrant of each dot plot. Positive controls are variant-specific antibodies to each parasite strain (top row). Negative controls are non-immunized rabbit IgG (bottom row). Antibodies to ITvar60 domains do not recognise any of these parasite strains.

Figure 13:
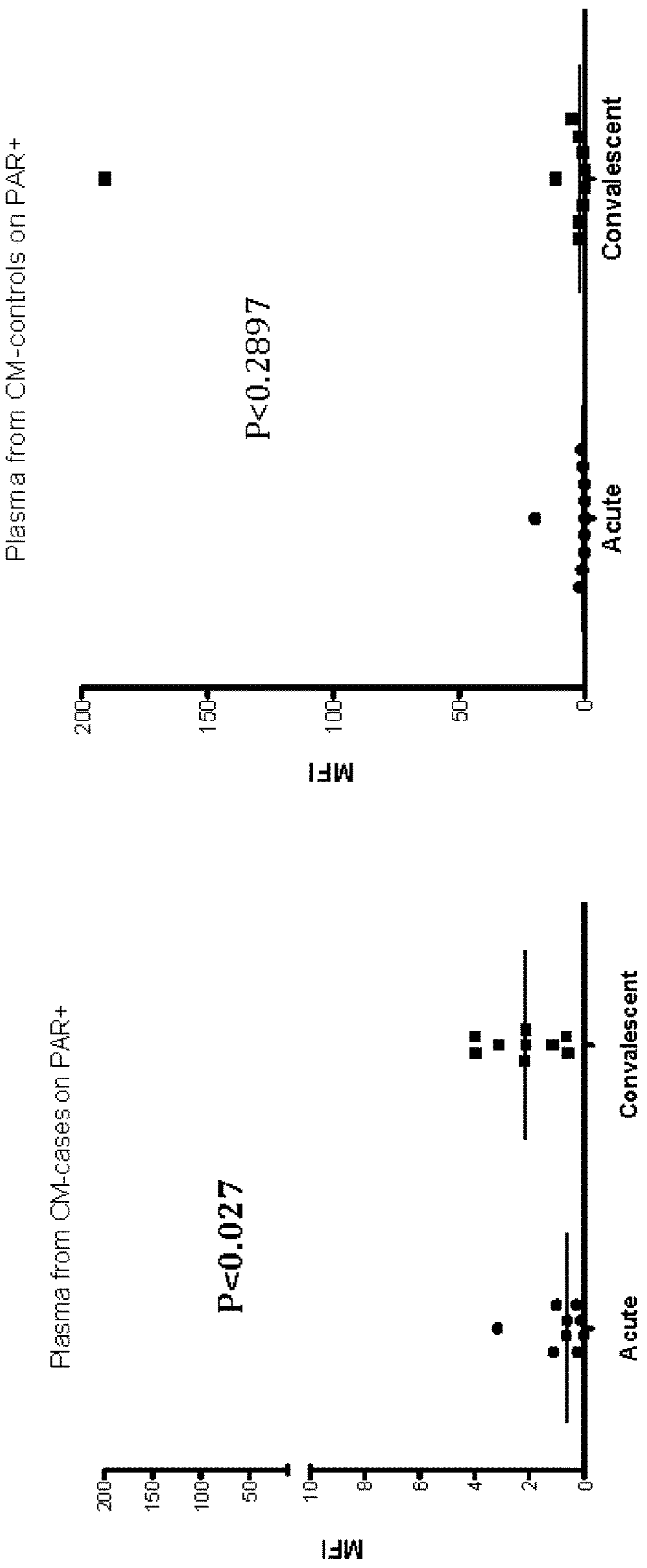

FIG. 13: Case-control study of recognition of live IT/PAR+ infected erythrocytes (expressing the ITvar60 antigen) by plasma samples from young Kenyan children with severe (cerebral) malaria (CM-cases) compared to age- and time of admission-matched controls (CM-controls). Data from flow cytometry; MFI: mean fluorescence intensity.

Figure 14:
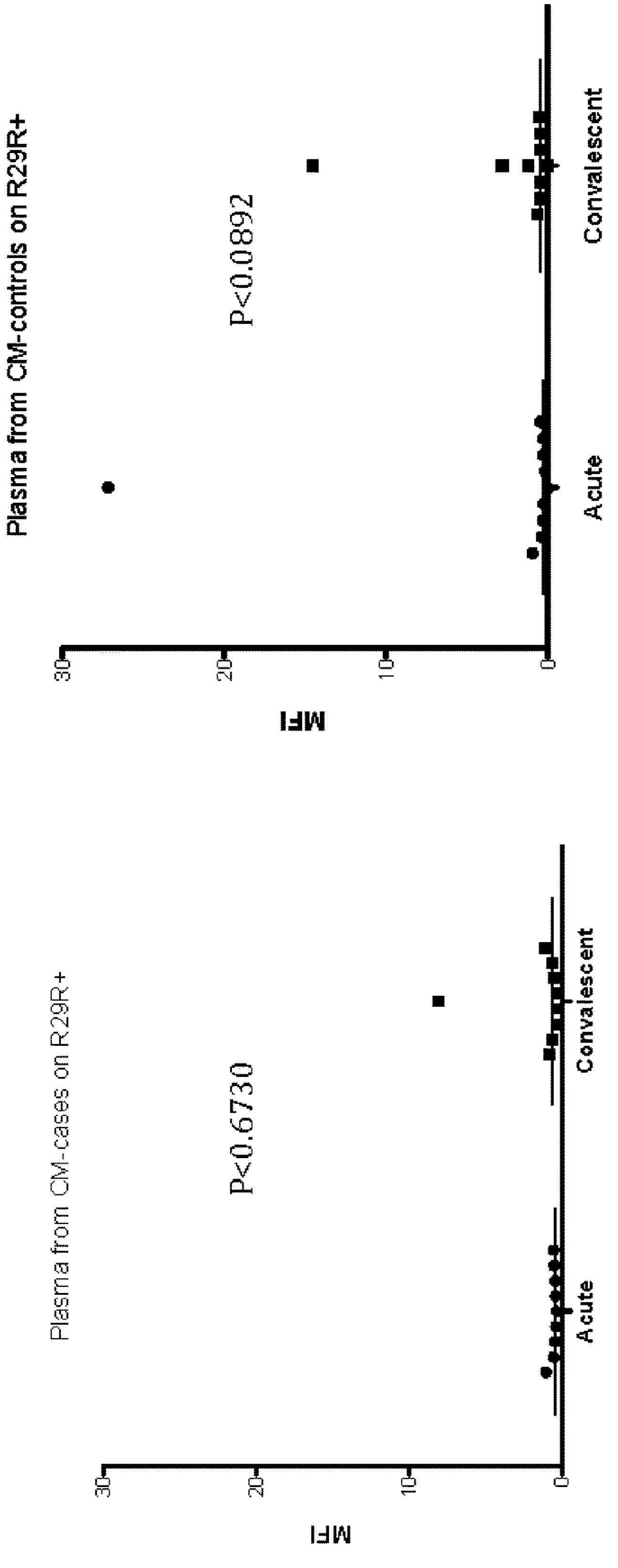

FIG. 14: Case-control study of recognition of live IT/R29 infected erythrocytes by plasma samples from young Kenyan children with severe (cerebral) malaria (CM-cases) compared to age- and time of admission-matched controls (CM-controls). Data from flow cytometry; MFI: mean fluorescence intensity.

Figure 15:
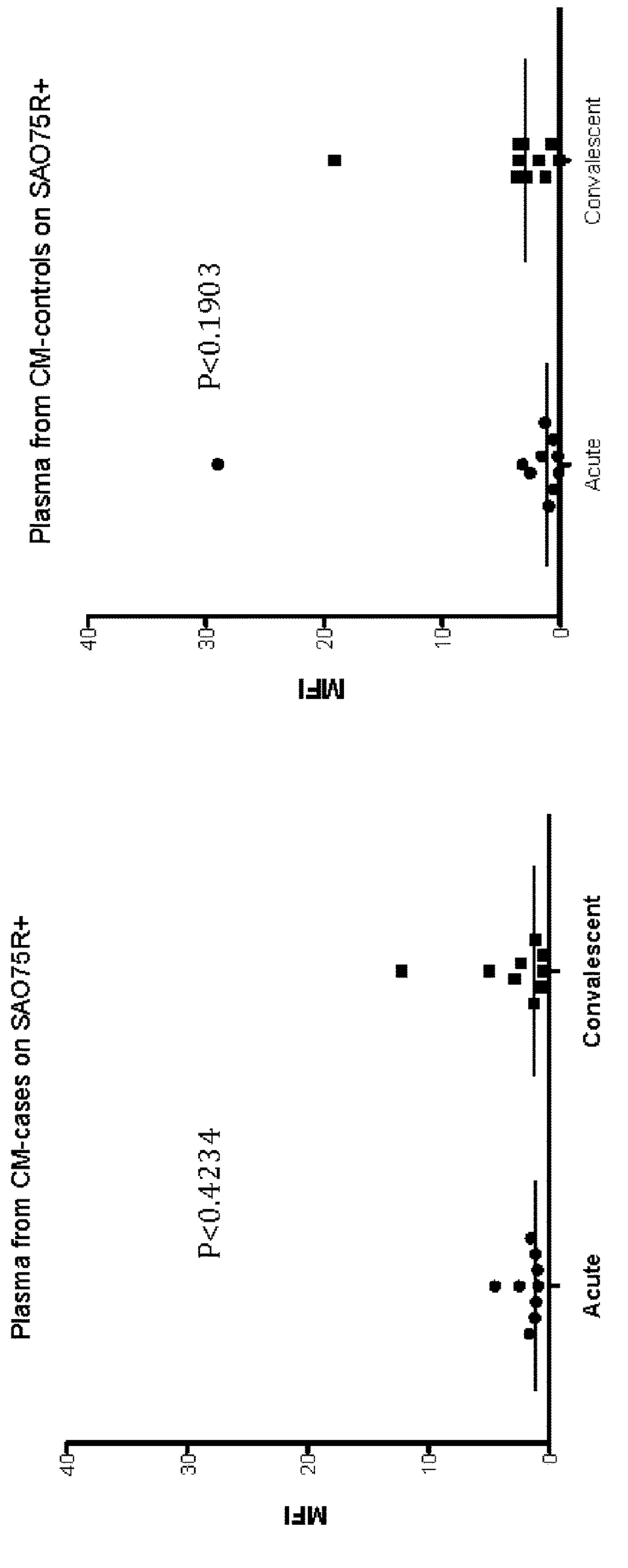

FIG. 15: Case-control study of recognition of live SA075R+ infected erythrocytes by plasma samples from young Kenyan children with severe (cerebral) malaria (CM-cases) compared to age- and time of admission-matched controls (CM-controls). Data from flow cytometry; MFI: mean fluorescence intensity.

Figure 16:
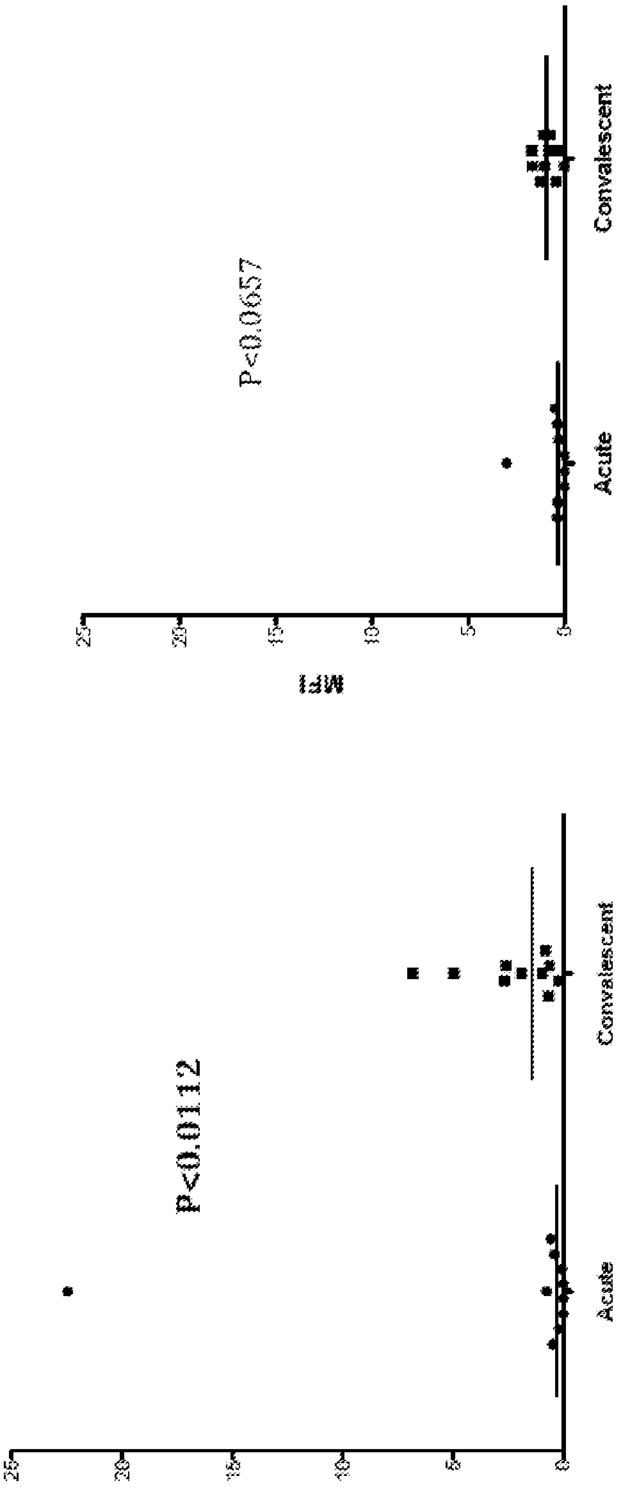

FIG. 16: A: Plasma from severe malaria cases tested on parasites expressing HB3var6; B: plasma from uncomplicated malaria controls tested on parasites expressing HB3var6.

Figure 17:
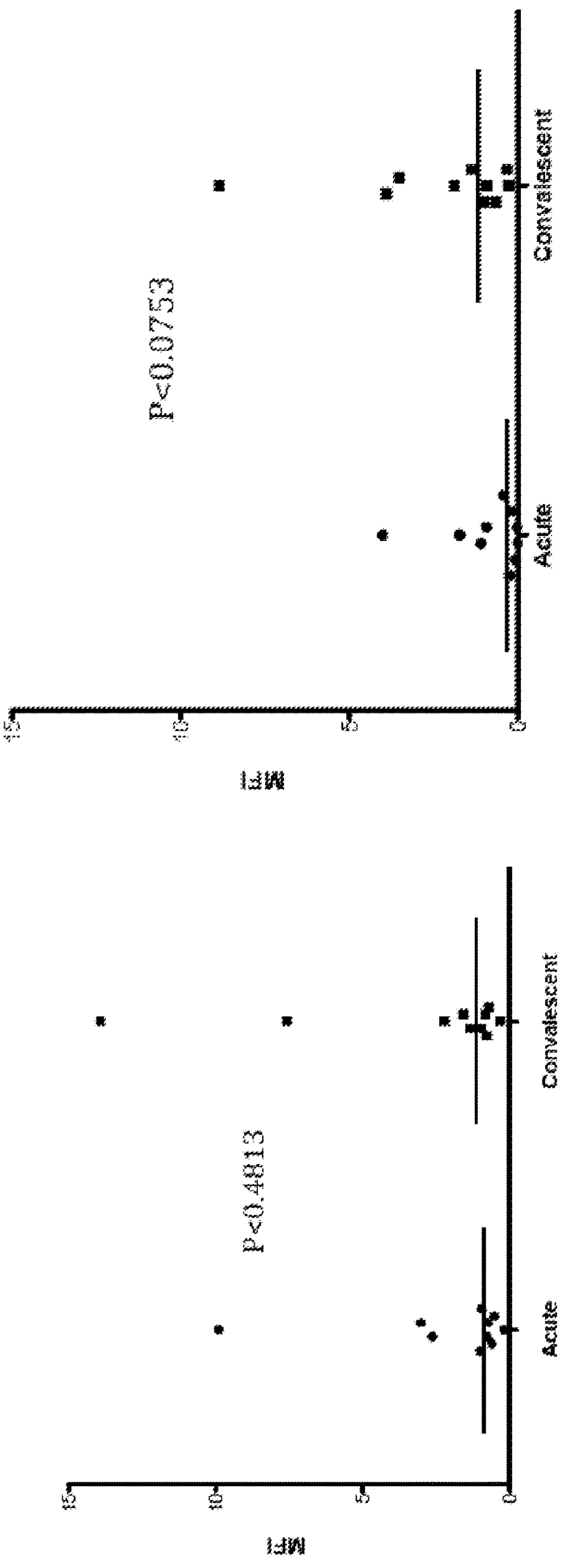

FIG. 17: A: Plasma from severe malaria cases tested on parasites expressing SA075var1; B: plasma from uncomplicated malaria controls tested on parasites expressing SA075var1.

Figure 18:
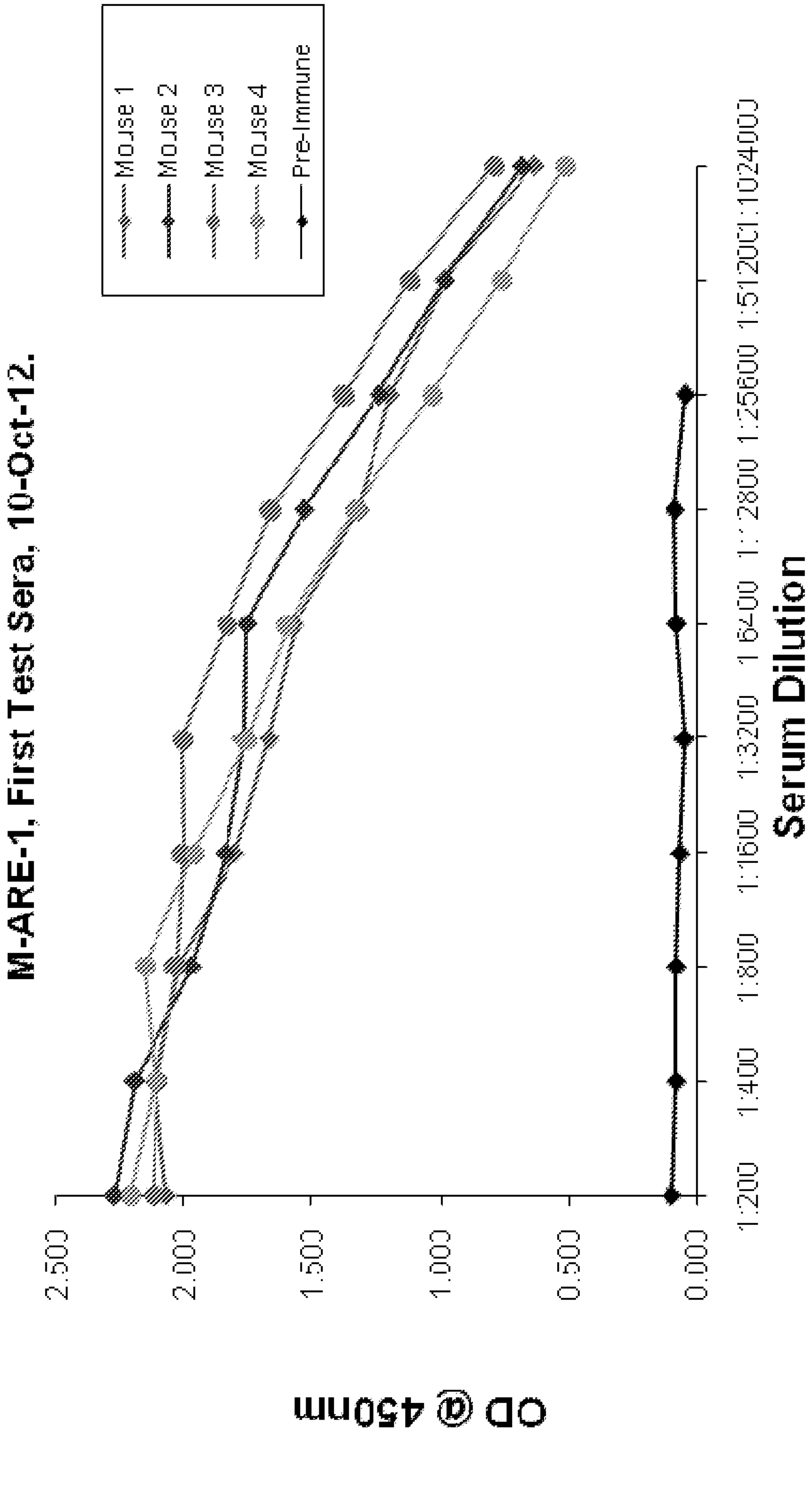

FIG. 18: ELISA showing polyclonal antibody response in mice immunised with TM284var1.

EXAMPLE 1

Materials and Methods

Parasites and Parasite Culture.

The *P. falciparum* laboratory strains (HB3, Muz12, IT/R29, IT/PAR+, TM180 and TM284) were cultured in supplemented RPMI [59] and selected for rosetting as described [60]. All cultures were checked regularly to exclude mycoplasma contamination [61]. The parasites were genotyped with primers to MSP1, MSP-2 and GLURP [62] and were genetically distinct apart from IT/PAR+ and IT/R29 which share the same genotype but transcribe different PfEMP1 variants. Other parasite strains used were unselected HB3 and 3D7 (CD36-binding), IT/A4 (CD36 and ICAM-1 binding) and three strains selected for binding to human brain endothelial cells (HB3-HBEC, 3D7-HBEC and IT-HBEC, Claessens et al, in press). Clinical isolates were from Cameroon (CAM1), Kenya (KEN7, KEN14, KEN17, 9197, SA075), Mali (MAL27, MAL34, MAL43, MAL81, MAL103) and The Gambia (GAM627). The Malian isolates and KEN7, KEN14 and KEN17 were cryopreserved from previous studies [30,46]. All clinical isolates were examined in the first cycle of in vitro growth except for KEN7, KEN14 and KEN17 (third cycle) and 9197 and SA075 which had been adapted to culture, cloned and selected for rosetting over 3-4 months of in vitro growth. The IgM binding phenotype of the rosetting strains was determined by immunofluorescence assay (IFA) with an anti-human IgM monoclonal antibody (Serotec MCA1662) as described [38,44].

Ethics Statement.

Collection of clinical isolates (blood samples) from malaria patients was carried out in accordance with the Declaration of Helsinki. Written informed consent was obtained from the patients' parents or guardians and was approved by the Lothian Regional Ethical Review Committee (LREC/2002/4/34), the KEMRI Ethical Review Committee, the Gambia Government/MRC Laboratories Joint Ethics Committee, the Cameroon Ministry of Public Health Regional Ethics committee and the University of Bamako Institutional Review Board. Animal immunisations were carried out commercially by BioGenes GmbH (Berlin, Germany) according to European Union guidelines 86/609/EWG of 24.11.1986 and the European Agreement of 18.3.1996 for protection of animals used for scientific purposes.

Var Gene Expression Profiling and Var Gene Sequencing.

RNA extraction and var gene expression profiling were carried out as described previously [24] and in Table S1. The full-length sequence of each predominant rosette-specific var gene was derived from the sequence tag by: a) extraction from parasite genome databases (HB3 at http://www.broadinstitute.org and IT at www.sanger.ac.uk) b) PCR-walking, cloning and sequencing using degenerate primers to upstream and downstream PfEMP1 regions [63] for Muz12var1. c) PCR-walking, cloning and sequencing using vectorette libraries [20] for TM284var1 and TM180var1.

Northern Blotting.

RNA extraction and Northern blotting of isogenic rosetting and non-rosetting pairs of parasites was carried out with Digoxigenin-labelled RNA probes as described [44]. RNA from each parasite strain was hybridised with a specific probe representing one DBL domain from the homologous rosette-specific var gene, as well as an exon II probe to detect all var genes.

Recombinant Proteins and Polyclonal Antibodies.

Recombinant proteins were produced as described previously [12]. The domain boundaries for the NTS-DBL1 recombinant proteins for each rosette-specific variant were as follows: HB3var6 Met1-Pro473; TM284var1 Met1-Pro457; ITvar60 Met1-Pro464; Muz12var1 Met1-Pro458; TM180var1 Met1-Pro485. The non-rosetting group A PfEMP1 variant HB3var3 (Met1-Pro468) was used as a control. Each protein was used to immunize two rabbits which had been pre-screened to avoid animals with pre-existing natural antibodies to human erythrocytes or malaria parasites. Immunization, serum collection and total IgG purification were carried out by BioGenes GmBH (Berlin, Germany).

Immunofluorescence Assays (IFA).

Immune and pre-immune sera were tested in IFA with live infected erythrocytes as described [12,44]. Out of each pair of immunized rabbits, the serum giving the brightest fluorescent signal with the lowest background was chosen for purification of total IgG. In all cases, both rabbit sera gave positive PfEMP1-staining, with only minor differences in intensity of staining.

Flow Cytometry.

Staining for flow cytometry was carried out as for IFA [12,44], except that Hoescht (1.25 μg/ml) was used instead of DAPI to stain infected erythrocytes and 50 μg/ml fucoidan was added after the secondary incubation washes to disrupt rosettes. Cells were fixed with 0.5% paraformaldehyde, with 50 μg/ml fucoidan added to prevent rosettes from re-forming, and 500,000 events per sample were analysed on a Becton-Dickinson LSRII flow cytometer.

Rosette Inhibition Experiments.

*P. falciparum* cultures at ring stage were incubated overnight with antibodies and controls at various dilutions, and rosetting assessed the next day by microscopy as described [12].

Phagocytosis Assays.

Phagocytosis experiments with Thp-1 cells were as described previously [12] except that fucoidan (200 μg/ml) was used for parasite purification and rosette disruption. The positive control was parasite culture opsonized with a rabbit anti-human erythrocyte antibody (ab34858, ABCAM, Cambridge, UK). Muz12var1 antibodies were not included in the phagocytosis assays because they show some background binding to uninfected erythrocytes.

IgM ELISA.

The ability of PfEMP1 antibodies to cross react with human IgM was tested using purified human IgM (5 μg/ml, Rockland) coated onto an ELISA plate at 4° C. overnight. After blocking for 1 hour in PBS containing 0.05% Tween 20 (PBST) and 5% milk, wells were incubated with 10, 1 and 0.1 μg/ml of rabbit anti-NTS DBL1α antibodies in PBST containing 1% milk (PBS™). After 1 hour incubation at room temperature, wells were washed with PBST and incubated with 1:10,000 anti-rabbit IgG-HRP (Sigma) in PBS™ for a further hour. After washing as above, reactions were developed by incubating the wells with substrate 3,3',5,5'-tetramethylbenzidinedihydrochloride (Sigma) according to the manufacturer's instructions and absorbance was measured at a wavelength of 450 nm. As a positive control, a rabbit anti-human IgM F(ab')2-HRP (DAKO) was used at 1:100 (10 μg/ml), 1:1000 (1 g/ml) and 1:10000 (0.1 μg/ml).

Surface Cross-Reactivity of PfEMP1 Antibodies in the Absence of IgM.

Pooled human serum was depleted of IgM by three successive rounds of incubation for 45 mins at room temperature on a rotating wheel (15 rpm) with an equal volume of anti-human IgM (μ-chain specific)-agarose (Sigma A9935). The absence of IgM in the absorbed serum was confirmed by western blotting with an anti-human IgM monoclonal antibody. IT/PAR+ parasites were grown from ring stage overnight in supplemented RPMI with 10% IgM-depleted serum, and an aliquot (positive control culture) was incubated with 1 mg/ml of human IgM (Calbiochem) for 1 hour at 37° C. The IgM-negative and IgM-positive cultures were then washed and testing for surface reactivity with cross-reactive PfEMP1 antibodies to TM284var1 NTS-DBL1α by flow cytometry as described above.

Selection for IgM-Positive Infected Erythrocytes.

Parasites were selected for IgM-positive infected erythrocytes using M-450 Epoxy Dynabeads (Dynal) coated with mouse anti-human IgM antibodies (Serotec MCA1662) as described [64].

Software.

Flow cytometry data were analysed using FlowJo software (Tree Star Inc.), DNA sequence analysis was done using DNAstar Lasergene (DNAstar Inc.) and graphing and statistical analysis using Prism (GraphPad Software).

Therapeutic mAbs.

Monoclonal antibodies with specificity for epitopes of the PfEMP1 variant, TM284var1 have been produced. These antibodies will be used to investigate possibility of developing a therapeutic monoclonal antibody cocktail to reverse rosetting.

Results

Identification of PfEMP1 Variants Transcribed by Rosetting Parasites

To identify the key surface antigens of rosetting parasites, five *P. falciparum* laboratory strains (three IgM binding, two non-IgM binding) originating from different countries were grown in vitro and selected for the rosetting phenotype. For each strain, isogenic rosette positive (R+) and rosette negative (R−) populations were selected in parallel [20], and their var gene transcription profiles examined by analysis of short PfEMP1 sequence tags [24]. The rosette-specific variant in each strain was identified as the predominant var gene transcribed by the rosetting population (comprising between one third to one half of all the var gene sequences detected) that was absent/rare in the non-rosetting population (an example is shown in Table S1). The full-length sequence of each predominant rosette-specific var gene was obtained from the sequence tag as described in the methods. The rosetting variants were mostly group A (FIG. 1*a*), defined by the presence of a conserved upstream sequence (UpsA) and a characteristic N-terminal domain type (called DBLα1 or "Cys2") that is associated with severe malaria [18,24,26]. The variants from the IgM binding rosetting parasites form a distinct subset that share an unusual PfEMP1 architecture, containing a triplet of domains that occur rarely in PfEMP1 (DBLE and DBLZ) [6]. The binding site for non-immune IgM lies within these DBLϵ/ζ domains [43,44](AG and JAR, unpublished data). The IgM binding domain triplet is linked via at least one other domain (DBLγ) to a typical group A PfEMP1 head-structure [16,18,45](FIG. 1*a*). DBLα domains from group A PfEMP1 variants fall into eight subclasses (DBLα1.1 to DBLα1.8) based on sequence homology [6]. The rosetting variants described previously (ITvar9, Palo Alto varO and PF13_0003) [11,20,21] are all of the DBLα1.6 subclass. The rosette-specific variants identified here are either DBLα1.5 (HB3var6 and Muz12var1), DBLα1.8 (TM284 and ITvar60) or DBLα2 (a non-group A type, TM180var1) [6].

Despite the observed similarities in PfEMP1 architecture, there was considerable sequence diversity amongst the rosette-specific variants from different parasite strains, with the rosette-mediating domain (NTS-DBLα) [11,20,21] showing pair-wise amino acid identities of between 38.9% (ITvar60:TM180var1) and 62.6% (ITvar60:TM284var1) (Table S2). The other extracellular domains from the rosetting variants do not show high levels of amino acid identity apart from the first CIDR domain of TM284var1 and ITvar60 (82.2%) and the first CIDR domain of HB3var6 and Muz12var1 (81.1%; see Tables S2-S7 for pair-wise amino acid identities for all domain types).

Figure 1B:
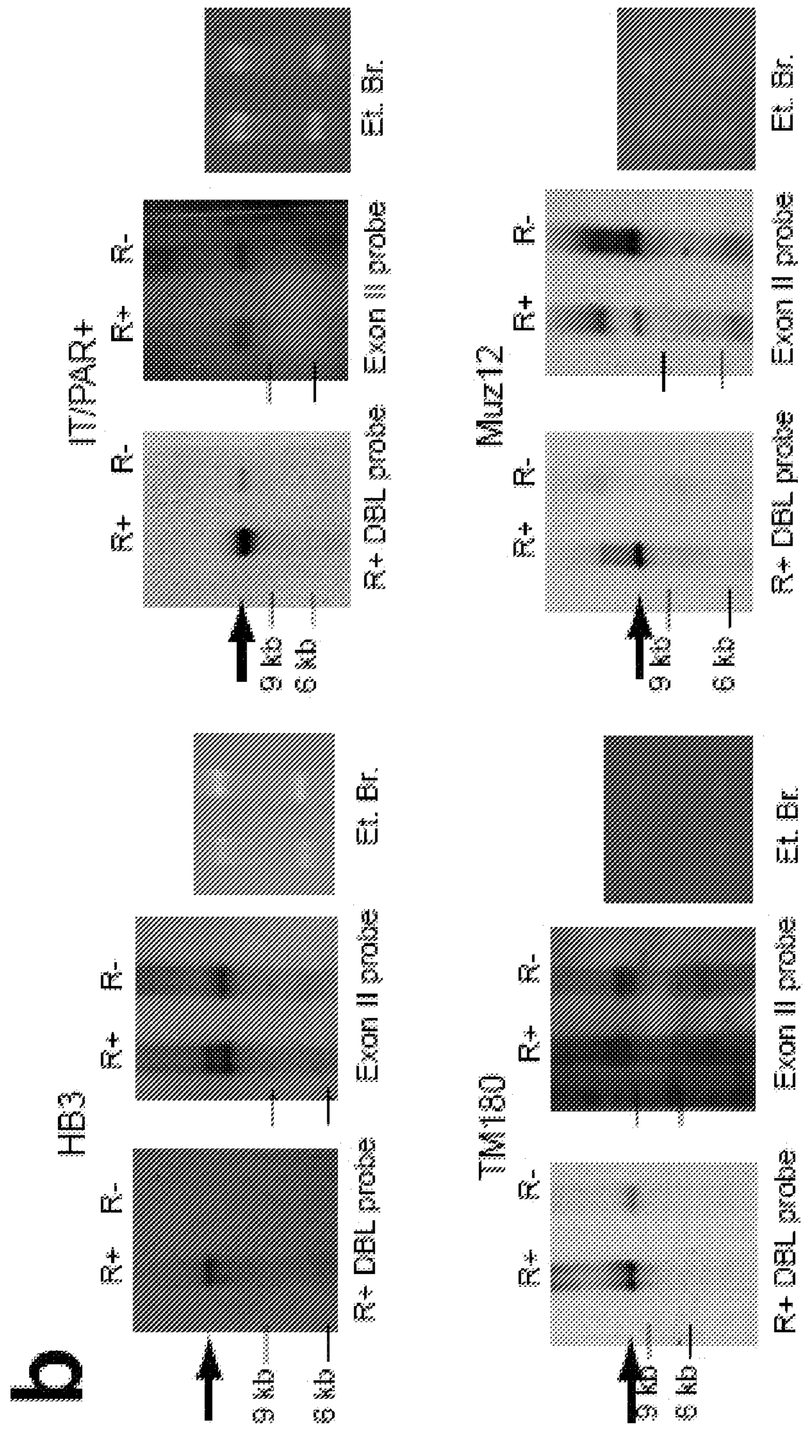

Correct identification of rosette-specific variants was confirmed by Northern blotting (FIG. 1*b*; shown previously for TM284 [44]). For each parasite strain, the rosette-specific PfEMP1 probe detected a transcript in rosetting parasites (arrowed) that was absent/weak in isogenic non-rosetting parasites. The presence of other transcribed var genes in the non-rosetting parasites was shown using an Exon II probe that identifies all var genes (FIG. 1*b*).

Figure 1C:
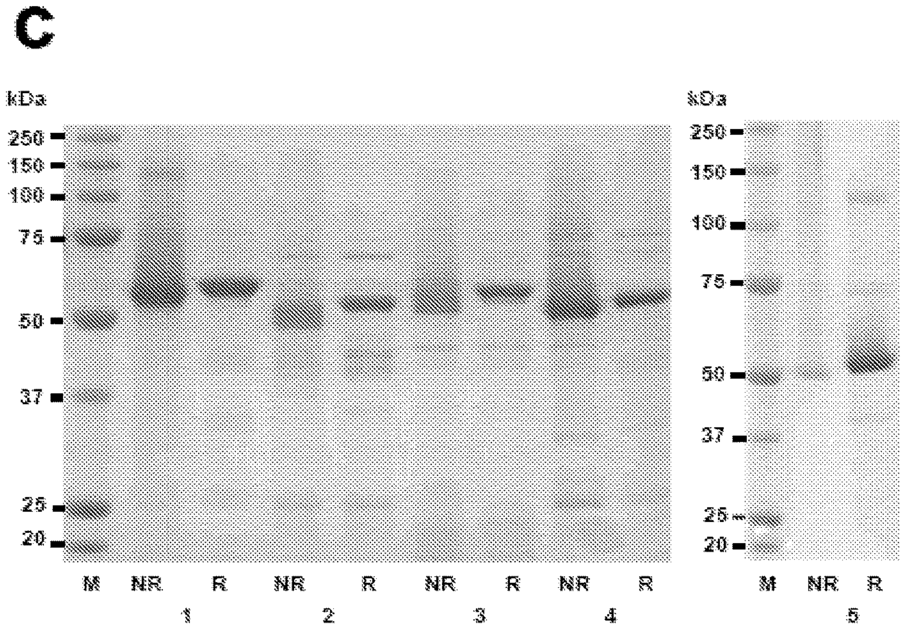

In order to raise antibodies against the rosetting PfEMP1 variants, the N-terminal NTS-DBLα region of each rosette-specific variant was expressed as a recombinant protein in *E. coli [*12], with a shift in mobility of the recombinant proteins upon reduction showing the presence of disulfide bonds in these cysteine-rich proteins (FIG. 1*c*). NTS-DBLα was chosen because it is the domain that binds erythrocytes to bring about rosetting [20,21], and variant-specific antibodies to this region were the most effective in inhibiting rosetting in previous studies [12,21].

Functional Activity and Cross-Reactivity of PfEMP1 Antibodies Against Laboratory-Adapted *P. falciparum* Strains The recombinant proteins were used to immunize rabbits [12], to elicit antibodies to determine whether the rosette-specific PfEMP1 variants from different *P. falciparum* strains share common epitopes. Immunofluorescence assays (IFA) showed that antisera to each of the five variants gave punctate fluorescence that is characteristic of PfEMP1 antibodies over the surface of live infected erythrocytes with the homologous parasite strain (shown for IT/PAR+ parasites with ITvar60 antibodies in FIG. 2*a*). Rabbit pre-immune sera and non-immunised rabbit control sera were negative by IFA. Titration of purified total IgG from each antiserum showed specific surface reactivity against homologous parasites down to low concentrations (end titres of 0.02-1.56 μg/ml of total IgG, FIG. 2*b* and FIG. 2*c*, rectangles in bold).

Figure 2C:
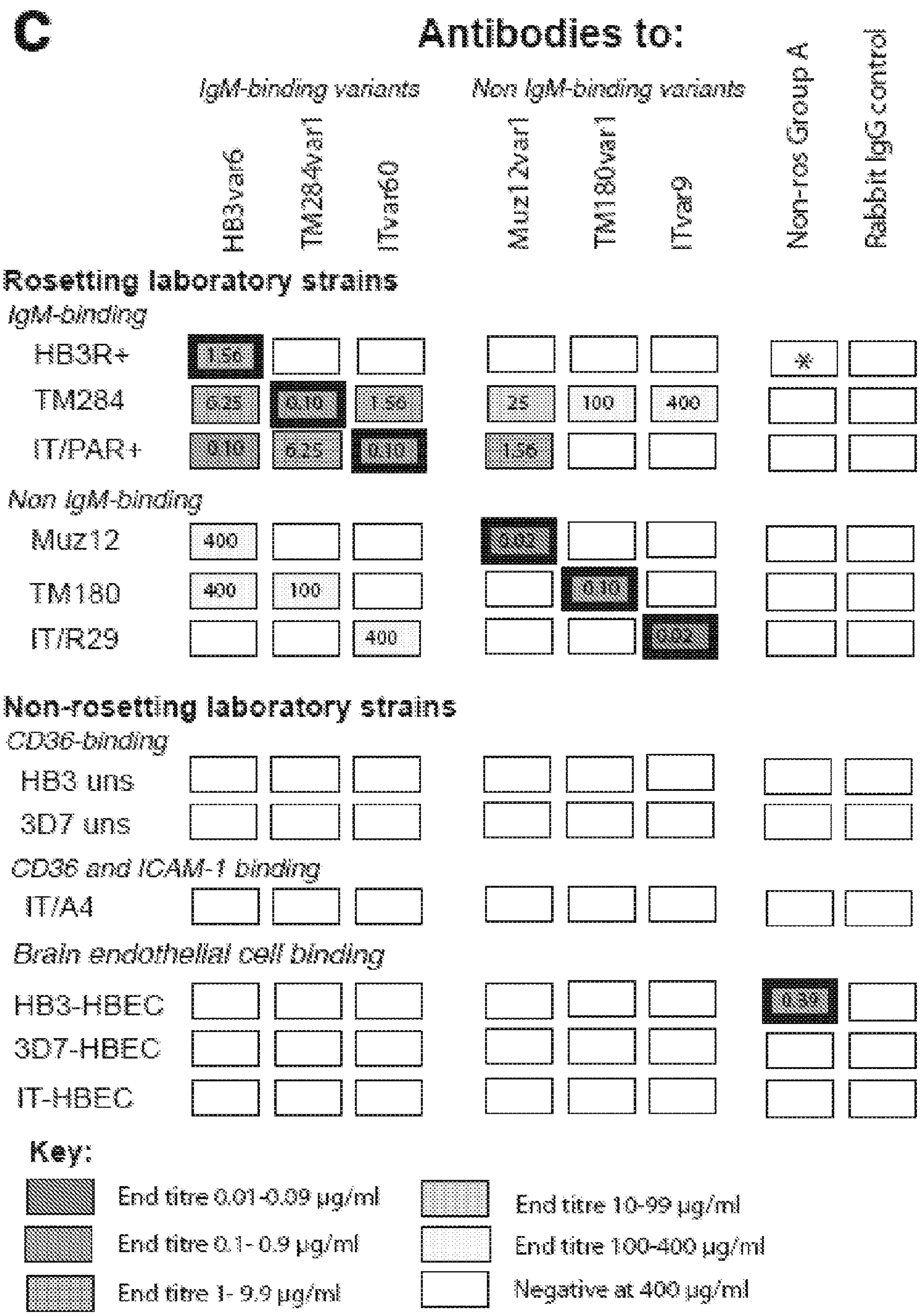

Importantly, the PfEMP1 antibodies also showed surface reactivity with heterologous rosetting strains. This was especially marked between the IgM binding rosetting strains (HB3R+, TM284 and IT/PAR+) and their antibodies (to variants HB3var6, TM284var1 and ITvar60 respectively), with surface reactivity at <10 μg/ml for heterologous antibody:parasite combinations (FIG. 2*c*). The non-IgM binding rosetting strains (Muz12, TM180 and IT/R29) were also recognised by antibodies to IgM binding rosetting variants, although higher concentrations were required (100-400 μg/ml of total IgG, FIG. 2*c*). Although these concentrations are high, they still represent a considerable dilution of whole serum (equivalent to 1/100 to 1/25 dilution) therefore they are potentially achievable in vivo.

The antibodies against rosetting PfEMP1 variants did not recognise parasites selected for other adhesion phenotypes (FIG. 2*c*), including binding to CD36 or ICAM-1 (parasites expressing Group B and C var genes) or binding to brain endothelial cells (parasites expressing an alternative sub-set of group A and B/A var genes). Thus, only parasites with a shared adhesion phenotype share epitopes that are recognised by cross-reactive antibodies to PfEMP1.

Figure 3A:
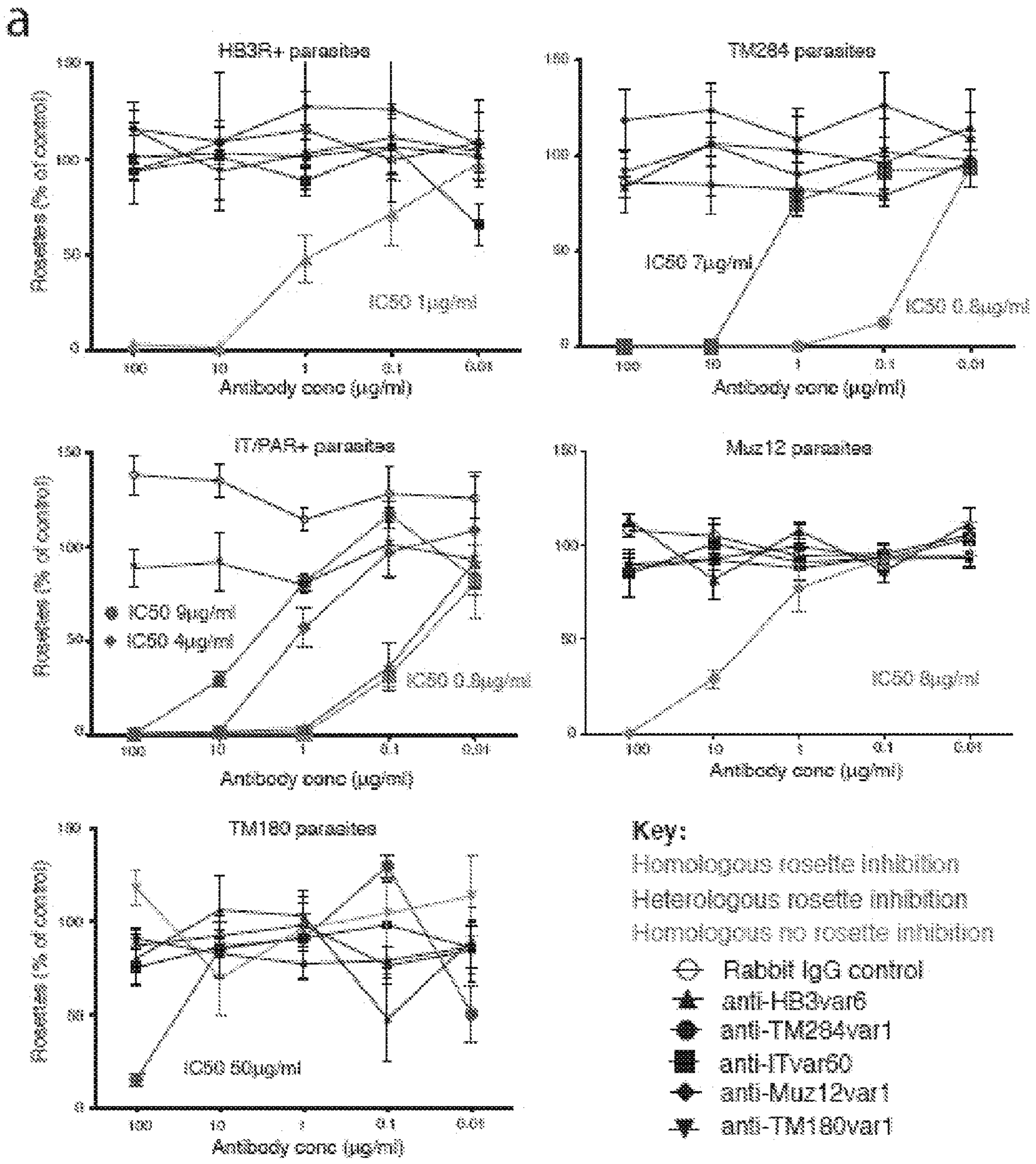
Figure 3B:
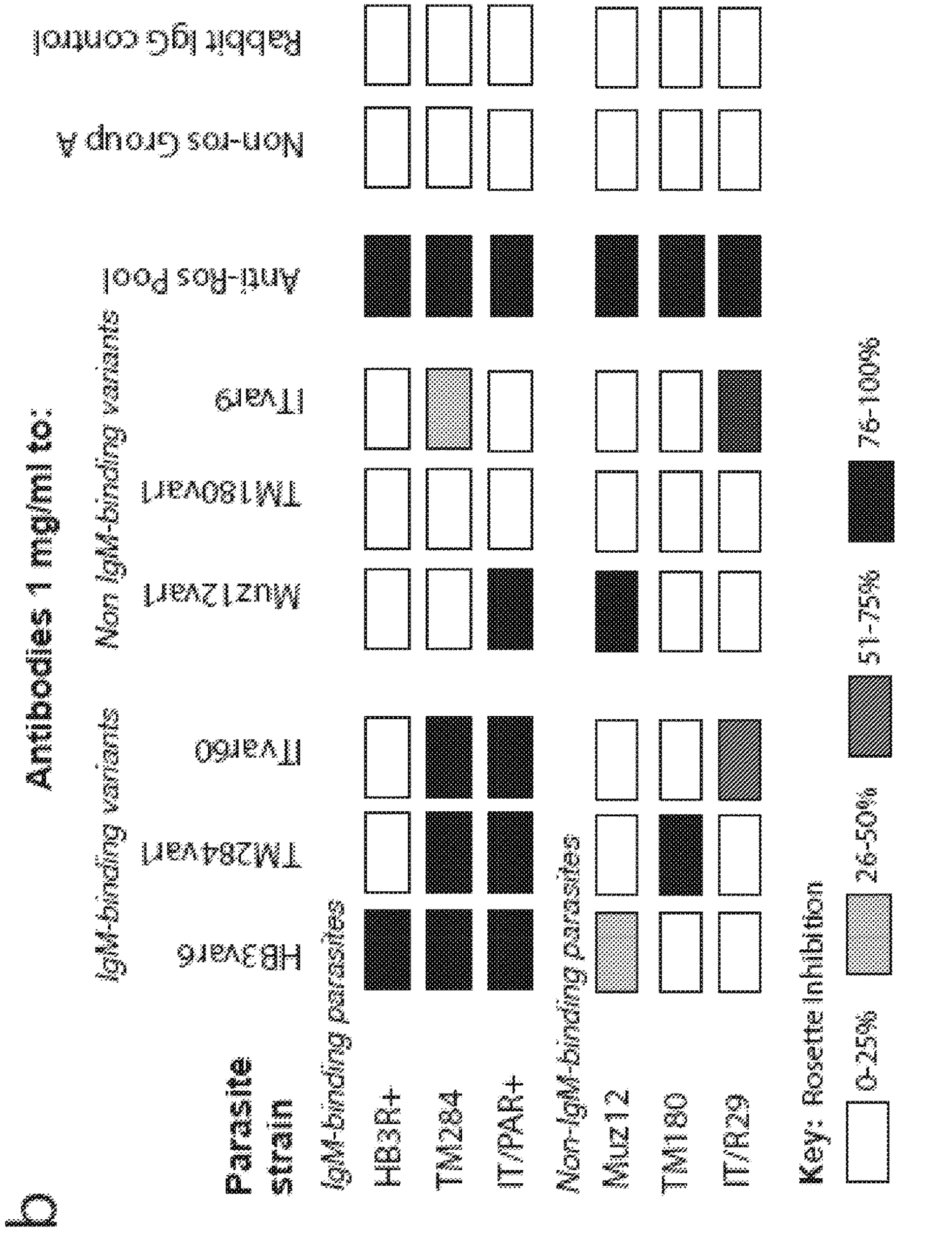

Surface recognition of live infected erythrocytes by antibodies in vivo is likely to lead to parasite clearance via effector mechanisms such as phagocytosis or complement-mediated lysis [13]. Rosette-inhibition may also be desirable in vivo to prevent pathological microvascular obstruction. We therefore examined whether the cross-reactive surface recognition by PfEMP1 antibodies shown in FIG. 2, translated into cross-reactivity in effector functions. The PfEMP1 antibodies showed potent rosette-inhibition against homologous parasite strains with 50% inhibitory concentrations (IC50) for rosetting between 0.8-8 μg/ml of total IgG (FIG. 3*a*, red curves), except for TM180, which was not inhibited (FIG. 3*a*, brown curve) despite good surface reactivity (FIG. 2*c*). Parasite strains TM284, IT/PAR+ and TM180 all showed rosette inhibition by heterologous antibodies (FIG. 3*a*, blue curves). At a higher concentration (1 mg/ml of total IgG) the cross-reactivity in rosette inhibition was even more marked, with all strains being inhibited by antibodies to at least one of the IgM-binding rosetting PfEMP1 variants (FIG. 3*b*).

Figure 3C:
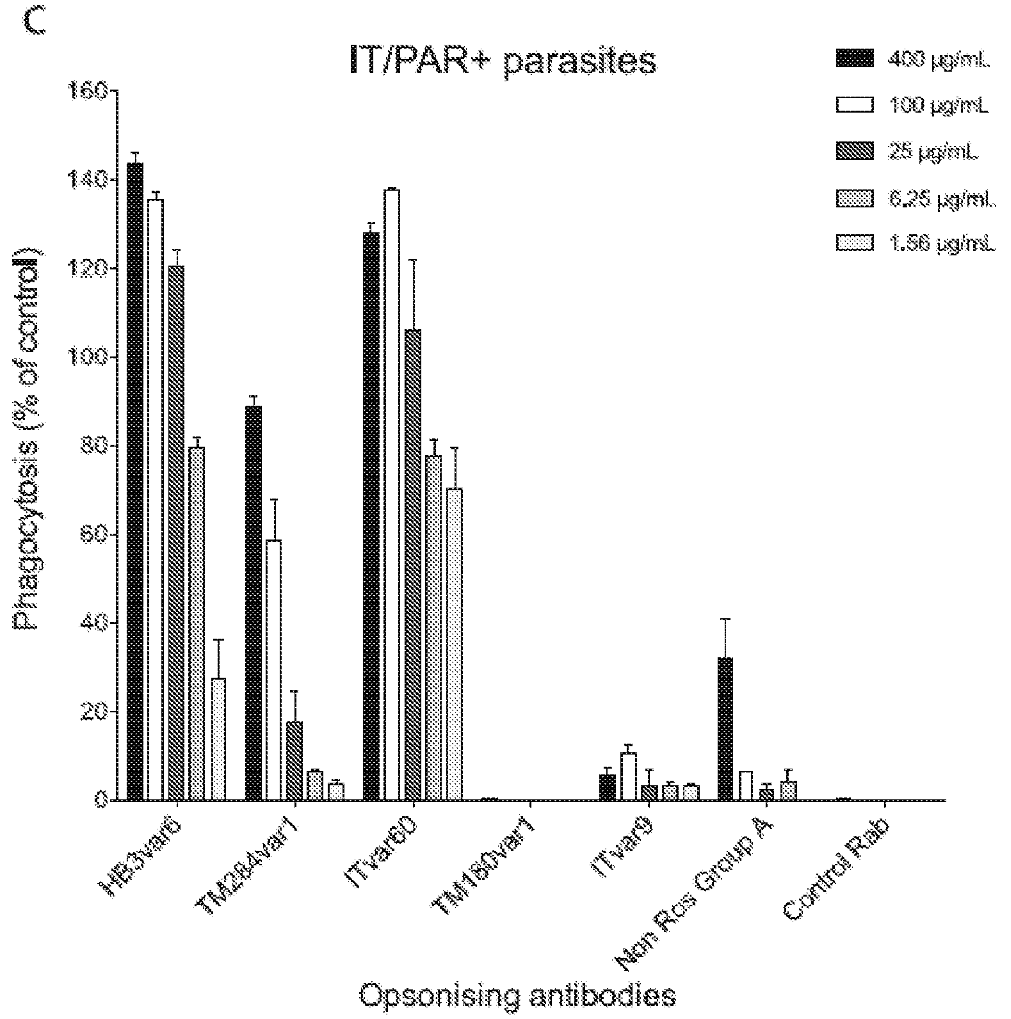

The antibodies to PfEMP1 variants from IgM binding rosetting parasites were also shown to have cross-reactive opsonising effects, by inducing the phagocytosis of homologous and heterologous infected erythrocytes (FIG. 3*c* and FIG. 7*a* and *b*). In contrast, antibodies to PfEMP1 variants from non-IgM binding rosetting parasites only effectively opsonised homologous parasites (FIG. 7*c* and *d*).

Functional Activity and Cross-Reactivity of Anti-PfEMP1 Antibodies Against *P. falciparum* Clinical Isolates Having shown surface recognition and biological effector functions of cross-reactive PfEMP1 antibodies in *P. falciparum* laboratory strains, we explored the geographical extent of the cross-reactivity using fresh clinical isolates from Cameroon, Kenya, Mali and The Gambia. The proportion of rosetting infected erythrocytes in the clinical isolates varies amongst isolates (15-40%), and was not as high as in the laboratory strains that undergo repeated selection for rosetting. The clinical isolates were selected because they contained at least 15% of infected erythrocytes in rosettes and all isolates tested are shown. Ten fresh clinical isolates were thawed, and all but one were found to be of the IgM binding rosetting phenotype (tested by detection of IgM on the surface of infected erythrocytes by IFA). This is consistent with previous data showing a strong positive correlation between rosette frequency and IgM binding in clinical isolates from Kenyan children [38].

Figure 4A:
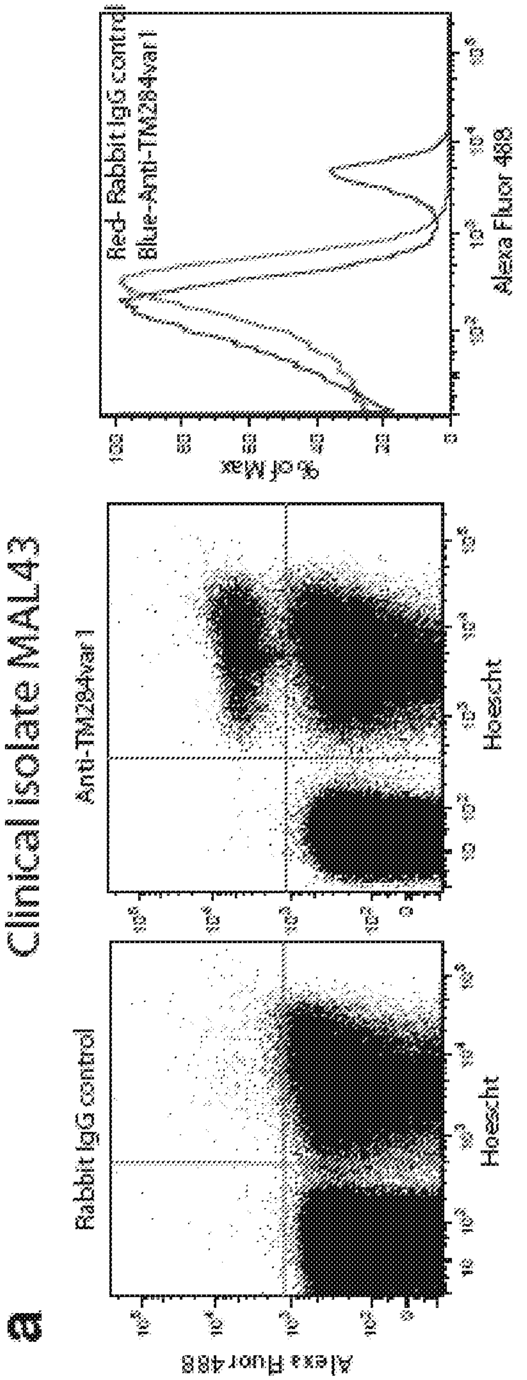
Figure 4B:
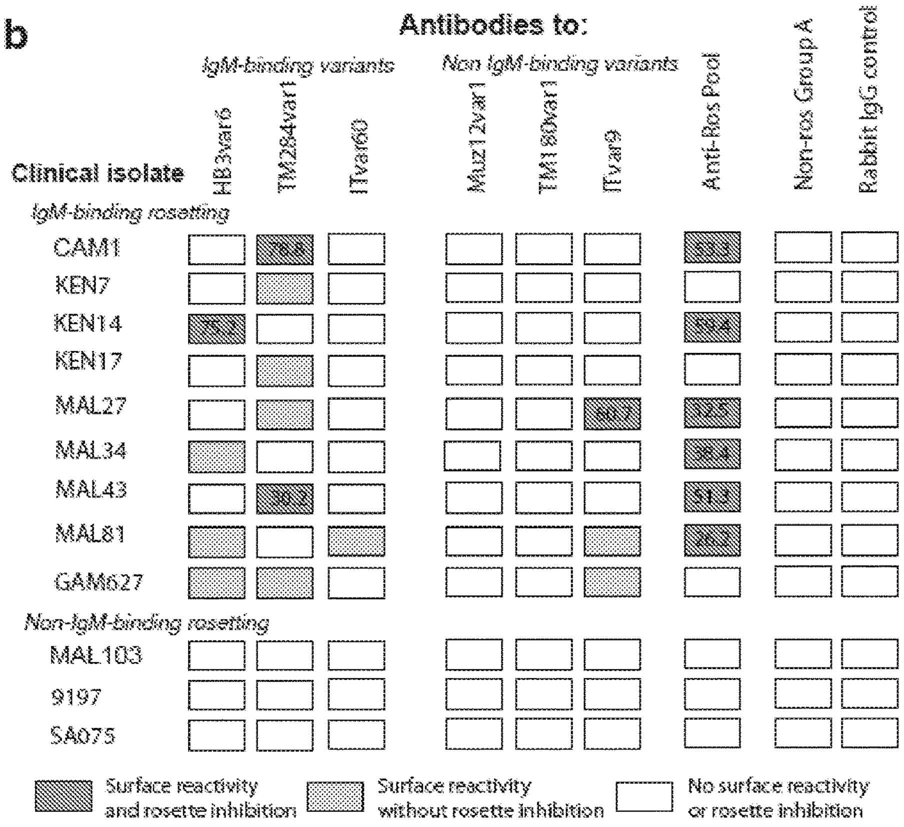
Figure 4C:
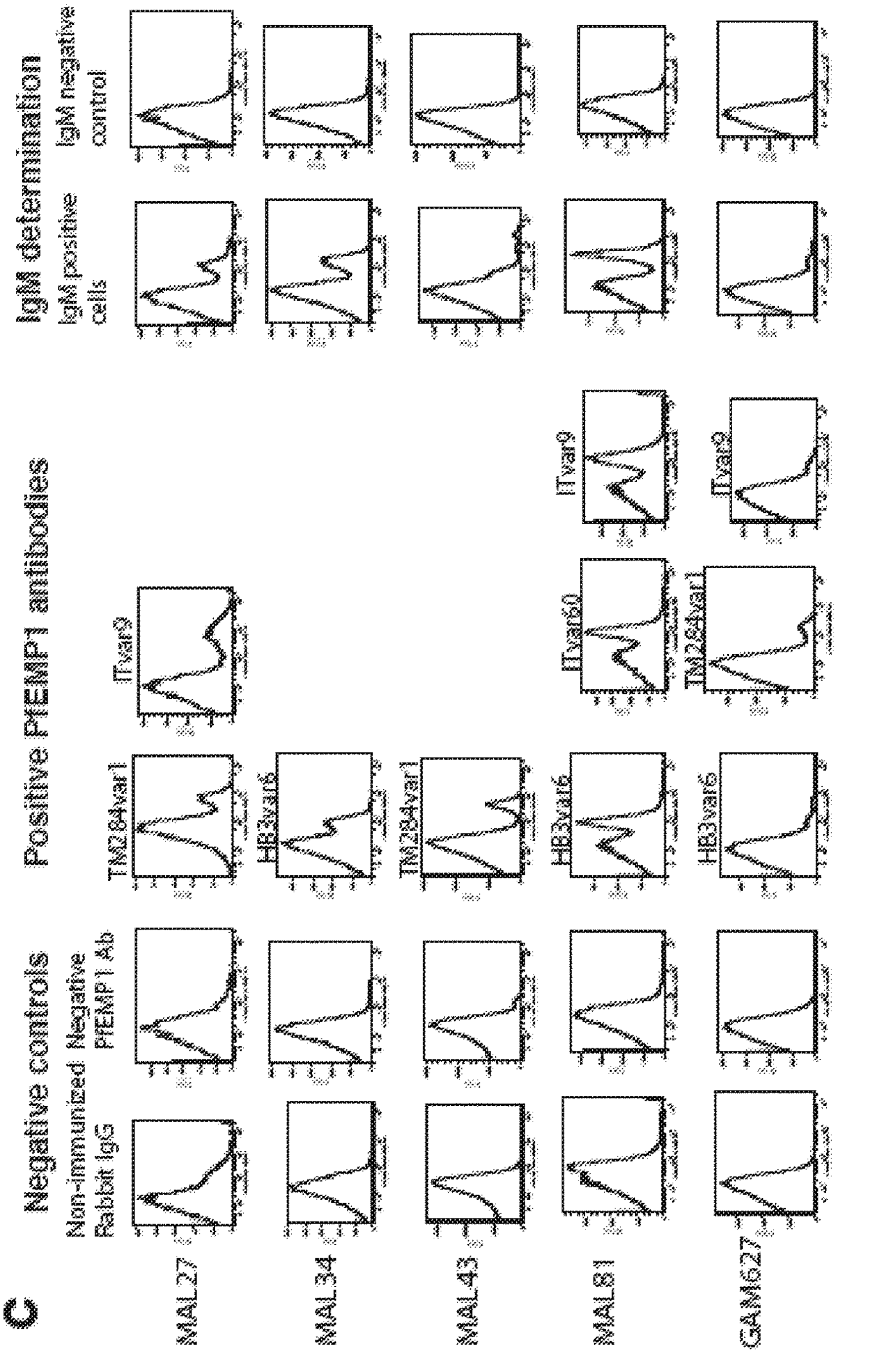

Surface reactivity with the panel of PfEMP1 antibodies was detected by punctate fluorescence of live infected erythrocytes by IFA (similar to FIG. 2*a*) and by flow cytometry (FIG. 4*a*). Remarkably, antibodies to two PfEMP1 variants (HB3var6 and TM284var1) were sufficient to provide surface reactivity against all of the geographically diverse IgM binding rosetting isolates (FIGS. 4*b* and *c*). The proportions of anti-PfEMP1 positive and IgM positive cells were closely matched in each isolate (Pearson correlation r=0.934, P=0.006; FIG. 4*c*, compare IgM positive cells with the positive PfEMP1 antibody stained cells). Rosette inhibition was also observed in four isolates, increasing to six isolates when a pool of anti-PfEMP1 antibodies was used (FIG. 4*b*). The non-IgM binding clinical isolate (MAL103) and two recently culture-adapted rosette-selected non-IgM binding Kenyan strains (9197 and SA075) were not recognized by the PfEMP1 antibodies (FIG. 4*b*). Therefore, in clinical isolates the cross-reactivity of PfEMP1 antibodies was only seen amongst parasites showing the IgM binding rosetting phenotype.

Figure 5B:
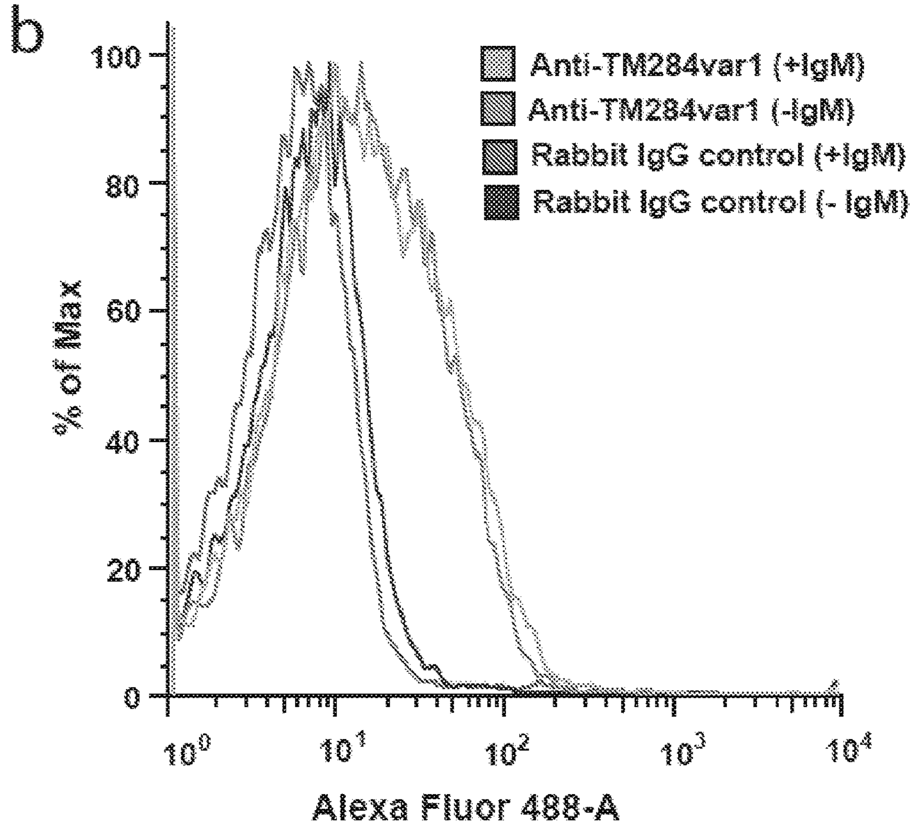

We considered the possibility that the above results could be explained by PfEMP1 antibodies cross-reacting with human IgM (which is bound to the surface of the infected erythrocytes from the culture medium) rather than due to shared epitopes within PfEMP1 itself. However, the PfEMP1 antibodies did not recognise human IgM in an ELISA (FIG. 5*a*), and the surface reactivity with heterologous parasite strains was maintained when the parasites were grown in the absence of IgM (for example, IT/PAR+ parasites show surface reactivity with TM284var1 antibodies in the absence of IgM as shown in FIG. 5*b*).

Figure 6B:
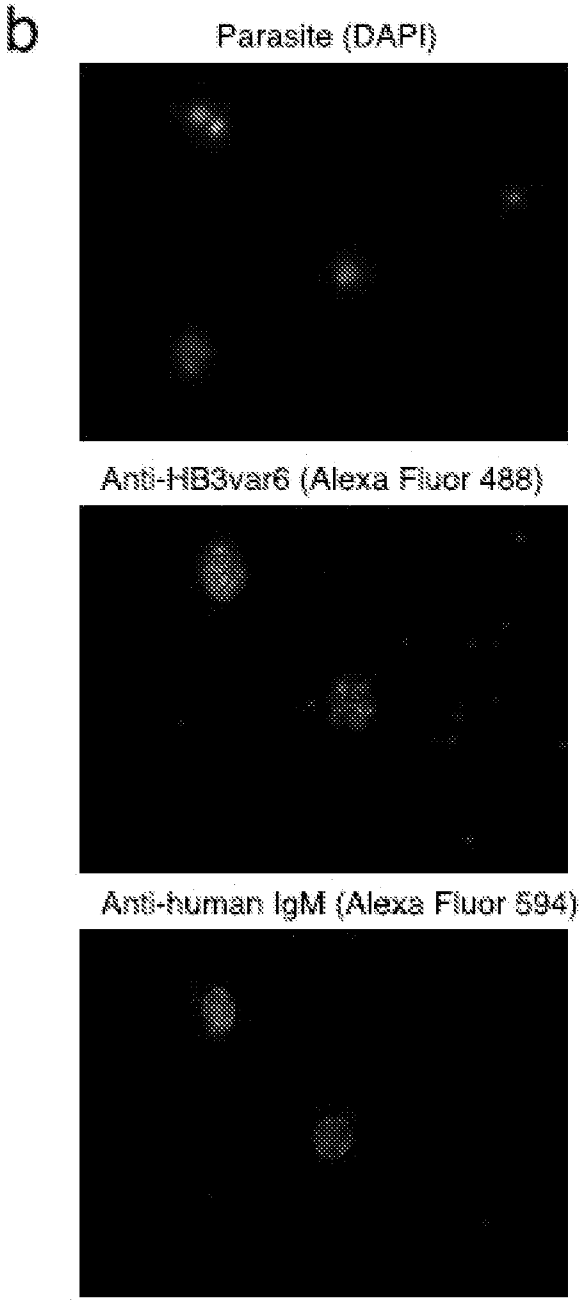

The presence of IgM binding rosetting variants in diverse parasite isolates was shown further by taking the two recently culture-adapted Kenyan strains 9197 and SA075 which showed non-IgM binding rosetting (FIG. 4*b*), and selecting them for IgM binding using magnetic beads coated with anti-human IgM antibodies. After three rounds of selection, a population of IgM binding rosetting parasites was obtained, which were recognised by antibodies to HB3var6 (9197 IgM-selected, FIG. 6) or by antibodies to TM284var1 (SA075 IgM-selected, data not shown). Dual staining showed that the same subpopulation of infected erythrocytes bound both IgM and HB3var6 antibodies (FIG. 6*b*).

Discussion

In this work the PfEMP1 variants expressed by *P. falciparum* strains representing two major rosetting phenotypes were examined. IgM binding rosetting parasites were found to express a distinct subset of group A PfEMP1 variants characterised by a DBLα1.5 or DBLα1.8 N-terminal domain and a triplet of DBLε/DBLζ domains adjacent to the transmembrane region. Antibodies raised against the N-terminal region of the IgM binding rosetting variants were potent inhibitors of rosetting when tested against homologous parasites (IC50 for rosette inhibition ≤1 μg/ml of total IgG, FIG. 3*a*), confirming the role of these variants in rosette formation. Furthermore, the antibodies against IgM binding rosetting variants were cross-reactive, showing surface recognition of live infected erythrocytes and rosette inhibition with globally diverse parasite isolates sharing the same adhesion phenotype. In contrast, antibodies raised against group A PfEMP1 variants from non-IgM binding rosetting parasites were variant specific, as described previously [11, 20,21]. These data indicate that not all group A PfEMP1 variants induce cross-reactive antibodies, and that certain subsets of group A variants may be particularly cross-reactive. To our knowledge, this is the first report to describe the successful induction of broadly cross-reactive surface-recognising antibodies to PfEMP1 variants implicated in severe childhood malaria. Broadly cross-reactive antibodies against var2CSA implicated in malaria in pregnancy have been described [47,48], however, var2CSA is a unique case of a strain-transcendent var gene with much more limited sequence diversity than that seen in group A PfEMP1 variants that are non-strain-transcendent [49].

Three PfEMP1 variants from IgM binding rosetting parasites were characterised in detail here: HB3var6 from strain HB3, TM284var1 from strain TM284 and ITvar60 from strain IT/PAR+. ITvar60 has previously been linked to rosetting in two other IT/FCR3-derived parasite lines [50, 51], and is confirmed here as an IgM binding rosetting variant. As expected for PfEMP1, the three distinct IgM binding rosetting variants show considerable diversity in amino acid sequence (Tables S2-S7), despite their similarities in PfEMP1 architecture (FIG. 1). Other variants with the same "rosetting IgM" type of domain architecture can be seen in the genome of a recently sequenced *P. falciparum* strain IGH (IGHvar12, IGHvar 22 and IGHvar 24 [6]). Furthermore, an ITvar60-like variant occurs in the sequenced *P. falciparum* strain D10 from Papua New Guinea (http://www.broadinstitute.org). Taken together, these data suggest that variants with the rosetting IgM-type of PfEMP1 architecture occur commonly in geographically diverse *P. falciparum* isolates. One limitation of the current study was that there was insufficient material from the clinical isolates to identify and sequence the PfEMP1 variants transcribed by the rosetting parasites to allow comparison with the laboratory strains. The selection of IgM binding rosetting parasites from two culture-adapted clinical isolates (FIG. 6) will allow us to examine their var genes in further detail. The correct identification of rosette-specific variants (Table S1) and sequencing of full-length var genes remains a laborious and time-consuming process for isolates that do not have a full genome sequence available. However, wider studies of PfEMP1 architecture and sequence from rosetting clinical isolates will be essential for a full understanding of how the antibody cross-reactivity documented here relates to sequence diversity and PfEMP1 type.

Previous studies of non-IgM binding rosetting parasites identified the parasite rosetting ligands as PfEMP1 variants (ITvar9, Palo Alto varO and PF13_0003) that show one out of eight possible subclasses of DBLα domain, DBLα1.6 [11,20,21]. In contrast, the group A rosetting variants described here have either DBLα1.5 (HB3var6 and Muz12var1) or DBLα1.8 (ITvar60 and TM284var1). The clinical isolates showed surface reactivity with either HB3var6 antibodies (DBLα1.5 type) or TM284var1 antibodies (DBLα1.8), but rarely with both (FIG. 4*b*). These data are suggestive that these two main DBLα1 types may underlie the IgM binding rosetting phenotype in diverse field isolates, although clearly further sequence information is needed to substantiate this idea. TM180var1 differs from the other rosette-associated variants as it has an UpsB sequence and a DBLα2 subtype, and this may represent a distinct type of rosetting phenotype that requires further investigation. Taking together the findings from this study and previously published work, we hypothesize that all group A PfEMP1 variants with DBLα1.5, DBLα1.6 or DBLα1.8 domains may be rosette-mediating variants. If true, this would indicate that a substantial proportion (approximately one third to one half) of the group A var gene repertoire from every *P. falciparum* isolate may encode rosetting variants [6]. This would represent a substantial investment by the parasite in an adhesion phenotype whose benefit to parasite fitness remains unknown.

Rask et al [6] recently presented an alternative way of assessing PfEMP1 types by looking at "domain cassettes" (sets of PfEMP1 domains that usually occur together). They identified seven domain cassettes commonly found in group A var genes [6]. Our data suggest that two of these domain cassettes are linked to the rosetting phenotype: domain cassette 16, characterised by DBLα1.5/6 linked to CIDRδ delta as seen in HB3var6, and domain cassette 11 characterised by DBLα1.8 linked to CIDRβ2 and DBLγ7 as seen in ITvar60 and TM284var1. Although much more work is needed to generalize these results and determine whether particular DBLα subclasses and domain cassettes are always linked to rosetting, our data represent an important step in relating PfEMP1 sequence to parasite adhesion phenotype.

One unexplained feature of the current data is why the IgM binding rosetting variants show cross-reactivity in recognition by PfEMP1 antibodies indicating shared epitopes, whereas the non-IgM binding variants do not, despite apparently equivalent amino acid diversity in the two sets of variants. We considered the possibility that the IgM itself could be the cause of the cross-reactivity, however we showed that the PfEMP1 antibodies did not recognise human IgM in an ELISA, and the PfEMP1 antibodies still recognized heterologous strains when the parasites were grown in the absence of human IgM (FIG. 5). It may be that a small sequence motif such as one of the homology blocks described by Rask et al [6] present only in the IgM binding variants explains the cross-reactivity. Additional examples of IgM binding rosetting variants will be needed to investigate this possibility. Alternatively, it is possible that the binding of IgM to PfEMP1 affects its tertiary or quaternary structure, making it more accessible to antibodies directed against the N-terminus of the molecule. However, recent data suggest that IgM-binding makes PfEMP1 less accessible to specific antibodies [41].

Previous work on PfEMP1 suggests that antibody responses are predominantly variant-specific [10,11,12] with little cross-reactivity between domains [52]. However, other reports suggest that cross-reactive antibodies can occur [53,54,55] and could play a role in structuring PfEMP1 expression during antigenic variation [56]. Whether the gradual acquisition of immunity to clinical malaria is linked to acquisition of a broad repertoire of antibodies to numerous distinct variant types, or due to development of cross-reactive responses remains unresolved. In the case of life-threatening malaria in particular, the role of antibodies to PfEMP1 is unclear. It is known that children become immune to severe malaria after a small number of infections [13,57], and that severe malaria is associated with the acquisition of antibodies to commonly recognised variants [14,15,58]. Current thinking suggests that severe malaria is caused by parasites expressing an antigenically-restricted subset of variant surface antigens [2], probably encoded by Group A var genes [26,27]. Such an "antigenically-restricted" subset of parasites would be expected to have variant surface antigens (probably PfEMP1) showing conserved sequence and/or conserved epitopes that would be recognised by antibodies that show surface reactivity with diverse parasite strains. The findings reported here of a subset of variants with shared epitopes underlying a virulence-associated phenotype may represent the first example of such an "antigenically-restricted" subset of parasites.

In summary, these data show that antibodies raised against a subset of Group A PfEMP1 variants from IgM binding rosetting laboratory strains are broadly cross-reactive against global parasite isolates that share the same adhesion phenotype. This discovery of shared epitopes amongst *P. falciparum* isolates with a shared virulence-associated phenotype may underlie the epidemiological observations that children acquire immunity to life-threatening malaria after a small number of infections [13,57]. Most importantly, the ability to elicit broadly cross-reactive antibodies by immunizing with key PfEMP1 variants underlying a virulence phenotype, suggests that designing interventions to prevent severe malaria is a realistic goal.

EXAMPLE 2

The data presented in Example 1 is focussed on antibodies to the N-terminal region (NTS-DBL1a) from the IgM-binding rosetting PfEMP1 variants. The experiments presented in Example 2, investigate whether antibodies to other DBL domains from these PfEMP1 variants would also show cross-reactivity. This would not be predicted from examination of the amino acid similarities between the domains (which are low, mostly between 20-40% amino acid identity).

Materials & Methods

Recombinant proteins were made in *E. coli* and antibodies generated in rabbits as described in the main manuscript. Surface reactivity assessed by flow cytometry, rosette inhibition and phagocytosis induction were as described in Example 1.

Results:

Antibodies were raised to all DBL domains from the ITvar60 variant (FIG. 1A and FIG. 8 below regions shown in red) and also to DBL4ϵ and DBL5e from the HB3var6 variant (FIG. 1A).

Tests of ITvar60 Antibodies Against the Homologous Parasite Strain (IT/PAR+)

The ITvar60 antibodies were tested for surface reactivity against live infected erythrocytes of the homologous parasite strain (IT/PAR+). All antibodies showed punctate fluorescence typical of PfEMP1, down to low concentrations (see Table 1) except the antibody to DBL3ζ which gave surface reactivity only at 100 μg/ml. The antibodies to other domains of ITvar60 inhibited rosetting, although none was as effective as the NTS-DBL1α antibody (see FIG. 10 and Table 1).

The ITvar60 antibodies were also tested for their ability to induce phagocytosis of infected erythrocytes (a function likely to be of importance in vivo). The antibodies to DBL2γ of ITvar60 were able to opsonize infected erythrocytes and induce phagocytosis similar to the NTS-DBL1α antibodies (see FIG. 11 below). Interestingly, despite good surface reactivity and rosette inhibiting capabilities, the antibodies to DBL4ϵ and DBL5ϵ of ITvar60 were unable to opsonize and induce phagocytosis.

TABLE 1

Effectiveness of ITvar60Abs in various assays against IT/PAR+ parasites.

| Antibody | Surface reactivity end titre (μg/ml) | Rosette Inhibition IC50 (μg/ml) | Phagocytosis ~50% of positive control (μg/ml) |
|---|---|---|---|
| Negative control rabbit IgG | Negative at 100 | Negative at 500 | Negative at 400 |
| Anti-NTS-DBL1α | 0.10 | 0.08 | <6.25 |
| Anti-DBL2γ | 0.02 | 0.80 | <6.25 |
| Anti-DBL3ζ | 100 | >100 | >400 |
| Anti-DBL4ϵ | 1.56 | 25 | >400 |
| Anti-DBL5ϵ | 1.56 | 9 | >400 |

Tests of ITvar60 Antibodies Against Other Parasite Strains

The antibodies were tested for surface reactivity with live infected erythrocytes from various rosetting parasite strains. Antibodies to DBL4ϵ of ITvar60 showed cross-reactivity against other IgM binding rosetting strains (see FIG. 11). This recognition was specific to IgM binding rosetting parasites, and was not seen with non-IgM binding rosetting parasites (see FIG. 12).

Discussion

These data show that it is not only the NTS-DBL1α region of PfEMP1 that can induce cross-reactive antibodies, but other domains from IgM-binding rosetting variants show the same effect. This raises the possibility that other domains could be included in a vaccine.

In terms of functional activity, antibodies to the NTS-DBL1α region are clearly the most effective in terms of rosette inhibition and phagocytosis (see Table 1). These activities are likely to be important for functional effectiveness of the antibodies in vivo, therefore these data argue for NTS-DBL1α being the most effective region to include in a vaccine. There are other possible mechanisms of antibody action in vivo (eg complement-mediated lysis of infected erythrocytes) that could be induced by all surface reactive antibodies.

TABLE S1

Identification of a rosette-specific var gene by transcriptional profiling of isogenic rosetting (R+) and non-rosetting (R−) HB3 parasites.

| HB3R+ Rosette frequency 58% | | | HB3R− Rosette frequency 2% | | |
|---|---|---|---|---|---|
| Number of recombinant plasmids | Gene name | Upstream sequence | Number of recombinant plasmids | Gene name | Upstream sequence |
| **14** | **HB3var6** | **A** | 11 | HB3var29 | C |
| 10 | HB3var3 | A | 7 | HB3var27 | B |
| 3 | HB3var31 | C | 5 | HB3var34 | C |
| 2 | HB3var29 | C | 2 | HB3var28 | C |
| 2 | HB3var34 | C | 2 | HB3var51 | C |
| 2 | HB3var27 | B | 2 | HB3var17 | B |
| 1 | HB3var1CSA | A | 1 | HB3var3 | A |
| 1 | HB3var7 | B | **1** | **HB3var6** | **A** |
| 1 | HB3var24 | B | 1 | HB3var11 | B |
| | | | 1 | HB3var14 | B |
| | | | 1 | HB3var19 | B |

To identify the predominant rosette-specific PfEMP1 variant, the var gene transcriptional profiles of isogenic rosetting (R+) and non-rosetting (R−) parasites were compared. RNA was extracted from late ring stage parasites and var gene transcription assessed by reverse-transcriptase (RT)-PCR with degenerate primers to DBL1α (1, 2). The RT-PCR products were cloned by TA cloning (Invitrogen), and 40 colonies picked for mini-prep DNA extraction and sequencing (3). From the HB3R+ line (rosette frequency 58%), 36 recombinant plasmids with var gene inserts were obtained, and the most common sequence (39% of clones) was the group A var gene HB3var6 (shown in bold). This gene was found in only one out of 34 var gene inserts sequenced from the HB3R− line (rosette frequency 2%), whereas several group B and C var genes were detected commonly in the non-rosetting line. Another group A var gene was also common in the HB3R+ line (HB3var3, 10/36 clones) and rare in the HB3R− line (1/34 clones). A second independent selection starting from a different cryostabilate of HB3 parasites showed HB3var6 in 5/16 clones from R+ parasites and 0/15 clones from R− parasites, whereas HB3var3 was not detected in either R+ or R− populations. These data show that the predominant var gene transcribed in HB3 rosetting parasites is HB3var6. The same procedure was followed for other *P. falciparum* rosetting strains, with at least two independent selections and RT-PCRs indicating a predominant var gene in each case.

REFERENCES FOR TABLE S1

1. Taylor H M, Kyes S A, Harris D, Kriek N, & Newbold C I (2000) A study of var gene transcription in vitro using universal var gene primers. Mol Biochem Parasitol 105: 13-23.
2. Bull P C, et al. (2005) *Plasmodium falciparum* Variant Surface Antigen Expression Patterns during Malaria. PLoS Pathog 1:e26.
3. Kyriacou H M, et al. (2006) Differential var gene transcription in *Plasmodium falciparum* isolates from patients with cerebral malaria compared to hyperparasitaemia. Mol Biochem Parasitol 150:211-218.

TABLE S2

Pair-wise amino acid identities for NTS-DBLα, CIDR1 and DBLγ from rosetting PfEMP1 variants[a]

| | HB3 var6 | TM284 var1 | IT var60 | Muz12 var1 | TM180 var1 | IT var9 | Palo AltoVarO | 3D7 PF13_0003 |
|---|---|---|---|---|---|---|---|---|
| Pair-wise amino acid identities for NTS-DBLα | | | | | | | | |
| HB3var6 | 100 | **50.8**[b] | **51.3** | 61.0 | 41.8 | 46.7 | 47.3 | 49.1 |
| TM284var1 | | 100 | **62.6** | 47.0 | 41.4 | 58.7 | 54.1 | 47.5 |
| ITvar60 | | | 100 | 43.6 | 38.9 | 53.8 | 55.3 | 52.5 |
| Muz12var1 | | | | 100 | 43.0 | 44.0 | 47.3 | 49.0 |
| TM180var1 | | | | | 100 | 40.8 | 42.6 | 39.3 |
| ITvar9 | | | | | | 100 | 61.6 | 53.9 |
| PA varO | | | | | | | 100 | 59.6 |
| 3D7 PF13 | | | | | | | | 100 |
| Pair-wise amino acid identities for CIDR1 | | | | | | | | |
| HB3var6 | 100 | **45.1** | **48.6** | 81.1 | 24.9 | 34.4 | 40.4 | 60.7 |
| TM284var1 | | 100 | **82.2** | 44.6 | 23.2 | 37.2 | 37.9 | 45.6 |
| ITvar60 | | | 100 | 46.7 | 25.3 | 40.0 | 38.6 | 48.4 |
| Muz12var1 | | | | 100 | 24.6 | 35.1 | 37.9 | 57.2 |
| TM180var1 | | | | | 100 | 21.4 | 20.7 | 24.6 |
| ITvar9 | | | | | | 100 | 35.8 | 35.4 |
| PA varO | | | | | | | 100 | 33.7 |
| 3D7 PF13 | | | | | | | | 100 |
| Pair-wise amino acid identities for DBLγ | | | | | | | | |
| HB3var6 | 100 | **38.3** | **38.1** | 38.9 | 46.6 | 34.1 | 40.9 | 49.4 |
| TM284var1 | | 100 | **56.5** | 38.3 | 36.3 | 29.3 | 40.1 | 37.8 |
| ITvar60 | | | 100 | 38.8 | 34.9 | 27.9 | 41.0 | 34.5 |
| Muz12var1 | | | | 100 | 45.4 | 31.1 | 43.8 | 40.6 |
| TM180var1 | | | | | 100 | 28.8 | 49.7 | 35.3 |
| ITvar9 | | | | | | 100 | 29.9 | 33.3 |
| PA varO | | | | | | | 100 | 37.3 |
| 3D7 PF13 | | | | | | | | 100 |

[a]Rosetting variants described in this work plus ITvar9 [1], Palo Alto Var O [2] and PF13_0003 [3].

[b]Pair-wise amino acid identities between the IgM-binding rosetting strains shown in bold References for Table S2

1. Rowe J A, Moulds J M, Newbold C I, Miller L H (1997) *P. falciparum* rosetting mediated by a parasite-variant erythrocyte membrane protein and complement-receptor 1. Nature 388: 292-295.
2. Vigan-Womas I, Guillotte M, Le Scanf C, Igonet S, Petres S, et al. (2008) An in vivo and in vitro model of *Plasmodium falciparum* rosetting and autoagglutination mediated by varO, a group A var gene encoding a frequent serotype. Infect Immun 76: 5565-5580.
3. Vigan-Womas I, Guillotte M, Juillerat A, Vallieres C, Lewit-Bentley A, et al. (2011) Allelic diversity of the *Plasmodium falciparum* erythrocyte membrane protein 1 entails variant-specific red cell surface epitopes. PLoS One 6: e16544.

TABLE S3

Pair-wise amino acid identities for DBLε from rosetting PfEMP1 variants

| | HB3 var6d3[a] | HB3 var6d6 | TM284 var1d3 | TM284 var1d5 | ITvar 60 d4 | ITvar 60 d5 | ITvar9 d3 | Palo Alto VarO d5 |
|---|---|---|---|---|---|---|---|---|
| HB3var6 d4 | 100 | **28.6** | **43.5** | 23.2 | 23.7 | 22.0 | 24.5 | 27.3 |
| HB3var6 d6 | | 100 | **30.5** | 29.9 | 30.5 | 28.6 | 38.8 | 38.5 |
| TM284var1 d3 | | | 100 | 25.3 | 22.7 | 26.1 | 26.3 | 28.6 |
| TM284var1 d5 | | | | 100 | 23.7 | 41.7 | 28.9 | 32.1 |
| ITvar60 d4 | | | | | 100 | 24.3 | 32.1 | 29.6 |
| ITvar60 d5 | | | | | | 100 | 27.6 | 31.5 |
| ITvar9 d3 | | | | | | | 100 | 30.9 |
| PA varO d5 | | | | | | | | 100 |

[a]d3: 3rd DBL domain from the N-terminus

TABLE S4

Pair-wise amino acid identities for DBLζ from rosetting PfEMP1 variants

| | HB3var6 | TM284var1 | ITvar60 | Palo Alto VarO |
|---|---|---|---|---|
| HB3var6 | 100 | **42.7** | **37.1** | 36.1 |
| TM284var1 | | 100 | **35.6** | 35.0 |
| ITvar60 | | | 100 | 36.8 |
| PA varO | | | | 100 |

TABLE S5

Pair-wise amino acid identities for DBLβ from rosetting PfEMP1 variants

| | Muz12var1 | TM180var1 | Palo Alto VarO | 3D7 PF13_0003 |
|---|---|---|---|---|
| Muz12var1 | 100 | 46.8 | 46.9 | 46.4 |
| TM180var1 | | 100 | 49.3 | 49.2 |

TABLE S5-continued

| Pair-wise amino acid identities for DBLβ from rosetting PfEMP1 variants | | | | |
|---|---|---|---|---|
| | Muz12var1 | TM180var1 | Palo Alto VarO | 3D7 PF13_0003 |
| PA VarO | | | 100 | 46.9 |
| 3D7 PF13 | | | | 100 |

TABLE S6

| Pair-wise amino acid identities for DBLδ from rosetting PfEMP1 variants | | | | | |
|---|---|---|---|---|---|
| | HB3var6 | Muz12var1 | TM180var1 | IT var9 | 3D7 PF13_0003 |
| HB3var6 | 100 | 42.9 | 37.0 | 36.4 | 48.1 |
| Muz12var1 | | 100 | 38.1 | 40.7 | 46.5 |
| TM180var1 | | | 100 | 47.5 | 37.9 |
| ITvar9 | | | | 100 | 37.6 |
| 3D7 PF13 | | | | | 100 |

TABLE S7

| Pair-wise amino acid identities for CIDR2 from rosetting PfEMP1 variants | | | | | | |
|---|---|---|---|---|---|---|
| | HB3var6 | Muz12var1 | TM180var1 | ITvar9 | Palo Alto VarO | 3D7 PF13 |
| HB3var6 | 100 | 28.1 | 30.9 | 26.7 | 53.0 | 32.3 |
| Muz12var1 | | 100 | 45.3 | 50.2 | 33.3 | 41.8 |
| TM180var1 | | | 100 | 37.9 | 34.4 | 48.1 |
| ITvar9 | | | | 100 | 29.8 | 36.8 |
| PA varO | | | | | 100 | 35.1 |
| 3D7 PF13 | | | | | | 100 |

EXAMPLE 3

Parasites Expressing ITvar60 are Specifically Recognized by Antibodies in Plasma from Children Recovering from Severe (Cerebral) Malaria Materials and Methods Plasma Samples Clinical plasma samples from 10 Kenyan cerebral malaria cases and 10 Kenyan non-severe controls (matched by age and date of admission) were collected at acute and convalescent stages. The acute sample (taken on hospital admission) reflects antibodies generated during prior malaria infections (i.e. this is the "baseline" sample); the convalescent sample (taken one month after admission) reflects antibodies generated to the parasites causing the recent clinical infection that resulted in hospitalization of the child.

Flow Cytometry

Recognition of surface antigens of live *P. falciparum* infected erythrocytes was tested by flow cytometry. Parasite strains tested were: IT/PAR+ (which are IgM-positive rosetting parasites that express the ITvar60 variant named in the patent), which we predict SHOULD be recognized by the severe malaria children's convalescent antibodies. IT/R29 and SA075R+, which are IgM-negative rosetting parasites that we predict should NOT be recognized by the severe malaria children's convalescent antibodies.

As predicted, IT/PAR+ parasites expressing the ITvar60 PfEMP1 variant are specifically recognized by antibodies in the plasma of children recovering from severe (cerebral) malaria (FIG. 13, CM cases). In contrast, age-matched control children with non-severe malaria do not show enhanced recognition of IT/PAR+ parasites in convalescent plasma (FIG. 13, CM-controls).

These data support the hypothesis that ITvar60-like antigens are involved in the pathogenesis of severe malaria, and that antibodies formed against this variant will protect against future episodes of severe malaria (because epidemiological studies show that children rapidly become immune to severe malaria in the first few years of life, and rarely develop severe malaria more than once, although they remain susceptible to mild clinical disease for many years).

In contrast to the above data, IgM-negative rosetting parasites (that we do not expect to be involved in severe malaria) are not specifically recognized by antibodies in the plasma of children recovering from severe malaria (FIGS. 1 and 15).

In a similar fashion, parasites expressing the HB3var6 antigen are specifically recognized by antibodies in the plasma of children recovering from severe malaria (FIGS. 16A & B), whereas, the control SA075var1 expressing parasites is not specifically recognized in this way (FIGS. 17 A & B).

Antibodies

Mice immunized with the TM284var1 antigen made excellent polyclonal antibody responses as shown by ELISA below. The polyclonal antibodies from each mouse also showed strong recognition of the native antigen on the surface of live infected erythrocytes down to at least 1/10,000 dilution, and completely disrupted rosettes at 1/1000 dilution (FIG. 18). In advance of screening for anti-PfEMP1 monoclonal antibodies, fusions have been prepared from mouse spleen.

General References.

1. Rappuoli R, Aderem A (2011) A 2020 vision for vaccines against HIV, tuberculosis and malaria. Nature 473: 463-469.
2. Hviid L (2010) The role of *Plasmodium falciparum* variant surface antigens in protective immunity and vaccine development. Hum Vaccin 6: 84-89.

3. Freitas-Junior L H, Bottius E, Pirrit L A, Deitsch K W, Scheidig C, et al. (2000) Frequent ectopic recombination of virulence factor genes in telomeric chromosome clusters of *P. falciparum*. Nature 407: 1018-1022.
4. Kraemer S M, Kyes S A, Aggarwal G, Springer A L, Nelson S O, et al. (2007) Patterns of gene recombination shape var gene repertoires in *Plasmodium falciparum*: comparisons of geographically diverse isolates. BMC Genomics 8: 45.
5. Barry A E, Leliwa-Sytek A, Tavul L, Imrie H, Migot-Nabias F, et al. (2007) Population genomics of the immune evasion (var) genes of *Plasmodium falciparum*. PLoS Pathog 3: e34.
6. Rask T S, Hansen D A, Theander T G, Gorm Pedersen A, Lavstsen T (2010) *Plasmodium falciparum* erythrocyte membrane protein 1 diversity in seven genomes—divide and conquer. PLoS Comput Biol 6.
7. Kyes S, Horrocks P, Newbold C (2001) Antigenic variation at the infected red cell surface in malaria. Annu Rev Microbiol 55: 673-707.
8. Chen D S, Barry A E, Leliwa-Sytek A, Smith T A, Peterson I, et al. (2011) A molecular epidemiological study of var gene diversity to characterize the reservoir of *Plasmodium falciparum* in humans in Africa. PLoS One 6: e16629.
9. Good M F, Doolan D L (2010) Malaria vaccine design: immunological considerations. Immunity 33: 555-566.
10. Newbold C I, Pinches R, Roberts D J, Marsh K (1992) *Plasmodium falciparum*; the human agglutinating antibody response to the infected red cell surface is predominantly variant specific. Experimental Parasitology 75: 281-292.
11. Vigan-Womas I, Guillotte M, Juillerat A, Vallieres C, Lewit-Bentley A, et al. (2011) Allelic diversity of the *Plasmodium falciparum* erythrocyte membrane protein 1 entails variant-specific red cell surface epitopes. PLoS One 6: e16544.
12. Ghumra A, Khunrae P, Ataide R, Raza A, Rogerson S J, et al. (2011) Immunisation with recombinant PfEMP1 domains elicits functional rosette-inhibiting and phagocytosis-inducing antibodies to *Plasmodium falciparum*. *PLoS One* 6: e16414.
13. Langhorne J, Ndungu F M, Sponaas A M, Marsh K (2008) Immunity to malaria: more questions than answers. Nat Immunol 9: 725-732.
14. Bull P C, Kortok M, Kai O, Ndungu F, Ross A, et al. (2000) *Plasmodium falciparum*-infected erythrocytes: agglutination by diverse Kenyan plasma is associated with severe disease and young host age. J Infect Dis 182: 252-259.
15. Nielsen M A, Staalsoe T, Kurtzhals J A, Goka B Q, Dodoo D, et al. (2002) *Plasmodium falciparum* variant surface antigen expression varies between isolates causing severe and nonsevere malaria and is modified by acquired immunity. J Immunol 168: 3444-3450.
16. Kraemer S M, Smith J D (2006) A family affair: var genes, PfEMP1 binding, and malaria disease. Curr Opin Microbiol 9: 374-380.
17. Rowe J A, Claessens A, Corrigan R A, Arman M (2009) Adhesion of *Plasmodium falciparum*-infected erythrocytes to human cells: molecular mechanisms and therapeutic implications. Expert Rev Mol Med 11: e16.
18. Robinson B A, Welch T L, Smith J D (2003) Widespread functional specialization of *Plasmodium falciparum* erythrocyte membrane protein 1 family members to bind C D36 analysed across a parasite genome. Mol Microbiol 47: 1265-1278.
19. Janes J H, Wang C P, Levin-Edens E, Vigan-Womas I, Guillotte M, et al. (2011) Investigating the Host Binding Signature on the *Plasmodium falciparum* PfEMP1 Protein Family. PLoS Pathog 7: e1002032.
20. Rowe J A, Moulds J M, Newbold C I, Miller L H (1997) *P. falciparum* rosetting mediated by a parasite-variant erythrocyte membrane protein and complement-receptor 1. Nature 388: 292-295.
21. Vigan-Womas I, Guillotte M, Le Scanf C, Igonet S, Petres S, et al. (2008) An in vivo and in vitro model of *Plasmodium falciparum* rosetting and autoagglutination mediated by varO, a group A var gene encoding a frequent serotype. Infect Immun 76: 5565-5580.
22. Udomsangpetch R, Wahlin B, Carlson J, Berzins K, Torii M, et al. (1989) *Plasmodium falciparum*-infected erythrocytes form spontaneous erythrocyte rosettes. Journal of Experimental Medicine 169: 1835-1840.
23. Kirchgatter K, Portillo Hdel A (2002) Association of severe noncerebral *Plasmodium falciparum* malaria in Brazil with expressed PfEMP1 DBL1 alpha sequences lacking cysteine residues. Mol Med 8: 16-23.
24. Kyriacou H M, Stone G N, Challis R J, Raza A, Lyke K E, et al. (2006) Differential var gene transcription in *Plasmodium falciparum* isolates from patients with cerebral malaria compared to hyperparasitaemia. Mol Biochem Parasitol 150: 211-218.
25. Rottmann M, Lavstsen T, Mugasa J P, Kaestli M, Jensen A T, et al. (2006) Differential Expression of var Gene Groups Is Associated with Morbidity Caused by *Plasmodium falciparum* Infection in Tanzanian Children. Infect Immun 74: 3904-3911.
26. Warimwe G M, Keane T M, Fegan G, Musyoki J N, Newton C R, et al. (2009) *Plasmodium falciparum* var gene expression is modified by host immunity. Proc Natl Acad Sci USA 106: 21801-21806.
27. Jensen A T, Magistrado P, Sharp S, Joergensen L, Lavstsen T, et al. (2004) *Plasmodium falciparum* associated with severe childhood malaria preferentially expresses PfEMP1 encoded by group A var genes. J Exp Med 199: 1179-1190.
28. Carlson J, Helmby H, Hill A V, Brewster D, Greenwood B M, et al. (1990) Human cerebral malaria: association with erythrocyte rosetting and lack of anti-rosetting antibodies. Lancet 336: 1457-1460.
29. Treutiger C J, Hedlund I, Helmby H, Carlson J, Jepson A, et al. (1992) Rosette formation in *Plasmodium falciparum* isolates and anti-rosette activity of sera from Gambians with cerebral or uncomplicated malaria. American Journal of Tropical Medicine and Hygiene 46: 503-510.
30. Rowe A, Obeiro J, Newbold C I, Marsh K (1995) *Plasmodium falciparum* rosetting is associated with malaria severity in Kenya. Infect Immun 63: 2323-2326.
31. Rowe J A, Obiero J, Marsh K, Raza A (2002) Positive correlation between rosetting and parasitemia in *Plasmodium falciparum* clinical isolates. Am J Trop Med Hyg 66: 458-460.
32. Doumbo O K, Thera M A, Kone A K, Raza A, Tempest L J, et al. (2009) High levels of *Plasmodium falciparum* rosetting in all clinical forms of severe malaria in African children. Am J Trop Med Hyg 81: 987-993.
33. Le Scanf C, Vigan-Womas I, Contamin H, Guillotte M, Bischoff E, et al. (2008) Rosetting is associated with increased *Plasmodium falciparum* in vivo multiplication rate in the Saimiri sciureus monkey. Microbes Infect 10: 447-451.

34. Kaul D K, Roth EFJ, Nagel R L, Howard R I, Handunnetti S M (1991) Rosetting of *Plasmodium falciparum*-infected red blood cells with uninfected red blood cells enhances microvascular obstruction under flow conditions. Blood 78: 812-819.

35. Cockburn I A, Mackinnon M J, O'Donnell A, Allen S J, Moulds J M, et al. (2004) A human complement receptor 1 polymorphism that reduces *Plasmodium falciparum* rosetting confers protection against severe malaria. Proc Natl Acad Sci USA 101: 272-277.

36. Rowe J A, Handel I G, Thera M A, Deans A M, Lyke K E, et al. (2007) Blood group O protects against severe *Plasmodium falciparum* malaria through the mechanism of reduced rosetting. Proc Natl Acad Sci USA 104: 17471-17476.

37. Scholander C, Treutiger C J, Hultenby K, Wahlgren M (1996) Novel fibrillar structure confers adhesive property to malaria-infected erythrocytes. Nature Medicine 2: 204-208.

38. Rowe J A, Shafi J, Kai O K, Marsh K, Raza A (2002) Nonimmune IgM, but not IgG binds to the surface of *Plasmodium falciparum*-infected erythrocytes and correlates with rosetting and severe malaria. Am J Trop Med Hyg 66: 692-699.

39. Clough B, Abiola Atilola F, Black J, Pasvol G (1998) *Plasmodium falciparum*: The Importance of IgM in the Rosetting of Parasite-Infected Erythrocytes. Experimental Parasitology 89: 129-132.

40. Somner E A, Black J, Pasvol G (2000) Multiple human serum components act as bridging molecules in rosette formation by *Plasmodium falciparum*-infected erythrocytes. Blood 95: 674-682.

41. Barfod L, Dalgaard M B, Pleman S T, Ofori M F, Pleass R J, et al. (2011) Evasion of immunity to *Plasmodium falciparum* malaria by IgM masking of protective IgG epitopes in infected erythrocyte surface-exposed PfEMP1. Proc Natl Acad Sci USA 108: 12485-12490.

42. Claessens A, Ghumra A, Gupta A P, Mok S, Bozdech Z, et al. (2011) Design of a variant surface antigen-supplemented microarray chip for whole transcriptome analysis of multiple *Plasmodium falciparum* cytoadherent strains, and identification of strain-transcendent rif and stevor genes. Malar J 10: 180.

43. Semblat J P, Raza A, Kyes S A, Rowe J A (2006) Identification of *Plasmodium falciparum* var1 CSA and var2CSA domains that bind IgM natural antibodies. Mol Biochem Parasitol 146: 192-197.

44. Ghumra A, Semblat J P, McIntosh R S, Raza A, Rasmussen I B, et al. (2008) Identification of residues in the Cmu4 domain of polymeric IgM essential for interaction with *Plasmodium falciparum* erythrocyte membrane protein 1 (PfEMP1). J Immunol 181: 1988-2000.

45. Smith J D, Subramanian G, Gamain B, Baruch D I, Miller L H (2000) Classification of adhesive domains in the *Plasmodium falciparum* erythrocyte membrane protein 1 family. Mol Biochem Parasitol 110: 293-310.

46. Deans A M, Lyke K E, Thera M A, Plowe C V, Kone A, et al. (2006) Low multiplication rates of African *Plasmodium falciparum* isolates and lack of association of multiplication rate and red blood cell selectivity with malaria virulence. Am J Trop Med Hyg 74: 554-563.

47. Avril M, Kulasekara B R, Gose S O, Rowe C, Dahlback M, et al. (2008) Evidence for globally shared, cross-reacting polymorphic epitopes in the pregnancy-associated malaria vaccine candidate VAR2CSA. Infect Immun 76: 1791-1800.

48. Barfod L, Dobrilovic T, Magistrado P, Khunrae P, Viwami F, et al. (2010) Chondroitin sulfate A-adhering *Plasmodium falciparum*-infected erythrocytes express functionally important antibody epitopes shared by multiple variants. J Immunol 185: 7553-7561.

49. Trimnell A R, Kraemer S M, Mukherjee S, Phippard D J, Janes J H, et al. (2006) Global genetic diversity and evolution of var genes associated with placental and severe childhood malaria. Mol Biochem Parasitol 148: 169-180.

50. Horrocks P, Pinches R, Christodoulou Z, Kyes S A, Newbold C I (2004) Variable var transition rates underlie antigenic variation in malaria. Proc Natl Acad Sci USA 101: 11129-11134.

51. Albrecht L, Moll K, Blomqvist K, Normark J, Chen Q, et al. (2011) var gene transcription and PfEMP1 expression in the rosetting and cytoadhesive *Plasmodium falciparum* clone FCR3S1.2. Malar J 10: 17.

52. Joergensen L, Turner L, Magistrado P, Dahlback M A, Vestergaard L S, et al. (2006) Limited cross-reactivity among domains of the *Plasmodium falciparum* clone 3D7 erythrocyte membrane protein 1 family. Infect Immun 74: 6778-6784.

53. Marsh K, Howard R J (1986) Antigens induced on erythrocytes by *P. falciparum*: expression of diverse and conserved determinants. Science 231: 150-153.

54. Chattopadhyay R, Sharma A, Srivastava V K, Pati S S, Sharma S K, et al. (2003) *Plasmodium falciparum* infection elicits both variant-specific and cross-reactive antibodies against variant surface antigens. Infect Immun 71: 597-604.

55. Gamain B, Miller L H, Baruch D I (2001) The surface variant antigens of *Plasmodium falciparum* contain cross-reactive epitopes. Proc Natl Acad Sci USA 98: 2664-2669.

56. Recker M, Gupta S (2006) Conflicting immune responses can prolong the length of infection in *Plasmodium falciparum* malaria. Bull Math Biol 68: 821-835.

57. Gupta S, Snow R W, Donnelly C A, Marsh K, Newbold C (1999) Immunity to non-cerebral severe malaria is acquired after one or two infections. Nat Med 5: 340-343.

58. Bull P C, Lowe B S, Kortok M, Marsh K (1999) Antibody recognition of *Plasmodium falciparum* erythrocyte surface antigens in Kenya: evidence for rare and prevalent variants. Infect Immun 67: 733-739.

59. Corrigan R A, Rowe J A (2010) Strain variation in early innate cytokine induction by *Plasmodium falciparum*. Parasite Immunol 32: 512-527.

60. Handunnetti S M, David P H, Perera KLRL, Mendis K N (1989) Uninfected erythrocytes form "rosettes" around *Plasmodium falciparum* infected erythrocytes. American Journal of Tropical Medicine and Hygiene 40: 115-118.

61. Rowe J A, Scragg I G, Kwiatkowski D, Ferguson D J P, Carucci D J, et al. (1998) Implications of mycoplasma contamination in *Plasmodium falciparum* cultures and methods for its detection and eradication. Molecular and Biochemical Parasitology 92: 177-180.

62. Farnert A, Arez A P, Babiker H A, Beck H P, Benito A, et al. (2001) Genotyping of *Plasmodium falciparum* infections by PCR: a comparative multicentre study. Trans R Soc Trop Med Hyg 95: 225-232.

63. Kraemer S M, Gupta L, Smith J D (2003) New tools to identify var sequence tags and clone full-length genes using type-specific primers to Duffy binding-like domains. Mol Biochem Parasitol 129: 91-102.

64. Heddini A, Treutiger C J, Wahlgren M (1998) Enrichment of immunoglobulin binding *Plasmodium falciparum*-infected erythrocytes using anti-immunoglobulin-coated magnetic beads. Am J Trop Med Hyg 59: 663-666.

65. Mu J, Awadalla P, Duan J, McGee K M, Joy D A, et al. (2005) Recombination hotspots and population structure in *Plasmodium falciparum*. PLoS Biol 3: e335.

The invention claimed is:

1. A method of raising an immune response in a human, the method comprising a step of administering an immunogenic amount of one or more Erythrocyte Membrane Protein-1 (PfEMP1) antigen(s) from *Plasmodium falciparum* (*P. falciparum*), to a human subject, wherein the PfEMP1 antigen(s) is:

(i) one or more PfEMP1 antigens having an amino acid sequence of SEQ ID NO:1, SEQ ID NO:3 or SEQ ID NO:5; or (ii) one or more PfEMP1 antigens having an amino acid sequence exhibiting at least 95% homology or identity to an amino acid sequence of SEQ ID NO:1, SEQ ID NO:3 or SEQ ID NO:5.

2. The method of claim 1, wherein the PfEMP1 antigen comprises a PfEMP1 Duffy Binding Like (DBL) domain, and wherein the DBL domain is one or more selected from the group consisting of:

(i) an NTS-DBL1α a domain from the PfEMP1 antigen having an amino acid sequence of SEQ ID NO:1, SEQ ID NO:3 and/or SEQ ID NO:5; and (ii) a DBL4ϵ domain from the PfEMP1 antigen having an amino acid sequence of SEQ ID NO:5.

3. The method of claim 1, wherein the immune response:

(i) is effective against diverse strains and isolates of the malaria parasite, *P. falciparum*; and (ii) comprises antibodies which exhibit a degree of affinity, selectivity and/or specificity to the PfEMP1 antigens having an amino acid sequence of SEQ ID NO:1, SEQ ID NO:3 and/or SEQ ID NO:5, and a degree of affinity, selectivity and/or specificity to PfEMP1 antigens other than the PfEMP1 antigens having an amino acid sequence of SEQ ID NO:1, SEQ ID NO:3 and/or SEQ ID NO:5.

4. A method of raising an immune response in a human comprising administering to a subject or a subject in need thereof, a vaccine or vaccine composition comprising one or more PfEMP1 antigens, or a DBL domain from one or more PfEMP1 antigens, selected from the group consisting of:

(i) a PfEMP1 antigen having an amino acid sequence of SEQ ID NO:1;

(ii) a PfEMP1 antigen having an amino acid sequence of SEQ ID NO:3;

(iii) a PfEMP1 antigen having an amino acid sequence of SEQ ID NO:5;

an NTS-DBL1α domain of the PfEMP1 antigen having an amino acid sequence of SEQ ID NO:1;

(v) an NTS-DBL1α domain of the PfEMP1 antigen having an amino acid sequence of SEQ ID NO:3:

(vi) an NTS-DBL1α domain of the PfEMP1 antigen having an amino acid sequence of SEQ ID NO:5; and (vii) a DBL4ϵ domain of the PfEMP1 antigen having an amino acid sequence of SEQ NO:5.

5. The method of claim 4, wherein the immune response is raised in a human or a juvenile human.

6. method of raising an immune response in a human comprising administering to a subject or a subject in need thereof, an antibody exhibiting a degree of affinity, specificity and/or selectivity for one or more of the PfEMP1 antigens, or a DBL domain from one or more PfEMP1 antigens, selected from the group consisting of:

(i) a PfEMP1 antigen having an amino acid sequence of SEQ ID NO:1;

(ii) a PfEMP1 antigen having an amino acid sequence of SEQ ID NO:3:

(iii) a PfEMP1 antigen having an amino acid sequence of SEQ ID NO:5;

(iv) an NTS-DBL1α domain of the PfEMP1 antigen having an amino acid sequence of SEQ ID NO:1;

(v) an NTS-DBL1== domain of the PfEMP1 antigen having an amino acid sequence of SEQ ID NO:3;

(vi) an NTS-DBL1α domain of the PfEMP1 antigen having an amino acid sequence of SEQ NO:5; and (vii) a DBL4ϵ domain of the PfEMP1 antigen having as amino acid sequence of SEQ ID NO:5.

7. The method of claim 6, wherein the immune response is raised in a human or a juvenile human.

* * * * *

UNITED STATES PATENT AND TRADEMARK OFFICE

CERTIFICATE OF CORRECTION

PATENT NO. : 9,878,025 B2
APPLICATION NO. : 14/360136
DATED : January 30, 2018
INVENTOR(S) : Rowe et al.

It is certified that error appears in the above-identified patent and that said Letters Patent is hereby corrected as shown below:

On the Title Page

Item (56) References Cited, Page 2, Column 2, Rowe et al. "Nonimmune..." reference:
Please correct "6696)" to read -- 66(6) --

In the Specification

Column 1, Line 18:
Please correct "9013-134TS_$_{ST}$25.txt" to read -- 9013-134TS_ST25.txt --

Column 28, Line 13:
Please correct "g/ml" to read -- μg/ml --

Column 31, Line 37:
Please correct "NTS-DBL1" to read -- NTS-DBL1α --

Column 32, Line 23:
Please correct "(PBS™)" to read -- (PBSTM) --

Column 32, Line 26:
Please correct "PBS™" to read -- PBSTM --

Column 32, Line 32:
Please correct "(1g/ml)" to read -- (1μg/ml) --

Column 33, Line 27:
Please correct "DBLZ" to read -- DBLζ --

Signed and Sealed this
Nineteenth Day of June, 2018

Andrei Iancu
*Director of the United States Patent and Trademark Office*

In the Claims

Column 152, Claim 4, Line 23:
Please correct “an NTS-DBL1α...” to read -- (iv) an NTS-DBL1α --

Column 152, Claim 6, Line 47:
Please correct “NTS-DBL1=” to read -- NTS-DBL1α --

Column 152, Claim 6, Line 51:
Please correct “as” to read -- an --

```
                              SEQUENCE LISTING


<160> NUMBER OF SEQ ID NOS: 6

<210> SEQ ID NO 1
<211> LENGTH: 3424
<212> TYPE: PRT
<213> ORGANISM: Plasmodium falciparum

<400> SEQUENCE: 1

Met Gly Asn Thr Ile Pro Lys Pro Pro Asp Pro Ile Tyr Ile Asn Glu
1               5                   10                  15

Ser Tyr Gln Ser Thr Arg Asn Val Leu Glu Arg Tyr Ala Glu Ser Ile
            20                  25                  30

Lys Gln Gln Ala Ala Ala Asp Ala Glu Lys Cys Glu Lys Ser Leu Lys
        35                  40                  45

Gly Asp Leu Thr Lys Ala Glu Phe Arg Gly Ala His Ile Glu Thr Val
    50                  55                  60

Gly Val Gln Lys Tyr Ser Tyr Ser Asn Pro Cys Gly Leu Asn His Thr
65                  70                  75                  80

Trp Asn Thr Asn Leu Leu His Asp Arg Val Lys Asp Arg Asp Pro Cys
                85                  90                  95

His Gly Arg Asn Gln Lys Arg Phe Asp Glu Gly Gln Val Tyr Glu Cys
            100                 105                 110

Gly Ser Gly Ile Ile Lys Gly Asn Gly Asn Asn Arg Asn Gly Gly Ser
        115                 120                 125

Tyr Ala Pro Pro Arg Arg Arg His Ile Cys Asp Lys Asn Leu Glu Ala
    130                 135                 140

Leu Thr Val Gln Asn Thr Lys Asn Ser Asn Asp Leu Leu Gly Asn Ile
145                 150                 155                 160

Leu Val Thr Ala Lys Tyr Glu Gly Glu Ser Ile Val Asn Ser Tyr Ala
                165                 170                 175

Asn Ser Gly Met Phe Asn Val Cys Thr Ala Leu Ala Arg Ser Phe Ala
            180                 185                 190

Asp Ile Gly Asp Ile Val Arg Gly Lys Asp Leu Tyr Ser Gly Asn Lys
        195                 200                 205

Gln Glu Lys Glu Lys Arg Lys Gln Leu Glu Lys Asn Leu Gln Lys Ile
    210                 215                 220

Phe Arg Asn Ile Tyr Asp Lys Leu Leu Glu Tyr Asn Lys Thr Asn Gly
225                 230                 235                 240

Glu Ile Glu Ala Arg Tyr Gly Ser Asp Lys Glu Asn Phe Phe Gln Leu
                245                 250                 255

Arg Glu Asp Trp Trp Lys Ala Asn Arg Asp Gln Val Trp Arg Ala Ile
            260                 265                 270

Thr Cys Lys Ala Pro Gln Asp Ala Asn Tyr Phe Arg Lys Ile Ser Gly
        275                 280                 285

Asp Thr Lys Val Phe Thr Ser Gln Gly Gln Cys Gly His Ser Glu Thr
    290                 295                 300

Asn Val Pro Thr Asn Leu Asp Tyr Val Pro Gln Phe Leu Arg Trp Phe
305                 310                 315                 320

Asp Glu Trp Ala Glu Glu Phe Cys Arg Val Arg Glu His Lys Leu Lys
                325                 330                 335

Lys Ile Lys Glu Ala Cys Arg Gly Lys Asn Asp Glu Lys Asp Cys Ser
            340                 345                 350

Arg Glu Gly Tyr Asp Cys Asn Lys Thr Asn Leu Arg Leu Asn Glu Ile
        355                 360                 365
```

-continued

```
Phe Met Asp Leu Glu Cys Pro Asn Cys Glu Lys Ala Cys Thr Ser Tyr
    370                 375                 380

Lys Glu Trp Ile Glu Asn Lys Gln Lys Glu Phe Asn Lys Gln Lys Lys
385                 390                 395                 400

Lys Tyr Glu Lys Glu Ile Glu Asn Asp Glu Ser Asn Ser His Ser Thr
                405                 410                 415

Tyr Asp Asn Glu Leu Tyr Asn Asn Leu Lys Arg Asn Tyr Pro Ser Phe
            420                 425                 430

Glu Asn Phe Val Glu Thr Leu Lys Glu Gly Ala Tyr Cys Thr Asn Gly
        435                 440                 445

Ile Ile Glu Gly Lys Ile Asp Phe Asn Lys Gln Tyr Asp Thr Phe Ser
    450                 455                 460

His Ser Gln Tyr Cys Lys Ser Cys Pro Ile Leu Gly Ala Lys Cys Lys
465                 470                 475                 480

Asn Gly Gln Cys Asn Ser Phe Asn Asp Ile Asn Cys Thr Lys Ile Pro
                485                 490                 495

Thr Met Thr Asn Ile Arg Ile His Ser Thr Glu Ser Pro Lys Asp Ile
            500                 505                 510

Tyr Ile Leu Val Asn Asp Lys Lys Asn Arg Glu His Ser Leu Glu Leu
        515                 520                 525

Lys Asp Ala Phe Asn Asp Cys Asp Ile Phe Lys Arg Ile Arg Lys Gln
    530                 535                 540

Lys Trp Tyr Cys Lys Tyr Lys Cys Asn Leu Asp Val Cys Glu Leu Lys
545                 550                 555                 560

Asn Phe Asn Arg Asp Met Asp Asp Glu Arg Leu Ile Ser Ile Glu Val
                565                 570                 575

Leu Ile Lys Arg Trp Leu Lys Tyr Phe Leu Asn Asp Tyr Asn Gln Ile
            580                 585                 590

Lys Glu Asn Leu Asn Gln Cys Ile Asn Asn Gly Thr Asn Thr Leu Cys
        595                 600                 605

Ile Asn Asp Cys His Lys Asn Cys Glu Cys Ile Glu Lys Trp Ile Lys
    610                 615                 620

Glu Lys Glu Lys Glu Trp Lys Val Ile Lys Asp Arg Tyr Val Glu Gln
625                 630                 635                 640

Tyr Asn Asn Asn Asp Lys Asp Val Ser Ser Lys Leu Lys Thr Phe Leu
                645                 650                 655

Lys Gln Asp Leu Phe Thr Asn Tyr Val Lys Asn Ala Leu Asp Pro Asp
            660                 665                 670

Glu Thr Leu Asp Lys Met Lys Glu Ser Ser Val Cys Asn Val Pro Asn
        675                 680                 685

Lys Leu Asn Gly Thr Ser Cys Lys Lys Lys Asp Val Ile Asn Ile Leu
    690                 695                 700

Leu Asn Arg Leu Asn Glu Lys Ile Asp Pro Cys Lys Asn Gln His Lys
705                 710                 715                 720

Ala Thr Lys Gly Lys Glu Cys Cys Asp Lys Leu Pro Lys Ile Ala Asp
                725                 730                 735

Gly Asp Thr Ser Asp Asp Glu Asp Asp Asp Glu Glu Asp Val Ser Val
            740                 745                 750

Thr Ser Gly Glu Lys Gln Asn Val Lys Gln Asp Cys Ala Gly Lys Lys
        755                 760                 765

Ser Asp Glu Val Cys Glu Met Val Lys Lys Leu Ile Gly Asp Asn Asn
    770                 775                 780

Gly Met Ser Gly Arg Ile Glu Ser Cys Asn Pro Lys Thr Gly Thr Tyr
```

-continued

```
785                 790                 795                 800

Pro Pro Trp Lys Asn His Ala Ser Leu Val Glu Asp Asn Arg Thr Trp
                805                 810                 815

Met Pro Pro Arg Arg Gln Lys Leu Cys Val Ser Ala Leu Thr Gln Glu
            820                 825                 830

Gly Lys Ile Lys Asn Lys Glu Asp Ile Arg Lys His Phe Ile Thr Cys
        835                 840                 845

Ala Ala Ile Glu Thr His Phe Ala Trp His Arg Tyr Lys Asn His Asn
    850                 855                 860

Ala Asn Ala Glu Ser Lys Leu Lys Thr Gly Lys Ile Pro Asp Asp Phe
865                 870                 875                 880

Leu Arg Ser Met Lys Tyr Thr Phe Gly Asp Tyr Arg Asp Ile Phe Phe
                885                 890                 895

Gly Thr Asp Ile Ser Ser Cys Asp Lys Ile Lys Asn Ala Ser Asn Thr
            900                 905                 910

Ile Lys Ser Ile Leu Glu Asn Lys Thr Lys Lys Lys Lys Gly Asp Lys
        915                 920                 925

Leu Ile Glu Asp Asn Glu Lys His Lys Glu Trp Trp Asn Glu His Gly
    930                 935                 940

Lys Glu Ile Trp Glu Gly Met Leu Cys Ala Leu Glu Lys Val Gly Gly
945                 950                 955                 960

Ser Val Asn Ile Lys Ser Thr Tyr Asn Tyr Asp Thr Ile Lys Asn Asp
                965                 970                 975

Leu Glu Asp Phe Ala Ser Arg Pro Gln Phe Leu Arg Trp Phe Thr Glu
            980                 985                 990

Trp Ser Asp Glu Phe Cys Gln Glu  Arg Lys Lys Leu Glu  Ala Lys Val
        995                 1000                1005

Lys Glu  Tyr Cys Lys Lys Asp  Tyr Val Gly Cys Asn  Lys Gln Asn
    1010                1015                1020

Thr Lys  Ala Asn Asn Ser Cys  Val Ser Ala Cys Glu  Ala Phe Gln
    1025                1030                1035

His Tyr  Met Lys Ser Lys Met  Ser Glu Tyr Asp Thr  Gln Lys Lys
    1040                1045                1050

Lys Phe  Glu Ala Glu Lys Ser  Gly Lys Glu Pro Glu  Tyr Glu Gly
    1055                1060                1065

Phe Ser  Thr Lys Asp Ala Ser  Glu Tyr Leu Lys Glu  Lys Cys Leu
    1070                1075                1080

His Gly  Thr Cys Asp Cys Met  Glu Lys Val Lys Asn  Ile Asp Asp
    1085                1090                1095

Tyr Trp  Lys Asn Pro His Lys  Thr Tyr Asp Asp Asn  Lys Leu Glu
    1100                1105                1110

Thr Lys  Cys Glu Cys Pro Gln  Thr Pro Pro Lys Pro  Cys Glu Ile
    1115                1120                1125

Val Lys  Thr Leu Leu Glu Asp  Asn Asn Gly Arg His  Val Asp Ala
    1130                1135                1140

Cys Asn  Leu Lys Tyr Glu Gly  Lys Lys Glu Lys His  Thr Ser Trp
    1145                1150                1155

Asn Cys  Asn Pro Asn Lys Phe  Lys Asn Gly Glu Glu  Gly Ala Cys
    1160                1165                1170

Ile Pro  Pro Arg Arg Gln Lys  Leu Tyr Ile Tyr Asn  Leu Glu Lys
    1175                1180                1185

Phe Thr  Gly Gly Thr Ser Glu  Ile Glu Leu Arg Lys  Ala Phe Ile
    1190                1195                1200
```

-continued

Glu Cys Ala Ala Ile Glu Thr Phe Phe Ser Trp His Lys Phe Lys
1205 1210 1215

Lys Asp Lys Glu Arg Glu Asp Lys Glu Lys Gln Asp Leu Val Gly
1220 1225 1230

Tyr Thr Ser Thr Val Asp Glu Lys His Gln Lys Asp Leu Gln Ser
1235 1240 1245

Gly Lys Ile Pro Glu Glu Phe Lys Arg Gln Met Phe Tyr Thr Phe
1250 1255 1260

Gly Asp Tyr Arg Asp Ile Cys Leu Gly Asn Asp Met Gly Asn Asp
1265 1270 1275

Asn Tyr Asn Lys Asn Ile Ser Thr Lys Val Arg Ser Ile Leu Asn
1280 1285 1290

Ser Gly Glu Thr Pro Glu Glu Trp Trp Gln Lys His Gly Pro Gln
1295 1300 1305

Ile Trp Glu Gly Met Leu Cys Ala Leu Ser Tyr Asp Thr Glu Lys
1310 1315 1320

Gln Lys Lys Val Gln Asp Val His Asn Asn Leu Ile Ala Pro Pro
1325 1330 1335

Asn Asn Asn Lys Tyr Asn Asp Val Lys Leu Val Ser Lys Ser Gly
1340 1345 1350

Lys Leu His Thr Ser Leu Ser Asp Phe Ala Thr Val Pro Gln Phe
1355 1360 1365

Leu Arg Trp Phe Glu Glu Trp Val Glu Glu Phe Cys Arg Lys Lys
1370 1375 1380

Lys Ile Lys Ile Asp Lys Ile Glu Asp Glu Cys Arg Gly Glu Tyr
1385 1390 1395

Asp Asn Gly Gly Lys Lys Tyr Cys Ser Gly Asp Gly Tyr Asp Cys
1400 1405 1410

Asp Lys Arg Tyr Leu Ser His Asn Lys Met Phe Ala Asp Leu Asn
1415 1420 1425

Cys Leu Gly Cys Glu Lys Glu Cys Arg Asn Tyr Lys Lys Trp Ile
1430 1435 1440

Glu Glu Lys Val Glu Glu Phe Tyr Lys Gln Lys Lys Lys Tyr Glu
1445 1450 1455

Lys Gly Phe Glu Asn Thr Arg Thr Asn Leu Asp Asn Lys Tyr Val
1460 1465 1470

Lys Glu Phe Tyr Glu Thr Ser Ala Gly Lys Tyr Lys Ser Val Asp
1475 1480 1485

Leu Phe Leu Asp Thr Leu Lys Glu Arg Ser His Cys Ser Met Gly
1490 1495 1500

Met Val Asn Arg Lys Ile Asp Phe Lys Asn Pro Leu Glu Thr Phe
1505 1510 1515

Ser Pro Ser Ile Tyr Cys Lys Thr Cys Pro Leu Tyr Gly Val Asn
1520 1525 1530

Cys Asn Ser Arg Glu Cys Val Asp Ile Thr Glu Asn Glu Phe Lys
1535 1540 1545

Lys Lys Asn Val Leu Asp Glu Ile Ile Ile Asn Asp Lys Ser His
1550 1555 1560

Thr Ser Ile Asp Ile Glu Met Ile Asp Arg Arg Gly Gln Tyr Met
1565 1570 1575

Gln Glu Asn Leu Asp Asn Pro Leu Phe Lys Glu Ser Tyr Leu Leu
1580 1585 1590

```
Lys Ser Val Arg Asp Gln Lys Trp Asp Cys Asn Phe Ile His Asn
    1595                1600                1605

Lys Ile Asp Leu Cys Glu Ile Asn Lys Phe Asn Glu Asn Ile Asp
    1610                1615                1620

Thr Asp Glu Ser Ile Thr Phe Lys Val Leu Ile Glu Arg Trp Leu
    1625                1630                1635

Gln Asp Phe Leu Glu Gly Tyr Tyr Ile Ser Lys Lys Gln Ile Asp
    1640                1645                1650

Leu Phe Thr Lys Lys Glu Glu Asn Lys Cys Glu Cys Val Lys Lys
    1655                1660                1665

Trp Ala Glu Lys Lys Glu Gly Glu Trp Glu Lys Ile Asn Glu His
    1670                1675                1680

Phe Asn Lys Gln Lys His Asp Asp Ala Phe Asp Met Asp Phe Lys
    1685                1690                1695

Val Lys Asn Tyr Phe Glu Lys Asn Ala Ser Asp Leu Lys Asp Trp
    1700                1705                1710

Ile Asp Asn Phe Lys Arg Leu Asn Asn Ile Asp Asp Tyr Gln Val
    1715                1720                1725

Cys Asn Val His Asn Asn Cys Lys Ser Ala Asp Lys Lys Asn Lys
    1730                1735                1740

Ile Asp Met Val Ser Ile Leu Leu Ser Glu Leu Lys Lys Glu Ile
    1745                1750                1755

Glu Thr Cys Lys Asn Gln Gly Asn Glu Lys Thr Lys Ile Lys Cys
    1760                1765                1770

Asp Ala Ser Pro Thr Asn Asp Glu Leu Asp Glu Glu Tyr Glu Leu
    1775                1780                1785

Gly Thr Thr Asp Thr Ser Pro Ser Ala Ala Pro Asp Ile Cys Lys
    1790                1795                1800

Asp Val Ile Gln Ser Lys Ser Glu Glu Thr Ile Cys Arg Asp Asp
    1805                1810                1815

Lys Arg Val Asp Cys Asn Lys Val Gly Lys Asp Asp Pro Ile Lys
    1820                1825                1830

Val Pro Met Asp Pro Lys Ser Gly Glu Asp His Leu Asn Glu Met
    1835                1840                1845

Gly Asp Lys His Asn Cys Ser Gly Ile Ile Ile Lys Thr Asn Gly
    1850                1855                1860

Glu Trp Lys Asn Thr Lys Gln Leu Asn Tyr Pro Asn Pro Cys Glu
    1865                1870                1875

Ser Ile Tyr Ala Ser Pro Arg Arg Gln Lys Phe Cys Val His Glu
    1880                1885                1890

Leu Asp Lys Ala Lys Asn Gln Lys Glu Leu Arg Thr Lys Leu Leu
    1895                1900                1905

Thr Val Ala Ala Asn Gln Gly Tyr Asn Leu Ala Ile Lys His His
    1910                1915                1920

Glu Tyr Lys Asp Lys Tyr Thr Val Asn Pro Cys Asn Ala Leu Lys
    1925                1930                1935

Tyr Ser Phe Tyr Asp Tyr Gln His Ile Ile Leu Gly Asp Asp Pro
    1940                1945                1950

Met Glu Pro Glu Lys Trp Asp Thr Glu Ser Ala Leu Lys Arg Ile
    1955                1960                1965

Phe Gly Asn Arg Asn Thr Glu Asp Ala Lys Pro Leu Ser Arg Lys
    1970                1975                1980

Arg Lys Asp Phe Trp Lys Glu Asn Lys Glu Cys Val Trp Ser Ala
```

-continued

```
    1985                1990                1995

Met Lys  Cys Gly Tyr Asn Glu  Gly Ile Lys Lys Gly  Asn Lys Ser
    2000                2005                2010

Asn Asn  Ile Pro Glu Cys Lys  Asp Ser Ile Pro Thr  Gln Phe Asp
    2015                2020                2025

Gly Val  Pro Gln Phe Leu Met  Trp Phe Thr Glu Trp  Ser Glu Asp
    2030                2035                2040

Phe Cys  Asn His Lys Lys Thr  His Leu Lys Lys Leu  Glu Gln Gly
    2045                2050                2055

Cys Arg  Gly Cys Thr Leu Arg  Ile Asp Gly Thr Cys  Glu Lys Asp
    2060                2065                2070

Gly Ser  Gly Cys Gln Lys Cys  Ser Gln Ala Cys Glu  Glu Tyr Lys
    2075                2080                2085

Ala Trp  Leu Gln Asn Trp Lys  Asp Gln Tyr Lys Lys  Gln Ser Lys
    2090                2095                2100

Lys Tyr  Ser Gly Asp Lys Lys  Lys Glu Leu Tyr Lys  Thr Val Pro
    2105                2110                2115

Lys Val  Lys Asn Ser Thr His  Ala Tyr Glu Tyr Leu  Gln Thr Gln
    2120                2125                2130

Leu Glu  Lys Leu Cys Glu Lys  Gly Lys Cys Asp Tyr  Thr Cys Met
    2135                2140                2145

Lys Asn  Pro Ser Thr Glu Asn  Ser Thr Glu Asn Met  Pro Glu Ser
    2150                2155                2160

Leu Asp  Val Lys Pro Asp Ile  Val Lys Asp Lys Cys  Pro Cys Pro
    2165                2170                2175

Pro Gln  Lys Ile Glu Lys Pro  Asp Ser Thr Leu Asn  Cys Ile Asp
    2180                2185                2190

Arg Ser  Ala Phe Glu Leu Tyr  Ala Lys Ala Lys Ser  Asp Leu His
    2195                2200                2205

Gly Val  Lys Asp Lys Leu Lys  Gly Asn Asn Thr Lys  Asn Ile Tyr
    2210                2215                2220

Glu Glu  Thr Thr Asn Gly Lys  Asn Asp Asp Asn Ile  Ile Cys Lys
    2225                2230                2235

Ile Asn  Glu Ser Ile Ser Lys  Gln Asn Asn Val Cys  Lys Lys Asn
    2240                2245                2250

Glu Asn  Leu Phe Asp Asp Ile  Asp Lys Trp Asp Cys  Lys Lys Arg
    2255                2260                2265

Thr Asn  Thr Val Pro Ile Glu  Asn Ile Cys Ile Pro  Pro Arg Arg
    2270                2275                2280

Lys Leu  Met Cys Ala Tyr Pro  Leu Lys Asn Leu Gly  Val Lys Lys
    2285                2290                2295

Asn Thr  Ser Glu Val Leu Phe  Asn Lys Val Leu Arg  Thr Ala Ala
    2300                2305                2310

Tyr Glu  Gly Lys His Ile Lys  Glu Ser Trp Glu Lys  Ala Glu Lys
    2315                2320                2325

Ser Lys  Lys Lys Lys Thr Gln  Ile Cys Asp Ala Met  Lys Tyr Ser
    2330                2335                2340

Phe Ala  Asp Leu Gly Asp Ile  Ile Arg Gly Arg Asp  Ile Leu Ile
    2345                2350                2355

Phe Asn  Asn Gly Asn Asn Glu  Ile Glu Arg Asp Leu  Lys Ala Val
    2360                2365                2370

Phe Gln  Ser Ile Tyr Asp Lys  Trp Lys Ser Asp Ser  Asn Asn Asn
    2375                2380                2385
```

-continued

```
Lys Asp  Lys Tyr Pro Asp Leu  Thr Ser Phe Arg Ser  Ala Trp Trp
    2390                 2395                 2400

Asp Ala  Asn Arg Lys Asp Ile  Trp Lys Ala Met Thr  Cys Gly Ala
    2405                 2410                 2415

Pro Glu  Asp Ala Thr Leu Phe  Lys Lys Leu Glu Lys  Trp Gly Ile
    2420                 2425                 2430

Pro Asn  Leu Ile Leu Ser Gln  His Lys Cys Gly His  Asn Asp Asp
    2435                 2440                 2445

Pro Pro  Ile Asp Asp Tyr Ile  Pro Gln Arg Leu Arg  Trp Met Lys
    2450                 2455                 2460

Glu Trp  Gly Glu Tyr Val Cys  Lys Ile Leu Asn Glu  Asn Val Asn
    2465                 2470                 2475

Asp Met  Lys Asn Asp Cys Asp  Lys Cys Thr Leu Asn  Asp Lys Lys
    2480                 2485                 2490

Cys Ser  Asp Glu Asp Asp Gly  Asn Lys Cys Arg Ser  Cys Lys Glu
    2495                 2500                 2505

Lys Cys  Lys Glu Tyr Thr Lys  Leu Ile Tyr Asn Leu  Lys Ser Gln
    2510                 2515                 2520

Phe Tyr  Ile Leu Glu Lys His  Tyr Asn Glu Leu Tyr  Thr Lys Ala
    2525                 2530                 2535

Gln Asn  Asn Thr Thr Tyr Phe  Thr Asn Asp Asn Asp  Lys Lys Val
    2540                 2545                 2550

Ile Glu  Phe Phe Lys Lys Val  Lys Lys Asp Cys Asp  Val Gly Thr
    2555                 2560                 2565

Pro Asp  Lys Tyr Leu Asp Lys  Ala Ile His Cys Ile  His Tyr Asp
    2570                 2575                 2580

Phe Thr  Lys Asn Gly Thr Lys  Ser Lys Pro Tyr Val  Phe Asn Asn
    2585                 2590                 2595

Gln Pro  Glu Lys Tyr Lys Asn  Leu Cys Ser Cys Thr  Ile Thr Asn
    2600                 2605                 2610

His Pro  Leu Asp Lys Cys Pro  Leu Pro Asp Lys Thr  Asp Asp Tyr
    2615                 2620                 2625

Cys Lys  Ile Ile Arg His Ile  Asn Pro Cys Ile Thr  Ile Asn Leu
    2630                 2635                 2640

Asp Asn  Asn Leu Asp Thr Trp  Thr Gly Phe Val Val  His Asn Ile
    2645                 2650                 2655

Ser His  Lys Asn Lys Gly Val  Leu Val Pro Pro Arg  Arg Arg His
    2660                 2665                 2670

Leu Cys  Thr Arg Glu Leu Thr  Gly Ile Arg Tyr Arg  Lys Asn Asp
    2675                 2680                 2685

Lys Asp  Asn Leu Lys Gln Asn  Leu Ile Asp Ser Ala  Phe Asn Gln
    2690                 2695                 2700

Gly Ile  Leu Leu Gly Lys Thr  Phe Lys Asp Tyr Ser  Asp Gln Gly
    2705                 2710                 2715

Leu Glu  Tyr Met Lys Tyr Ser  Phe Ala Asp Tyr Gly  Asp Ile Ile
    2720                 2725                 2730

Lys Ala  Lys Asp Met Ile Gly  Gly Ser Asn Ile Asp  Asp Phe Asn
    2735                 2740                 2745

Asn Asp  Leu Lys Lys Met Phe  Pro Glu His His Ser  Glu Asn Met
    2750                 2755                 2760

Gly Lys  Thr Thr Ile Ser Arg  Glu Gln Trp Trp Glu  Ala Asn Lys
    2765                 2770                 2775
```

-continued

```
Thr His  Val Trp His Ala Met  Leu Cys Gly Tyr His  Gln Gly Ile
    2780                 2785                 2790

Ile Asn  Pro Asn Leu Ser Arg  Arg Arg Pro Lys Pro  Leu Glu Glu
    2795                 2800                 2805

Gly Thr  Gln Ser Ser Ile Ala  Thr Lys Thr Ile Pro  Ser Asn Trp
    2810                 2815                 2820

Cys Gln  Leu Pro Asn Asp Tyr  Ser Thr Asp Gln Phe  Leu Arg Trp
    2825                 2830                 2835

Phe Gln  Glu Trp Ile Glu Asn  Phe Cys Thr Arg Lys  Lys Val Leu
    2840                 2845                 2850

Glu Lys  Glu Ala Gln Glu Gln  Cys Lys Asn Ile Thr  Cys Asn Asn
    2855                 2860                 2865

Asp Thr  Gly Lys Thr Asn Thr  Lys Cys Thr Glu Ala  Cys Lys Asn
    2870                 2875                 2880

Tyr Ser  Asn Phe Ile Leu Ile  Lys Lys Lys Glu Tyr  Glu Ser Leu
    2885                 2890                 2895

Asn Ser  Gln Tyr Asp Met Asn  Tyr Lys Lys Ile Val  Glu His Lys
    2900                 2905                 2910

Asn Ala  Leu Glu Tyr Phe Lys  Asp Lys Cys Lys Asn  Asn Cys Glu
    2915                 2920                 2925

Cys Leu  Ser Lys His Ile Asp  Asn Gly Lys Asn Trp  Lys Glu Pro
    2930                 2935                 2940

Tyr Glu  Thr Ile Asp Asp Ser  Glu Leu Ile Gly Lys  Cys Lys Cys
    2945                 2950                 2955

Lys Lys  Val Lys Pro Lys Thr  Pro Asp Val Ile Pro  Ala Gly Ala
    2960                 2965                 2970

Thr Glu  Thr Lys Glu Lys Asp  Thr Pro His Ala Pro  Glu Lys Pro
    2975                 2980                 2985

Gln Gln  Pro Pro Gln Pro Leu  Pro Pro Ser Asp Glu  Pro Phe Asp
    2990                 2995                 3000

Pro Thr  Ile Leu Gln Thr Thr  Ile Pro Phe Gly Ile  Ala Leu Ala
    3005                 3010                 3015

Leu Gly  Ser Ile Ala Phe Leu  Phe Met Lys Lys Lys  Pro Lys Ser
    3020                 3025                 3030

Pro Val  Asp Leu Leu Arg Val  Leu Asn Ile Pro Lys  Arg Asp Tyr
    3035                 3040                 3045

Glu Met  Pro Thr Leu Lys Ser  Lys Asn Arg Tyr Ile  Pro Tyr Ala
    3050                 3055                 3060

Ser Asp  Arg Tyr Lys Gly Lys  Thr Tyr Ile Tyr Met  Glu Gly Asp
    3065                 3070                 3075

Ser Ser  Gly Asp Glu Lys Tyr  Ala Phe Met Ser Asp  Thr Thr Asp
    3080                 3085                 3090

Val Thr  Ser Ser Glu Ser Glu  Tyr Glu Glu Leu Asp  Ile Asn Asp
    3095                 3100                 3105

Ile Tyr  Val Pro Gly Ser Pro  Lys Tyr Lys Thr Leu  Ile Glu Val
    3110                 3115                 3120

Val Leu  Glu Pro Ser Lys Ser  Asn Gly Asn Thr Leu  Gly Asp Asp
    3125                 3130                 3135

Met Val  Pro Thr Thr Asn Thr  Phe Thr Asp Glu Glu  Trp Asn Glu
    3140                 3145                 3150

Leu Lys  His Asp Phe Ile Ser  Gln Tyr Val Gln Arg  Glu Pro Leu
    3155                 3160                 3165

Asp Val  Pro Gln Tyr Asp Glu  Ser Thr Gln Leu Pro  Met Asn Ile
```

-continued

```
    3170                3175                3180

Val Gly  Asn Val Leu Asp Asp  Gly Met Asp Glu Lys  Pro Phe Ile
    3185                3190                3195

Thr Ser  Ile His Asp Arg Asp  Leu Tyr Thr Gly Glu  Glu Ile Ser
    3200                3205                3210

Tyr Asn  Ile Asn Met Ser Thr  Asn Ser Met Asp Asp  Pro Lys Tyr
    3215                3220                3225

Val Ser  Asn Asn Val Tyr Ser  Gly Ile Asp Leu Ile  Asn Asp Thr
    3230                3235                3240

Leu Ser  Gly Asp Arg Ile Asp  Ile Tyr Asp Glu Leu  Leu Lys Arg
    3245                3250                3255

Lys Glu  Asn Glu Leu Phe Gly  Thr Asn His Val Lys  Gln Thr Ser
    3260                3265                3270

Ile His  Ser Val Ala Lys Leu  Thr Asn Ser Asp Pro  Ile His Asn
    3275                3280                3285

Gln Leu  Asp Leu Phe His Thr  Trp Leu Asp Arg His  Arg Asp Met
    3290                3295                3300

Cys Asn  Thr Trp Asn Thr Lys  Glu Glu Leu Leu Asp  Lys Leu Asn
    3305                3310                3315

Glu Gln  Trp Asn Lys Asp Asn  Asp Gly Gly Asp Ile  Pro Asn Asp
    3320                3325                3330

Asn Lys  Lys Leu Asn Thr Asp  Val Ser Phe Glu Ile  Asp Met Asp
    3335                3340                3345

Glu Thr  Lys Gly Lys Lys Glu  Phe Ser Asn Met Asp  Thr Ile Leu
    3350                3355                3360

Asp Asp  Met Glu Asp Asp Ile  Tyr Tyr Asp Val Asn  Asp Glu Asn
    3365                3370                3375

Pro Ser  Val Asp Asn Ile Pro  Met Asp His Asn Lys  Val Asp Val
    3380                3385                3390

Pro Lys  Lys Val His Val Glu  Met Lys Ile Leu Asn  Asn Thr Ser
    3395                3400                3405

Asn Gly  Ser Leu Glu Gln Glu  Phe Pro Ile Ser Asp  Val Trp Asn
    3410                3415                3420

Ile


<210> SEQ ID NO 2
<211> LENGTH: 10275
<212> TYPE: DNA
<213> ORGANISM: Plasmodium falciparum

<400> SEQUENCE: 2

atggggaata caataccaaa gcctccggat ccaatttata taaatgaaag ttatcaaagt      60

accagaaatg ttttggaacg ttatgccgaa agtataaagc aacaggcagc tgctgatgca     120

gaaaaatgtg agaaatcgtt gaaaggagat ttgacaaaag cagaatttcg tggtgctcat     180

atagagacag ttggtgtcca gaaatatagt tattctaatc catgtggttt gaatcataca     240

tggaatacta atttattgca tgatagagtg aaggatagag atccgtgcca tggtagaaat     300

caaaaacgtt ttgatgaagg tcaagtatat gaatgtggta gtggtataat caaaggtaat     360

ggaaataaca gaaatggggg atcctatgcg ccacccagaa gaagacatat atgtgataaa     420

aacttggaag ctctaactgt gcaaaataca aaaaattcta acgacttgtt aggaaatatc     480

ttggtcacag caaaatatga aggcgaatct attgtgaata gttatgcaaa tagcggaatg     540

ttcaatgtat gtactgcact tgcacgaagt tttgcagata taggtgatat cgtacgcggc     600
```

-continued

```
aaagatctat atagtggtaa taaacaagaa aaagaaaaaa gaaaacaatt agagaagaat    660
ttacaaaaaa tttttaggaa tatatatgac aaattattag agtataacaa gacgaatggg    720
gagatagaag ctcgctacgg aagtgataaa gaaaattttt ttcaattaag agaagattgg    780
tggaaagcga acagagatca agtatggaga gctataacat gtaaagctcc acaagacgct    840
aattatttta gaaaaatttc aggagatact aaggtgttta caagtcaagg acaatgtggg    900
catagtgaaa caaacgttcc tacgaatcta gattatgtcc ctcaattttt acgatggttt    960
gatgaatggg cagaagagtt ttgcagagta agagaacata agttgaaaaa gattaaagaa   1020
gcgtgtcgtg ggaaaaatga tgaaaaagat tgtagtcgtg agggttacga ttgtaataaa   1080
acaaatctaa gacttaatga aatttttatg gatttagaat gtccaaattg tgaaaaagcg   1140
tgtacaagtt ataaggaatg gatagaaaat aaacaaaagg aatttaataa acaaaagaaa   1200
aaatacgaaa aggaaataga aaatgatgaa agtaattctc atagtacata tgataacgaa   1260
ttatataata atctgaaaag aaattatcct tcctttgaaa attttgtaga aacattaaaa   1320
gaaggagcgt attgtactaa tggcattata gaaggtaaaa tagattttaa taaacaatat   1380
gacacttttt cccattcaca gtactgtaaa tcatgtccta tattaggtgc caaatgcaag   1440
aatggacaat gcaattcatt taatgatata aattgtacaa aaataccgac tatgactaat   1500
ataagaattc acagcactga aagtcctaag gatatttata ttctggtgaa tgataaaaaa   1560
aatagagaac attctcttga attaaaggat gcttttaatg attgtgatat ttttaaaaga   1620
ataagaaaac aaaaatggta ttgtaaatat aaatgtaact tagatgtatg tgaactaaaa   1680
aattttaata gggatatgga tgatgaaaga ttaatttcaa tcgaagtatt gattaaacgt   1740
tggttaaagt attttttaaa tgattataat caaataaaag aaaatttaaa tcaatgtata   1800
aataatggaa caaatacatt atgtataaac gattgtcata aaaattgtga atgcatagag   1860
aaatggataa aagaaaaaga gaaagagtgg aaagttataa aagatcgtta tgtagaacaa   1920
tataataata acgataaaga cgtttcttct aaacttaaaa ctttttgaa acaggatttg   1980
tttactaact atgttaaaaa tgccttggac cccgatgaaa cgttagataa gatgaaagaa   2040
tctagtgtat gcaatgtacc taataaactc aatggaacat catgtaaaaa aaaggacgtg   2100
ataaatattt tacttaatag acttaatgaa aaaatagatc cttgcaaaaa tcaacataaa   2160
gcaaccaaag gtaaagaatg ttgtgataaa ttacctaaaa ttgcagatgg tgatacatca   2220
gacgatgaag atgacgatga agaggatgtt tctgtgactt ctggagaaaa acaaaatgta   2280
aaacaagatt gtgctggtaa gaaatcggat gaggtgtgcg aaatggtgaa gaaacttatt   2340
ggagataaca atggaatgag tggtcgaata gagagttgta atccaaaaac tggaacttat   2400
cctccatgga aaaaccacgc aagtttagtg gaagacaaca gaacgtggat gcctccaaga   2460
agacagaaat tatgcgtaag tgctttaaca caagaaggta aaataaaaaa taaagaagat   2520
ataagaaaac attttattac atgtgcggct atagaaacac attttgcgtg gcatagatat   2580
aaaaaccata atgcgaatgc tgaaagcaaa ttaaaaactg gaaaaattcc tgatgatttt   2640
ttaagatcca tgaaatatac ttttggtgat tatagagata tattttttgg aacagatatt   2700
tcatcatgtg ataaaattaa aaatgcctca aatactataa aatctatatt agaaaataaa   2760
acaaagaaga aaaaaggaga taaactcatt gaagataatg aaaaacacaa agagtggtgg   2820
aatgaacatg ggaaggagat atgggaagga atgttatgtg cactagaaaa agttggagga   2880
agcgtcaata tcaaatccac gtacaactac gatactataa aaaatgatct agaagacttt   2940
```

-continued

```
gcatctaggc cacaattttt acggtggttc accgaatgga gtgatgaatt ttgtcaggaa   3000
cggaagaaat tggaggcaaa ggttaaagaa tattgtaaga aggattatgt cggatgtaat   3060
aaacaaaaca cgaaggctaa taatagttgt gttagcgctt gtgaagcatt tcaacattac   3120
atgaagtcca aaatgtcaga atacgataca caaaaaaaaa aatttgaggc tgaaaaaagc   3180
gggaaggaac cagaatatga aggtttttca actaaagacg cttctgaata cttaaaagaa   3240
aaatgtttgc atggtacatg tgattgtatg gagaaagtaa aaaacattga tgattattgg   3300
aaaaatcctc ataaaacgta tgacgataac aaacttgaaa ctaaatgtga gtgtcctcaa   3360
acaccaccaa aaccatgtga aatagtaaaa acacttttgg aagataacaa tggaagacat   3420
gtagatgctt gcaatctcaa atatgagggt aaaaaagaaa aacatacttc atggaattgt   3480
aatccaaata agtttaaaaa tggagaagaa ggtgcctgta tacctccgag aagacaaaaa   3540
ttatacatat ataatttaga gaaattcact ggtggaacat cagaaattga attgagaaaa   3600
gcttttattg aatgtgctgc aatagaaacg tttttttctt ggcataaatt taaaaaggat   3660
aaagaaagag aggataaaga aaaacaagat ctagtaggat atacatcaac cgtcgatgaa   3720
aaacatcaaa aggatttaca aagtggaaaa attcctgaag aatttaaacg tcaaatgttc   3780
tatacatttg gtgattatag agatatatgt ttaggaaacg atatgggtaa tgataactat   3840
aataaaaata tatctacaaa agttaggagt attttaaata gtggggaaac acctgaagaa   3900
tggtggcaaa aacatggacc tcagatatgg gaaggtatgt tatgtgcttt aagttacgat   3960
accgaaaaac aaaaaaaggt tcaagatgtg cacaataatc ttatagcccc cccaaacaac   4020
aacaagtaca acgacgtaaa attggtttcg aaaagtggga aacttcatac ctctttatcc   4080
gattttgcaa ctgttccgca gtttttaaga tggttcgaag aatgggtcga agagttttgt   4140
agaaaaaaaa aaattaaaat tgataaaatt gaagacgaat gtcgtggaga atatgataat   4200
ggtggtaaaa aatattgtag tggtgatggt tatgattgtg acaaaagata tttatcccat   4260
aataaaatgt ttgcagattt aaattgtcta ggttgtgaga aagaatgtag aaattataaa   4320
aaatggatag aagaaaaagt agaagaattt tataaacaaa aaaagaaata cgaaaagggg   4380
tttgagaaca cacgaactaa ccttgataat aaatatgtta aagaatttta tgaaacatct   4440
gctggaaaat ataagtctgt tgacttattt ttagatacat tgaaagaaag atctcattgt   4500
agtatgggta tggtaaatag aaaaatagat tttaagaatc cgctcgaaac attttcccct   4560
tcaatatatt gtaaaacgtg ccctttatat ggagttaact gtaattcgag agaatgtgta   4620
gacattactg aaaatgagtt taagaaaaaa aatgttttag atgagattat tataaacgat   4680
aagtcacata caagtattga tatcgaaatg attgatcgta ggggacagta tatgcaagag   4740
aatttagaca atcctttgtt taaagaatca tatcttttaa aaagtgtcag agatcaaaaa   4800
tgggattgta actttattca taataagatc gatttatgtg aaataaataa gtttaatgaa   4860
aacatagaca ctgatgaaag cattacattt aaggttttga tagaacggtg gttacaagat   4920
ttcttagaag gatattatat atcaaaaaaa caaatcgatc tatttacaaa aaaagaagaa   4980
aataaatgtg aatgcgtgaa gaaatgggca gaaaaaaagg aaggagaatg ggaaaaaata   5040
aacgaacatt ttaataaaca aaaacatgat gatgcatttg atatggattt taaagtcaaa   5100
aattattttg agaaaaatgc aagtgattta aaggattgga tagataattt taaacgtcta   5160
aacaatatag atgattatca ggtttgcaat gttcataaca attgtaaaag tgcggataaa   5220
aaaaataaaa tagatatggt atctatttta ctttctgagc ttaaaaaaga aatagaaact   5280
tgtaaaaatc aaggtaacga aaaaacaaaa ataaaatgtg atgcatcacc tacaaacgac   5340
```

-continued

```
gaactagatg aagaatacga actaggcaca acggacacat ctccatccgc agctccggat   5400
atttgtaagg atgtgatcca aagtaaatct gaagaaacaa tatgtagaga tgataaaagg   5460
gtagattgta acaaggtggg taaagatgat ccaataaagg tccctatgga tccaaaatct   5520
ggtgaagatc atctcaacga gatgggagat aaacataatt gtagtggaat tatcattaaa   5580
acaaatggtg aatggaaaaa tacaaaacaa ttaaattacc cgaacccatg tgaaagcata   5640
tatgcttcac ctcgaagaca aaaattctgt gtacatgaac ttgacaaagc aaaaaaccaa   5700
aaggaattaa gaactaaatt attgactgtt gctgcaaatc aaggatataa tctagctatt   5760
aaacatcatg aatataaaga caaatatact gttaatcctt gtaatgcatt gaaatatagt   5820
ttttacgatt atcagcatat aattctagga gatgacccga tggaacctga aaaatgggat   5880
acggaaagtg cattgaaaag aatatttgga aatagaaata cagaagatgc caaacctctt   5940
agtagaaaac gtaaagattt ttggaaagaa aacaaagaat gcgtttggtc agcaatgaaa   6000
tgtggttaca acgaaggaat aaaaaagggt aataagagta ataatattcc agaatgtaag   6060
gacagtatac ctacccaatt tgatggtgtt cctcaatttt tgatgtggtt tactgaatgg   6120
agtgaagatt tttgtaatca taagaagaca catttgaaaa aattggagca ggggtgtagg   6180
ggatgtactc ttcgtattga tggcacatgt gagaaagatg gctcaggatg ccaaaaatgt   6240
tcacaagcgt gtgaagaata taaagcatgg cttcaaaatt ggaaagacca atataagaaa   6300
caaagcaaaa aatatagtgg tgataaaaaa aaagagctat ataaaactgt tcctaaagta   6360
aaaaattcaa cacatgccta tgaatattta caaacacaat tagaaaaact ttgtgaaaaa   6420
ggtaaatgtg attatacttg tatgaaaaac ccatcgacag aaaatagtac tgaaaatatg   6480
cccgaatcat tggacgtaaa acccgatata gttaaggata aatgcccttg tccaccacag   6540
aaaatagaaa aacccgattc cacattaaat tgcatagata gaagtgcatt tgaattatat   6600
gcaaaagcaa aaagtgattt acatggtgta aaagataaat taaagggtaa taatacaaaa   6660
aatatatacg aagaaacaac taatggtaaa aatgatgata atattatctg taaaattaat   6720
gagagtattt ctaaacaaaa caatgtatgt aaaaaaaatg aaaatctttt tgatgatata   6780
gacaaatggg actgtaaaaa acgaacaaat acagtgccca ttgaaaatat atgtattcct   6840
ccaagaagga aacttatgtg tgcatatcca ttaaaaaatt taggagtaaa aaaaaatact   6900
tcagaagtat tgttcaacaa agtattgcgt acagcagcat atgaaggaaa acatataaag   6960
gaatcatggg aaaaagcaga aaaatccaag aaaaaaaaaa cccaaatatg tgatgctatg   7020
aaatacagtt ttgcagattt aggagatata attagaggaa gagatatatt gatatttaat   7080
aatggtaata atgaaattga gagagactta aaagctgttt ttcagtcaat atacgataaa   7140
tggaaatctg acagtaataa taataaagat aaatacccg  acttaacctc ttttcgttct   7200
gcctggtggg atgctaatag aaaagatatt tggaaagcta tgacatgtgg tgcaccggaa   7260
gatgctacgc tttttaaaaa actagaaaaa tggggaattc ctaatttaat tttgtcacaa   7320
cataaatgtg ggcataatga cgatcctcct attgatgatt acatacctca acggttaaga   7380
tggatgaagg aatggggaga atatgtttgc aaaatattaa atgaaaacgt gaatgatatg   7440
aagaacgatt gtgataaatg tacactaaat gataaaaaat gttcagatga agatgatggt   7500
aataaatgta gaagttgtaa agaaaaatgt aaagaatata ctaaacttat atacaatctg   7560
aaatcacaat tttatatact agaaaaacat tataacgaat tatatacaaa agcacaaaat   7620
aatacaacat attttacaaa tgataacgat aaaaaggtta ttgaattttt taaaaaagtt   7680
```

-continued

```
aaaaaggatt gtgatgtggg aactcctgat aaatatctcg ataaagctat tcattgtatc   7740
cattatgatt ttactaaaaa tggaaccaaa tctaagccat atgtcttcaa caatcaacca   7800
gaaaagtata aaaatctttg tagttgtact attactaatc atccgttaga caaatgtcct   7860
ttacctgata aaacagatga ttattgcaaa atcattagac atattaatcc gtgtataaca   7920
ataaatttgg ataataattt ggatacgtgg actggatttg ttgtgcataa tataagtcac   7980
aaaaataaag gtgtgcttgt acctccaaga agaagacatt tatgtacaag agaattaact   8040
ggaattagat atcgtaaaaa tgataaagat aatttgaaac aaaatcttat tgattctgct   8100
tttaatcaag gaatactttt aggaaaaaca tttaaagatt acagcgatca aggtttggaa   8160
tatatgaaat atagttttgc tgattatgga gatataatta aagctaaaga tatgatagga   8220
ggttcaaata ttgatgattt caataatgat ttaaaaaaaa tgtttccaga acatcatagt   8280
gagaatatgg gaaaaactac tattagtcgt gaacagtggt gggaagcaaa taaaacacac   8340
gtatggcacg ctatgttatg cgggtatcat caaggaataa ttaatccaaa cttatcaaga   8400
agaagaccaa aaccattaga agaaggaaca caatcgtcga tagcaactaa aactattcct   8460
tcaaattggt gtcaattacc taatgattat agcactgatc agtttcttcg ttggtttcag   8520
gaatggattg aaaatttttg tacaaggaaa aaagtattag agaaagaagc acaagaacaa   8580
tgtaagaata ttacatgtaa taacgatact ggaaaaacga acactaaatg tactgaagca   8640
tgtaaaaatt atagtaattt tattttaata aaaaaaaagg agtatgagtc actaaatagt   8700
caatacgata tgaattataa aaaaatagta gaacataaaa atgccctaga atatttcaaa   8760
gataaatgta aaaataattg tgaatgtctc tctaaacata ttgataatgg aaaaaattgg   8820
aaagaaccat atgaaactat cgatgactca gaactcatag gtaaatgtaa atgcaaaaaa   8880
gttaaaccca aaactcctga cgtaattcct gcaggggcaa ctgaaacaaa agaaaaagat   8940
acacctcatg cacctgaaaa acctcaacaa cccccacaac ccttaccacc atccgacgaa   9000
ccctttgacc cgaccatcct acaaacgacc attccttttg gaatcgcttt ggcattagga   9060
tcgatagcgt ttcttttcat gaaaaaaaaa ccgaaatctc cagttgacct cttacgtgta   9120
ctgaatatcc cgaaacgaga ttatgaaatg cctacgttga aatcaaaaaa tcgatatata   9180
ccctatgcta gtgatcgata taaaggtaaa acatacattt atatggaagg agatagcagt   9240
ggagatgaaa aatatgcatt tatgtctgat actactgatg taacttcctc agaaagtgaa   9300
tatgaagaat tggatattaa tgatatatat gtaccaggta gtcctaaata taaaacattg   9360
atagaagtag tattggaacc atcaaaaagt aatggtaaca cactaggtga tgatatggta   9420
cctaccacta atacatttac agatgaggaa tggaatgaat tgaaacatga ttttatatca   9480
caatatgtac aacgtgaacc actggatgta ccacaatatg atgaatcaac acagttacca   9540
atgaatatag taggtaacgt tttagatgat ggtatggatg aaaaaccttt tattacttct   9600
attcatgata gagatttata tactggagaa gaaattagtt ataatattaa tatgagtact   9660
aatagtatgg atgatccaaa atatgtatca aataatgtat attctggtat agatttaatt   9720
aatgatacat taagtggtga tcgtattgat atatatgatg aattattgaa acgaaaagaa   9780
aatgaattat ttggtacaaa tcatgtgaaa caaacaagta tacatagtgt tgccaaacta   9840
acaaatagtg accccatcca caaccaatta gatttgttcc atacatggtt agatagacat   9900
agagatatgt gcaatacgtg gaataccaag gaagaattat tagataaatt gaatgaacaa   9960
tggaataaag ataatgatgg tggtgatata ccaaatgata acaaaaagtt gaatacggat  10020
gtttcgtttg aaatagatat ggatgaaact aaaggaaaga aggaatttag taatatggat  10080
```

```
actatcttgg atgatatgga agatgatata tattatgatg taaatgatga aaacccatct  10140

gtggataata tacctatgga tcataataaa gtagatgtac caaagaaagt acatgttgaa  10200

atgaaaatcc ttaataatac atccaatgga tcgttggaac aagaatttcc catatcggat  10260

gtatggaata tataa                                                   10275


<210> SEQ ID NO 3
<211> LENGTH: 2790
<212> TYPE: PRT
<213> ORGANISM: Plasmodium falciparum

<400> SEQUENCE: 3

Met Thr Ser Lys Arg Gly Asn Arg Thr Val Ile Asn Leu Ser Val Thr
1               5                   10                  15

Asp Val Leu Glu Lys Ile Ala Leu Gln Ile Tyr Lys Glu Glu Asn Glu
            20                  25                  30

Lys Lys Ile Pro His Glu Ser Glu Leu Ile Gly Thr Leu Trp Lys Ala
        35                  40                  45

Gln Phe Ser Asp Gly Leu Ser Gly Ser Phe Gly Asp Val Arg Ser Gly
    50                  55                  60

Pro Ser Asn Ser Cys Asn Leu His His Lys Tyr Tyr Thr Asn Ile Lys
65                  70                  75                  80

Asn Gly Tyr Pro Pro Ala Arg Asn Pro Cys Asp Gly Arg Asn Glu Lys
                85                  90                  95

Arg Phe Ser Asn Glu Gly Glu Ala Glu Cys Gly Ser Asp Lys Ile Arg
            100                 105                 110

Val Ile Gly Lys Gly Asp Gly Thr Ala Cys Val Pro Phe Arg Arg Gln
        115                 120                 125

Asn Met Cys Asp Lys Asn Leu Glu Tyr Leu Ile Asn Lys Asn Thr Lys
    130                 135                 140

Thr Thr His Asp Leu Leu Gly Asn Val Leu Val Thr Ala Lys Tyr Glu
145                 150                 155                 160

Gly Ala Ser Ile Val Ala Lys His Pro His Lys Asp Thr Ser Glu Val
                165                 170                 175

Cys Thr Ala Leu Ala Arg Ser Phe Ala Asp Ile Gly Asp Ile Val Arg
            180                 185                 190

Gly Arg Asp Met Phe Leu Pro Asn Lys Asp Asp Lys Val Gln Lys Gly
        195                 200                 205

Leu Arg Glu Val Phe Lys Lys Ile His Asp Asn Leu Ser Ser Ser Val
    210                 215                 220

Lys Pro His Tyr Lys Asp Asp Gly Ser Gly Asn Tyr Val Lys Leu Arg
225                 230                 235                 240

Glu Asp Trp Trp Ala Ile Asn Arg Lys Glu Val Trp Asn Ala Leu Thr
                245                 250                 255

Cys Glu Ala Pro Gln Ser Val His Tyr Phe Ile Lys Thr Ser His Gly
            260                 265                 270

Thr Arg Gly Phe Thr Ser Gln Gly Lys Cys Gly Arg Asn Glu Thr Asn
        275                 280                 285

Val Pro Thr Asn Leu Asp Tyr Val Pro Gln Tyr Leu Arg Trp Phe Asp
    290                 295                 300

Glu Trp Ala Glu Glu Phe Cys Arg Leu Arg Asn His Lys Leu Gln Asn
305                 310                 315                 320

Val Lys Lys Glu Cys Arg Gly Glu Asn Ile Gly Asp Lys Tyr Cys Ser
                325                 330                 335
```

-continued

```
Gly Asp Gly Glu Asp Cys Glu Lys Ile Val Arg Gln Asp Tyr Asn Ile
            340                 345                 350

Arg Ser Asp Phe Leu Cys Pro Ser Cys Lys Lys Glu Cys Thr Asn Tyr
        355                 360                 365

Lys Lys Trp Ile Asp Thr Lys Gln Gly Glu Phe Asn Lys Gln Lys Lys
    370                 375                 380

Lys Tyr Glu Lys Glu Ile Lys Lys Val Glu Ser Asn Ser Asp Thr Thr
385                 390                 395                 400

Tyr Asp Lys Lys Val Tyr Lys Ile Leu Lys Glu Met Tyr Pro Leu Asn
                405                 410                 415

Ser Glu Phe Val Ala Thr Leu Lys Glu Ala Pro Tyr Cys Asn Asn Asn
            420                 425                 430

Asn Val Asp Gly Thr Ile Asp Phe Asn Lys Pro Asp Asp Thr Phe Ser
        435                 440                 445

Arg Ser Asp Tyr Cys Lys Ser Cys Pro Val Phe Gly Val Ile Cys Thr
    450                 455                 460

Arg Gly Glu Cys Thr Glu Val Lys Glu Asp Thr Cys Ser Lys Met Asn
465                 470                 475                 480

Val Lys Val Pro Lys Lys Ile Thr Asn Lys Glu Asp Pro Ile Asn Ile
                485                 490                 495

Gly Ile Leu Val Ser Asp Asp Arg Val Ser Val Ile Pro Asn Glu Leu
            500                 505                 510

Glu Asn Val Cys Lys Asp Thr Gly Leu Phe Lys Gly Ile Arg Lys Asp
        515                 520                 525

Gln Arg Ser Cys Asn Tyr Leu Cys Asn Leu Asp Val Cys Asp Leu Ser
    530                 535                 540

His Asn Lys Asn Asn Thr His Ile Asp Lys Arg Ile Ser Ile Arg Val
545                 550                 555                 560

Leu Phe Lys Arg Trp Leu Glu Tyr Phe Phe Lys Asp Tyr Ser Lys Leu
                565                 570                 575

Lys Lys Lys Leu Asn Ser Cys Thr Asn Asn Gly Glu Lys Ser Ile Cys
            580                 585                 590

Ile Asn Lys Cys Lys Lys Lys Cys Glu Cys Val Gly Lys Trp Val Glu
        595                 600                 605

Glu Lys Arg Thr Glu Trp Glu Lys Val Arg Lys Arg Tyr Phe Ser Gln
    610                 615                 620

Tyr Asn Val Asp Asp Ser Gln Lys Ser Tyr Thr Val Lys Ser Ile Val
625                 630                 635                 640

Asn Gly Asn Val Asp Arg Ser Asp Ile Asn Asn Ser Leu Asp Glu Ser
                645                 650                 655

Glu Asp Ile Glu Thr Leu Lys Glu Ser Asp Thr Cys Tyr Asn Ser Asp
            660                 665                 670

Ser Ala Lys Lys Gln Lys Cys Glu Lys Asn Asp Val Ile Thr Ile Leu
        675                 680                 685

Ile Asp Arg Leu Lys Lys Lys Ile Asp Asp Cys Glu Lys Gln His Asp
    690                 695                 700

Asn Arg Thr Asn Gln Ile Cys Cys Asp Glu Leu Pro Glu Ser Lys Glu
705                 710                 715                 720

Asp Asp Glu Asp Glu Glu Glu Glu Gly Lys Lys Lys Lys Asn Ala Lys
                725                 730                 735

Gln Leu Glu Val Thr Asn Glu Lys Lys Glu Gln Glu Asp Lys Asn Leu
            740                 745                 750
```

-continued

```
Phe Gln Val Cys Gln Lys Met Lys Lys Val Ile Thr Asp Asn Asn Gly
        755                 760                 765

Glu Arg Ile Arg Asn Gln Arg Cys Asn Glu Lys Thr Asp Arg Lys Trp
    770                 775                 780

Asp Cys Ser Thr Asn Glu Ile Pro Thr Asn His Thr Gly Ala Cys Met
785                 790                 795                 800

Pro Pro Arg Arg Ile Ser Leu Cys Ile Arg Pro Leu Arg Tyr Leu Val
                805                 810                 815

Asp Asn Gly Gly Lys Lys Ser Ile Asp Asp Tyr Lys Asn Ala Phe Thr
            820                 825                 830

Glu Cys Ala Ser Ile Glu Thr Tyr Leu Leu Trp Gln Lys Tyr Lys Arg
        835                 840                 845

Thr Asn Gly Ala Glu Asp Lys Leu Lys Asp Gly Glu Ile Pro Asn Asp
    850                 855                 860

Phe Leu Arg Ile Met Tyr Tyr Thr Tyr Gly Asp Tyr Arg Asp Ile Phe
865                 870                 875                 880

Leu Gly Thr Asp Ile Ser Lys Asn Pro Asn Ile Lys Asn Ile Ser Asn
                885                 890                 895

Lys Val Lys Asn Ile Leu Lys Phe Lys Lys Ser Met Asp Glu Ser Gly
            900                 905                 910

Lys Asn Gln Asp Glu Asn Ala Lys Val Gln Ser Ser Trp Asp Glu His
        915                 920                 925

Lys Arg Asp Ile Trp Lys Gly Met Leu Cys Gly Leu Thr Tyr Asp Ile
    930                 935                 940

Gln Asn Glu Lys Lys Asp Ile Leu Lys Ile Leu Asn Asn Lys Tyr Asn
945                 950                 955                 960

Tyr Pro Cys Asp Leu Glu Val Phe Ala Ser Lys Pro Gln Phe Phe Arg
                965                 970                 975

Trp Phe Ile Glu Trp Ala Glu Asp Tyr Cys Arg Lys Tyr Asn Asp Glu
            980                 985                 990

Tyr Glu Lys Leu Gln Thr Ala Cys  Ser Thr Val Asp Cys  Ser Lys Asp
        995                 1000                1005

Pro Thr  Asp Ser Glu Lys Gln  Lys Cys Lys Asn Ala  Cys Asp Asn
    1010                1015                1020

Phe Lys  Thr Phe Val Glu Gly  Trp Lys Lys Gln Tyr  Asp Ser Gln
    1025                1030                1035

Lys Asn  Lys Phe Asn Lys Ile  Lys Ile Glu Ala Asn  Ile Lys Asn
    1040                1045                1050

Thr Tyr  Lys Gly Ile Glu Asn  Lys Glu Ala Tyr Val  Phe Leu Ser
    1055                1060                1065

Glu Glu  Cys Lys Gly Lys Cys  Asp Cys Ile Lys Tyr  Lys Thr Asp
    1070                1075                1080

Tyr Asp  Thr Asn Ala Asn Asp  Pro Lys Gly Phe Asp  Thr Pro Pro
    1085                1090                1095

Lys Glu  Gln Lys Asp Asn Cys  Glu Cys Val Leu Arg  Lys Lys Ser
    1100                1105                1110

Ala Cys  Glu Asn Asn Glu Val  Pro Lys Gly Arg Thr  Gln Ser Gln
    1115                1120                1125

Met Thr  Cys Ala Asp Leu Lys  Asn Glu Ser Pro Ser  Lys Gly Asn
    1130                1135                1140

Asn Asn  Thr Gly Asn Asn His  Lys Glu Thr Ile Thr  Phe Ser Cys
    1145                1150                1155

Asn Lys  Ser Asn Leu Ile Gly  Leu Gly Ala Gln Trp  Lys Lys Ile
```

-continued

```
    1160                1165                1170

Thr Asp  Asp Gly Leu Tyr Ala  Ser Pro Arg Thr Arg  Gln Leu Cys
    1175                1180                1185

Leu Lys  His Val Ile Asp Ile  Gly Arg Asn Asn Thr  Lys Lys Asn
    1190                1195                1200

Asn Ile  Thr Glu Glu Glu Phe  Ile Asn Val Leu Gln  Lys Asp Ala
    1205                1210                1215

Tyr Ala  Glu Gly Lys Leu Leu  Tyr Met Tyr Tyr Asn  Ser Asn Gly
    1220                1225                1230

Lys Ile  Ser Ile Phe Gln Asn  Gly Glu Lys Leu Lys  Leu Asp Asp
    1235                1240                1245

Ile Glu  Lys His Thr His Glu  Ala Met Lys Arg Ser  Tyr Ala Asp
    1250                1255                1260

Tyr Gly  Asp Leu Ile Lys Gly  Thr Thr Lys Tyr Thr  Gln Tyr Asn
    1265                1270                1275

Asp Tyr  Asn Lys Ile Ser Asp  Ile Ile Asn Val Val  Thr Lys Lys
    1280                1285                1290

Lys Asn  Ser Ala Ser Ile Asn  Asp Ile Tyr Glu Arg  Glu Glu Phe
    1295                1300                1305

Trp Glu  Lys Tyr Arg Ala Asp  Val Trp Asn Ala Met  Leu Cys Gly
    1310                1315                1320

Tyr Lys  Asp Val Ser Asn Lys  Thr Phe Asp Gly Asn  Asp Asp Met
    1325                1330                1335

Cys Asn  Leu Pro Asn Thr Asp  Lys Glu Glu Glu Phe  Leu Arg Trp
    1340                1345                1350

Phe Lys  Glu Trp Asn Glu Asn  Phe Cys Ile Thr Gln  Ile Lys Arg
    1355                1360                1365

Ala Glu  Lys Leu Lys Asn Glu  Cys Asn Asn Phe Asn  Cys Ser Ser
    1370                1375                1380

Ile Lys  Ser Lys Lys Asp Asp  Ile Lys Ser Lys Cys  Val Lys Ala
    1385                1390                1395

Cys Ile  Asn Tyr Lys Lys Phe  Val Lys Glu Ser Lys  Thr Gln Tyr
    1400                1405                1410

Glu Asp  Gln Lys Arg Thr Tyr  Asn Glu Arg His Asn  Lys Thr Asn
    1415                1420                1425

Lys Asp  Ile Pro Thr Phe Leu  Lys Asp Asn Cys Ile  His Lys Asn
    1430                1435                1440

Cys Asp  Cys Ile Ser Ile Lys  Phe Asn His Lys Asp  Asn Trp Glu
    1445                1450                1455

Lys Ser  Phe Phe Glu Ser Leu  Asp Ser Ser Asp Ile  Lys Asn Lys
    1460                1465                1470

Cys Glu  Cys Leu Lys Leu Glu  Glu Glu Ser Asn Thr  Thr Glu Arg
    1475                1480                1485

Tyr Ile  Ser Lys Glu Asp Pro  Gln Tyr His Pro Glu  Tyr Lys Gly
    1490                1495                1500

Asp Gly  Lys Val Asn Tyr Lys  Tyr Glu Lys Gly Lys  Pro Lys Ala
    1505                1510                1515

Leu Pro  Ser Ile Tyr Pro Leu  Asn Cys Ala Glu Lys  Val Ala Asp
    1520                1525                1530

Glu Leu  Arg Met Tyr Ala Glu  Asn Ser Leu Asp Thr  Asn Thr Lys
    1535                1540                1545

Leu Lys  Ala Lys Ile Ser Lys  Ser Ile Asp Thr Asn  Glu Gln Asn
    1550                1555                1560
```

```
Ala Thr Asn Asp Glu Ile Asp Cys Asn Ile Tyr Asn Asn Ile Ser
    1565                1570                1575

Asn Gly Gln Lys Asn Thr Cys Glu His Asn Gly Asn Thr Phe His
    1580                1585                1590

Asp Lys Asp Glu Trp Asp Cys Asn Lys Gly Thr Asn Lys Leu Tyr
    1595                1600                1605

Glu Asn Asp Ile Cys Leu Pro Pro Arg Arg Lys His Met Cys Thr
    1610                1615                1620

Lys Gln Leu Glu Asn Ile Ser Thr Ala Ser Ile Thr Thr Thr Asp
    1625                1630                1635

Asp Leu Leu Lys Glu Val Leu Ile Thr Ala Val Asn Glu Gly Lys
    1640                1645                1650

Arg Leu Lys Gln Gln Trp Glu Lys Thr Glu Asn Glu Ala Gln Lys
    1655                1660                1665

Lys Lys His Phe Leu Cys Asp Ala Met Lys Tyr Ser Phe Ala Asp
    1670                1675                1680

Leu Ala Asp Ile Ile Arg Gly Thr Asp Ile Trp Lys Gly Asn Arg
    1685                1690                1695

Glu Gln Gln Lys Ile Gln Glu Arg Leu Val Lys Ile Phe Arg Asn
    1700                1705                1710

Ile Tyr Asp Asn Leu Glu Lys Asp Glu Tyr Glu Lys Tyr Lys Tyr
    1715                1720                1725

Gly Thr Lys Tyr Gln Asn Leu Arg Ser Ala Trp Trp Asp Ala His
    1730                1735                1740

Arg Lys Lys Ile Trp Asn Ala Met Thr Cys Ser Ala Pro Gly Asp
    1745                1750                1755

Phe Leu Phe Val Lys Arg Gly Lys Gly Asp Gly Ser Asp Ile Glu
    1760                1765                1770

Phe Leu Thr Phe Ser Glu His Lys Lys Cys Gly His Asp Lys Glu
    1775                1780                1785

Pro Pro Val Tyr Asp Tyr Val Pro Gln Ile Leu Arg Trp Ile Thr
    1790                1795                1800

Glu Trp Ser Glu His Phe Cys Glu Leu Gln Glu Lys Asn Tyr Tyr
    1805                1810                1815

Leu Leu Lys Glu Lys Cys Ala Asp Tyr Ile Gln Lys Asp Ser Lys
    1820                1825                1830

Pro Ile Asp Asp Ser His Asn Ile Lys Cys Asn Thr Cys Lys Thr
    1835                1840                1845

Lys Cys Glu Glu Tyr Ser Lys Phe Ile Lys Lys Trp Asn Ser Gln
    1850                1855                1860

Tyr Ile Asn Leu Glu Lys Lys Phe Lys Glu Leu Tyr Asp Glu Ala
    1865                1870                1875

Asn Asn Thr Lys Ser Tyr Glu Glu Leu Tyr Arg Ile Gly Lys Pro
    1880                1885                1890

Ser His Arg Asn His Tyr Glu Asp Glu Asn Leu Ile Gln Phe Leu
    1895                1900                1905

Gln Asn Val Lys Ser Glu Cys Asn Glu Pro Asn Thr Val Asp Lys
    1910                1915                1920

Tyr Leu Met Tyr Thr Ser Asp Cys Arg Arg Val Lys Phe Ser Asn
    1925                1930                1935

Thr Ile Asp Thr Asn Val Asn Lys Pro Thr Ala Asp Val Thr His
    1940                1945                1950
```

-continued

```
Asn Thr  Ile Asn Gly Pro Ser  Ser Asn Leu Pro Val  Val Thr Glu
    1955                 1960                 1965

Thr Asn  Ile Lys Asn Glu Leu  Arg Glu Tyr Ala Phe  Leu Glu Thr
    1970                 1975                 1980

Pro Glu  Gly Tyr Gly Asn Ala  Cys Lys Cys Lys Gly  Pro Glu Pro
    1985                 1990                 1995

Leu Asp  Arg Cys Pro Glu Asn  Asp Asn Ile Ser Asn  Tyr Cys Asn
    2000                 2005                 2010

Asp Phe  Val Ser Val Pro Glu  Cys Thr Ala Lys Ile  Tyr Lys Asp
    2015                 2020                 2025

Glu Ile  Asp His Trp Asn Asn  Ala Asn Val Lys Phe  Lys Thr Ser
    2030                 2035                 2040

Ile Asn  Asn Gly Val Leu Val  Pro Pro Arg Arg Ser  His Ile Cys
    2045                 2050                 2055

Leu Lys  Asn Met Ile Thr Lys  Asn Tyr Asp Lys Lys  Lys Asn Gly
    2060                 2065                 2070

Met Glu  Lys Phe Lys Thr Asp  Leu Leu Gln Val Ala  Tyr Asn Glu
    2075                 2080                 2085

Gly Tyr  Phe Leu Cys Gln Lys  Tyr Asp Lys Gln Pro  Arg Asp Val
    2090                 2095                 2100

Leu Glu  Ala Met Lys Tyr Thr  Phe Ala Asp Ile Ala  Asp Ile Val
    2105                 2110                 2115

Lys Gly  Arg Asp Met Ile Asn  Lys Asp Ile Ser Ala  Lys Leu Arg
    2120                 2125                 2130

Lys Leu  Leu Asp Ile Lys Val  Glu Pro Lys Ala Pro  Arg Lys Trp
    2135                 2140                 2145

Trp Lys  Tyr Asn Lys Ala His  Val Trp His Ala Met  Leu Cys Gly
    2150                 2155                 2160

Tyr Arg  Lys Gly Gly Gly Thr  Ile Thr Asn Asp Glu  Cys Asn Val
    2165                 2170                 2175

Pro Asp  Glu Glu Tyr Thr Tyr  Gln Phe Leu Arg Trp  Phe Gln Glu
    2180                 2185                 2190

Trp Ile  Lys Lys Phe Cys Thr  Gly Gln Gln Lys Leu  Tyr Asp Asp
    2195                 2200                 2205

Val Gln  Thr Lys Cys Ser Ser  Ala Asn Cys Asn Arg  Asp Asp Gly
    2210                 2215                 2220

Thr Ile  Ser Leu Pro Glu Cys  Glu Ser Ser Cys Val  Gln Tyr Lys
    2225                 2230                 2235

Asn Tyr  Ile Thr Arg Lys Arg  Gln Glu Tyr Arg Ser  Leu Asn His
    2240                 2245                 2250

Gln Tyr  Asn Met Asn Phe Lys  Glu Gln Lys Ala Gln  Gly Met Lys
    2255                 2260                 2265

Ala Thr  Gln Tyr Ile Asp Asp  Lys Cys Asn Ser Lys  Cys Asp Cys
    2270                 2275                 2280

Leu Ile  Lys Tyr Ile Asp Arg  Glu Lys Glu Trp Thr  Asn Ile Tyr
    2285                 2290                 2295

Asp Ser  Leu Glu Asn Asn Asp  Leu Lys Asn Lys Cys  Asp Cys Lys
    2300                 2305                 2310

Gln Ile  Lys Pro Lys Arg His  Pro Lys Glu Val Asn  Pro Glu Glu
    2315                 2320                 2325

Glu Pro  Ala Asn Ser Glu Pro  Asp Tyr Ile Val Pro  Leu Val Pro
    2330                 2335                 2340

Gln Lys  Pro Ser Thr Pro Glu  Val Pro Pro Pro Pro  Pro Pro Pro
```

```
    2345                2350                2355

Leu Pro  Thr Pro Ser Asp Glu  Pro Phe Asn Arg Asp  Ile Leu Glu
    2360                2365                2370

Lys Thr  Ile Pro Phe Gly Ile  Ala Leu Ala Leu Cys  Ser Ile Ala
    2375                2380                2385

Phe Leu  Phe Ile Lys Lys Lys  Pro Lys Ser Ser Val  Asp Leu Leu
    2390                2395                2400

Arg Val  Ile Asp Ile His Lys  Gly Asp Tyr Asp Ile  Pro Thr Leu
    2405                2410                2415

Lys Ser  Lys Asn Arg Tyr Ile  Pro Tyr Lys Ser Ala  Gln Tyr Lys
    2420                2425                2430

Gly Lys  Thr Tyr Ile Tyr Met  Glu Gly Asp Ser Asp  Ser Gly His
    2435                2440                2445

Tyr Tyr  Glu Asp Thr Thr Asp  Ile Thr Ser Ser Glu  Ser Glu Tyr
    2450                2455                2460

Glu Glu  Met Asp Ile Asn Asp  Ile Tyr Val Pro Gly  Ser Pro Lys
    2465                2470                2475

Tyr Lys  Thr Leu Ile Glu Val  Val Leu Glu Pro Ser  Lys Arg Asp
    2480                2485                2490

Thr Gln  Asn Asp Ile Pro Ser  Asp Asn Thr Pro Ser  Tyr Lys Leu
    2495                2500                2505

Thr Asp  Glu Glu Trp Asn Gln  Leu Lys His Asp Phe  Ile Ser Gln
    2510                2515                2520

Tyr Leu  Pro Asn Thr Glu Pro  Asn Asn Asn Tyr Arg  Ser Gly Asn
    2525                2530                2535

Ser Pro  Thr Asn Thr Asn Asn  Thr Thr Thr Ser His  Asp Asn Met
    2540                2545                2550

Gly Glu  Lys Pro Phe Ile Thr  Ser Ile His Asp Arg  Asp Leu Tyr
    2555                2560                2565

Thr Gly  Glu Glu Ile Ser Tyr  Asn Ile Asn Met Ser  Thr Asn Thr
    2570                2575                2580

Asn Asn  Asp Ile Pro Lys Tyr  Val Ser Asn Asn Val  Tyr Ser Gly
    2585                2590                2595

Ile Asp  Leu Ile Asn Asp Thr  Leu Ser Gly Asn Lys  His Ile Asp
    2600                2605                2610

Ile Tyr  Asp Glu Val Leu Lys  Arg Lys Glu Asn Glu  Leu Phe Gly
    2615                2620                2625

Thr Asn  His Pro Lys Asn Thr  Ser Asn Asn Ser Val  Ala Lys Leu
    2630                2635                2640

Thr Asn  Ser Asp Pro Ile Met  Asn Gln Leu Asp Leu  Leu His Lys
    2645                2650                2655

Trp Leu  Asp Arg His Arg Asp  Met Cys Asp Lys Trp  Asn Thr Lys
    2660                2665                2670

Glu Glu  Leu Leu Asp Lys Leu  Asn Glu Gln Trp Asn  Lys Asp Asn
    2675                2680                2685

Asp Val  Gly Gly Asp Ile Ser  Thr Ser Asn Gly Asn  Lys Thr Leu
    2690                2695                2700

Asn Thr  Asn Val Ser Ile Glu  Ile Asp Met Asp Glu  Thr Lys Gly
    2705                2710                2715

Lys Lys  Glu Phe Ser Asn Met  Asp Thr Ile Leu Asp  Asn Ile Glu
    2720                2725                2730

Asp Asp  Ile Tyr Tyr Asp Val  Asn Asp Glu Asn Pro  Ser Met Asp
    2735                2740                2745
```

```
Asp Ile  Pro Met Asp His Asn  Lys Val Asp Val Pro  Lys Lys Val
    2750                 2755                 2760

His Val  Glu Met Lys Ile Leu  Asn Asn Thr Phe Asn  Gly Ser Leu
    2765                 2770                 2775

Glu Pro  Glu Phe Pro Ile Ser  Asp Val Trp Asn Ile
    2780                 2785                 2790
```

```
<210> SEQ ID NO 4
<211> LENGTH: 8373
<212> TYPE: DNA
<213> ORGANISM: Plasmodium falciparum

<400> SEQUENCE: 4

atgacgtcaa aacgtggaaa tcgaactgta attaatctta gtgtaacgga tgttctagaa     60
aaaattgcat tacaaatata taaagaggaa aatgaaaaaa agattccaca tgaaagtgaa    120
ttgataggca cattatggaa agcacaattt tctgatggct tgagtggttc atttggtgat    180
gtaaggtctg gtccttcaaa ttcatgcaat cttcatcaca aatactatac taatataaag    240
aatggatatc cacccgcaag gaatccttgc gatggtagaa atgaaaaacg tttttcaaac    300
gaaggtgaag cagaatgtgg tagtgataaa ataagggtta ttggaaaagg tgatggtaca    360
gcatgtgtac catttagaag gcaaaatatg tgtgataaaa atttagaata tttgattaat    420
aaaaacacga aaactactca tgatttattg ggaaatgtat tagttacagc aaaatatgaa    480
ggtgcctcta ttgttgcaaa gcatccacat aaagatactt cagaagtatg tactgcactt    540
gcacgaagtt ttgcagatat aggtgatatt gtaagaggaa gagatatgtt tttacctaat    600
aaggatgata aagtacaaaa aggtctaaga gaagttttca agaaaataca tgataatttg    660
tcatcttccg taaaaccaca ttacaaagat gatggatctg gaaattacgt caaattaaga    720
gaagattggt gggcaattaa tagaaaggag gtatggaatg cattaacatg tgaagctcca    780
caaagtgttc attattttat aaaaacgtca catggaacaa gaggttttac aagtcaagga    840
aaatgtggcc gtaatgaaac aaacgttcct acaaatcttg actatgttcc tcaatattta    900
cgctggttcg atgaatgggc agaagagttt tgtcgattaa ggaatcataa gttacaaaac    960
gttaagaaag agtgtcgtgg agaaaatata ggtgacaaat attgtagtgg tgatggtgag   1020
gattgtgaaa agattgttcg tcaggattat aatattcgtt cggatttttt atgtccgagc   1080
tgtaaaaagg aatgtacaaa ttataaaaaa tggatagaca caaaacaggg agaatttaat   1140
aaacagaaaa aaaaatacga aaaagaaatt aaaaaagttg aaagtaattc tgataccaca   1200
tatgataaaa aagtttataa aattctaaaa gaaatgtacc ctttaaattc agaatttgta   1260
gcaacattaa aagaagctcc ctattgtaat aacaataatg tagacggtac aatagatttt   1320
aataaaccag atgatacatt ttctcgttca gactattgta aatcatgtcc tgtatttggt   1380
gttatttgta caagaggtga gtgtactgaa gttaaggaag atacatgtag taaaatgaat   1440
gttaaggttc cgaaaaaaat tacaaataag gaagatccta ttaatatagg tattcttgtt   1500
agtgatgaca gagtaagtgt aattccaaat gaattagaga atgtttgcaa agatacaggt   1560
ctctttaaag gtattagaaa agatcaacgg tcatgtaatt acttatgtaa tttagatgta   1620
tgtgacctga gtcataataa aaacaataca catatagata aacgtatttc tattagagta   1680
ttgtttaaac gttggttaga atattttttt aaagattata gtaaattaaa aaaaaaactg   1740
aattcatgta caaataatgg agaaaaatcc atatgtataa ataaatgtaa aaaaaaatgt   1800
gaatgtgtgg gaaaatgggt agaagaaaaa aggacagaat gggaaaaagt aagaaagcgt   1860
```

```
tacttcagtc aatataatgt tgatgattca caaaaatcgt atacagtgaa aagtattgta   1920
aatggaaatg tagatcgtag tgatattaat aattcattag atgagagcga agatatagaa   1980
acgttgaaag aatcagatac atgttataat tctgatagcg caaaaaaaca aaaatgtgaa   2040
aaaaacgacg tcataactat tttaattgat agacttaaaa aaaaaattga tgattgtgaa   2100
aagcaacatg ataatagaac taatcaaatt tgttgtgatg agttacctga aagtaaagaa   2160
gatgatgaag atgaagagga agaagggaaa aagaaaaaaa atgcaaagca attggaagta   2220
actaatgaga aaaaagaaca agaagacaaa aacttgtttc aagtgtgcca aaaaatgaag   2280
aaggtaatta cggataataa tggagaaaga atcagaaacc agcgttgcaa tgaaaaaact   2340
gatagaaaat gggattgtag tactaatgaa attcctacaa atcatactgg agcttgtatg   2400
ccaccaagaa gaatatcatt atgtattcgg cctttacgat atttggtaga taacggagga   2460
aaaaaaagca tagatgatta taaaaatgcg tttactgaat gtgcatcaat agaaacgtat   2520
ttgttatggc aaaaatacaa aagaactaat ggagcagaag ataaattaaa agatggagag   2580
attccaaatg attttctaag aataatgtat tatacatatg gagattatag agatatattt   2640
ttgggaacag atatttctaa aaatcctaat attaaaaata tatcaaataa ggttaaaaat   2700
atattgaaat tcaaaaagag catggacgaa tcaggtaaaa atcaggatga aaatgcgaaa   2760
gttcaatctt cgtgggatga acataaaagg gacatatgga aaggaatgtt atgtggatta   2820
acctatgata tccaaaatga aaagaaagat attctcaaaa ttctcaataa caagtacaat   2880
tacccatgcg atcttgaagt gtttgcatct aaaccacaat tttttcgttg gtttattgaa   2940
tgggcagaag attattgtag aaaatacaat gatgagtatg aaaaattaca gacggcgtgt   3000
agtacggtag attgtagtaa agaccctact gattctgaaa aacaaaaatg taaaaacgct   3060
tgtgataatt tcaaaacatt cgttgaaggt tggaaaaaac aatatgatag tcaaaaaaat   3120
aaatttaata agataaaaat tgaagctaat ataaagaata catataaagg tatagaaaat   3180
aaagaagctt atgtattttt aagtgaagaa tgtaaaggaa aatgtgactg tataaaatat   3240
aaaacagact atgatacaaa tgcaaatgat cctaaaggtt tcgatacacc accgaaagaa   3300
caaaaagata attgtgaatg tgtgttgaga aaaaaatcgg catgtgaaaa taatgaagta   3360
cctaaaggtc gaacacaatc tcaaatgaca tgtgctgatc taaaaaatga atctcctagt   3420
aaaggaaata ataatactgg gaacaatcat aaagaaacca ttacattctc gtgcaataaa   3480
agcaatttaa ttggcttagg agcacaatgg aaaaaaataa ctgatgatgg tttatatgct   3540
tctccaagaa ctcgacaatt atgtttgaaa cacgtaatag acataggaag gaataatact   3600
aaaaaaaaca atataacaga agaagagttc attaatgtat tacaaaaaga tgcatatgct   3660
gaaggtaaat tactttatat gtactacaac agtaatggta aaatatctat atttcaaaat   3720
ggcgaaaagt taaaattgga tgacatagaa aaacatacac atgaagccat gaaaagatca   3780
tatgctgatt atggtgattt aattaaagga acaacaaaat atacacaata caatgattat   3840
aacaaaatta gcgatattat aaacgttgtg actaaaaaga aaaattccgc ttcaattaat   3900
gatatttatg agcgtgaaga attttgggaa aaatatagag ctgatgtatg gaatgctatg   3960
ttatgtggtt acaaagatgt atcaaataaa acatttgatg gaaacgatga tatgtgtaac   4020
ttaccaaata ctgataagga ggaagaattt ctcagatggt ttaaggaatg gaatgaaaat   4080
ttttgtatta cacaaataaa acgcgcagag aaattaaaaa atgaatgcaa taattttaac   4140
tgttcttcca ttaagagtaa aaaggacgat attaaatcta aatgtgtaaa agcatgtata   4200
```

-continued

```
aattataaaa agtttgtaaa ggaatcaaaa acgcaatatg aagatcaaaa gagaacatac   4260
aatgaaagac ataataagac aaataaggat attcctactt ttttgaaaga taattgtatt   4320
cataaaaact gtgattgtat ttctataaaa tttaatcata aagataattg ggaaaaatct   4380
ttttttgaga gtttagatag ttccgatatt aaaaataagt gtgaatgttt aaaacttgaa   4440
gaagagtcaa atactacaga acgatatatt tctaaagaag acccacaata tcatccagaa   4500
tataaaggtg atggaaaggt taattataaa tatgagaaag gaaaaccaaa agctcttcct   4560
tctatatacc ctttgaactg tgctgaaaag gttgctgacg agttacgaat gtatgctgaa   4620
aattctttgg atactaatac taaattgaag gcaaaaatat caaaaagtat agatacaaat   4680
gaacaaaatg ctacgaatga tgagattgat tgcaatattt acaataatat atctaatgga   4740
cagaaaaata cttgtgaaca taatggaaac acttttcatg ataaggatga atgggattgt   4800
aacaaaggaa caaataaatt atatgaaaat gatatttgtt tacctccaag aagaaaacat   4860
atgtgtacaa aacaactaga aaatatcagc acggcatcaa ttacaactac ggatgattta   4920
ctgaaagaag tgttaattac agctgtaaat gaaggaaagc gtttaaaaca gcaatgggag   4980
aaaacagaaa atgaagcaca aaaaaagaaa cactttttat gtgatgctat gaaatatagt   5040
tttgctgatt tagctgatat tataagagga acagacatat ggaaaggaaa tagagagcaa   5100
caaaaaatac aagaaagatt agtaaaaatc ttcagaaata tatatgataa cttagagaag   5160
gatgaatatg agaaatataa atatggtaca aaatatcaaa atttaagatc ggcttggtgg   5220
gatgcacata gaaagaaaat atggaatgct atgacatgtt cagcaccagg tgatttcctt   5280
tttgtaaaaa gaggaaaagg agatggaagt gacatcgaat ttttaacttt ttcagaacat   5340
aaaaaatgtg gacatgataa agaaccacct gtttatgatt atgtgcctca aatacttaga   5400
tggattacag aatggtctga acatttttgt gaattgcaag aaaaaaatta ttatcttcta   5460
aaagaaaaat gtgctgatta tatacaaaag gattccaaac ctattgatga ttcacataat   5520
ataaaatgta atacttgtaa gacgaaatgt gaagaatata gtaaatttat taagaaatgg   5580
aactctcagt atataaatct ggaaaaaaaa tttaaagaat tatatgacga ggcaaataat   5640
actaaaagtt atgaagaact ttacagaatt gggaagcctt cacacagaaa ccactatgaa   5700
gatgaaaacc tgattcagtt cttacaaaat gtaaaatctg agtgtaacga acctaacact   5760
gttgataaat atcttatgta tacaagtgat tgtagaagag ttaaattttc taatactatc   5820
gatacaaatg ttaacaaacc tactgcggat gttactcata atactattaa tggtcctagt   5880
agtaacctcc cagttgttac tgaaacaaat attaaaaatg aactaagaga atatgctttc   5940
ttagaaacac cagaaggata tggtaatgct tgtaaatgta agggtcctga accattagat   6000
cgttgccctg aaaatgataa tattagtaat tactgtaacg attttgttag tgttcctgaa   6060
tgcacagcaa aaatatataa agatgaaatt gatcattgga ataatgcaaa tgtaaaattt   6120
aagacatcaa taaataacgg tgtgttagtt cctccaagaa gaagtcatat atgtcttaag   6180
aatatgataa caaaaaacta tgataaaaag aaaaatggga tggaaaaatt taaaactgat   6240
cttctacagg ttgcatacaa tgaaggttat ttcctatgtc aaaaatatga taagcaacct   6300
agagacgtat tggaagcgat gaaatacaca tttgcagata ttgctgatat agtaaaaggt   6360
agagatatga ttaacaaaga tatatccgca aaactacgaa aattattgga tattaaggtt   6420
gaacccaaag ctcctagaaa atggtggaaa tacaataaag cacatgtatg gcacgctatg   6480
ttatgtggat atagaaaagg tggaggaaca attacgaatg atgagtgtaa tgttccagat   6540
gaagagtaca cttatcaatt tcttcgatgg tttcaagaat ggattaaaaa attttgtact   6600
```

ggacaacaaa aattatatga cgacgtacaa acgaaatgtt catctgccaa ttgtaataga 6660
gatgatggga cgattagcct acctgaatgt gaaagttctt gtgttcaata taagaattac 6720
attacaagga agagacaaga gtatcggtca ctaaaccatc aatataacat gaattttaaa 6780
gaacaaaagg cacaaggtat gaaagccaca cagtacatag atgataaatg taatagtaaa 6840
tgtgattgtc tcattaaata tattgataga gaaaaagaat ggacaaacat atatgactca 6900
ttggaaaata atgatctgaa aaataaatgt gattgtaagc aaattaaacc caaacgtcat 6960
ccaaaagaag taaatcctga ggaagaacct gctaattctg aacccgatta cattgttccc 7020
cttgtaccac aaaaaccttc aacaccagag gtaccccac ctcctcctcc acctttacca 7080
accccttcgg acgaaccatt caatcgtgac attctggaaa aaaccattcc ttttggaatt 7140
gcattggcat tatgttcgat agcttttctc ttcataaaga aaaaacctaa atcatctgtt 7200
gacctcttgc gagtaattga catccacaaa ggagattatg atatacctac attgaaatcc 7260
aaaaataggt acataccata taaaagtgct caatataaag gtaaaacata catttatatg 7320
gaaggagata gtgatagtgg acactactac gaagatacaa ctgatattac ttcctccgaa 7380
agtgaatatg aagagatgga tattaatgat atatatgttc ctggtagtcc aaaatacaaa 7440
acgttgatag aagttgttct ggagccatca aaaagagata cacaaaatga tatacctagt 7500
gataatacac ctagttataa acttacagat gaggaatgga atcaattgaa acatgatttt 7560
atatcacaat atttaccaaa tacagaacca aataataatt atagaagtgg aaatagtcca 7620
acaaatacca ataatactac cacgtcacat gataatatgg gagaaaaacc ttttattact 7680
tctattcatg atagggattt atatactgga gaagaaatta gttataatat taatatgagt 7740
actaacacta ataatgatat tccaaaatat gtatcaaata atgtatattc tggtatagat 7800
ttaattaatg acacattaag tggtaacaaa catattgata tatatgatga agtgctaaaa 7860
agaaaagaaa atgaattatt tggaacaaat catccgaaaa atacatcaaa caatagtgta 7920
gctaaattaa caaatagtga tccaattatg aaccaattag atttgttaca taaatggtta 7980
gatagacata gagatatgtg cgataaatgg aataccaagg aagaattgtt agataaatta 8040
aatgaacaat ggaataaaga taatgatgtt ggtggtgata tttccactag taatggtaat 8100
aaaacgttga atactaatgt ttcgattgaa atagatatgg atgaaactaa aggaaagaag 8160
gaatttagta atatggatac tatcttggat aatatagaag atgatatata ttatgatgta 8220
aatgatgaaa acccatctat ggatgatata cctatggatc ataataaagt agatgtacct 8280
aagaaagtac atgttgaaat gaaaatcctt aataatacat tcaatggatc cttggaacca 8340
gaatttccca tatcggatgt atggaatata taa 8373

<210> SEQ ID NO 5
<211> LENGTH: 2716
<212> TYPE: PRT
<213> ORGANISM: Plasmodium falciparum

<400> SEQUENCE: 5

Met Ala Pro Lys Gly Arg Ser Thr Asn Glu Ile Glu Leu Ser Ala Arg
1 5 10 15

Asp Val Leu Glu Asn Ile Gly Ile Gly Ile Tyr Asn Gln Glu Lys Ile
20 25 30

Lys Lys Asn Pro Tyr Glu Gln Gln Leu Lys Gly Thr Leu Ser Asn Ala
35 40 45

Arg Phe His Asp Gly Leu His Lys Ala Ala Asp Leu Gly Val Ile Pro

-continued

```
    50                  55                  60

Gly Pro Ser His Phe Ser Gln Leu Tyr Tyr Lys Lys His Thr Asn Asn
65                  70                  75                  80

Thr Lys Tyr Tyr Lys Asp Asp Arg His Pro Cys His Gly Arg Gln Gly
                85                  90                  95

Lys Arg Phe Asp Glu Gly Gln Lys Phe Glu Cys Gly Asn Asp Lys Ile
            100                 105                 110

Ile Gly Asn Ser Asp Lys Tyr Gly Ser Cys Ala Pro Pro Arg Arg Arg
        115                 120                 125

His Ile Cys Asp Gln Asn Leu Glu Phe Leu Asp Asn Asn His Thr Asp
    130                 135                 140

Thr Ile His Asp Val Leu Gly Asn Val Leu Val Thr Ala Lys Tyr Glu
145                 150                 155                 160

Gly Glu Ser Ile Val Asn Asp His Pro Asp Lys Lys Asn Asn Gly Asn
                165                 170                 175

Lys Ser Gly Ile Cys Thr Ser Leu Ala Arg Ser Phe Ala Asp Ile Gly
            180                 185                 190

Asp Ile Val Arg Gly Arg Asp Met Phe Lys Pro Asn Asp Lys Asp Ala
        195                 200                 205

Val Arg His Gly Leu Lys Val Val Phe Lys Lys Ile Tyr Asp Lys Leu
    210                 215                 220

Ser Pro Lys Val Gln Glu His Tyr Lys Asp Val Asp Gly Ser Gly Asn
225                 230                 235                 240

Tyr Tyr Lys Leu Arg Glu Asp Trp Trp Thr Ala Asn Arg Asp Gln Val
                245                 250                 255

Trp Lys Ala Ile Thr Tyr Lys Ala Pro Gln Asp Ala Asn Tyr Phe Arg
            260                 265                 270

Asn Val Ser Gly Thr Thr Met Ala Phe Thr Ser Ala Gly Lys Cys Arg
        275                 280                 285

His Asn Asp Asn Ser Val Pro Thr Asn Leu Asp Tyr Val Pro Gln Phe
    290                 295                 300

Leu Arg Trp Tyr Asp Glu Trp Ala Asp Asp Phe Cys Arg Ile Arg Asn
305                 310                 315                 320

His Lys Leu Gln Lys Val Lys Asp Thr Cys Gln Gly Tyr Asn Asn Ser
                325                 330                 335

Gly Tyr Arg Ile Tyr Cys Ser Gly Asp Gly Glu Asp Cys Thr Asn Ile
            340                 345                 350

Leu Lys Gln Asn Phe Asn Ile Val Ser Asp Phe Phe Cys Pro Ser Cys
        355                 360                 365

Lys Thr Glu Cys Thr Asn Tyr Lys Lys Trp Ile Asn Lys Lys Gln Gly
    370                 375                 380

Glu Phe Asn Lys Gln Lys Lys Lys Tyr Glu Lys Glu Ile Asn Asn Ile
385                 390                 395                 400

Ala Ser Asn Ser Asp Asn Thr Tyr Asp Lys Lys Val Tyr Lys Thr Leu
                405                 410                 415

Lys Ser Met Tyr Pro Leu Asp Thr Lys Phe Val Ala Thr Leu Lys Glu
            420                 425                 430

Ala Pro Phe Cys Asn Asn Asn Asn Val Asp Gly Ile Ile Asp Phe Asn
        435                 440                 445

Lys Pro Asp Asp Thr Phe Ser Ser Ser Thr Tyr Cys Asp Ser Cys Pro
    450                 455                 460

Ala Phe Gly Val Ile Cys Glu Asn Gly Thr Cys Thr Lys Val Asn Glu
465                 470                 475                 480
```

-continued

```
Asp Thr Cys Ser Lys Met Asn Val Gln Val Pro Lys Ile Ile Thr Asn
                485                 490                 495

Lys Glu Asp Pro Thr Asn Ile Gly Ile Leu Val Ser Asp Asp Arg Val
            500                 505                 510

Asn Val Ile Pro Asn Glu Leu Glu Asn Val Cys Lys Asn Thr Gly Ile
        515                 520                 525

Phe Lys Gly Ile Arg Lys Asp Glu Trp Ser Cys Lys Tyr Leu Cys Asn
    530                 535                 540

Leu Asp Val Cys Asp Leu Ser His Asn Lys Asn Asn Thr His Ile Asp
545                 550                 555                 560

Lys Arg Ile Ser Ile Arg Val Leu Phe Lys Arg Trp Leu Glu Tyr Phe
                565                 570                 575

Leu Lys Asp Tyr Ser Lys Leu Lys Lys Lys Leu Asn Ser Cys Thr Asn
            580                 585                 590

Asn Gly Lys Glu Ser Ile Cys Ile Asn Glu Cys Lys Lys Lys Cys Glu
        595                 600                 605

Cys Val Gly Lys Trp Ala Glu Glu Lys Arg Lys Glu Trp Glu Lys Val
    610                 615                 620

Arg Lys Arg Phe Phe Asn Gln Tyr Asn Val Asp Asp Ser Leu Lys Ser
625                 630                 635                 640

Tyr Glu Val Lys Thr Phe Val Asn Gly Asn Val Asp Arg Ser Asp Ile
                645                 650                 655

Lys Asn Ala Leu Asn Glu Gly Glu Asn Leu Glu Ala Leu Gln Asp Ser
            660                 665                 670

Asp Glu Cys Ile Lys Pro His Asn Ser Lys Lys Asp Thr Cys Val Lys
        675                 680                 685

Asn Asp Val Val Asn Ile Leu Ile Asn Arg Leu Lys Lys Lys Ile Asp
    690                 695                 700

Asp Cys Lys Ile Gln His Asp Asn Arg Thr Asn Gln Ile Cys Cys Asp
705                 710                 715                 720

Glu Leu Pro Glu Ser Lys Glu Asp Asn Glu Asp Glu Glu Glu Glu Gly
                725                 730                 735

Glu Lys Lys Lys Asn Ser Lys His Leu Glu Glu Thr Lys Glu Lys Lys
            740                 745                 750

Glu Leu Asp Asp Asn Asn Phe Leu Asp Leu Cys Asn Asn Val Lys Lys
        755                 760                 765

Tyr Ile Glu Asp Asn Asn Lys Gln Ile Ser Ile Gln His Lys Cys Asn
    770                 775                 780

Thr Lys Gly Asp Gly Asn Trp Asn Asp Ser Thr Lys Lys Ile Asp Ile
785                 790                 795                 800

Gln His Thr Gly Ala His Met Pro Pro Arg Arg Lys Ser Leu Cys Ile
                805                 810                 815

Arg Glu Leu Arg Tyr Leu Val Glu Ile Gly Gly Asp Lys Asn Ile Asp
            820                 825                 830

Asp Tyr Lys Asn Ala Phe Thr Lys Cys Ala Ser Ile Glu Thr Tyr Leu
        835                 840                 845

Leu Trp Gln Lys Tyr Lys Lys Ser Asn Arg Ser Glu Glu Asp Lys Leu
    850                 855                 860

Lys Gly Gly Glu Ile Pro Glu Asp Phe Arg Gly Ile Met Tyr Tyr Thr
865                 870                 875                 880

Phe Gly Asp Tyr Arg Asp Ile Phe Leu Gly Thr Asp Ile Ser Ser Asp
                885                 890                 895
```

-continued

```
Gly Asn Ile Lys Asn Ile Ser Asn Lys Ile Lys Asp Leu Met Lys Glu
            900                 905                 910

Lys Tyr Ser Lys Ala Thr Gly His Lys Gly Glu Asn His Asn Ser Asn
        915                 920                 925

Leu Gln Ser Ser Trp Asp Glu His Lys Arg Thr Ile Trp Lys Gly Met
    930                 935                 940

Leu Cys Gly Leu Thr Tyr Gly Ile Ser Asn Glu Gln Gln Lys Lys Asn
945                 950                 955                 960

Ile Arg Lys Met Leu Asn Asn Lys Tyr Lys Tyr Pro Cys Asp Leu Glu
                965                 970                 975

Thr Phe Ser Lys Lys Pro Gln Phe Leu Arg Trp Phe Asn Glu Trp Ser
            980                 985                 990

Glu Asp Phe Cys Lys Asn Tyr Lys  Asn Ala Ile Asp Ile  Leu Lys Lys
        995                 1000                1005

Asp Cys  Thr Glu Ala Asp Cys  Met Asn Lys Leu Val  Asn Asn Arg
    1010                1015                1020

Glu Lys  Asn Lys Lys Cys Lys  Glu Ala Cys Glu His  Phe Lys Glu
    1025                1030                1035

Trp Ile  Lys Gly Trp Lys Asn  Gln Tyr Glu Gln Gln  Arg Lys Lys
    1040                1045                1050

Phe Asn  Ile Asp Lys Asn Val  Glu Gln Lys Glu Thr  Ala Tyr Ile
    1055                1060                1065

Asn Val  Asn Gly Leu Glu Pro  Tyr Glu Phe Phe Gln  Asn Gln Tyr
    1070                1075                1080

Phe Val  Gly Thr Cys Glu Cys  Met Lys Asn Lys Ser  Glu Ser Ser
    1085                1090                1095

Ala Asn  Asn Asp Glu Asn Ile  Pro Glu Ala Phe Asp  Glu Lys Pro
    1100                1105                1110

Lys Glu  Phe Lys Asp Lys Cys  Pro Cys Thr Tyr Asp  Ile Pro Glu
    1115                1120                1125

Pro Ser  Glu Thr Met Ser Cys  Ile Glu Lys Ala Ala  Phe Lys Leu
    1130                1135                1140

Arg Tyr  Ala Ser Glu Asp Lys  Ile His Ser Lys Ile  Ser Ser Lys
    1145                1150                1155

Leu Lys  Gly Asn Gly Ser Ala  Phe Ser Cys Thr Asn  Ser Ala Ser
    1160                1165                1170

Asp Asn  Ile Phe Asp Glu Thr  Ser Cys Tyr Lys Asn  Glu Phe Asn
    1175                1180                1185

Lys Thr  Glu Asn Ile Asn Ser  Val Lys Ala Ser Asn  Met Asn Arg
    1190                1195                1200

Phe Asp  Thr Asn Ile Ile Trp  Asp Cys Asp Gly Lys  Thr Lys Tyr
    1205                1210                1215

Glu Gln  Ile Asn Leu Cys Val  Pro Pro Arg Arg Glu  Asn Met Cys
    1220                1225                1230

Ile Lys  Gly Leu Glu His Leu  Asn Glu Thr Lys His  Ser Asp Asn
    1235                1240                1245

Lys Thr  Leu Leu Lys Glu Leu  Gln Glu Ile Ala Ser  Thr Glu Gly
    1250                1255                1260

Lys Gly  Ile Ser Lys Asn Phe  Lys Gln Met Asp Arg  Glu Asn Asp
    1265                1270                1275

Asp Gly  Ile Cys Asp Ala Met  Lys Tyr Ser Phe Ala  Asp Leu Ala
    1280                1285                1290

Asp Ile  Val Arg Gly Thr Asp  Asn Tyr Lys Asn Ser  Asn Gly Asn
```

```
    1295                1300                1305

Asn Asn  Lys Val Glu Glu Asn  Leu Lys Lys Ile Phe  Glu Lys Ile
    1310                1315                1320

His Asn  Ile Asn Ser Leu Lys  Lys Glu Tyr Ser Lys  Asp Lys Pro
    1325                1330                1335

Asp Tyr  Gln Arg Leu Arg Ser  Asp Trp Trp Asp Thr  Asn Arg Lys
    1340                1345                1350

Glu Ile  Trp Lys Ala Leu Thr  Cys Ser Ala Arg Asp  Asn Asn Lys
    1355                1360                1365

Ile Tyr  Lys Lys Gly Gln Lys  Asn Thr Asn Asn Gly  Lys Asn Lys
    1370                1375                1380

Cys Gly  Asn Glu Glu Asp Pro  Pro Asp Asp Asp Tyr  Ile Pro Gln
    1385                1390                1395

Pro Phe  Arg Trp Leu Gln Glu  Trp Ser Glu His Phe  Cys Arg Val
    1400                1405                1410

Gln Tyr  Asp Asn Leu Asn Lys  Leu Lys Glu Glu Cys  Gly Glu Cys
    1415                1420                1425

Asn Glu  Asn Lys Asn Gly Leu  Ala Cys Met Met Asn  Ser Asn Ile
    1430                1435                1440

Lys Asp  Thr Lys Cys Met Asn  Cys Lys Asp Ala Cys  Lys Asp Tyr
    1445                1450                1455

Arg Asn  Met Ile Asn Thr Trp  Asn Ser Gln Trp Lys  Lys Gln Gln
    1460                1465                1470

Glu Ile  Tyr Lys Glu Leu Tyr  Asn Thr Lys Asn Lys  Ile Asn Ile
    1475                1480                1485

Asn Lys  Cys Lys Val Ile Glu  Phe Leu Asp Lys Thr  Asn Asp Thr
    1490                1495                1500

Cys His  Tyr Lys Pro Gly Ser  Ala Glu Lys Phe Leu  Lys Glu Ser
    1505                1510                1515

Ser His  Cys Thr Asp Leu Thr  Phe Asp Lys Thr Lys  Asn Ser Asn
    1520                1525                1530

Asn Ile  Pro Tyr Ala Phe Glu  Asn Pro Pro Asp Gly  Tyr Lys Val
    1535                1540                1545

Leu Cys  Gly Thr Thr Tyr Arg  Lys Ser Cys Lys Lys  Leu Lys Lys
    1550                1555                1560

Leu Gly  Met Asn Tyr Thr Ser  Glu Asn Lys Ile Asp  Leu Ser Gly
    1565                1570                1575

Glu Asn  Ala Lys Trp Glu Lys  Leu Asn Asp Leu Ile  Tyr Val Pro
    1580                1585                1590

Pro Arg  Thr Gln Gln Leu Cys  Leu Gln Pro Leu Gln  Thr Leu Ile
    1595                1600                1605

Ser Arg  Thr Asn Lys Thr Thr  Lys Val Thr Glu Tyr  Asp Phe Ser
    1610                1615                1620

Arg Ala  Leu Gln Ile Cys Ala  Tyr Asn Glu Ala Asn  Ser Leu His
    1625                1630                1635

Asn Tyr  Tyr Ser Lys Tyr Gly  Lys Asp Phe Val Phe  Ser Ala Gly
    1640                1645                1650

Lys Ser  Gln Asp Thr Lys Asp  Glu Ile Lys Thr His  Ile Leu Glu
    1655                1660                1665

Asn Met  Lys Arg Ser Phe Ala  Asp Tyr Gly Asn Leu  Ile Lys Gly
    1670                1675                1680

Lys Thr  Gln Tyr Glu Tyr Asn  Gly Leu Asn Lys Lys  Leu Gln Asp
    1685                1690                1695
```

```
Tyr Ile Lys Thr Asn Leu Lys Tyr Asn Gly Thr Asp Arg Lys Thr
    1700                1705                1710

Gly Glu Asp Leu Trp Asn Lys His Lys Ser Asp Ile Trp Asn Ser
    1715                1720                1725

Met Leu Cys Gly Tyr Asn Glu Glu Asn Pro Ser Glu Pro Leu His
    1730                1735                1740

Asp Lys Asp Ile Arg Cys Lys Leu Pro Asp Asn Asp Ser Glu Asp
    1745                1750                1755

Glu Phe Leu Arg Trp Phe Gln Glu Trp Arg Glu Asp Phe Cys Val
    1760                1765                1770

Ile Lys Gly Ile Leu Ile Gln Asn Val Lys Asp Ala Cys Asn Phe
    1775                1780                1785

Asn Asn Cys Glu Asp Ala Asn Asn Lys Ser Ile Arg Ser Cys Gln
    1790                1795                1800

Lys Pro Cys Val Lys Tyr Lys Thr Trp Val Glu Gln Arg Lys Ile
    1805                1810                1815

Glu Tyr Glu Asn Gln Ile Gln Lys Tyr Lys Asn Leu Asn Asn Asn
    1820                1825                1830

Ser Asn Glu Gly Lys Glu Ser Leu Leu Phe Leu Asn Asp Lys Cys
    1835                1840                1845

Lys Gly Lys Cys Glu Cys Ile Val Gln Lys Lys Ser Thr Asp Asn
    1850                1855                1860

Ile Asp Lys Ile Phe Glu Glu Tyr Pro Glu Glu Tyr Lys Thr Gln
    1865                1870                1875

Cys Glu Cys Gln Pro Asp Pro Cys Ser Asp Leu Ser Ile Thr Asp
    1880                1885                1890

Ser Gly Phe Pro Asp Ala Ser Pro Phe Gly Gly Gly Gln Pro Arg
    1895                1900                1905

Ser Ala Cys Pro Thr Arg Arg Gly Asn His Asn Asn Cys Pro Thr
    1910                1915                1920

Glu Glu Ile Cys Lys Lys Tyr Asp Ser Tyr Ile Asn Gly Cys Arg
    1925                1930                1935

Pro Lys Thr Tyr His Asp Asn Thr Asn Asn Trp Asp Ser Arg Gly
    1940                1945                1950

Met Leu Asn Ser Ser Ser Glu Asn Glu Gly Val Leu Ile Pro Pro
    1955                1960                1965

Arg Arg Arg His Leu Cys Thr Arg Asn Ile Ile Lys Asn Leu Ser
    1970                1975                1980

Arg Ile Lys Asn Lys Asp His Phe Lys Asp Tyr Leu Met Lys Ser
    1985                1990                1995

Ala Tyr Glu Glu Gly Lys Leu Leu Arg Glu Lys Tyr Arg Asn Asn
    2000                2005                2010

Ser Arg Asp Gly Leu Asn Ala Met Met Phe Thr Phe Ala Asp Tyr
    2015                2020                2025

Ala Asp Ile Val Lys Gly Thr Asp Ile Phe Gly Ser Ile Leu Ser
    2030                2035                2040

Gln Lys Leu Gly Glu Ile Thr Gly Ile Ser Asn Asp Ile Asn Glu
    2045                2050                2055

Arg Lys Lys Trp Trp Ser Glu Ile Lys Asn Asn Ile Trp Glu Val
    2060                2065                2070

Met Leu Cys Ser Tyr Asn Arg Thr Lys Asn Asn Asn Asn Phe Phe
    2075                2080                2085
```

```
Gly Asn  Ile Val Arg Glu Asn  Cys Asn Val Pro Asn  Thr Asp Glu
    2090                 2095                 2100

Lys Asp  Gln Phe Leu Arg Trp  Leu Leu Glu Trp Gly  Ile Gln Ala
    2105                 2110                 2115

Cys Lys  Glu Lys Lys Ile Arg  Lys Gln Ala Leu Gln  Thr Lys Cys
    2120                 2125                 2130

Tyr Cys  Ser Asn Pro Asn Glu  Ile Ser Gly Ser Asp  Ile Ile Lys
    2135                 2140                 2145

His Tyr  Pro Cys Lys Ser Glu  Leu Thr Lys Tyr Ile  Gln Trp Asn
    2150                 2155                 2160

Leu Met  Ile Lys Glu Leu Leu  Asp Gln Leu Asn Ile  Lys Tyr Gln
    2165                 2170                 2175

Asn Ile  Lys Ala Ser Asn Asn  Pro Lys Asn Pro Ser  Glu Ile Asn
    2180                 2185                 2190

Ala Glu  Glu Tyr Ile Glu Thr  Glu Leu Lys Glu Gly  Glu Cys Asn
    2195                 2200                 2205

Leu Val  Asp Ile Glu Arg Ile  Tyr Asn Lys Ile Lys  Gln Glu His
    2210                 2215                 2220

Asn Pro  Leu Lys Glu Ile Leu  Met Tyr Leu Cys Pro  Asn Leu Glu
    2225                 2230                 2235

Phe Pro  Asp Asp Thr Phe Glu  Tyr Ile Gly Lys Thr  Glu Thr Glu
    2240                 2245                 2250

Asp Thr  Thr Ile Glu Pro Glu  Thr Pro Thr Ser Asp  Asn Pro Glu
    2255                 2260                 2265

Asp Ser  Ile Pro Ser Ile Ser  Pro Glu Asp Val His  Pro Thr Thr
    2270                 2275                 2280

Gly Glu  Asp Thr Asn Ile Phe  Asn Ser Asn Ile Leu  Ser Ser Thr
    2285                 2290                 2295

Ile Pro  Phe Gly Ile Ala Leu  Ala Leu Ser Ser Ile  Ala Phe Leu
    2300                 2305                 2310

Phe Leu  Lys Lys Lys Thr Leu  Ser Pro Val Asp Leu  Leu Arg Val
    2315                 2320                 2325

Leu Asp  Ile His Lys Gly Asp  Tyr Gly Ile Pro Thr  Leu Lys Ser
    2330                 2335                 2340

Lys Asn  Arg Tyr Ile Pro Tyr  Arg Ser Gly Thr Tyr  Lys Gly Lys
    2345                 2350                 2355

Thr Tyr  Leu Tyr Val Glu Gly  Asp Ser Asp Ser Gly  His Tyr Tyr
    2360                 2365                 2370

Glu Asp  Thr Thr Asp Ile Thr  Ser Ser Glu Ser Glu  Tyr Glu Glu
    2375                 2380                 2385

Met Asp  Ile Asn Asp Ile Tyr  Val Pro Gly Ser Pro  Lys Tyr Lys
    2390                 2395                 2400

Thr Leu  Ile Glu Val Val Leu  Glu Pro Ser Lys Ser  Asp Gly His
    2405                 2410                 2415

Ile Pro  His Ser Ala Gly Glu  Pro Leu Asp Asp Met  Val Gly Thr
    2420                 2425                 2430

Thr Ile  Phe Thr Asp Glu Glu  Trp Asn Glu Leu Lys  His Asp Phe
    2435                 2440                 2445

Ile Ser  Gln Tyr Val Gln Arg  Glu Ser Met Gly Val  Pro Gln Tyr
    2450                 2455                 2460

Asp Val  Ser Thr Glu Leu Pro  Met Asn Ile Gly Gly  Asn Val Leu
    2465                 2470                 2475

Asp Asp  Gly Met Glu Glu Lys  Pro Phe Ile Thr Ser  Ile His Asp
```

```
    2480                2485                2490

Arg Asp  Leu Tyr Thr Gly Glu  Glu Phe Ser Tyr Asn  Ile Asn Met
    2495                2500                2505

Gly Thr  Asn Ser Met Asp Asp  Pro Lys Tyr Val Ser  Asn Asn Val
    2510                2515                2520

Tyr Ser  Gly Ile Asp Leu Ile  Asn Asp Thr Leu Ser  Gly Asn Gln
    2525                2530                2535

His Ile  Asp Ile Tyr Asp Glu  Val Leu Lys Arg Lys  Glu Asn Glu
    2540                2545                2550

Leu Phe  Gly Thr Asn Tyr Lys  Lys Asn Ile Ser Asn  Asn Arg Val
    2555                2560                2565

Ala Lys  Leu Thr Asn Asn Asp  Pro Ile Met Asn Gln  Leu Asp Leu
    2570                2575                2580

Leu His  Lys Trp Leu Asp Arg  His Arg Asp Met Cys  Asn Thr Trp
    2585                2590                2595

Asn Thr  Lys Glu Glu Leu Leu  Asp Lys Leu Asn Glu  Gln Trp Asn
    2600                2605                2610

Lys Asp  Asn Asp Ala Gly Asp  Ile Pro Ser Asp Ser  Asn Lys Lys
    2615                2620                2625

Leu Asn  Thr Asp Val Ser Ile  Gln Ile Asp Met Asp  Asp Pro Lys
    2630                2635                2640

Gly Lys  Lys Glu Phe Ser Asn  Met Asp Thr Ile Leu  Asp Asp Ile
    2645                2650                2655

Glu Asp  Asp Ile Tyr Tyr Asp  Val Asn Asp Glu Asn  Pro Phe Val
    2660                2665                2670

Asp Asp  Ile Pro Met Asp His  Asn Lys Val Asp Val  Pro Lys Lys
    2675                2680                2685

Val His  Val Glu Met Lys Ile  Leu Asn Asn Thr Ser  Asn Gly Ser
    2690                2695                2700

Leu Glu  Pro Glu Phe Pro Ile  Ser Asp Val Trp Asn  Ile
    2705                2710                2715


<210> SEQ ID NO 6
<211> LENGTH: 8151
<212> TYPE: PRT
<213> ORGANISM: Plasmodium falciparum

<400> SEQUENCE: 6

Ala Thr Gly Gly Cys Ala Cys Cys Ala Ala Ala Gly Gly Gly Thr Ala
1               5                   10                  15

Gly Ala Ala Gly Thr Ala Cys Ala Ala Ala Thr Gly Ala Ala Ala Thr
            20                  25                  30

Thr Gly Ala Ala Cys Thr Thr Ala Gly Cys Gly Cys Ala Ala Gly Ala
        35                  40                  45

Gly Ala Thr Gly Thr Thr Thr Thr Gly Gly Ala Ala Ala Ala Thr Ala
    50                  55                  60

Thr Thr Gly Gly Ala Ala Thr Ala Gly Gly Ala Ala Thr Ala Thr Ala
65                  70                  75                  80

Thr Ala Ala Thr Cys Ala Gly Gly Ala Ala Ala Ala Ala Ala Thr Ala
                85                  90                  95

Ala Ala Ala Ala Ala Gly Ala Ala Thr Cys Cys Ala Thr Ala Thr Gly
            100                 105                 110

Ala Ala Cys Ala Ala Cys Ala Ala Thr Thr Gly Ala Ala Ala Gly Gly
        115                 120                 125
```

```
Cys Ala Cys Ala Thr Thr Ala Thr Cys Ala Ala Ala Cys Gly Cys Cys
    130                 135                 140

Cys Gly Ala Thr Thr Thr Cys Ala Thr Gly Ala Thr Gly Gly Cys Thr
145                 150                 155                 160

Thr Gly Cys Ala Cys Ala Ala Gly Gly Cys Ala Gly Cys Thr Gly Ala
                165                 170                 175

Thr Thr Thr Gly Gly Gly Gly Gly Thr Ala Ala Thr Ala Cys Cys Thr
            180                 185                 190

Gly Gly Thr Cys Cys Thr Thr Cys Ala Cys Ala Thr Thr Thr Thr Thr
        195                 200                 205

Cys Thr Cys Ala Gly Cys Thr Thr Thr Ala Thr Thr Ala Cys Ala Ala
    210                 215                 220

Ala Ala Ala Gly Cys Ala Thr Ala Cys Thr Ala Ala Thr Ala Ala Cys
225                 230                 235                 240

Ala Cys Ala Ala Ala Ala Thr Ala Thr Thr Ala Thr Ala Ala Gly Gly
                245                 250                 255

Ala Thr Gly Ala Thr Ala Gly Gly Cys Ala Thr Cys Cys Thr Thr Gly
            260                 265                 270

Thr Cys Ala Thr Gly Gly Thr Ala Gly Ala Cys Ala Ala Gly Gly Ala
        275                 280                 285

Ala Ala Ala Cys Gly Thr Thr Thr Thr Gly Ala Thr Gly Ala Ala Gly
    290                 295                 300

Gly Thr Cys Ala Ala Ala Ala Ala Thr Thr Thr Gly Ala Ala Thr Gly
305                 310                 315                 320

Thr Gly Gly Thr Ala Ala Thr Gly Ala Thr Ala Ala Ala Ala Thr Ala
                325                 330                 335

Ala Thr Thr Gly Gly Thr Ala Ala Thr Ala Gly Cys Gly Ala Thr Ala
            340                 345                 350

Ala Ala Thr Ala Thr Gly Gly Ala Thr Cys Cys Thr Gly Thr Gly Cys
        355                 360                 365

Thr Cys Cys Ala Cys Cys Thr Ala Gly Ala Ala Gly Ala Ala Gly Ala
    370                 375                 380

Cys Ala Thr Ala Thr Ala Thr Gly Thr Gly Ala Thr Cys Ala Ala Ala
385                 390                 395                 400

Ala Thr Thr Thr Ala Gly Ala Ala Thr Thr Cys Thr Thr Ala Gly Ala
                405                 410                 415

Thr Ala Ala Cys Ala Ala Thr Cys Ala Thr Ala Cys Thr Gly Ala Thr
            420                 425                 430

Ala Cys Thr Ala Thr Thr Cys Ala Thr Gly Ala Thr Gly Thr Ala Thr
        435                 440                 445

Thr Gly Gly Gly Ala Ala Ala Thr Gly Thr Gly Thr Thr Gly Gly Thr
    450                 455                 460

Cys Ala Cys Ala Gly Cys Ala Ala Ala Ala Thr Ala Thr Gly Ala Ala
465                 470                 475                 480

Gly Gly Thr Gly Ala Ala Thr Cys Thr Ala Thr Thr Gly Thr Thr Ala
                485                 490                 495

Ala Thr Gly Ala Thr Cys Ala Thr Cys Cys Ala Gly Ala Thr Ala Ala
            500                 505                 510

Ala Ala Ala Gly Ala Ala Cys Ala Ala Thr Gly Gly Thr Ala Ala Thr
        515                 520                 525

Ala Ala Ala Thr Cys Ala Gly Gly Thr Ala Thr Ala Thr Gly Thr Ala
    530                 535                 540

Cys Thr Thr Cys Thr Cys Thr Thr Gly Cys Ala Cys Gly Ala Ala Gly
```

```
545                 550                 555                 560

Thr Thr Thr Thr Gly Cys Cys Gly Ala Thr Ala Thr Ala Gly Gly Thr
                565                 570                 575

Gly Ala Thr Ala Thr Thr Gly Thr Ala Ala Gly Ala Gly Gly Ala Ala
            580                 585                 590

Gly Ala Gly Ala Thr Ala Thr Gly Thr Thr Thr Ala Ala Ala Cys Cys
        595                 600                 605

Thr Ala Ala Thr Gly Ala Cys Ala Ala Ala Gly Ala Thr Gly Cys Ala
    610                 615                 620

Gly Thr Gly Cys Gly Gly Cys Ala Thr Gly Gly Thr Thr Thr Ala Ala
625                 630                 635                 640

Ala Gly Gly Thr Ala Gly Thr Thr Thr Thr Thr Ala Ala Gly Ala Ala
                645                 650                 655

Ala Ala Thr Ala Thr Ala Thr Gly Ala Thr Ala Ala Ala Thr Thr Gly
            660                 665                 670

Thr Cys Ala Cys Cys Thr Ala Ala Ala Gly Thr Ala Cys Ala Ala Gly
        675                 680                 685

Ala Ala Cys Ala Thr Thr Ala Cys Ala Ala Ala Gly Ala Thr Gly Thr
    690                 695                 700

Thr Gly Ala Thr Gly Gly Ala Thr Cys Thr Gly Gly Ala Ala Ala Thr
705                 710                 715                 720

Thr Ala Cys Thr Ala Thr Ala Ala Ala Thr Thr Ala Ala Gly Gly Gly
                725                 730                 735

Ala Ala Gly Ala Thr Thr Gly Gly Thr Gly Gly Ala Cys Ala Gly Cys
            740                 745                 750

Gly Ala Ala Cys Ala Gly Ala Gly Ala Thr Cys Ala Ala Gly Thr Ala
        755                 760                 765

Thr Gly Gly Ala Ala Ala Gly Cys Cys Ala Thr Ala Ala Cys Ala Thr
    770                 775                 780

Ala Thr Ala Ala Ala Gly Cys Thr Cys Cys Ala Cys Ala Ala Gly Ala
785                 790                 795                 800

Cys Gly Cys Thr Ala Ala Thr Thr Ala Thr Thr Thr Thr Ala Gly Ala
                805                 810                 815

Ala Ala Thr Gly Thr Thr Thr Cys Ala Gly Gly Ala Ala Cys Ala Ala
            820                 825                 830

Cys Thr Ala Thr Gly Gly Cys Gly Thr Thr Thr Ala Cys Ala Ala Gly
        835                 840                 845

Thr Gly Cys Ala Gly Gly Ala Ala Ala Ala Thr Gly Thr Ala Gly Ala
    850                 855                 860

Cys Ala Cys Ala Ala Thr Gly Ala Cys Ala Ala Thr Ala Gly Cys Gly
865                 870                 875                 880

Thr Cys Cys Cys Ala Ala Cys Gly Ala Ala Thr Cys Thr Ala Gly Ala
                885                 890                 895

Thr Thr Ala Thr Gly Thr Cys Cys Cys Thr Cys Ala Ala Thr Thr Thr
            900                 905                 910

Thr Thr Ala Cys Gly Thr Thr Gly Gly Thr Ala Cys Gly Ala Thr Gly
        915                 920                 925

Ala Ala Thr Gly Gly Gly Cys Ala Gly Ala Thr Gly Ala Thr Thr Thr
    930                 935                 940

Thr Thr Gly Thr Cys Gly Ala Ala Thr Ala Ala Gly Ala Ala Ala Thr
945                 950                 955                 960

Cys Ala Thr Ala Ala Gly Thr Thr Gly Cys Ala Ala Ala Ala Gly Gly
                965                 970                 975
```

-continued

```
Thr Thr Ala Ala Ala Gly Ala Cys Ala Cys Ala Thr Gly Thr Cys Ala
            980                 985                 990

Gly Gly Gly Ala Thr Ala Thr Ala  Ala Thr Ala Ala Thr  Ala Gly Thr
        995                 1000                 1005

Gly Gly  Thr Thr Ala Thr Ala  Gly Ala Ala Thr Ala  Thr Ala Thr
    1010                 1015                 1020

Thr Gly  Thr Ala Gly Thr Gly  Gly Thr Gly Ala Thr  Gly Gly Thr
    1025                 1030                 1035

Gly Ala  Gly Gly Ala Thr Thr  Gly Thr Ala Cys Ala  Ala Ala Thr
    1040                 1045                 1050

Ala Thr  Thr Cys Thr Thr Ala  Ala Ala Cys Ala Gly  Ala Ala Thr
    1055                 1060                 1065

Thr Thr  Thr Ala Ala Thr Ala  Thr Thr Gly Thr Thr  Thr Cys Gly
    1070                 1075                 1080

Gly Ala  Thr Thr Thr Thr Thr  Thr Thr Thr Gly Thr  Cys Cys Gly
    1085                 1090                 1095

Ala Gly  Cys Thr Gly Thr Ala  Ala Ala Ala Cys Cys  Gly Ala Ala
    1100                 1105                 1110

Thr Gly  Thr Ala Cys Ala Ala  Ala Thr Thr Ala Thr  Ala Ala Ala
    1115                 1120                 1125

Ala Ala  Ala Thr Gly Gly Ala  Thr Ala Ala Ala Thr  Ala Ala Ala
    1130                 1135                 1140

Ala Ala  Ala Cys Ala Ala Gly  Gly Thr Gly Ala Ala  Thr Thr Thr
    1145                 1150                 1155

Ala Ala  Thr Ala Ala Ala Cys  Ala Ala Ala Ala Ala  Ala Ala Ala
    1160                 1165                 1170

Ala Ala  Ala Thr Ala Cys Gly  Ala Ala Ala Ala Gly  Gly Ala Ala
    1175                 1180                 1185

Ala Thr  Thr Ala Ala Cys Ala  Ala Thr Ala Thr Thr  Gly Cys Ala
    1190                 1195                 1200

Ala Gly  Thr Ala Ala Thr Thr  Cys Thr Gly Ala Thr  Ala Ala Cys
    1205                 1210                 1215

Ala Cys  Ala Thr Ala Thr Gly  Ala Thr Ala Ala Ala  Ala Ala Ala
    1220                 1225                 1230

Gly Thr  Thr Thr Ala Thr Ala  Ala Ala Ala Cys Thr  Cys Thr Ala
    1235                 1240                 1245

Ala Ala  Ala Ala Gly Cys Ala  Thr Gly Thr Ala Cys  Cys Cys Thr
    1250                 1255                 1260

Thr Thr  Ala Gly Ala Thr Ala  Cys Ala Ala Ala Ala  Thr Thr Thr
    1265                 1270                 1275

Gly Thr  Ala Gly Cys Ala Ala  Cys Ala Cys Thr Ala  Ala Ala Ala
    1280                 1285                 1290

Gly Ala  Gly Gly Cys Thr Cys  Cys Cys Thr Thr Thr  Thr Gly Cys
    1295                 1300                 1305

Ala Ala  Thr Ala Ala Cys Ala  Ala Thr Ala Ala Thr  Gly Thr Ala
    1310                 1315                 1320

Gly Ala  Thr Gly Gly Thr Ala  Thr Ala Ala Thr Ala  Gly Ala Thr
    1325                 1330                 1335

Thr Thr  Thr Ala Ala Thr Ala  Ala Ala Cys Cys Ala  Gly Ala Thr
    1340                 1345                 1350

Gly Ala  Thr Ala Cys Ala Thr  Thr Thr Thr Cys Thr  Ala Gly Thr
    1355                 1360                 1365
```

-continued

```
Thr Cys  Ala Ala Cys Ala Thr  Ala Thr Thr Gly Thr  Gly Ala Thr
    1370                 1375                 1380

Thr Cys  Ala Thr Gly Thr Cys  Cys Thr Gly Cys Ala  Thr Thr Thr
    1385                 1390                 1395

Gly Gly  Thr Gly Thr Thr Ala  Thr Thr Thr Gly Thr  Gly Ala Ala
    1400                 1405                 1410

Ala Ala  Thr Gly Gly Thr Ala  Cys Gly Thr Gly Thr  Ala Cys Thr
    1415                 1420                 1425

Ala Ala  Gly Gly Thr Thr Ala  Ala Thr Gly Ala Ala  Gly Ala Thr
    1430                 1435                 1440

Ala Cys  Ala Thr Gly Thr Ala  Gly Thr Ala Ala Ala  Ala Thr Gly
    1445                 1450                 1455

Ala Ala  Thr Gly Thr Thr Cys  Ala Gly Gly Thr Thr  Cys Cys Ala
    1460                 1465                 1470

Ala Ala  Ala Ala Thr Ala Ala  Thr Thr Ala Cys Ala  Ala Ala Thr
    1475                 1480                 1485

Ala Ala  Gly Gly Ala Ala Gly  Ala Thr Cys Cys Thr  Ala Cys Thr
    1490                 1495                 1500

Ala Ala  Thr Ala Thr Ala Gly  Gly Thr Ala Thr Thr  Cys Thr Thr
    1505                 1510                 1515

Gly Thr  Thr Ala Gly Thr Gly  Ala Thr Gly Ala Cys  Ala Gly Ala
    1520                 1525                 1530

Gly Thr  Ala Ala Ala Thr Gly  Thr Ala Ala Thr Thr  Cys Cys Ala
    1535                 1540                 1545

Ala Ala  Thr Gly Ala Ala Thr  Thr Ala Gly Ala Gly  Ala Ala Thr
    1550                 1555                 1560

Gly Thr  Thr Thr Gly Cys Ala  Ala Ala Ala Ala Thr  Ala Cys Ala
    1565                 1570                 1575

Gly Gly  Thr Ala Thr Cys Thr  Thr Thr Ala Ala Ala  Gly Gly Thr
    1580                 1585                 1590

Ala Thr  Thr Ala Gly Ala Ala  Ala Ala Gly Ala Thr  Gly Ala Ala
    1595                 1600                 1605

Thr Gly  Gly Thr Cys Ala Thr  Gly Thr Ala Ala Ala  Thr Ala Thr
    1610                 1615                 1620

Thr Thr  Ala Thr Gly Thr Ala  Ala Thr Thr Thr Ala  Gly Ala Thr
    1625                 1630                 1635

Gly Thr  Cys Thr Gly Thr Gly  Ala Cys Cys Thr Gly  Ala Gly Thr
    1640                 1645                 1650

Cys Ala  Thr Ala Ala Thr Ala  Ala Ala Ala Ala Cys  Ala Ala Thr
    1655                 1660                 1665

Ala Cys  Ala Cys Ala Thr Ala  Thr Ala Gly Ala Thr  Ala Ala Ala
    1670                 1675                 1680

Cys Gly  Thr Ala Thr Thr Thr  Cys Ala Ala Thr Thr  Ala Gly Ala
    1685                 1690                 1695

Gly Thr  Ala Cys Thr Gly Thr  Thr Thr Ala Ala Ala  Cys Gly Thr
    1700                 1705                 1710

Thr Gly  Gly Thr Thr Ala Gly  Ala Ala Thr Ala Thr  Thr Thr Thr
    1715                 1720                 1725

Thr Thr  Ala Ala Ala Ala Gly  Ala Thr Thr Ala Thr  Ala Gly Thr
    1730                 1735                 1740

Ala Ala  Ala Thr Thr Ala Ala  Ala Ala Ala Ala Ala  Ala Ala Ala
    1745                 1750                 1755

Cys Thr  Gly Ala Ala Thr Thr  Cys Ala Thr Gly Thr  Ala Cys Ala
```

```
    1760                1765                1770

Ala Ala  Thr Ala Ala Thr Gly  Gly Ala Ala Ala Ala  Gly Ala Ala
    1775                1780                1785

Thr Cys  Cys Ala Thr Ala Thr  Gly Thr Ala Thr Ala  Ala Ala Thr
    1790                1795                1800

Gly Ala  Ala Thr Gly Thr Ala  Ala Ala Ala Ala Ala  Ala Ala Ala
    1805                1810                1815

Thr Gly  Thr Gly Ala Ala Thr  Gly Thr Gly Thr Gly  Gly Gly Ala
    1820                1825                1830

Ala Ala  Ala Thr Gly Gly Gly  Cys Ala Gly Ala Ala  Gly Ala Gly
    1835                1840                1845

Ala Ala  Ala Ala Gly Ala Ala  Ala Ala Gly Ala Ala  Thr Gly Gly
    1850                1855                1860

Gly Ala  Ala Ala Ala Ala Gly  Thr Ala Ala Gly Ala  Ala Ala Gly
    1865                1870                1875

Cys Gly  Thr Thr Thr Cys Thr  Thr Thr Ala Ala Thr  Cys Ala Ala
    1880                1885                1890

Thr Ala  Thr Ala Ala Thr Gly  Thr Thr Gly Ala Thr  Gly Ala Thr
    1895                1900                1905

Thr Cys  Ala Cys Thr Ala Ala  Ala Ala Thr Cys Thr  Thr Ala Cys
    1910                1915                1920

Gly Ala  Ala Gly Thr Gly Ala  Ala Ala Ala Cys Ala  Thr Thr Thr
    1925                1930                1935

Gly Thr  Ala Ala Ala Thr Gly  Gly Ala Ala Ala Thr  Gly Thr Ala
    1940                1945                1950

Gly Ala  Thr Cys Gly Thr Ala  Gly Thr Gly Ala Thr  Ala Thr Thr
    1955                1960                1965

Ala Ala  Gly Ala Ala Thr Gly  Cys Ala Thr Thr Ala  Ala Ala Thr
    1970                1975                1980

Gly Ala  Gly Gly Gly Thr Gly  Ala Ala Ala Ala Thr  Thr Thr Ala
    1985                1990                1995

Gly Ala  Ala Gly Cys Gly Thr  Thr Gly Cys Ala Ala  Gly Ala Thr
    2000                2005                2010

Thr Cys  Thr Gly Ala Thr Gly  Ala Ala Thr Gly Thr  Ala Thr Thr
    2015                2020                2025

Ala Ala  Ala Cys Cys Thr Cys  Ala Thr Ala Ala Thr  Thr Cys Cys
    2030                2035                2040

Ala Ala  Gly Ala Ala Ala Gly  Ala Cys Ala Cys Ala  Thr Gly Thr
    2045                2050                2055

Gly Thr  Ala Ala Ala Ala Ala  Ala Thr Gly Ala Cys  Gly Thr Cys
    2060                2065                2070

Gly Thr  Ala Ala Ala Thr Ala  Thr Thr Thr Thr Ala  Ala Thr Thr
    2075                2080                2085

Ala Ala  Thr Ala Gly Ala Cys  Thr Thr Ala Ala Ala  Ala Ala Ala
    2090                2095                2100

Ala Ala  Ala Ala Thr Thr Gly  Ala Thr Gly Ala Thr  Thr Gly Thr
    2105                2110                2115

Ala Ala  Ala Ala Thr Cys Cys  Ala Ala Cys Ala Thr  Gly Ala Thr
    2120                2125                2130

Ala Ala  Thr Ala Gly Ala Ala  Cys Thr Ala Ala Thr  Cys Ala Ala
    2135                2140                2145

Ala Thr  Thr Thr Gly Thr Thr  Gly Thr Gly Ala Thr  Gly Ala Gly
    2150                2155                2160
```

-continued

```
Thr Thr  Ala Cys Cys Thr Gly  Ala Ala Ala Gly Thr  Ala Ala Ala
    2165                 2170                 2175

Gly Ala  Ala Gly Ala Thr Ala  Ala Thr Gly Ala Ala  Gly Ala Thr
    2180                 2185                 2190

Gly Ala  Ala Gly Ala Gly Gly  Ala Ala Gly Ala Ala  Gly Gly Gly
    2195                 2200                 2205

Gly Ala  Ala Ala Ala Gly Ala  Ala Ala Ala Ala Ala  Ala Ala Thr
    2210                 2215                 2220

Thr Cys  Ala Ala Ala Ala Cys  Ala Thr Thr Thr Gly  Gly Ala Gly
    2225                 2230                 2235

Gly Ala  Gly Ala Cys Thr Ala  Ala Ala Gly Ala Gly  Ala Ala Ala
    2240                 2245                 2250

Ala Ala  Ala Gly Ala Ala Cys  Thr Gly Gly Ala Thr  Gly Ala Cys
    2255                 2260                 2265

Ala Ala  Cys Ala Ala Thr Thr  Thr Thr Thr Thr Gly  Gly Ala Thr
    2270                 2275                 2280

Thr Thr  Gly Thr Gly Cys Ala  Ala Cys Ala Ala Thr  Gly Thr Gly
    2285                 2290                 2295

Ala Ala  Gly Ala Ala Ala Thr  Ala Thr Ala Thr Thr  Gly Ala Gly
    2300                 2305                 2310

Gly Ala  Thr Ala Ala Thr Ala  Ala Thr Ala Ala Gly  Cys Ala Ala
    2315                 2320                 2325

Ala Thr  Ala Ala Gly Thr Ala  Thr Ala Cys Ala Ala  Cys Ala Thr
    2330                 2335                 2340

Ala Ala  Ala Thr Gly Cys Ala  Ala Thr Ala Cys Gly  Ala Ala Ala
    2345                 2350                 2355

Gly Gly  Ala Gly Ala Thr Gly  Gly Ala Ala Ala Thr  Thr Gly Gly
    2360                 2365                 2370

Ala Ala  Thr Gly Ala Thr Ala  Gly Thr Ala Cys Ala  Ala Ala Ala
    2375                 2380                 2385

Ala Ala  Gly Ala Thr Cys Gly  Ala Thr Ala Thr Thr  Cys Ala Ala
    2390                 2395                 2400

Cys Ala  Thr Ala Cys Thr Gly  Gly Ala Gly Cys Thr  Cys Ala Thr
    2405                 2410                 2415

Ala Thr  Gly Cys Cys Ala Cys  Cys Ala Ala Gly Ala  Ala Gly Ala
    2420                 2425                 2430

Ala Ala  Ala Thr Cys Ala Thr  Thr Ala Thr Gly Thr  Ala Thr Thr
    2435                 2440                 2445

Cys Gly  Thr Gly Ala Gly Thr  Thr Ala Cys Gly Ala  Thr Ala Thr
    2450                 2455                 2460

Thr Thr  Gly Gly Thr Ala Gly  Ala Ala Ala Thr Thr  Gly Gly Ala
    2465                 2470                 2475

Gly Gly  Ala Gly Ala Thr Ala  Ala Ala Ala Ala Cys  Ala Thr Ala
    2480                 2485                 2490

Gly Ala  Thr Gly Ala Thr Thr  Ala Thr Ala Ala Ala  Ala Ala Thr
    2495                 2500                 2505

Gly Cys  Gly Thr Thr Thr Ala  Cys Thr Ala Ala Ala  Thr Gly Thr
    2510                 2515                 2520

Gly Cys  Ala Thr Cys Ala Ala  Thr Ala Gly Ala Ala  Ala Cys Ala
    2525                 2530                 2535

Thr Ala  Thr Thr Thr Gly Thr  Thr Ala Thr Gly Gly  Cys Ala Ala
    2540                 2545                 2550
```

-continued

```
Ala Ala Ala Thr Ala Cys Ala Ala Ala Ala Ala Ala Thr Cys Thr
    2555                2560                2565

Ala Ala Thr Ala Gly Ala Thr Cys Ala Gly Ala Ala Gly Ala Ala
    2570                2575                2580

Gly Ala Thr Ala Ala Ala Thr Thr Ala Ala Ala Ala Gly Gly Thr
    2585                2590                2595

Gly Gly Ala Gly Ala Gly Ala Thr Thr Cys Cys Ala Gly Ala Ala
    2600                2605                2610

Gly Ala Thr Thr Thr Thr Ala Gly Ala Gly Gly Ala Ala Thr Ala
    2615                2620                2625

Ala Thr Gly Thr Ala Thr Thr Ala Thr Ala Cys Ala Thr Thr Thr
    2630                2635                2640

Gly Gly Thr Gly Ala Thr Thr Ala Cys Ala Gly Ala Gly Ala Thr
    2645                2650                2655

Ala Thr Ala Thr Thr Thr Thr Thr Gly Gly Gly Ala Ala Cys Ala
    2660                2665                2670

Gly Ala Thr Ala Thr Thr Thr Cys Thr Thr Cys Ala Gly Ala Thr
    2675                2680                2685

Gly Gly Thr Ala Ala Thr Ala Thr Thr Ala Ala Ala Ala Ala Thr
    2690                2695                2700

Ala Thr Ala Thr Cys Ala Ala Ala Thr Ala Ala Ala Ala Thr Ala
    2705                2710                2715

Ala Ala Ala Gly Ala Thr Thr Thr Ala Ala Thr Gly Ala Ala Ala
    2720                2725                2730

Gly Ala Ala Ala Ala Gly Thr Ala Thr Ala Gly Thr Ala Ala Ala
    2735                2740                2745

Gly Cys Ala Ala Cys Ala Gly Gly Thr Cys Ala Thr Ala Ala Ala
    2750                2755                2760

Gly Gly Ala Gly Ala Ala Ala Ala Cys Cys Ala Thr Ala Ala Thr
    2765                2770                2775

Thr Cys Ala Ala Ala Thr Cys Thr Thr Cys Ala Ala Thr Cys Thr
    2780                2785                2790

Thr Cys Gly Thr Gly Gly Gly Ala Thr Gly Ala Ala Cys Ala Thr
    2795                2800                2805

Ala Ala Ala Ala Gly Gly Ala Cys Cys Ala Thr Ala Thr Gly Gly
    2810                2815                2820

Ala Ala Ala Gly Gly Ala Ala Thr Gly Thr Thr Ala Thr Gly Thr
    2825                2830                2835

Gly Gly Ala Thr Thr Ala Ala Cys Cys Thr Ala Thr Gly Gly Thr
    2840                2845                2850

Ala Thr Ala Thr Cys Ala Ala Ala Thr Gly Ala Ala Cys Ala Ala
    2855                2860                2865

Cys Ala Ala Ala Ala Ala Ala Ala Ala Ala Ala Thr Ala Thr Thr
    2870                2875                2880

Cys Gly Cys Ala Ala Ala Ala Thr Gly Cys Thr Cys Ala Ala Cys
    2885                2890                2895

Ala Ala Cys Ala Ala Gly Thr Ala Cys Ala Ala Ala Thr Ala Cys
    2900                2905                2910

Cys Cys Ala Thr Gly Cys Gly Ala Thr Cys Thr Ala Gly Ala Ala
    2915                2920                2925

Ala Cys Ala Thr Thr Thr Thr Cys Ala Ala Ala Gly Ala Ala Ala
    2930                2935                2940

Cys Cys Ala Cys Ala Ala Thr Thr Thr Cys Thr Thr Cys Gly Thr
```

```
    2945                2950                2955

Thr Gly  Gly Thr Thr Thr Ala  Ala Cys Gly Ala Ala  Thr Gly Gly
    2960                2965                2970

Ala Gly  Thr Gly Ala Ala Gly  Ala Thr Thr Thr Thr  Thr Gly Thr
    2975                2980                2985

Ala Ala  Ala Ala Ala Thr Thr  Ala Cys Ala Ala Ala  Ala Ala Thr
    2990                2995                3000

Gly Cys  Thr Ala Thr Thr Gly  Ala Thr Ala Thr Ala  Thr Thr Ala
    3005                3010                3015

Ala Ala  Ala Ala Ala Gly Gly  Ala Thr Thr Gly Thr  Ala Cys Ala
    3020                3025                3030

Gly Ala  Ala Gly Cys Ala Gly  Ala Thr Thr Gly Thr  Ala Thr Gly
    3035                3040                3045

Ala Ala  Thr Ala Ala Ala Thr  Thr Ala Gly Thr Ala  Ala Ala Thr
    3050                3055                3060

Ala Ala  Thr Cys Gly Thr Gly  Ala Ala Ala Ala Ala  Ala Ala Cys
    3065                3070                3075

Ala Ala  Gly Ala Ala Ala Thr  Gly Thr Ala Ala Ala  Gly Ala Ala
    3080                3085                3090

Gly Cys  Gly Thr Gly Thr Gly  Ala Ala Cys Ala Thr  Thr Thr Thr
    3095                3100                3105

Ala Ala  Ala Gly Ala Gly Thr  Gly Gly Ala Thr Ala  Ala Ala Ala
    3110                3115                3120

Gly Gly  Ala Thr Gly Gly Ala  Ala Ala Ala Ala Thr  Cys Ala Ala
    3125                3130                3135

Thr Ala  Thr Gly Ala Ala Cys  Ala Ala Cys Ala Ala  Ala Gly Ala
    3140                3145                3150

Ala Ala  Ala Ala Ala Ala Thr  Thr Thr Ala Ala Thr  Ala Thr Thr
    3155                3160                3165

Gly Ala  Thr Ala Ala Ala Ala  Ala Thr Gly Thr Thr  Gly Ala Ala
    3170                3175                3180

Cys Ala  Ala Ala Ala Gly Gly  Ala Gly Ala Cys Ala  Gly Cys Ala
    3185                3190                3195

Thr Ala  Thr Ala Thr Ala Ala  Ala Cys Gly Thr Ala  Ala Ala Thr
    3200                3205                3210

Gly Gly  Thr Cys Thr Gly Gly  Ala Ala Cys Cys Cys  Thr Ala Thr
    3215                3220                3225

Gly Ala  Ala Thr Thr Thr Thr  Thr Thr Cys Ala Ala  Ala Ala Cys
    3230                3235                3240

Cys Ala  Ala Thr Ala Thr Thr  Thr Thr Gly Thr Gly  Gly Gly Ala
    3245                3250                3255

Ala Cys  Ala Thr Gly Thr Gly  Ala Ala Thr Gly Cys  Ala Thr Gly
    3260                3265                3270

Ala Ala  Ala Ala Ala Thr Ala  Ala Ala Thr Cys Ala  Gly Ala Gly
    3275                3280                3285

Thr Cys  Ala Thr Cys Thr Gly  Cys Ala Ala Ala Thr  Ala Ala Thr
    3290                3295                3300

Gly Ala  Thr Gly Ala Ala Ala  Ala Thr Ala Thr Ala  Cys Cys Ala
    3305                3310                3315

Gly Ala  Ala Gly Cys Ala Thr  Thr Cys Gly Ala Thr  Gly Ala Ala
    3320                3325                3330

Ala Ala  Ala Cys Cys Ala Ala  Ala Ala Gly Ala Gly  Thr Thr Cys
    3335                3340                3345
```

-continued

```
Ala Ala  Gly Gly Ala Cys Ala  Ala Ala Thr Gly Thr  Cys Cys Ala
    3350                 3355                 3360

Thr Gly  Thr Ala Cys Thr Thr  Ala Thr Gly Ala Thr  Ala Thr Ala
    3365                 3370                 3375

Cys Cys  Thr Gly Ala Ala Cys  Cys Thr Ala Gly Cys  Gly Ala Ala
    3380                 3385                 3390

Ala Cys  Thr Ala Thr Gly Ala  Gly Thr Thr Gly Thr  Ala Thr Ala
    3395                 3400                 3405

Gly Ala  Gly Ala Ala Ala Gly  Cys Thr Gly Cys Cys  Thr Thr Cys
    3410                 3415                 3420

Ala Ala  Ala Thr Thr Ala Cys  Gly Thr Thr Ala Thr  Gly Cys Thr
    3425                 3430                 3435

Thr Cys  Thr Gly Ala Ala Gly  Ala Thr Ala Ala Ala  Ala Thr Thr
    3440                 3445                 3450

Cys Ala  Thr Ala Gly Thr Ala  Ala Ala Ala Thr Thr  Ala Gly Thr
    3455                 3460                 3465

Ala Gly  Thr Ala Ala Ala Thr  Thr Gly Ala Ala Ala  Gly Gly Ala
    3470                 3475                 3480

Ala Ala  Cys Gly Gly Thr Thr  Cys Ala Gly Cys Gly  Thr Thr Thr
    3485                 3490                 3495

Thr Cys  Ala Thr Gly Thr Ala  Cys Gly Ala Ala Cys  Ala Gly Cys
    3500                 3505                 3510

Gly Cys  Ala Ala Gly Thr Gly  Ala Cys Ala Ala Thr  Ala Thr Thr
    3515                 3520                 3525

Thr Thr  Thr Gly Ala Thr Gly  Ala Gly Ala Cys Ala  Ala Gly Thr
    3530                 3535                 3540

Thr Gly  Thr Thr Ala Thr Ala  Ala Gly Ala Ala Thr  Gly Ala Ala
    3545                 3550                 3555

Thr Thr  Thr Ala Ala Cys Ala  Ala Ala Ala Cys Ala  Gly Ala Ala
    3560                 3565                 3570

Ala Ala  Thr Ala Thr Thr Ala  Ala Thr Thr Cys Ala  Gly Thr Gly
    3575                 3580                 3585

Ala Ala  Ala Gly Cys Thr Thr  Cys Ala Ala Ala Cys  Ala Thr Gly
    3590                 3595                 3600

Ala Ala  Thr Cys Gly Thr Thr  Thr Thr Gly Ala Thr  Ala Cys Ala
    3605                 3610                 3615

Ala Ala  Thr Ala Thr Thr Ala  Thr Ala Thr Gly Gly  Gly Ala Thr
    3620                 3625                 3630

Thr Gly  Thr Gly Ala Thr Gly  Gly Ala Ala Ala Ala  Ala Cys Ala
    3635                 3640                 3645

Ala Ala  Ala Thr Ala Thr Gly  Ala Gly Cys Ala Ala  Ala Thr Thr
    3650                 3655                 3660

Ala Ala  Thr Thr Thr Ala Thr  Gly Thr Gly Thr Thr  Cys Cys Gly
    3665                 3670                 3675

Cys Cys  Thr Ala Gly Ala Ala  Gly Ala Gly Ala Ala  Ala Ala Thr
    3680                 3685                 3690

Ala Thr  Gly Thr Gly Thr Ala  Thr Ala Ala Ala Gly  Gly Gly Gly
    3695                 3700                 3705

Cys Thr  Ala Gly Ala Ala Cys  Ala Cys Thr Thr Gly  Ala Ala Cys
    3710                 3715                 3720

Gly Ala  Ala Ala Cys Thr Ala  Ala Ala Cys Ala Thr  Thr Cys Thr
    3725                 3730                 3735
```

Gly Ala Thr Ala Ala Thr Ala Ala Ala Ala Cys Gly Cys Thr Ala
3740 3745 3750

Thr Thr Ala Ala Ala Ala Gly Ala Gly Cys Thr Thr Cys Ala Ala
3755 3760 3765

Gly Ala Ala Ala Thr Thr Gly Cys Ala Ala Gly Thr Ala Cys Thr
3770 3775 3780

Gly Ala Ala Gly Gly Gly Ala Ala Ala Gly Gly Cys Ala Thr Ala
3785 3790 3795

Thr Cys Ala Ala Ala Ala Ala Ala Thr Thr Thr Thr Ala Ala Ala
3800 3805 3810

Cys Ala Ala Ala Thr Gly Gly Ala Thr Ala Gly Ala Gly Ala Ala
3815 3820 3825

Ala Ala Thr Gly Ala Thr Gly Ala Cys Gly Gly Ala Ala Thr Ala
3830 3835 3840

Thr Gly Thr Gly Ala Thr Gly Cys Cys Ala Thr Gly Ala Ala Gly
3845 3850 3855

Thr Ala Cys Ala Gly Thr Thr Thr Thr Gly Cys Cys Gly Ala Thr
3860 3865 3870

Thr Thr Gly Gly Cys Ala Gly Ala Thr Ala Thr Ala Gly Thr Ala
3875 3880 3885

Ala Gly Ala Gly Gly Thr Ala Cys Ala Gly Ala Thr Ala Ala Thr
3890 3895 3900

Thr Ala Cys Ala Ala Ala Ala Ala Thr Thr Cys Thr Ala Ala Thr
3905 3910 3915

Gly Gly Thr Ala Ala Thr Ala Ala Thr Ala Ala Thr Ala Ala Ala
3920 3925 3930

Gly Thr Ala Gly Ala Gly Gly Ala Ala Ala Ala Cys Cys Thr Thr
3935 3940 3945

Ala Ala Ala Ala Ala Ala Ala Thr Thr Thr Thr Cys Gly Ala Ala
3950 3955 3960

Ala Ala Ala Ala Thr Ala Cys Ala Cys Ala Ala Thr Ala Thr Thr
3965 3970 3975

Ala Ala Thr Ala Gly Thr Cys Thr Thr Ala Ala Ala Ala Ala Ala
3980 3985 3990

Gly Ala Ala Thr Ala Thr Ala Gly Thr Ala Ala Gly Gly Ala Cys
3995 4000 4005

Ala Ala Ala Cys Cys Gly Gly Ala Thr Thr Ala Thr Cys Ala Ala
4010 4015 4020

Ala Gly Ala Thr Thr Ala Cys Gly Ala Thr Cys Thr Gly Ala Cys
4025 4030 4035

Thr Gly Gly Thr Gly Gly Gly Ala Thr Ala Cys Gly Ala Ala Thr
4040 4045 4050

Ala Gly Ala Ala Ala Ala Gly Ala Ala Ala Thr Ala Thr Gly Gly
4055 4060 4065

Ala Ala Ala Gly Cys Ala Thr Thr Ala Ala Cys Gly Thr Gly Thr
4070 4075 4080

Thr Cys Ala Gly Cys Ala Ala Gly Gly Gly Ala Thr Ala Ala Thr
4085 4090 4095

Ala Ala Thr Ala Ala Ala Ala Thr Ala Thr Ala Cys Ala Ala Gly
4100 4105 4110

Ala Ala Ala Gly Gly Gly Cys Ala Ala Ala Ala Ala Ala Ala Thr
4115 4120 4125

Ala Cys Thr Ala Ala Thr Ala Ala Thr Gly Gly Ala Ala Ala Gly

-continued

```
    4130                4135                4140

Ala Ala  Thr Ala Ala Ala Thr  Gly Thr Gly Gly Ala  Ala Ala Thr
    4145                4150                4155

Gly Ala  Ala Gly Ala Gly Gly  Ala Thr Cys Cys Thr  Cys Cys Thr
    4160                4165                4170

Gly Ala  Thr Gly Ala Thr Gly  Ala Thr Thr Ala Thr  Ala Thr Thr
    4175                4180                4185

Cys Cys  Ala Cys Ala Ala Cys  Cys Thr Thr Thr Thr  Cys Gly Thr
    4190                4195                4200

Thr Gly  Gly Thr Thr Ala Cys  Ala Ala Gly Ala Ala  Thr Gly Gly
    4205                4210                4215

Ala Gly  Thr Gly Ala Ala Cys  Ala Thr Thr Thr Thr  Thr Gly Thr
    4220                4225                4230

Ala Gly  Ala Gly Thr Thr Cys  Ala Ala Thr Ala Thr  Gly Ala Thr
    4235                4240                4245

Ala Ala  Thr Cys Thr Gly Ala  Ala Thr Ala Ala Ala  Cys Thr Gly
    4250                4255                4260

Ala Ala  Ala Gly Ala Ala Gly  Ala Ala Thr Gly Thr  Gly Gly Ala
    4265                4270                4275

Gly Ala  Ala Thr Gly Thr Ala  Ala Thr Gly Ala Ala  Ala Ala Thr
    4280                4285                4290

Ala Ala  Ala Ala Ala Thr Gly  Gly Thr Thr Thr Ala  Gly Cys Thr
    4295                4300                4305

Thr Gly  Thr Ala Thr Gly Ala  Thr Gly Ala Ala Thr  Thr Cys Ala
    4310                4315                4320

Ala Ala  Thr Ala Thr Thr Ala  Ala Ala Gly Ala Thr  Ala Cys Ala
    4325                4330                4335

Ala Ala  Ala Thr Gly Thr Ala  Thr Gly Ala Ala Thr  Thr Gly Cys
    4340                4345                4350

Ala Ala  Ala Gly Ala Thr Gly  Cys Ala Thr Gly Cys  Ala Ala Gly
    4355                4360                4365

Gly Ala  Cys Thr Ala Cys Ala  Gly Ala Ala Ala Thr  Ala Thr Gly
    4370                4375                4380

Ala Thr  Thr Ala Ala Cys Ala  Cys Ala Thr Gly Gly  Ala Ala Thr
    4385                4390                4395

Ala Gly  Thr Cys Ala Ala Thr  Gly Gly Ala Ala Ala  Ala Ala Ala
    4400                4405                4410

Cys Ala  Ala Cys Ala Ala Gly  Ala Ala Ala Thr Ala  Thr Ala Thr
    4415                4420                4425

Ala Ala  Ala Gly Ala Ala Thr  Thr Ala Thr Ala Thr  Ala Ala Thr
    4430                4435                4440

Ala Cys  Thr Ala Ala Ala Ala  Ala Thr Ala Ala Ala  Ala Thr Ala
    4445                4450                4455

Ala Ala  Thr Ala Thr Thr Ala  Ala Thr Ala Ala Ala  Thr Gly Thr
    4460                4465                4470

Ala Ala  Gly Gly Thr Gly Ala  Thr Ala Gly Ala Ala  Thr Thr Thr
    4475                4480                4485

Thr Thr  Ala Gly Ala Thr Ala  Ala Ala Ala Cys Ala  Ala Ala Thr
    4490                4495                4500

Gly Ala  Thr Ala Cys Gly Thr  Gly Thr Cys Ala Cys  Thr Ala Thr
    4505                4510                4515

Ala Ala  Ala Cys Cys Ala Gly  Gly Ala Ala Gly Thr  Gly Cys Ala
    4520                4525                4530
```

Gly Ala Ala Ala Ala Gly Thr Thr Thr Cys Thr Thr Ala Ala Ala
4535 4540 4545

Gly Ala Ala Thr Cys Thr Ala Gly Thr Cys Ala Thr Thr Gly Thr
4550 4555 4560

Ala Cys Thr Gly Ala Cys Cys Thr Thr Ala Cys Ala Thr Thr Cys
4565 4570 4575

Gly Ala Cys Ala Ala Ala Ala Cys Ala Ala Ala Gly Ala Ala Thr
4580 4585 4590

Thr Cys Ala Ala Ala Thr Ala Ala Thr Ala Thr Thr Cys Cys Thr
4595 4600 4605

Thr Ala Thr Gly Cys Cys Thr Thr Thr Gly Ala Ala Ala Ala Thr
4610 4615 4620

Cys Cys Ala Cys Cys Thr Gly Ala Thr Gly Gly Ala Thr Ala Thr
4625 4630 4635

Ala Ala Ala Gly Thr Thr Thr Thr Ala Thr Gly Thr Gly Gly Thr
4640 4645 4650

Ala Cys Ala Ala Cys Ala Thr Ala Thr Ala Gly Ala Ala Ala Ala
4655 4660 4665

Thr Cys Ala Thr Gly Thr Ala Ala Ala Ala Ala Gly Cys Thr Ala
4670 4675 4680

Ala Ala Ala Ala Ala Ala Thr Thr Ala Gly Gly Gly Ala Thr Gly
4685 4690 4695

Ala Ala Thr Thr Ala Thr Ala Cys Gly Thr Cys Ala Gly Ala Ala
4700 4705 4710

Ala Ala Cys Ala Ala Ala Ala Thr Thr Gly Ala Thr Thr Thr Ala
4715 4720 4725

Ala Gly Thr Gly Gly Ala Gly Ala Ala Ala Ala Cys Gly Cys Thr
4730 4735 4740

Ala Ala Gly Thr Gly Gly Gly Ala Ala Ala Ala Ala Cys Thr Thr
4745 4750 4755

Ala Ala Thr Gly Ala Thr Thr Thr Gly Ala Thr Ala Thr Ala Thr
4760 4765 4770

Gly Thr Cys Cys Cys Thr Cys Cys Ala Cys Gly Ala Ala Cys Ala
4775 4780 4785

Cys Ala Ala Cys Ala Ala Thr Thr Ala Thr Gly Thr Thr Thr Ala
4790 4795 4800

Cys Ala Ala Cys Cys Thr Thr Thr Gly Cys Ala Ala Ala Cys Gly
4805 4810 4815

Thr Thr Gly Ala Thr Ala Thr Cys Ala Cys Gly Thr Ala Cys Cys
4820 4825 4830

Ala Ala Thr Ala Ala Ala Ala Cys Cys Ala Cys Gly Ala Ala Ala
4835 4840 4845

Gly Thr Ala Ala Cys Ala Gly Ala Ala Thr Ala Thr Gly Ala Thr
4850 4855 4860

Thr Thr Cys Thr Cys Cys Ala Gly Ala Gly Cys Ala Thr Thr Ala
4865 4870 4875

Cys Ala Ala Ala Thr Ala Thr Gly Thr Gly Cys Ala Thr Ala Thr
4880 4885 4890

Ala Ala Thr Gly Ala Ala Gly Cys Ala Ala Ala Thr Thr Cys Thr
4895 4900 4905

Cys Thr Thr Cys Ala Cys Ala Ala Thr Thr Ala Thr Thr Ala Thr
4910 4915 4920

```
Ala Gly  Thr Ala Ala Gly Thr  Ala Thr Gly Gly Cys  Ala Ala Ala
    4925                 4930                 4935

Gly Ala  Thr Thr Thr Thr Gly  Thr Ala Thr Thr Thr  Ala Gly Thr
    4940                 4945                 4950

Gly Cys  Thr Gly Gly Thr Ala  Ala Gly Thr Cys Thr  Cys Ala Ala
    4955                 4960                 4965

Gly Ala  Thr Ala Cys Thr Ala  Ala Ala Gly Ala Thr  Gly Ala Ala
    4970                 4975                 4980

Ala Thr  Ala Ala Ala Ala Ala  Cys Ala Cys Ala Cys  Ala Thr Thr
    4985                 4990                 4995

Cys Thr  Thr Gly Ala Ala Ala  Ala Thr Ala Thr Gly  Ala Ala Ala
    5000                 5005                 5010

Ala Gly  Ala Ala Gly Cys Thr  Thr Thr Gly Cys Thr  Gly Ala Thr
    5015                 5020                 5025

Thr Ala  Thr Gly Gly Thr Ala  Ala Thr Thr Thr Ala  Ala Thr Thr
    5030                 5035                 5040

Ala Ala  Ala Gly Gly Ala Ala  Ala Gly Ala Cys Cys  Cys Ala Ala
    5045                 5050                 5055

Thr Ala  Cys Gly Ala Ala Thr  Ala Thr Ala Ala Thr  Gly Gly Thr
    5060                 5065                 5070

Thr Thr  Ala Ala Ala Cys Ala  Ala Ala Ala Ala Gly  Cys Thr Thr
    5075                 5080                 5085

Cys Ala  Gly Gly Ala Thr Thr  Ala Cys Ala Thr Ala  Ala Ala Gly
    5090                 5095                 5100

Ala Cys  Thr Ala Ala Thr Thr  Thr Ala Ala Ala Ala  Thr Ala Thr
    5105                 5110                 5115

Ala Ala  Thr Gly Gly Ala Ala  Cys Thr Gly Ala Cys  Ala Gly Ala
    5120                 5125                 5130

Ala Ala  Ala Ala Cys Ala Gly  Gly Thr Gly Ala Ala  Gly Ala Thr
    5135                 5140                 5145

Cys Thr  Thr Thr Gly Gly Ala  Ala Thr Ala Ala Ala  Cys Ala Thr
    5150                 5155                 5160

Ala Ala  Ala Thr Cys Cys Gly  Ala Thr Ala Thr Thr  Thr Gly Gly
    5165                 5170                 5175

Ala Ala  Thr Thr Cys Thr Ala  Thr Gly Cys Thr Ala  Thr Gly Thr
    5180                 5185                 5190

Gly Gly  Ala Thr Ala Thr Ala  Ala Thr Gly Ala Ala  Gly Ala Ala
    5195                 5200                 5205

Ala Ala  Cys Cys Cys Ala Ala  Gly Thr Gly Ala Ala  Cys Cys Ala
    5210                 5215                 5220

Cys Thr  Thr Cys Ala Thr Gly  Ala Thr Ala Ala Ala  Gly Ala Cys
    5225                 5230                 5235

Ala Thr  Ala Ala Gly Ala Thr  Gly Thr Ala Ala Ala  Thr Thr Ala
    5240                 5245                 5250

Cys Cys  Thr Gly Ala Thr Ala  Ala Thr Gly Ala Thr  Ala Gly Thr
    5255                 5260                 5265

Gly Ala  Ala Gly Ala Thr Gly  Ala Ala Thr Thr Thr  Thr Thr Ala
    5270                 5275                 5280

Cys Gly  Thr Thr Gly Gly Thr  Thr Thr Cys Ala Ala  Gly Ala Ala
    5285                 5290                 5295

Thr Gly  Gly Ala Gly Ala Gly  Ala Ala Gly Ala Thr  Thr Thr Thr
    5300                 5305                 5310

Thr Gly  Thr Gly Thr Thr Ala  Thr Cys Ala Ala Ala  Gly Gly Thr
```

-continued

```
    5315                5320                5325

Ala Thr  Ala Cys Thr Gly Ala  Thr Ala Cys Ala Ala  Ala Ala Thr
    5330                5335                5340

Gly Thr  Gly Ala Ala Ala Gly  Ala Thr Gly Cys Ala  Thr Gly Thr
    5345                5350                5355

Ala Ala  Thr Thr Thr Thr Ala  Ala Thr Ala Ala Thr  Thr Gly Thr
    5360                5365                5370

Gly Ala  Ala Gly Ala Thr Gly  Cys Ala Ala Ala Thr  Ala Ala Thr
    5375                5380                5385

Ala Ala  Ala Thr Cys Cys Ala  Thr Ala Ala Gly Ala  Thr Cys Thr
    5390                5395                5400

Thr Gly  Thr Cys Ala Ala Ala  Ala Ala Cys Cys Ala  Thr Gly Thr
    5405                5410                5415

Gly Thr  Cys Ala Ala Ala Thr  Ala Cys Ala Ala Ala  Ala Cys Ala
    5420                5425                5430

Thr Gly  Gly Gly Thr Thr Gly  Ala Ala Cys Ala Ala  Ala Gly Ala
    5435                5440                5445

Ala Ala  Ala Ala Thr Thr Gly  Ala Ala Thr Ala Cys  Gly Ala Ala
    5450                5455                5460

Ala Ala  Thr Cys Ala Ala Ala  Thr Cys Cys Ala Gly  Ala Ala Ala
    5465                5470                5475

Thr Ala  Thr Ala Ala Ala Ala  Ala Thr Cys Thr Cys  Ala Ala Cys
    5480                5485                5490

Ala Ala  Thr Ala Ala Thr Thr  Cys Ala Ala Ala Thr  Gly Ala Ala
    5495                5500                5505

Gly Gly  Ala Ala Ala Ala Gly  Ala Ala Thr Cys Ala  Cys Thr Thr
    5510                5515                5520

Thr Thr  Ala Thr Thr Thr Thr  Thr Ala Ala Ala Cys  Gly Ala Thr
    5525                5530                5535

Ala Ala  Ala Thr Gly Thr Ala  Ala Ala Gly Gly Gly  Ala Ala Ala
    5540                5545                5550

Thr Gly  Thr Gly Ala Ala Thr  Gly Thr Ala Thr Ala  Gly Thr Thr
    5555                5560                5565

Cys Ala  Ala Ala Ala Ala Ala  Ala Ala Ala Gly Thr  Ala Cys Thr
    5570                5575                5580

Gly Ala  Thr Ala Ala Thr Ala  Thr Cys Gly Ala Thr  Ala Ala Gly
    5585                5590                5595

Ala Thr  Thr Thr Thr Thr Gly  Ala Gly Gly Ala Ala  Thr Ala Thr
    5600                5605                5610

Cys Cys  Thr Gly Ala Ala Gly  Ala Ala Thr Ala Cys  Ala Ala Ala
    5615                5620                5625

Ala Cys  Gly Cys Ala Ala Thr  Gly Thr Gly Ala Ala  Thr Gly Thr
    5630                5635                5640

Cys Ala  Gly Cys Cys Thr Gly  Ala Thr Cys Cys Ala  Thr Gly Thr
    5645                5650                5655

Ala Gly  Thr Gly Ala Cys Cys  Thr Ala Ala Gly Thr  Ala Thr Thr
    5660                5665                5670

Ala Cys  Ala Gly Ala Thr Ala  Gly Thr Gly Gly Ala  Thr Thr Thr
    5675                5680                5685

Cys Cys  Thr Gly Ala Thr Gly  Cys Ala Ala Gly Thr  Cys Cys Thr
    5690                5695                5700

Thr Thr  Thr Gly Gly Thr Gly  Gly Ala Gly Gly Thr  Cys Ala Ala
    5705                5710                5715
```

```
Cys Cys  Ala Cys Gly Thr Thr  Cys Cys Gly Cys Gly  Thr Gly Thr
    5720                 5725                 5730

Cys Cys  Thr Ala Cys Ala Ala  Gly Gly Cys Gly Ala  Gly Gly Ala
    5735                 5740                 5745

Ala Ala  Thr Cys Ala Thr Ala  Ala Thr Ala Ala Thr  Thr Gly Cys
    5750                 5755                 5760

Cys Cys  Thr Ala Cys Thr Gly  Ala Ala Gly Ala Ala  Ala Thr Ala
    5765                 5770                 5775

Thr Gly  Thr Ala Ala Ala Ala  Ala Ala Thr Ala Thr  Gly Ala Thr
    5780                 5785                 5790

Ala Gly  Cys Thr Ala Thr Ala  Thr Thr Ala Ala Thr  Gly Gly Thr
    5795                 5800                 5805

Thr Gly  Thr Cys Gly Cys Cys  Cys Thr Ala Ala Ala  Ala Cys Ala
    5810                 5815                 5820

Thr Ala  Thr Cys Ala Cys Gly  Ala Cys Ala Ala Thr  Ala Cys Ala
    5825                 5830                 5835

Ala Ala  Thr Ala Ala Thr Thr  Gly Gly Gly Ala Thr  Ala Gly Cys
    5840                 5845                 5850

Ala Gly  Ala Gly Gly Cys Ala  Thr Gly Cys Thr Ala  Ala Ala Cys
    5855                 5860                 5865

Ala Gly  Thr Thr Cys Ala Thr  Cys Thr Gly Ala Ala  Ala Ala Thr
    5870                 5875                 5880

Gly Ala  Ala Gly Gly Thr Gly  Thr Ala Thr Thr Ala  Ala Thr Thr
    5885                 5890                 5895

Cys Cys  Thr Cys Cys Thr Ala  Gly Ala Ala Gly Gly  Cys Gly Ala
    5900                 5905                 5910

Cys Ala  Thr Thr Thr Ala Thr  Gly Cys Ala Cys Ala  Ala Gly Ala
    5915                 5920                 5925

Ala Ala  Thr Ala Thr Ala Ala  Thr Thr Ala Ala Ala  Ala Ala Thr
    5930                 5935                 5940

Thr Thr  Gly Thr Cys Ala Cys  Gly Thr Ala Thr Thr  Ala Ala Ala
    5945                 5950                 5955

Ala Ala  Thr Ala Ala Ala Gly  Ala Thr Cys Ala Thr  Thr Thr Thr
    5960                 5965                 5970

Ala Ala  Ala Gly Ala Thr Thr  Ala Cys Cys Thr Ala  Ala Thr Gly
    5975                 5980                 5985

Ala Ala  Ala Thr Cys Thr Gly  Cys Thr Thr Ala Thr  Gly Ala Ala
    5990                 5995                 6000

Gly Ala  Ala Gly Gly Ala Ala  Ala Ala Cys Thr Thr  Thr Thr Ala
    6005                 6010                 6015

Ala Gly  Gly Gly Ala Ala Ala  Ala Ala Thr Ala Thr  Ala Gly Ala
    6020                 6025                 6030

Ala Ala  Thr Ala Ala Thr Ala  Gly Thr Ala Gly Ala  Gly Ala Thr
    6035                 6040                 6045

Gly Gly  Ala Thr Thr Ala Ala  Ala Thr Gly Cys Ala  Ala Thr Gly
    6050                 6055                 6060

Ala Thr  Gly Thr Thr Cys Ala  Cys Thr Thr Thr Thr  Gly Cys Thr
    6065                 6070                 6075

Gly Ala  Thr Thr Ala Thr Gly  Cys Ala Gly Ala Thr  Ala Thr Ala
    6080                 6085                 6090

Gly Thr  Thr Ala Ala Ala Gly  Gly Thr Ala Cys Thr  Gly Ala Thr
    6095                 6100                 6105
```

-continued

Ala Thr Ala Thr Thr Thr Gly Gly Cys Ala Gly Thr Ala Thr Ala
6110 6115 6120

Thr Thr Ala Thr Cys Thr Cys Ala Ala Ala Ala Ala Thr Thr Ala
6125 6130 6135

Gly Gly Thr Gly Ala Ala Ala Thr Ala Ala Cys Thr Gly Gly Ala
6140 6145 6150

Ala Thr Ala Ala Gly Cys Ala Ala Thr Gly Ala Thr Ala Thr Ala
6155 6160 6165

Ala Ala Thr Gly Ala Gly Cys Gly Thr Ala Ala Ala Ala Ala Ala
6170 6175 6180

Thr Gly Gly Thr Gly Gly Ala Gly Thr Gly Ala Ala Ala Thr Thr
6185 6190 6195

Ala Ala Ala Ala Ala Thr Ala Ala Thr Ala Thr Ala Thr Gly Gly
6200 6205 6210

Gly Ala Ala Gly Thr Thr Ala Thr Gly Thr Thr Gly Thr Gly Thr
6215 6220 6225

Thr Cys Thr Thr Ala Thr Ala Ala Thr Ala Gly Ala Ala Cys Ala
6230 6235 6240

Ala Ala Gly Ala Ala Thr Ala Ala Thr Ala Ala Thr Ala Ala Thr
6245 6250 6255

Thr Thr Thr Thr Thr Cys Gly Gly Ala Ala Ala Cys Ala Thr Thr
6260 6265 6270

Gly Thr Gly Ala Gly Ala Gly Ala Ala Ala Ala Cys Thr Gly Thr
6275 6280 6285

Ala Ala Thr Gly Thr Thr Cys Cys Thr Ala Ala Cys Ala Cys Ala
6290 6295 6300

Gly Ala Thr Gly Ala Ala Ala Ala Gly Gly Ala Cys Cys Ala Ala
6305 6310 6315

Thr Thr Thr Thr Thr Gly Ala Gly Ala Thr Gly Gly Thr Thr Ala
6320 6325 6330

Cys Thr Thr Gly Ala Ala Thr Gly Gly Gly Gly Thr Ala Thr Ala
6335 6340 6345

Cys Ala Ala Gly Cys Ala Thr Gly Thr Ala Ala Ala Gly Ala Ala
6350 6355 6360

Ala Ala Ala Ala Ala Ala Ala Thr Cys Ala Gly Ala Ala Ala Ala
6365 6370 6375

Cys Ala Ala Gly Cys Cys Cys Thr Thr Cys Ala Ala Ala Cys Gly
6380 6385 6390

Ala Ala Gly Thr Gly Thr Thr Ala Cys Thr Gly Thr Thr Cys Ala
6395 6400 6405

Ala Ala Cys Cys Cys Ala Ala Ala Cys Gly Ala Ala Ala Thr Ala
6410 6415 6420

Thr Cys Gly Gly Gly Thr Thr Cys Cys Gly Ala Thr Ala Thr Thr
6425 6430 6435

Ala Thr Ala Ala Ala Ala Cys Ala Thr Thr Ala Cys Cys Cys Thr
6440 6445 6450

Thr Gly Thr Ala Ala Ala Ala Gly Thr Gly Ala Ala Cys Thr Cys
6455 6460 6465

Ala Cys Cys Ala Ala Ala Thr Ala Thr Ala Thr Ala Cys Ala Ala
6470 6475 6480

Thr Gly Gly Ala Ala Thr Thr Thr Ala Ala Thr Gly Ala Thr Thr
6485 6490 6495

Ala Ala Ala Gly Ala Ala Thr Thr Ala Thr Thr Ala Gly Ala Thr

```
    6500                6505                6510

Cys Ala  Ala Thr Thr Ala Ala  Ala Thr Ala Thr Ala  Ala Ala Ala
    6515                6520                6525

Thr Ala  Thr Cys Ala Ala Ala  Ala Thr Ala Thr Ala  Ala Ala Ala
    6530                6535                6540

Gly Cys  Ala Thr Cys Thr Ala  Ala Thr Ala Ala Thr  Cys Cys Gly
    6545                6550                6555

Ala Ala  Ala Ala Ala Thr Cys  Cys Cys Thr Cys Gly  Gly Ala Ala
    6560                6565                6570

Ala Thr  Ala Ala Ala Thr Gly  Cys Ala Gly Ala Gly  Gly Ala Ala
    6575                6580                6585

Thr Ala  Cys Ala Thr Ala Gly  Ala Ala Ala Cys Ala  Gly Ala Ala
    6590                6595                6600

Cys Thr  Thr Ala Ala Gly Gly  Ala Ala Gly Gly Thr  Gly Ala Ala
    6605                6610                6615

Thr Gly  Thr Ala Ala Thr Thr  Thr Gly Gly Thr Thr  Gly Ala Thr
    6620                6625                6630

Ala Thr  Ala Gly Ala Ala Cys  Gly Ala Ala Thr Ala  Thr Ala Thr
    6635                6640                6645

Ala Ala  Thr Ala Ala Ala Ala  Thr Thr Ala Ala Ala  Cys Ala Ala
    6650                6655                6660

Gly Ala  Ala Cys Ala Thr Ala  Ala Thr Cys Cys Ala  Thr Thr Ala
    6665                6670                6675

Ala Ala  Ala Gly Ala Ala Ala  Thr Ala Thr Thr Ala  Ala Thr Gly
    6680                6685                6690

Thr Ala  Thr Thr Thr Ala Thr  Gly Thr Cys Cys Thr  Ala Ala Thr
    6695                6700                6705

Thr Thr  Ala Gly Ala Ala Thr  Thr Thr Cys Cys Thr  Gly Ala Thr
    6710                6715                6720

Gly Ala  Thr Ala Cys Ala Thr  Thr Cys Gly Ala Ala  Thr Ala Cys
    6725                6730                6735

Ala Thr  Thr Gly Gly Gly Ala  Ala Ala Ala Cys Cys  Gly Ala Ala
    6740                6745                6750

Ala Cys  Thr Gly Ala Ala Gly  Ala Thr Ala Cys Ala  Ala Cys Thr
    6755                6760                6765

Ala Thr  Thr Gly Ala Ala Cys  Cys Ala Gly Ala Ala  Ala Cys Cys
    6770                6775                6780

Cys Cys  Thr Ala Cys Ala Thr  Cys Cys Gly Ala Thr  Ala Ala Cys
    6785                6790                6795

Cys Cys  Thr Gly Ala Gly Gly  Ala Thr Ala Gly Thr  Ala Thr Thr
    6800                6805                6810

Cys Cys  Thr Thr Cys Cys Ala  Thr Thr Thr Cys Ala  Cys Cys Thr
    6815                6820                6825

Gly Ala  Ala Gly Ala Cys Gly  Thr Thr Cys Ala Cys  Cys Cys Ala
    6830                6835                6840

Ala Cys  Ala Ala Cys Ala Gly  Gly Ala Gly Ala Ala  Gly Ala Cys
    6845                6850                6855

Ala Cys  Ala Ala Ala Cys Ala  Thr Thr Thr Thr Cys  Ala Ala Cys
    6860                6865                6870

Ala Gly  Thr Ala Ala Cys Ala  Thr Ala Thr Thr Ala  Thr Cys Ala
    6875                6880                6885

Thr Cys  Thr Ala Cys Thr Ala  Thr Cys Cys Cys Thr  Thr Thr Thr
    6890                6895                6900
```

```
Gly Gly Ala Ala Thr Thr Gly Cys Thr Thr Thr Gly Gly Cys Cys
    6905                6910                6915

Thr Thr Ala Ala Gly Thr Thr Cys Gly Ala Thr Cys Gly Cys Thr
    6920                6925                6930

Thr Thr Cys Cys Thr Gly Thr Thr Cys Cys Thr Gly Ala Ala Gly
    6935                6940                6945

Ala Ala Ala Ala Ala Ala Ala Cys Cys Cys Thr Ala Thr Cys Cys
    6950                6955                6960

Cys Cys Thr Gly Thr Gly Gly Ala Cys Cys Thr Cys Thr Thr Ala
    6965                6970                6975

Cys Gly Thr Gly Thr Ala Cys Thr Thr Gly Ala Thr Ala Thr Cys
    6980                6985                6990

Cys Ala Thr Ala Ala Ala Gly Gly Cys Gly Ala Thr Thr Ala Thr
    6995                7000                7005

Gly Gly Ala Ala Thr Ala Cys Cys Thr Ala Cys Ala Cys Thr Gly
    7010                7015                7020

Ala Ala Ala Thr Cys Cys Ala Ala Ala Ala Ala Thr Ala Gly Gly
    7025                7030                7035

Thr Ala Thr Ala Thr Ala Cys Cys Ala Thr Ala Thr Ala Gly Ala
    7040                7045                7050

Ala Gly Thr Gly Gly Thr Ala Cys Ala Thr Ala Thr Ala Ala Ala
    7055                7060                7065

Gly Gly Cys Ala Ala Ala Ala Cys Ala Thr Ala Thr Thr Thr Ala
    7070                7075                7080

Thr Ala Thr Gly Thr Thr Gly Ala Ala Gly Gly Ala Gly Ala Thr
    7085                7090                7095

Ala Gly Thr Gly Ala Thr Ala Gly Thr Gly Gly Ala Cys Ala Cys
    7100                7105                7110

Thr Ala Cys Thr Ala Cys Gly Ala Ala Gly Ala Thr Ala Cys Ala
    7115                7120                7125

Ala Cys Thr Gly Ala Thr Ala Thr Thr Ala Cys Thr Thr Cys Ala
    7130                7135                7140

Thr Cys Cys Gly Ala Ala Ala Gly Thr Gly Ala Ala Thr Ala Thr
    7145                7150                7155

Gly Ala Ala Gly Ala Ala Ala Thr Gly Gly Ala Thr Ala Thr Cys
    7160                7165                7170

Ala Ala Thr Gly Ala Thr Ala Thr Ala Thr Ala Thr Gly Thr Ala
    7175                7180                7185

Cys Cys Ala Gly Gly Thr Ala Gly Thr Cys Cys Thr Ala Ala Ala
    7190                7195                7200

Thr Ala Thr Ala Ala Ala Ala Cys Ala Thr Thr Gly Ala Thr Ala
    7205                7210                7215

Gly Ala Ala Gly Thr Ala Gly Thr Ala Cys Thr Gly Gly Ala Ala
    7220                7225                7230

Cys Cys Ala Thr Cys Cys Ala Ala Ala Ala Gly Thr Gly Ala Thr
    7235                7240                7245

Gly Gly Thr Cys Ala Thr Ala Thr Ala Cys Cys Ala Cys Ala Thr
    7250                7255                7260

Ala Gly Thr Gly Cys Thr Gly Gly Thr Gly Ala Ala Cys Cys Ala
    7265                7270                7275

Cys Thr Ala Gly Ala Thr Gly Ala Thr Ala Thr Gly Gly Thr Ala
    7280                7285                7290
```

```
Gly Gly  Thr Ala Cys Cys Ala  Cys Thr Ala Thr Ala  Thr Thr Thr
    7295                 7300                 7305

Ala Cys  Ala Gly Ala Thr Gly  Ala Gly Gly Ala Ala  Thr Gly Gly
    7310                 7315                 7320

Ala Ala  Thr Gly Ala Ala Cys  Thr Gly Ala Ala Ala  Cys Ala Cys
    7325                 7330                 7335

Gly Ala  Thr Thr Thr Thr Ala  Thr Ala Thr Cys Ala  Cys Ala Ala
    7340                 7345                 7350

Thr Ala  Thr Gly Thr Gly Cys  Ala Ala Cys Gly Thr  Gly Ala Ala
    7355                 7360                 7365

Thr Cys  Ala Ala Thr Gly Gly  Gly Thr Gly Thr Ala  Cys Cys Ala
    7370                 7375                 7380

Cys Ala  Ala Thr Ala Thr Gly  Ala Thr Gly Thr Ala  Thr Cys Ala
    7385                 7390                 7395

Ala Cys  Cys Gly Ala Gly Thr  Thr Ala Cys Cys Ala  Ala Thr Gly
    7400                 7405                 7410

Ala Ala  Thr Ala Thr Ala Gly  Gly Ala Gly Gly Thr  Ala Ala Thr
    7415                 7420                 7425

Gly Thr  Thr Thr Thr Ala Gly  Ala Thr Gly Ala Thr  Gly Gly Cys
    7430                 7435                 7440

Ala Thr  Gly Gly Ala Ala Gly  Ala Ala Ala Ala Ala  Cys Cys Thr
    7445                 7450                 7455

Thr Thr  Thr Ala Thr Thr Ala  Cys Thr Thr Cys Thr  Ala Thr Thr
    7460                 7465                 7470

Cys Ala  Thr Gly Ala Thr Ala  Gly Gly Gly Ala Thr  Thr Thr Ala
    7475                 7480                 7485

Thr Ala  Thr Ala Cys Thr Gly  Gly Ala Gly Ala Ala  Gly Ala Ala
    7490                 7495                 7500

Thr Thr  Thr Ala Gly Thr Thr  Ala Thr Ala Ala Thr  Ala Thr Thr
    7505                 7510                 7515

Ala Ala  Thr Ala Thr Gly Gly  Gly Thr Ala Cys Thr  Ala Ala Thr
    7520                 7525                 7530

Ala Gly  Thr Ala Thr Gly Gly  Ala Thr Gly Ala Thr  Cys Cys Ala
    7535                 7540                 7545

Ala Ala  Ala Thr Ala Thr Gly  Thr Ala Thr Cys Ala  Ala Ala Thr
    7550                 7555                 7560

Ala Ala  Thr Gly Thr Ala Thr  Ala Thr Thr Cys Thr  Gly Gly Thr
    7565                 7570                 7575

Ala Thr  Cys Gly Ala Thr Thr  Thr Ala Ala Thr Thr  Ala Ala Thr
    7580                 7585                 7590

Gly Ala  Cys Ala Cys Ala Thr  Thr Ala Ala Gly Thr  Gly Gly Thr
    7595                 7600                 7605

Ala Ala  Thr Cys Ala Ala Cys  Ala Thr Ala Thr Thr  Gly Ala Thr
    7610                 7615                 7620

Ala Thr  Ala Thr Ala Thr Gly  Ala Thr Gly Ala Ala  Gly Thr Ala
    7625                 7630                 7635

Thr Thr  Gly Ala Ala Ala Ala  Gly Ala Ala Ala Ala  Gly Ala Ala
    7640                 7645                 7650

Ala Ala  Thr Gly Ala Ala Thr  Thr Ala Thr Thr Thr  Gly Gly Gly
    7655                 7660                 7665

Ala Cys  Ala Ala Ala Thr Thr  Ala Thr Ala Ala Gly  Ala Ala Ala
    7670                 7675                 7680

Ala Ala  Thr Ala Thr Ala Thr  Cys Gly Ala Ala Thr  Ala Ala Cys
```

```
    7685                7690                7695

Cys Gly  Thr Gly Thr Ala Gly  Cys Thr Ala Ala Ala  Thr Thr Ala
    7700                7705                7710

Ala Cys  Ala Ala Ala Thr Ala  Ala Thr Gly Ala Thr  Cys Cys Ala
    7715                7720                7725

Ala Thr  Thr Ala Thr Gly Ala  Ala Cys Cys Ala Ala  Thr Thr Ala
    7730                7735                7740

Gly Ala  Thr Thr Thr Gly Thr  Thr Ala Cys Ala Thr  Ala Ala Ala
    7745                7750                7755

Thr Gly  Gly Thr Thr Ala Gly  Ala Thr Ala Gly Ala  Cys Ala Thr
    7760                7765                7770

Ala Gly  Ala Gly Ala Thr Ala  Thr Gly Thr Gly Cys  Ala Ala Thr
    7775                7780                7785

Ala Cys  Gly Thr Gly Gly Ala  Ala Thr Ala Cys Cys  Ala Ala Gly
    7790                7795                7800

Gly Ala  Ala Gly Ala Ala Thr  Thr Ala Thr Thr Ala  Gly Ala Thr
    7805                7810                7815

Ala Ala  Ala Thr Thr Gly Ala  Ala Thr Gly Ala Ala  Cys Ala Ala
    7820                7825                7830

Thr Gly  Gly Ala Ala Thr Ala  Ala Ala Gly Ala Thr  Ala Ala Thr
    7835                7840                7845

Gly Ala  Thr Gly Cys Thr Gly  Gly Thr Gly Ala Thr  Ala Thr Ala
    7850                7855                7860

Cys Cys  Ala Ala Gly Thr Gly  Ala Thr Ala Gly Thr  Ala Ala Cys
    7865                7870                7875

Ala Ala  Ala Ala Ala Gly Thr  Thr Gly Ala Ala Thr  Ala Cys Gly
    7880                7885                7890

Gly Ala  Thr Gly Thr Thr Thr  Cys Gly Ala Thr Ala  Cys Ala Ala
    7895                7900                7905

Ala Thr  Ala Gly Ala Thr Ala  Thr Gly Gly Ala Thr  Gly Ala Thr
    7910                7915                7920

Cys Cys  Thr Ala Ala Ala Gly  Gly Ala Ala Ala Gly  Ala Ala Gly
    7925                7930                7935

Gly Ala  Ala Thr Thr Thr Ala  Gly Thr Ala Ala Thr  Ala Thr Gly
    7940                7945                7950

Gly Ala  Thr Ala Cys Thr Ala  Thr Cys Thr Thr Gly  Gly Ala Thr
    7955                7960                7965

Gly Ala  Thr Ala Thr Ala Gly  Ala Ala Gly Ala Thr  Gly Ala Thr
    7970                7975                7980

Ala Thr  Ala Thr Ala Thr Thr  Ala Thr Gly Ala Thr  Gly Thr Ala
    7985                7990                7995

Ala Ala  Thr Gly Ala Thr Gly  Ala Ala Ala Ala Cys  Cys Cys Ala
    8000                8005                8010

Thr Thr  Thr Gly Thr Gly Gly  Ala Thr Gly Ala Thr  Ala Thr Ala
    8015                8020                8025

Cys Cys  Thr Ala Thr Gly Gly  Ala Thr Cys Ala Thr  Ala Ala Thr
    8030                8035                8040

Ala Ala  Ala Gly Thr Ala Gly  Ala Thr Gly Thr Ala  Cys Cys Ala
    8045                8050                8055

Ala Ala  Gly Ala Ala Ala Gly  Thr Ala Cys Ala Thr  Gly Thr Thr
    8060                8065                8070

Gly Ala  Ala Ala Thr Gly Ala  Ala Ala Ala Thr Cys  Cys Thr Thr
    8075                8080                8085
```

-continued

```
Ala Ala  Thr Ala Ala Thr Ala  Cys Ala Thr Cys Cys  Ala Ala Thr
    8090                 8095                 8100

Gly Gly  Ala Thr Cys Cys Thr  Thr Gly Gly Ala Ala  Cys Cys Ala
    8105                 8110                 8115

Gly Ala  Ala Thr Thr Thr Cys  Cys Thr Ala Thr Ala  Thr Cys Gly
    8120                 8125                 8130

Gly Ala  Thr Gly Thr Ala Thr  Gly Gly Ala Ala Thr  Ala Thr Ala
    8135                 8140                 8145

Thr Ala  Ala
    8150
```